US012290561B2

(12) United States Patent
Ertl et al.

(10) Patent No.: US 12,290,561 B2
(45) Date of Patent: May 6, 2025

(54) ADENOVIRAL VECTORS ENCODING HEPATITIS B VIRAL ANTIGENS FUSED TO HERPES VIRUS GLYCOPROTEIN D AND METHODS OF USING THE SAME

(71) Applicants: Virion Therapeutics, LLC, Newark, DE (US); The Wistar Institute, Philadelphia, PA (US)

(72) Inventors: Hildegund C J Ertl, Villanova, PA (US); Colin Stephen Magowan, Bishop, CA (US)

(73) Assignees: Virion Therapeutics, LLC, Newark, DE (US); The Wistar Institute, Philadelphia, PA (US)

( * ) Notice: Subject to any disclaimer, the term of this patent is extended or adjusted under 35 U.S.C. 154(b) by 0 days.

(21) Appl. No.: 18/492,945

(22) Filed: Oct. 24, 2023

(65) Prior Publication Data
US 2024/0091347 A1 Mar. 21, 2024

Related U.S. Application Data

(63) Continuation of application No. 17/679,356, filed on Feb. 24, 2022, now Pat. No. 11,850,282, which is a continuation of application No. 17/459,313, filed on Aug. 27, 2021, now Pat. No. 11,291,716, which is a continuation of application No. PCT/US2021/012630, filed on Jan. 8, 2021.

(60) Provisional application No. 63/112,219, filed on Nov. 11, 2020, provisional application No. 63/112,202, filed on Nov. 11, 2020, provisional application No. 63/064,506, filed on Aug. 12, 2020, provisional application No. 63/064,571, filed on Aug. 12, 2020, provisional application No. 62/967,104, filed on Jan. 29, 2020, provisional application No. 62/967,242, filed on Jan. 29, 2020, provisional application No. 62/958,809, filed on Jan. 9, 2020, provisional application No. 62/958,827, filed on Jan. 9, 2020.

(51) Int. Cl.
| | |
|---|---|
| *A61K 39/29* | (2006.01) |
| *A61K 35/761* | (2015.01) |
| *A61K 38/00* | (2006.01) |
| *A61K 39/00* | (2006.01) |
| *A61K 39/12* | (2006.01) |
| *A61P 31/12* | (2006.01) |
| *C12N 7/00* | (2006.01) |
| *C12N 15/86* | (2006.01) |

(52) U.S. Cl.
CPC ............ *A61K 39/292* (2013.01); *A61P 31/12* (2018.01); *C12N 7/00* (2013.01); *C12N 15/86* (2013.01); *A61K 2039/53* (2013.01); *C12N 2710/10343* (2013.01); *C12N 2730/10122* (2013.01); *C12N 2730/10134* (2013.01)

(58) Field of Classification Search
CPC .. A61K 2039/53; A61K 39/12; A61K 39/292; A61K 39/29; A61P 31/12
See application file for complete search history.

(56) References Cited

U.S. PATENT DOCUMENTS

2007/0054262 A1 3/2007 Baker et al.

FOREIGN PATENT DOCUMENTS

| | | |
|---|---|---|
| JP | 2014507144 A | 3/2014 |
| WO | 2012109404 A1 | 8/2012 |
| WO | 2018026547 A1 | 2/2018 |

OTHER PUBLICATIONS

Barbara Rehermann, et al.; "The Cytotoxic T Lymphocyte Response to Multiple Hepatitis B Virus Polymerase Epitopes During and After Acute Viral Hepatitis"; The Journal of Experimental Medicine; vol. 181, Mar. 1995; pp. 1047-1059.
Nanna-Sophie Brinck-Jensen, et al.; "Immunogenicity of twenty peptides representing epitopes of the hepatitis B core and surface antigens by IFN-γ response in chronic and resolved HBV"; BMC Immunology; 2015; pp. 1-12.
Brinck-Jensen, Nanna-Sophie et al.; "Immunogenicity of Twenty Peptides Representing Epitopes of the Hepatitis B Core and Surface Antigens by IFN-γ Response in Chronic and Resolved HBV", BMC Immunology (2015) vol. 16, No. 65, 2015; pp. 1-12.
Farina, Steven F., et al., "Replication-Defective Vector Based on a Chimpanzee Adenovirus", Journal of Virology (2001) vol. 75, No. 23, pp. 11603-11613.
Hu, Yue, et al., LBP-25—A Phase 1 Clinical Trial of Therapeutic Vaccine t101 in Chronic Hepatitis b(chb) Patients: a Randomized, Double-Blind, Placebo-Controlled, Single and Multiple Injections, Journal of Hepatology, vol. 70, pp. e153-e154.
Jian, Li et al., "The Prevalence of Neutralizing Antibodies to Chimpanzee Adenovirus Type 6 and Type 7 in Healthy Adult Volunteers, Patients with Chronic Hepatitis B and Patients with Primary Hepatocellular Carcinoma in China", Archives of Virology, vol. 159 (2014), pp. 465-470.
Martin, Perrine et al., "TG1050, An Immunotherapeutic to Treat Chronic Hepatitis B, Induces Robust T Cells and Exerts an Antiviral Effect in HBV-Persistent Mice", GUT 2015, vol. 64, No. 12, pp. 1961-1971.

(Continued)

*Primary Examiner* — Barry A Chestnut
(74) *Attorney, Agent, or Firm* — BakerHostetler

(57) ABSTRACT

Provided herein are non-naturally occurring variants of the hepatitis B virus (HBV) Core protein, the HBV polymerase N-terminal domain, and the HBV polymerase C-terminal domain, as well as immunogenic fragments thereof. Fusion proteins comprising the HBV variants fused to a herpes simplex virus (HSV) glycoprotein (gD) sequence, as well as methods of using the fusion proteins, are also provided.

20 Claims, 49 Drawing Sheets

Specification includes a Sequence Listing.

(56) References Cited

OTHER PUBLICATIONS

Pinto, Arguinaldo R., et al., "Induction of CD8+ T Cells to an HIV-1 Antigen Through a Prime Boost Regimen with Heterologous E1-Deleted Adenoviral Vaccine Carriers", Journal of Immunology (2003) vol. 171, No. 12, pp. 6774-6779.

Rehermann, Barbara, et al.; "The Cytotoxic T Lymphocyte Response to Multiple Hepatitis B Virus Polymerase Epitopes During and After Acute Viral Hepatitis"; The Journal of Experimental Medicine, (1995) vol. 181, No. 3, pp. 1047-1058.

Reyes-Sandoval, A., et al., "Human Immunodeficiency Virus Type 1-Specific Immune Responses in Primates Upon Sequential Immunization with Adenoviral Vaccine Carriers of Human Simian Serotypes", Journal of Virology, (2004) vol. 78, pp. 7392-7399.

Zheng, Bojian, et al., "Immunogenicity in Mice of Tandem Repeats of an Epitope From Herpes Simplex gD Protein When Expressed by Recombinant Adenovirus Vectors", Vaccine (1993), vol. 11, No. 12, pp. 1191-1198.

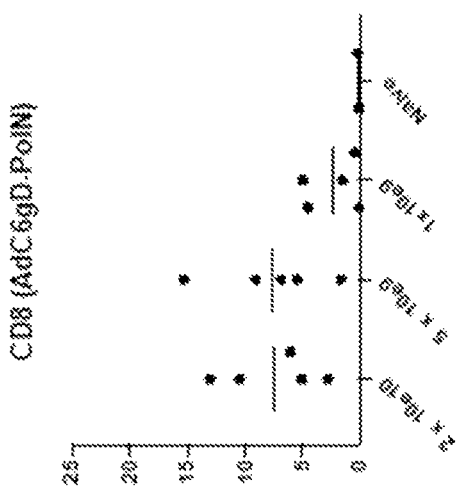
FIG. 2A  FIG. 2B  FIG. 2C
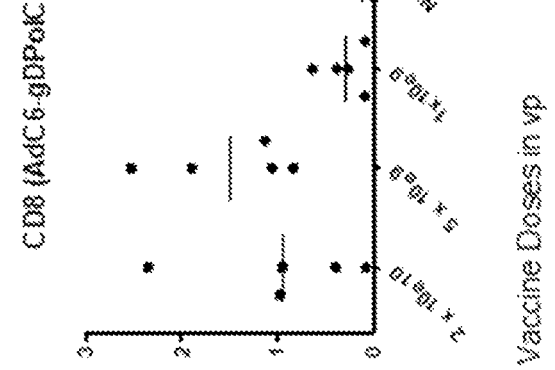
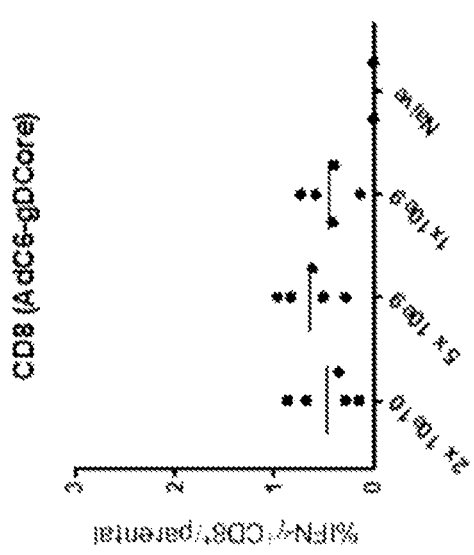

FIG. 7A
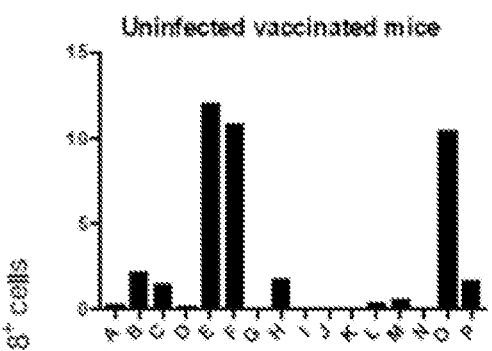
FIG. 7D
FIG. 7B
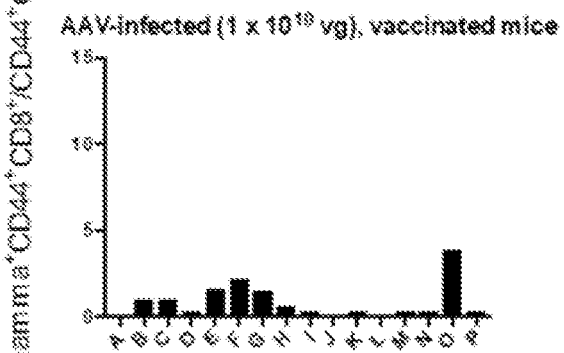
FIG. 7C
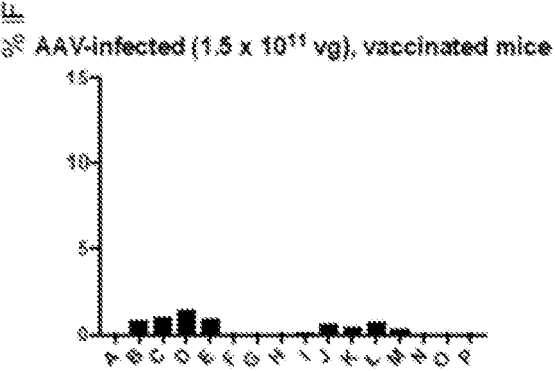

FIG. 7E

| 1 | PLSYQ HFRKL LLLDE |
|---|---|
| 2 | HFRKL LLLDE EAGPL |
| 3 | LLLDE EAGPL EEELP |
| 4 | EAGPL EEELP RLADE |
| 5 | EEELP RLADE GLNRR |
| 6 | RLADE GLNRR VAEDL |
| 7 | GLNRR VAEDL NLGNL |
| 8 | VAEDL NLGNL NVSIP |
| 9 | NLGNL NVSIP WTHKV |
| 10 | NVSIP WTHKV GNFTG |
| 11 | WTHKV GNFTG LYSST |
| 12 | GNFTG LYSST VPVFN |
| 13 | LYSST VPVFN PEWQT |
| 14 | VPVFN PEWQT PSFPK |
| 15 | PEWQT PSFPK IHLQE |
| 16 | PSFPK IHLQE DIVDR |
| 17 | IHLQE DIVDR CKQFV |
| 18 | DIVDR CKQFV GPLTV |
| 19 | CKQFV GPLTV NEKRR |
| 20 | GPLTV NEKRR LKLIM |
| 21 | NEKRR LKLIM PARFY |
| 22 | LKLIM PARFY PNVTK |
| 23 | PARFY PNVTK YLPLD |
| 24 | PNVTK YLPLD KGIKP |
| 25 | YLPLD KGIKP YYPEH |
| 26 | KGIKP YYPEH AVNHY |
| 27 | YYPEH AVNHY FQTRH |
| 28 | AVNHY FQTRH YLHTL |
| 29 | FQTRH YLHTL WKAGI |
| 30 | YLHTL WKAGI LYKRE |
| 31 | WKAGI LYKRE TTRSA |
| 32 | LYKRE TTRSA SFCGS |
| 33 | TTRSA SFCGS PYSWE |
| 34 | SFCGS PYSWE QELQH |
| 35 | PYSWE QELQH GSCWW |
| 36 | QELQH GSCWW LQFRN |
| 37 | GSCWW LQFRN SKPCS |
| 38 | LQFRN SKPCS EYCLT |
| 39 | SKPCS EYCLT HLVNL |
| 40 | EYCLT HLVNL LEDWG |
| 41 | HLVNL LEDWG PCDEH |
| 42 | LEDWG PCDEH GEHHI |
| 43 | PCDEH GEHHI RIPRT |
| 44 | GEHHI RIPRT PARVT |
| 45 | RIPRT PARVT GGVFL |
| 46 | PARVT GGVFL VDKNP |
| 47 | GGVFL VDKNP HNTAE |
| 48 | VDKNP HNTAE SRLVV |
| 49 | HNTAE SRLVV DFSQF |
| 50 | SRLVV DFSQF SRGIT |
| 51 | DFSQF SRGIT RVSWP |
| 52 | SRGIT RVSWP KFAVP |
| 53 | RVSWP KFAVP NLQSL |
| 54 | KFAVP NLQSL TNLLS |
| 55 | NLQSL TNLLS SNLSW |
| 56 | TNLLS SNLSW LSLDV |
| 57 | SNLSW LSLDV SAAFY |
| 58 | LSLDV SAAFY HIPLH |
| 59 | SAAFYHIPLHPAAMP |

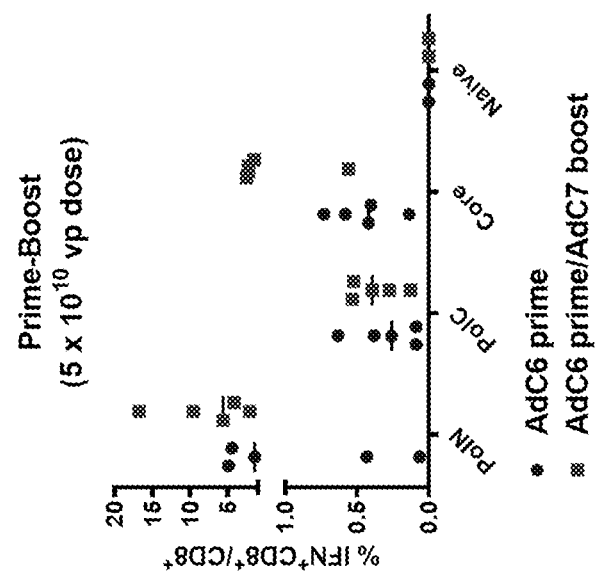
FIG. 9A  FIG. 9B  FIG. 9C
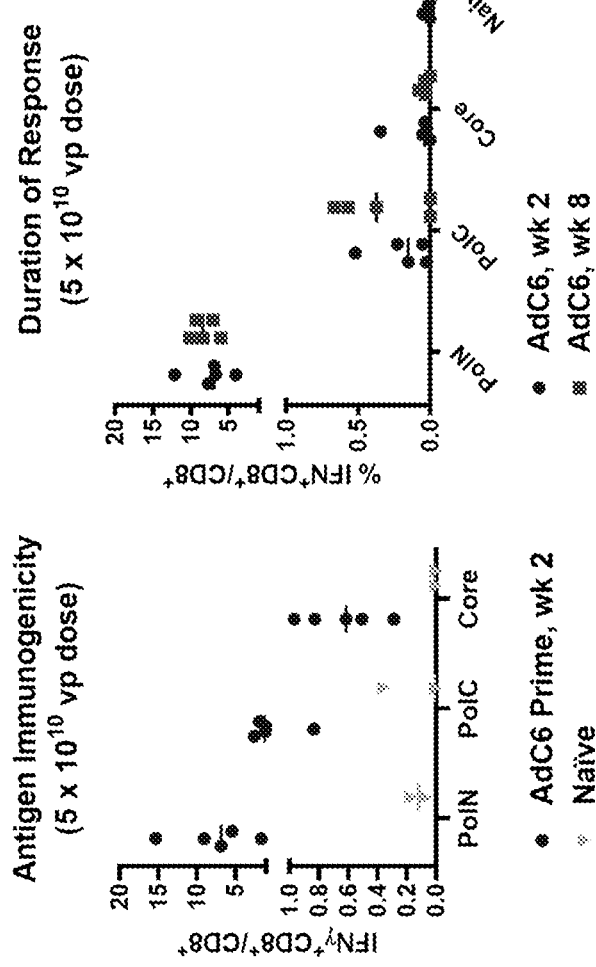

FIG. 12A
FIG. 12B
FIG. 12C
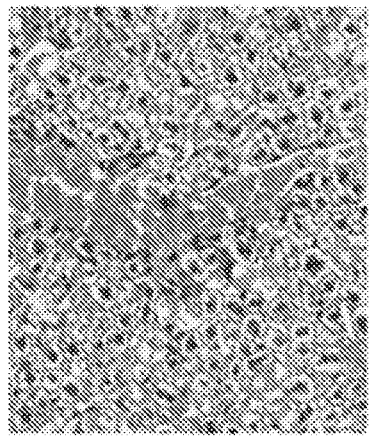
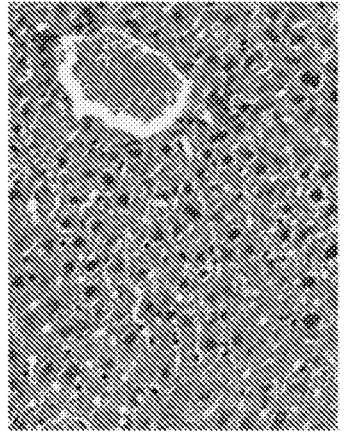
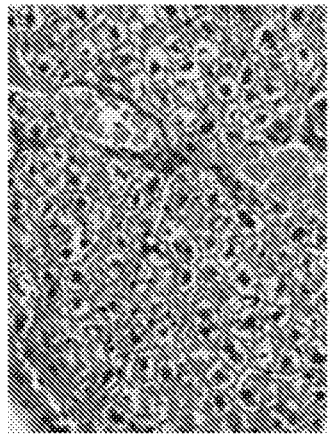
-/AdC6-gDPolN
$10^{11}$ vg AAV8-1.3HBV
FIG. 12D
FIG. 12E
FIG. 12F
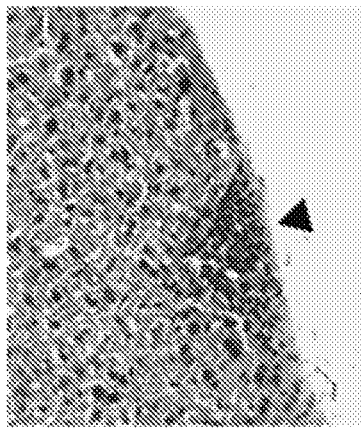
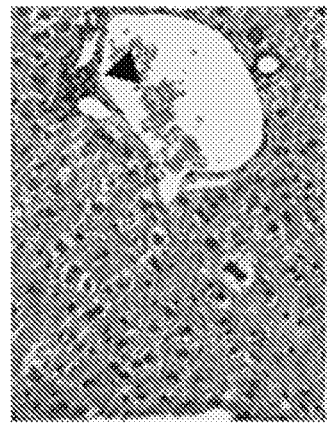
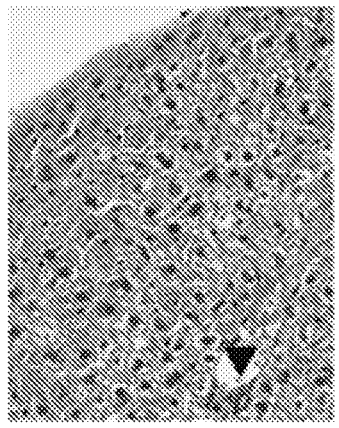
$10^{11}$ vg AAV8-1.3HBV / AdC6-gDPolN

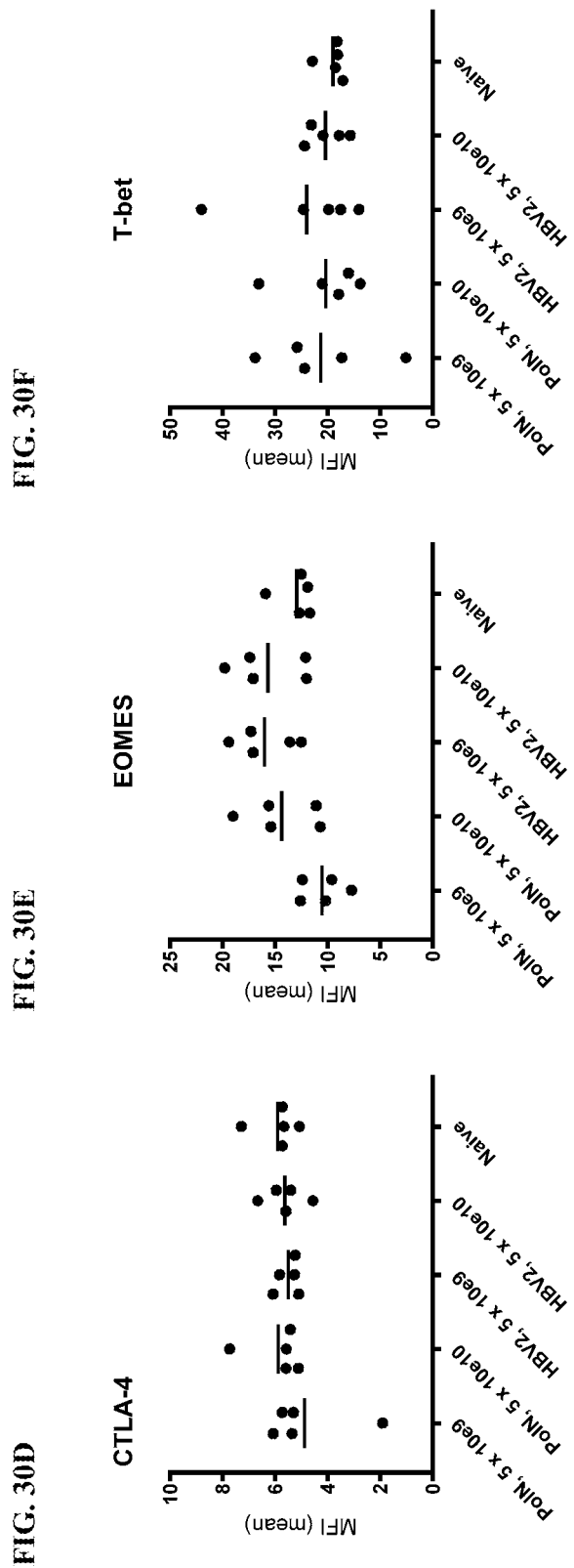

SEQUENCE LISTING

```
Sequence total quantity: 233
SEQ ID NO: 1           moltype = AA  length = 185
FEATURE                Location/Qualifiers
REGION                 1..185
                       note = source = /note="Description of Artificial Sequence:
                       Synthetic polypeptide"
source                 1..185
                       mol_type = protein
                       organism = synthetic construct
SEQUENCE: 1
MDIDPYKEFG ATVELLSFLP SDFFPSVRDL LDTASALYRE ALESPEHCSP HHTALRQAIL   60
CWGELMTLAT WVGNNLEDPA SRDLVVNYVN TNMGLKIRQL LWFHISCLTF GRETVLEYLV  120
SFGVWIRTPP AYRPPNAPIL STLPETTVVR RRDRGRSPRR RTPSPRRRRS QSPRRRRSQS  180
```

```
RESQC                                                                            185

SEQ ID NO: 2              moltype = AA  length = 183
FEATURE                   Location/Qualifiers
REGION                    1..183
                          note = source = /note="Description of Artificial Sequence:
                           Synthetic polypeptide"
source                    1..183
                          mol_type = protein
                          organism = synthetic construct
SEQUENCE: 2
MDIDPYKEFG ASVELLSFLP SDFFPSIRDL LDTASALYRE ALESPEHCSP HHTALRQAIL    60
CWGELMNLAT WVGSNLEDPA SRELVVSYVN VNMGLKIRQL LWFHISCLTF GRETVLEYLV    120
SFGVWIRTPP AYRPPNAPIL STLPETTVVR RRGRSPRRRT PSPRRRRSQS PRRRRSQSRE    180
SQC                                                                 183

SEQ ID NO: 3              moltype = AA  length = 182
FEATURE                   Location/Qualifiers
REGION                    1..182
                          note = source = /note="Description of Artificial Sequence:
                           Synthetic polypeptide"
source                    1..182
                          mol_type = protein
                          organism = synthetic construct
SEQUENCE: 3
MDIDPYKEFG ASVELLSFLP SDFFPSIRDL LDTASALYRE ALESPEHCSP HHTALRQAIL    60
CWGELMNLAT WVGSNLEDPA SRELVVSYVN VNMGLKIRQL LWFHISCLTF GRETVLEYLV    120
SFGVWIRTPP AYRPPNAPIL STLPETTVVR RRGRSPRRRT PSPRRRRSQS PRRRSQSRES    180
QC                                                                  182

SEQ ID NO: 4              moltype = AA  length = 183
FEATURE                   Location/Qualifiers
REGION                    1..183
                          note = source = /note="Description of Artificial Sequence:
                           Synthetic polypeptide"
source                    1..183
                          mol_type = protein
                          organism = synthetic construct
SEQUENCE: 4
MDIDPYKEFG ATVELLSFLP SDFFPSVRDL LDTASALYRE ALESPEHCSP HHTALRQAIL    60
CWGELMTLAT WVGGNLEDPA SRDLVVSYVN TNMGLKFRQL LWFHISCLTF GRETVIEYLV    120
SFGVWIRTPP AYRPPNAPIL STLPETTVVR RRGRSPRRRT PSPRRRRSQS PRRRRSQSRE    180
SQC                                                                 183

SEQ ID NO: 5              moltype = AA  length = 184
FEATURE                   Location/Qualifiers
VARIANT                   12
                          note = /replace="S"
VARIANT                   27
                          note = /replace="I"
VARIANT                   66
                          note = /replace="N"
VARIANT                   73
                          note = /replace="S" or "G"
VARIANT                   82
                          note = /replace="E"
VARIANT                   86
                          note = /replace="S"
VARIANT                   90
                          note = /replace="V"
VARIANT                   96
                          note = /replace="F"
VARIANT                   115
                          note = /replace="I"
VARIANT                   152..153
                          note = /replace=" "
SITE                      1..184
                          note = /note="Variant residues given in the sequence have
                           no preference with respect to those in the annotations for
                           variant positions"
REGION                    1..184
                          note = source = /note="Description of Artificial Sequence:
                           Synthetic polypeptide"
source                    1..184
                          mol_type = protein
                          organism = synthetic construct
SEQUENCE: 5
MDIDPYKEFG ATVELLSFLP SDFFPSVDLL DTASALYREA LESPEHCSPH HTALRQAILC    60
WGELMTLATW VGNNLEDPAS RDLVNYVNT NMGLKIRQLL WFHISCLTFG RETVLEYLVS    120
```

```
FGVWIRTPPA YRPPNAPILS TLPETTVVRR RDRGRSPRRR TPSPRRRRSQ SPRRRRSQSR    180
ESQC                                                                184

SEQ ID NO: 6              moltype = AA  length = 184
FEATURE                   Location/Qualifiers
REGION                    1..184
                          note = source = /note="Description of Artificial Sequence:
                          Synthetic polypeptide"
source                    1..184
                          mol_type = protein
                          organism = synthetic construct
SEQUENCE: 6
DIDPYKEFGA TVELLSFLPS DFFPSIRDLL DTASALYREA LESPEHCSPH HTALRQAILC    60
WGELMTLATW VGSNLEDPAS RELVVSYVNV NMGLKIRQLL WFHISCLTFG RETVIEYLVS    120
FGVWIRTPPA YRPPNAPILS TLPETTVVRR RDRGRSPRRR TPSPRRRRSQ SPRRRRSQSR    180
ESQC                                                                184

SEQ ID NO: 7              moltype = DNA  length = 552
FEATURE                   Location/Qualifiers
misc_feature              1..552
                          note = source = /note="Description of Artificial Sequence:
                          Synthetic polynucleotide"
source                    1..552
                          mol_type = other DNA
                          organism = synthetic construct
SEQUENCE: 7
gacatcgacc cctacaagga gttcggcgcc accgtggagc tgctgagctt cctgcccagc    60
gacttcttcc ccagcatcag ggacctgctg gacaccgcca gcgccctgta cagggaggcc    120
ctggagagcc cgagcactg cagccccac acaccgccc tgaggcaggc catcctgtgc       180
tggggcgagc tgatgaccct ggccacctgg gtgggcagca acctggagga ccccgccagc    240
agggagctgg tggtgagcta cgtgaacgtg aacatgggcc tgaagatcag gcagctgctg    300
tggttccaca tcagctgcct gaccttcggc agggagaccg tgatcgagta cctggtgagc    360
ttcggcgtgt ggatcaggac cccccccgcc tacaggcccc caacgcccc catcctgagc     420
accctgcccg agaccaccgt ggtgaggagg agggacaggg gcaggagccc caggaggagg    480
accccagcc ccaggaggag gaggagccag agccccagga ggaggaggag ccagagcagg     540
gagagccagt gc                                                       552

SEQ ID NO: 8              moltype = AA  length = 305
FEATURE                   Location/Qualifiers
REGION                    1..305
                          note = source = /note="Description of Artificial Sequence:
                          Synthetic polypeptide"
source                    1..305
                          mol_type = protein
                          organism = synthetic construct
SEQUENCE: 8
PLSYQHFRKL LLLDEEAGPL EEELPRLADE GLNRRVAEDL NLGNLNVSIP WTHKVGNFTG    60
LYSSTVPVFN PEWQTPSFPK IHLQEDIVDR CKQFVGPLTV NEKRRLKLIM PARFYPNVTK    120
YLPLDKGIKP YYPEHAVNHY FQTRHYLHTL WKAGILYKRE TTRSASFCGS PYSWEQELQH    180
GSCWWLQFRN SKPCSEYCLT HLVNLLEDWG PCDEHGEHHI RIPRTPARVT GGVFLVDKNP    240
HNTAESRLVV DFSQFSRGIT RVSWPKFAVP NLQSLTNLLS SNLSWLSLDV SAAFYHIPLH    300
PAAMP                                                               305

SEQ ID NO: 9              moltype = DNA  length = 915
FEATURE                   Location/Qualifiers
misc_feature              1..915
                          note = source = /note="Description of Artificial Sequence:
                          Synthetic polynucleotide"
source                    1..915
                          mol_type = other DNA
                          organism = synthetic construct
SEQUENCE: 9
cccctgagct accagcactt caggaagctg ctgctgctgg acgaggaggc cggccccctg    60
gaggaggagc tgcccaggct ggccgacgag ggcctgaaca ggcgggtggc cgaggacctg    120
aacctgggca acctgaacgt gagcatcccc tggacccaca aggtgggcaa cttcaccggc    180
ctgtacagca gcaccgtgcc cgtgttcaac cccgagtggc agacccccag cttccccaag    240
atccacctgc aggaggacat cgtggacagg tgcaagcagt tcgtgggccc cctgaccgtg    300
aacgagaaga ggaggctgaa gctgatcatg cccgccaggt tctaccccaa cgtgaccaag    360
tacctgcccc tggacaaggg catcaagccc tactacccg agcacgccgt gaaccactac    420
ttccagacca ggcactacct gcacaccctg tggaaggccg gcatcctgta caagagggag    480
accaccagga gcgccagctt ctgcggcagc ccctacagct gggagcagga gctgcagcac    540
ggcagctgct ggtggctgca gttcaggaac agcaagccct gcagcgagta ctgcctgacc    600
cacctggtga acctgctgga ggactggggc cctgcgacg agcacggcga gcaccacatc     660
aggatcccca ggaccccgc cagggtgacc ggcggcgtgt tcctggtgga caagaaccc      720
cacaacaccg ccgagagcag gctggtggtg gacttcagcc agttcagcag gggcatcacc    780
agggtgagct ggcccaagtt cgccgtgccc aacctgcaga gctgaccaa cctgctgagc    840
agcaacctga gctggctgag cctggacgtg agcgccgcct tctaccacat cccccctgcac    900
cccgccgcca tgccc                                                    915
```

| | | |
|---|---|---|
| SEQ ID NO: 10 | moltype = AA  length = 303 | |
| FEATURE | Location/Qualifiers | |
| REGION | 1..303 | |
| | note = source = /note="Description of Artificial Sequence: Synthetic polypeptide" | |
| source | 1..303 | |
| | mol_type = protein | |
| | organism = synthetic construct | |
| SEQUENCE: 10 | | |

```
HLLVGSSGLS RYVARLSSNS RIINHQHGTM QNLHDSCSRN LYVSLLLLYK TFGRKLHLYS    60
HPIILKTKRW GYSLNFMGYV IGSWGSLPQD HIIQKIKECF RKLPVNRPID WKVCQRIVGL   120
LGFAAPFTQC GYPALMPLYA CIQSKQAFTF SPTYKAFLSK QYLNLYPVAR QRPGLCQVFA   180
DATPTGWGLA MGHQRMRGTF VAPLPIHTAE LLAACFARSR SGAKILGTDN SVVLSRKYTS   240
FPWLLGCAAN WILRGTSFVY VPSALNPADD PSRGRLGLSR PLLRLPFRPT TGRTSLYAVS   300
PSV                                                                303
```

| | | |
|---|---|---|
| SEQ ID NO: 11 | moltype = DNA  length = 909 | |
| FEATURE | Location/Qualifiers | |
| misc_feature | 1..909 | |
| | note = source = /note="Description of Artificial Sequence: Synthetic polynucleotide" | |
| source | 1..909 | |
| | mol_type = other DNA | |
| | organism = synthetic construct | |
| SEQUENCE: 11 | | |

```
cacctgctgg tgggcagcag cggcctgagc aggtacgtgg ccaggctgag cagcaacagc    60
aggatcatca accaccagca cggcaccatg cagaacctgc acgacagctg cagcaggaac   120
ctgtacgtga gcctgctgct gctgtacaag accttcggca ggaagctgca cctgtacagc   180
caccccatca tcctgaagac caagaggtgg ggctacagcc tgaacttcat gggctacgtg   240
atcggcagct ggggcagcct gccccaggac cacatcatcc agaagatcaa ggagtgcttc   300
aggaagctgc ccgtgaacag gcccatcgac tggaaggtgt gccagaggat cgtgggcctg   360
ctgggcttcg ccgcccccct cacccagtgc ggctaccccg ccctgatgcc cctgtacgcc   420
tgcatccaga gcaagcaggc cttcaccttc agcccacct acaaggcctt cctgagcaag   480
cagtacctga acctgtaccc cgtggccagg cagaggcccg gcctgtgcca ggtgttcgcc   540
gacgccaccc ccaccggctg gggcctggcc atgggccacc agaggatgag gggcaccttc   600
gtggcccccc tgcccatcca caccgccgag ctgctggccg cctgcttcgc caggagcagg   660
agcggcgcca agatcctggg caccgacaac agcgtggtgc tgagcaggaa gtacaccagc   720
ttccctggc tgctgggctg cgccgccaac tggatcctga gggcaccag cttcgtgtac   780
gtgcccagcg ccctgaaccc cgccgacgac cccagcaggg gcaggctggg cctgagcagg   840
cccctgctga ggctgccctt caggcccacc accggcagga ccagcctgta cgccgtgagc   900
cccagcgtg                                                          909
```

| | | |
|---|---|---|
| SEQ ID NO: 12 | moltype = AA  length = 269 | |
| FEATURE | Location/Qualifiers | |
| REGION | 1..269 | |
| | note = source = /note="Description of Artificial Sequence: Synthetic polypeptide" | |
| source | 1..269 | |
| | mol_type = protein | |
| | organism = synthetic construct | |
| SEQUENCE: 12 | | |

```
MGGAAARLGA VILFVVIVGL HGVRGKYALA DASLKMADPN RFRGKDLPVL DQLTDPPGVR    60
RVYHIQAGLP DPFQPPSLPI TVYYAVLERA CRSVLLNAPS EAPQIVRGAS EDVRKQPYNL   120
TIAWFRMGGN CAIPITVMEY TECSYNKSLG ACPIRTQPRW NYYDSFSAVS EDNLGFLMHA   180
PAFETAGTYL RLVKINDWTE ITQFILEHRA KGSCKYALPL RIPPSACLSP QAYQQGVTVD   240
SIGMLPRFIP ENQRTVAVYS LKIAGWHGP                                     269
```

| | | |
|---|---|---|
| SEQ ID NO: 13 | moltype = AA  length = 127 | |
| FEATURE | Location/Qualifiers | |
| REGION | 1..127 | |
| | note = source = /note="Description of Artificial Sequence: Synthetic polypeptide" | |
| source | 1..127 | |
| | mol_type = protein | |
| | organism = synthetic construct | |
| SEQUENCE: 13 | | |

```
GPKAPYTSTL LPPELSETPN ATQPELAPED PEDSALLEDP VGTVAPQIPP NWHIPSIQDA    60
ATPYHPPATP NNMGLIAGAV GGSLLAALVI CGIVYWMHRR TRKAPKRIRL PHIREDDQPS   120
SHQPLFY                                                             127
```

| | | |
|---|---|---|
| SEQ ID NO: 14 | moltype = AA  length = 580 | |
| FEATURE | Location/Qualifiers | |
| REGION | 1..580 | |
| | note = source = /note="Description of Artificial Sequence: Synthetic polypeptide" | |
| source | 1..580 | |
| | mol_type = protein | |
| | organism = synthetic construct | |
| SEQUENCE: 14 | | |

```
MGGAAARLGA VILFVVIVGL HGVRGKYALA DASLKMADPN RFRGKDLPVL DQLTDPPGVR    60
RVYHIQAGLP DPFQPPSLPI TVYYAVLERA CRSVLLNAPS EAPQIVRGAS EDVRKQPYNL   120
TIAWFRMGGN CAIPITVMEY TECSYNKSLG ACPIRTQPRW NYYDSFSAVS EDNLGFLMHA   180
PAFETAGTYL RLVKINDWTE ITQFILEHRA KGSCKYALPL RIPPSACLSP QAYQQGVTVD   240
SIGMLPRFIP ENQRTVAVYS LKIAGWHGPD IDPYKEFGAT VELLSFLPSD FFPSIRDLLD   300
TASALYREAL ESPEHCSPHH TALRQAILCW GELMTLATWV GSNLEDPASR ELVVSYVNVN   360
MGLKIRQLLW FHISCLTFGR ETVIEYLVSF GVWIRTPPAY RPPNAPILST LPETTVVRRR   420
DRGRSPRRRT PSPRRRRSQS PRRRRSQSRE SQCGPKAPYT STLLPPELSE TPNATQPELA   480
PEDPEDSALL EDPVGTVAPQ IPPNWHIPSI QDAATPYHPP ATPNNMGLIA GAVGGSLLAA   540
LVICGIVYWM HRRTRKAPKR IRLPHIREDD QPSSHQPLFY                         580
```

```
SEQ ID NO: 15            moltype = DNA   length = 1743
FEATURE                  Location/Qualifiers
misc_feature             1..1743
                         note = source = /note="Description of Artificial Sequence:
                         Synthetic polynucleotide"
source                   1..1743
                         mol_type = other DNA
                         organism = synthetic construct
SEQUENCE: 15
atggggggg ctgccgccag gttggggggcc gtgattttgt ttgtcgtcat agtgggcctc    60
catggggtcc gcggcaaata tgccttggcg gatgcctctc tcaagatgcg cgaccccaat   120
cgctttcgcg gcaaagacct tccggtcctg gaccagctga ccgaccctcc ggggtccgg    180
cgcgtgtacc acatccaggc ggggctaccg gacccgttcc agccccccag cctcccgatc   240
acggtttact acgccgtgtt ggagcgcgcc tgccgcagcg tgctcctaaa cgcaccgtcg   300
gaggcccccc agattgtccg cggggcctcc gaagacgtcc ggaaacaacc ctacaacctg   360
accatcgctt ggtttcggat gggaggcaac tgtgctatcc ccatcacggt catggagtac   420
accgaatgct cctacaacaa gtctctgggg gcctgtccca tccgaacgca gccccgctgg   480
aactactatg acagcttcag cgccgtcagc gaggataacc tggggttcct gatgcacgcc   540
cccgcgtttg agaccgccgg cacgtacctg cggctcgtga agataaacga ctggacggag   600
attacacagt ttatcctgga gcaccgagcg aagggctcct gtaagtacgc cctcccgctg   660
cgcatcccc cgtcagcctg cctctccccc caggcctacc agcaggggt gacggtggac     720
agcatcggga tgctgccccg cttcatcccc gagaaccagc gcaccgtcgc cgtatacagc   780
ttgaagatcg ccgggtggca cgggcccgac atcgacccct acaaggagtt cggcgccacc   840
gtggagctgc tgagcttcct gccccagcga ttcttcccca gcatcaggga cctgctggac   900
accgccagcg ccctgtacag ggaggccctg gagagccccg agcactgcag cccccaccac   960
accgccctga ggcaggccat cctgtgctgg ggcgagctga tgaccctggc cacctggtg   1020
ggcagcaacc tggaggaccc cgccagcagg gagctggtgg tgagctacgt gaacgtgaac   1080
atgggcctga agatcaggca gctgctgtgg ttccacatca gctgcctgac cttcggcagg   1140
gagaccgtga tcgagtacct ggtgagcttc ggcgtgtgga tcaggacccc ccccgcctac   1200
aggcccccca acgccccat cctgagcacc ctgcccgaga ccaccgtggt gaggaggagg   1260
gacagggca ggagccccag gaggaggacc cccagcccca ggaggaggag gagccagagc    1320
ccaggaggag gaggagccca gagcagtgcg ggccaaggc cccatacacg                1380
agcaccctgc tgcccccgga gctgtccgag accccaacg ccacgcagcc agaactcgcc    1440
ccggaagacc ccgaggattc ggcccctctg gaggaccccg tggggacggt ggcgccgcaa   1500
atcccaccaa actggcacat cccgtcgatc caggacgccg cgacgcctta ccatccccg    1560
gccaccccga acaacatggg cctgatcgcc ggcgcggcg cggcagtct cctggcagcc    1620
ctggtcattt gcggaattgt gtactgatg caccgccgca ctcggaaagc cccaaagcgc    1680
atacgcctcc cccacatccg ggaagacgac cagccgtcct cgcaccagcc cttgtttac    1740
tag                                                                1743
```

```
SEQ ID NO: 16            moltype = AA   length = 701
FEATURE                  Location/Qualifiers
REGION                   1..701
                         note = source = /note="Description of Artificial Sequence:
                         Synthetic polypeptide"
source                   1..701
                         mol_type = protein
                         organism = synthetic construct
SEQUENCE: 16
MGGAAARLGA VILFVVIVGL HGVRGKYALA DASLKMADPN RFRGKDLPVL DQLTDPPGVR    60
RVYHIQAGLP DPFQPPSLPI TVYYAVLERA CRSVLLNAPS EAPQIVRGAS EDVRKQPYNL   120
TIAWFRMGGN CAIPITVMEY TECSYNKSLG ACPIRTQPRW NYYDSFSAVS EDNLGFLMHA   180
PAFETAGTYL RLVKINDWTE ITQFILEHRA KGSCKYALPL RIPPSACLSP QAYQQGVTVD   240
SIGMLPRFIP ENQRTVAVYS LKIAGWHGPP LSYQHFRKLL LLDEEAGPLE EELPRLADEG   300
LNRRVAEDLN LGNLNVSIPW THKVGNFTGL YSSTVPVFNP EWQTPSFPKI HLQEDIVDRC   360
KQFVGPLTVN EKRRLKLIMP ARFYPNVTKY LPLDKGIKPY YPEHAVNHYF QTRHYLHTLW   420
KAGILYKRET TRSASPFCGSP YSWEQELQHG SCWWLQFRNS KPCSEYCLTH LVNLLEDWGP   480
CDEHGEHHIR IPRTPARVTG GVFLVDKNPH NTAESRLVVD FSQFSRGITR VSWPKFAVPN   540
LQSLTNLLSS NLSWLSLDVS AAFYHIPLHP AAMPGPKAPY TSTLLPPELS ETPNATQPEL   600
APEDPEDSAL LEDPVGTVAP QIPPNWHIPS IQDAATPYHP PATPNNMGLI AGAVGGSLLA   660
ALVICGIVYW MHRRTRKAPK RIRLPHIRED DQPSSHQPLF Y                       701
```

```
SEQ ID NO: 17            moltype = DNA   length = 2106
FEATURE                  Location/Qualifiers
misc_feature             1..2106
                         note = source = /note="Description of Artificial Sequence:
                         Synthetic polynucleotide"
source                   1..2106
```

```
                        mol_type = other DNA
                        organism = synthetic construct
SEQUENCE: 17
atggggggg   ctgccgccag  gttggggcc   gtgattttgt  ttgtcgtcat  agtgggcctc   60
catggggtcc  gcggcaaata  tgccttggcg  gatgcctctc  tcaagatggc  cgaccccaat  120
cgctttcgcg  gcaaagacct  tccggtcctg  gaccagctga  ccgaccctcc  ggggtccgg   180
cgcgtgtacc  acatccaggc  gggcctaccg  gacccgttcc  agcccccag   cctcccgatc  240
acggtttact  acgccgtgtt  ggagcgcgcc  tgccgcagcg  tgctcctaaa  cgcaccgtcg  300
gaggccccc   agattgtccg  cggggcctcc  gaagacgtcc  ggaaacaacc  ctacaacctg  360
accatcgctt  ggtttcggat  gggaggcaac  tgtgctatcc  ccatcacggt  catggagtac  420
accgaatgct  cctacaacaa  gtctctgggg  gcctgtccca  tccgaacgca  gccccgctgg  480
aactactatg  acagcttcag  cgccgtcagc  gaggataacc  tggggttcct  gatgcacgcc  540
cccgcgtttg  agaccgccgg  cacgtacctg  cggctcgtga  agataaacga  ctggacggag  600
attacacagt  ttatcctgga  gcaccgagcc  aagggctcct  gtaagtacgc  cctcccgctg  660
cgcatcccc   cgtcagcctg  cctctccccc  caggcctacc  agcagggggt  gaccgtggac  720
agcatcggga  tgctgcccg   cttcatcccc  gagaaccagc  gcaccgtcgc  cgtatacagc  780
ttgaagatcg  ccgggtggca  cgggccccc   ctgagctacc  agcacttcag  gaagctgctg  840
ctgctggacg  aggaggccgg  ccccctggag  gaggagctgc  cgacgagggc  900
ctgaacagga  gggtggccga  ggacctgaac  ctgggcaacc  tgaacgtgag  catccccctg  960
acccacaagg  tgggcaactt  caccggcctg  tacagcagca  ccgtgccgt   gttcaacccc  1020
gagtggcaga  ccccagctt   ccccaagatc  cacctgcagg  aggacatcgt  ggacaggtgc  1080
aagcagttcg  tgggtcccct  gaccgtgaac  gagaagagga  gctgaagct   gatcatgccc  1140
gccaggttct  accccaacgt  gaccaagtac  ctgcccctgg  acaagggcat  caagcccta   1200
taccccgagc  acgccgtgaa  ccactactcc  agaccaggc   actacctgca  caccctgtgg  1260
aaggccggca  tcctgtacaa  gagggagacc  accaggagcg  ccagcttctg  cggcagcccc  1320
tacagctggg  agcaggagct  gcagcacggc  agctgctggt  gcagtt      caggaacagc  1380
aagccctgca  gcgagtactg  cctgaccac   ctggtgaacc  tgctggagga  ctggggtccc  1440
tgcgacgagc  acggcgagca  ccacatcagg  atccccagga  cccccgccag  ggtgaccggc  1500
ggcgtgttcc  tggtggacaa  gaaccccac   aacaccgccg  agagcaggct  ggtggtggac  1560
ttcagccagt  tcagcagggg  catccagac   gtgagctgac  ccaagttcgc  cgtgcccaac  1620
ctgcagagcc  tgaccaacct  gctgagcagc  aacctgagct  ggctgagcct  ggacgtgagc  1680
gccgccttct  accacatccc  cctgcacccc  gccgccatgc  ccgggcccaa  ggcccatac   1740
acgagcaccc  tgctgcccc   ggagctgtcc  gagacccca   acgccacgca  gccagaactc  1800
gccccggaag  accccgagga  ttcggccctc  ttggaggacc  ccgtggggac  ggtggcgccg  1860
caaatcccac  caaactggca  catcccgtcg  atccaggacg  ccgcgacgcc  ttaccatccc  1920
ccggccaccc  cgaacaacat  gggcctgatc  gccggcgcgg  tgggcggcag  tctcctggca  1980
gccctggtca  tttgcggaat  tgtgtactgg  atgcaccgcc  gcactcggaa  agccccaaag  2040
cgcatacgcc  tcccccacat  ccgggaagac  gaccagccgt  cctcgcacca  gcccttgttt  2100
tactag                                                                  2106

SEQ ID NO: 18           moltype = AA  length = 699
FEATURE                 Location/Qualifiers
REGION                  1..699
                        note = source = /note="Description of Artificial Sequence:
                        Synthetic polypeptide"
source                  1..699
                        mol_type = protein
                        organism = synthetic construct
SEQUENCE: 18
MGGAAARLGA  VILFVVIVGL  HGVRGKYALA  DASLKMADPN  RFRGKDLPVL  DQLTDPPGVR   60
RVYHIQAGLP  DPFQPPSLPI  TVYYAVLERA  CRSVLLNAPS  EAPQIVRGAS  EDVRKQPYNL  120
TIAWFRMGGN  CAIPITVMEY  TECSYNKSLG  ACPIRTQPRW  NYYDSFSAVS  EDNLGFLMHA  180
PAFETAGTYL  RLVKINDWTE  ITQFILEHRA  KGSCKYALPL  RIPPSACLSP  QAYQQGVTVD  240
SIGMLPRFIP  ENQRTVAVYS  LKIAGWHGPH  LLVGSSGLSR  YVARLSSNSR  IINHQHGTMQ  300
NLHDSCSRNL  YVSLLLLYKT  FGRKLHLYSH  PIILKTKRWG  YSLNFMGYVI  GSWGSLPQDH  360
IIQKIKECFR  KLPVNRPIDW  KVCQRIVGLL  GFAAPFTQCG  YPALMPLYAC  IQSKQAFTFS  420
PTYKAFLSKQ  YLNLYPVARQ  RPGLCQVFAD  ATPTGWGLAM  GHQRMRGTFV  APLPIHTAEL  480
LAACFARSRS  GAKILGTDNS  VVLSRKYTSF  PWLLGCAANW  ILRGTSFVYV  PSALNPADDP  540
SRGRLGLSRP  LLRLPFRPTT  GRTSLYAVSP  SVGPKAPYTS  TLLPPELSET  PNATQPELAP  600
EDPEDSALLE  DPVGTVAPQI  PPNWHIPSIQ  DAATPYHPAP  TPNNMGLIAG  AVGGSLLAAL  660
VICGIVYWMH  RRTRKAPKRI  RLPHIREDDQ  PSSHQPLFY                            699

SEQ ID NO: 19           moltype = DNA  length = 2100
FEATURE                 Location/Qualifiers
misc_feature            1..2100
                        note = source = /note="Description of Artificial Sequence:
                        Synthetic polynucleotide"
source                  1..2100
                        mol_type = other DNA
                        organism = synthetic construct
SEQUENCE: 19
atggggggg   ctgccgccag  gttggggcc   gtgattttgt  ttgtcgtcat  agtgggcctc   60
catggggtcc  gcggcaaata  tgccttggcg  gatgcctctc  tcaagatggc  cgaccccaat  120
cgctttcgcg  gcaaagacct  tccggtcctg  gaccagctga  ccgaccctcc  ggggtccgg   180
cgcgtgtacc  acatccaggc  gggcctaccg  gacccgttcc  agcccccag   cctcccgatc  240
acggtttact  acgccgtgtt  ggagcgcgcc  tgccgcagcg  tgctcctaaa  cgcaccgtcg  300
gaggccccc   agattgtccg  cggggcctcc  gaagacgtcc  ggaaacaacc  ctacaacctg  360
accatcgctt  ggtttcggat  gggaggcaac  tgtgctatcc  ccatcacggt  catggagtac  420
accgaatgct  cctacaacaa  gtctctgggg  gcctgtccca  tccgaacgca  gccccgctgg  480
```

```
aactactatg acagcttcag cgccgtcagc gaggataacc tgggggttcct gatgcacgcc    540
cccgcgtttg agaccgccgg cacgtacctg cggctcgtga agataaacga ctggacggag    600
attacacagt ttatcctgga gcaccgagcc aagggctcct gtaagtacgc cctcccgctg    660
cgcatccccc cgtcagcctg cctctccccc caggcctacc agcaggggg t gacggtggac    720
agcatcggga tgctgccccg cttcatcccc gagaaccagc gcaccgtcgc cgtatacagc    780
ttgaagatcg ccggggtggca cgggccccac ctgctggtgg gcagcagcgg cctgagcagg    840
tacgtggcca ggctgagcag caacagcagg atcatcaacc accagcacgg caccatgcag    900
aacctgcacg acagctgcag caggaacctg tacgtgagcc tgctgctgct gtacaagacc    960
ttcggcagga agctgcacct gtacagccac cccatcatcc tgaagaccaa gaggtggggc   1020
tacagcctga acttcatggg ctacgtgatc ggcagctggg gcagcctgcc ccaggaccac   1080
atcatccaga agatcaagga gtgcttcagg aagctgcccg tgaacaggcc catcgactgg   1140
aaggtgtgcc agaggatcgt gggcctgctg ggcttcgccg ccccccttca c ccagtgcggc   1200
taccccgccc tgatgcccct gtacgcctgc atccagagca agcaggcctt caccttcagc   1260
cccaccta ca aggccttcct gagcaagcag tacctgaacc tgtacccgt ggccaggcag   1320
aggcccggcc tgtgccaggt gttcgccgac gccaccccca ccggctgggg cctggcatg    1380
ggccaccaga ggatgagggg caccttcgtg gccccccctgc ccatccacac cgccgagctg   1440
ctggccgcct gcttcgccag gagcaggagc ggcgccaaga tcctgggcac cgacaacagc   1500
gtggtgctga gcaggaagta caccgccttc ccctggctgc tgggctgcgc cgccaactgc   1560
atcctgaggg gcaccagctt cgtgtacgtg cccagcgccc tgaacccgc c gacgacccc    1620
agcaggggca ggctgggcct gagcaggccc ctgctgaggc tgcccttcag gcccaccacc   1680
ggcaggacca gcctgtacgc cgtgagcccc agcgtggggc ccaaggcccc atacacgagc   1740
accctgctgc ccccggagct gtccgagacc cccaacgcca gcagccaga actcgccccg    1800
gaagaccccg aggattcggc cctcttggag gaccccgtgg ggacggtggc gccgcaaatc   1860
ccaccaaact ggcacatccc gtcgatccag gacgccgcga cgccttacca tccccggcc    1920
accccgaaca acatgggcct gatcgccggc gcggtgggcg gcagtctcct ggcagccctg   1980
gtcattttgcg gaattgtgta ctggatgcac cgccgcactc ggaaagcccc aaagcgcata   2040
cgcctccccc acatccggga agacgaccag ccgtcctcgc accagccctt gttttactag   2100
```

```
SEQ ID NO: 20            moltype = AA   length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 20
DIDPYKEFGA TVELL                                                        15

SEQ ID NO: 21            moltype = AA   length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 21
KEFGATVELL SFLPS                                                        15

SEQ ID NO: 22            moltype = AA   length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 22
TVELLSFLPS DFFPS                                                        15

SEQ ID NO: 23            moltype = AA   length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 23
SFLPSDFFPS IRDLL                                                        15

SEQ ID NO: 24            moltype = AA   length = 15
FEATURE                  Location/Qualifiers
REGION                   1..15
                         note = source = /note="Description of Artificial Sequence:
                         Synthetic peptide"
source                   1..15
                         mol_type = protein
```

```
                        organism = synthetic construct
SEQUENCE: 24
DFFPSIRDLL DTASA                                                           15

SEQ ID NO: 25           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 25
IRDLLDTASA LYREA                                                           15

SEQ ID NO: 26           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 26
DTASALYREA LESPE                                                           15

SEQ ID NO: 27           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 27
LYREALESPE HCSPH                                                           15

SEQ ID NO: 28           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 28
LESPEHCSPH HTALR                                                           15

SEQ ID NO: 29           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 29
HCSPHHTALR QAILC                                                           15

SEQ ID NO: 30           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 30
HTALRQAILC WGELM                                                           15

SEQ ID NO: 31           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 31
```

QAILCWGELM TLATW                                                15

SEQ ID NO: 32           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 32
WGELMTLATW VGSNL                                                15

SEQ ID NO: 33           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 33
TLATWVGSNL EDPAS                                                15

SEQ ID NO: 34           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 34
VGSNLEDPAS RELVV                                                15

SEQ ID NO: 35           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 35
EDPASRELVV SYVNV                                                15

SEQ ID NO: 36           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 36
RELVVSYVNV NMGLK                                                15

SEQ ID NO: 37           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 37
SYVNVNMGLK IRQLL                                                15

SEQ ID NO: 38           moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 38
NMGLKIRQLL WFHIS                                                15

```
SEQ ID NO: 39            moltype = AA  length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 39
IRQLLWFHIS CLTFG                                                            15

SEQ ID NO: 40            moltype = AA  length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 40
WFHISCLTFG RETVI                                                            15

SEQ ID NO: 41            moltype = AA  length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 41
CLTFGRETVI EYLVS                                                            15

SEQ ID NO: 42            moltype = AA  length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 42
RETVIEYLVS FGVWI                                                            15

SEQ ID NO: 43            moltype = AA  length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 43
EYLVSFGVWI RTPPA                                                            15

SEQ ID NO: 44            moltype = AA  length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 44
FGVWIRTPPA YRPPN                                                            15

SEQ ID NO: 45            moltype = AA  length = 15
FEATURE                  Location/Qualifiers
REGION                   1..15
                         note = source = /note="Description of Artificial Sequence:
                         Synthetic peptide"
source                   1..15
                         mol_type = protein
                         organism = synthetic construct
SEQUENCE: 45
RTPPAYRPPN APILS                                                            15

SEQ ID NO: 46            moltype = AA  length = 15
FEATURE                  Location/Qualifiers
```

```
REGION                      1..15
                            note = source = /note="Description of Artificial Sequence:
                             Synthetic peptide"
source                      1..15
                            mol_type = protein
                            organism = synthetic construct
SEQUENCE: 46
YRPPNAPILS TLPET                                                              15

SEQ ID NO: 47               moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 47
APILSTLPET TVVRR                                                              15

SEQ ID NO: 48               moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 48
TLPETTVVRR RDRGR                                                              15

SEQ ID NO: 49               moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 49
TVVRRRDRGR SPRRR                                                              15

SEQ ID NO: 50               moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 50
RDRGRSPRRR TPSPR                                                              15

SEQ ID NO: 51               moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 51
SPRRRTPSPR RRRSQ                                                              15

SEQ ID NO: 52               moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 52
TPSPRRRRSQ SPRRR                                                              15

SEQ ID NO: 53               moltype = AA  length = 16
FEATURE                     Location/Qualifiers
REGION                      1..16
                            note = source = /note="Description of Artificial Sequence:
```

```
                            Synthetic peptide"
source                      1..16
                            mol_type = protein
                            organism = synthetic construct
SEQUENCE: 53
RRRSQSPRRR RRSQSR                                                             16

SEQ ID NO: 54               moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 54
SPRRRRRSQS RESQC                                                              15

SEQ ID NO: 55               moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 55
PLSYQHFRKL LLLDE                                                              15

SEQ ID NO: 56               moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 56
HFRKLLLLDE EAGPL                                                              15

SEQ ID NO: 57               moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 57
LLLDEEAGPL EEELP                                                              15

SEQ ID NO: 58               moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 58
EAGPLEEELP RLADE                                                              15

SEQ ID NO: 59               moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 59
EEELPRLADE GLNRR                                                              15

SEQ ID NO: 60               moltype = AA  length = 15
FEATURE                     Location/Qualifiers
REGION                      1..15
                            note = source = /note="Description of Artificial Sequence:
                            Synthetic peptide"
source                      1..15
```

```
                             mol_type = protein
                             organism = synthetic construct
SEQUENCE: 60
RLADEGLNRR VAEDL                                                    15

SEQ ID NO: 61                moltype = AA  length = 15
FEATURE                      Location/Qualifiers
REGION                       1..15
                             note = source = /note="Description of Artificial Sequence:
                              Synthetic peptide"
source                       1..15
                             mol_type = protein
                             organism = synthetic construct
SEQUENCE: 61
GLNRRVAEDL NLGNL                                                    15

SEQ ID NO: 62                moltype = AA  length = 15
FEATURE                      Location/Qualifiers
REGION                       1..15
                             note = source = /note="Description of Artificial Sequence:
                              Synthetic peptide"
source                       1..15
                             mol_type = protein
                             organism = synthetic construct
SEQUENCE: 62
VAEDLNLGNL NVSIP                                                    15

SEQ ID NO: 63                moltype = AA  length = 15
FEATURE                      Location/Qualifiers
REGION                       1..15
                             note = source = /note="Description of Artificial Sequence:
                              Synthetic peptide"
source                       1..15
                             mol_type = protein
                             organism = synthetic construct
SEQUENCE: 63
NLGNLNVSIP WTHKV                                                    15

SEQ ID NO: 64                moltype = AA  length = 15
FEATURE                      Location/Qualifiers
REGION                       1..15
                             note = source = /note="Description of Artificial Sequence:
                              Synthetic peptide"
source                       1..15
                             mol_type = protein
                             organism = synthetic construct
SEQUENCE: 64
NVSIPWTHKV GNFTG                                                    15

SEQ ID NO: 65                moltype = AA  length = 15
FEATURE                      Location/Qualifiers
REGION                       1..15
                             note = source = /note="Description of Artificial Sequence:
                              Synthetic peptide"
source                       1..15
                             mol_type = protein
                             organism = synthetic construct
SEQUENCE: 65
WTHKVGNFTG LYSST                                                    15

SEQ ID NO: 66                moltype = AA  length = 15
FEATURE                      Location/Qualifiers
REGION                       1..15
                             note = source = /note="Description of Artificial Sequence:
                              Synthetic peptide"
source                       1..15
                             mol_type = protein
                             organism = synthetic construct
SEQUENCE: 66
GNFTGLYSST VPVFN                                                    15

SEQ ID NO: 67                moltype = AA  length = 15
FEATURE                      Location/Qualifiers
REGION                       1..15
                             note = source = /note="Description of Artificial Sequence:
                              Synthetic peptide"
source                       1..15
                             mol_type = protein
                             organism = synthetic construct
```

```
                                    -continued

SEQUENCE: 67
LYSSTVPVFN PEWQT                                                              15

SEQ ID NO: 68          moltype = AA   length = 15
FEATURE                Location/Qualifiers
REGION                 1..15
                       note = source = /note="Description of Artificial Sequence:
                        Synthetic peptide"
source                 1..15
                       mol_type = protein
                       organism = synthetic construct
SEQUENCE: 68
VPVFNPEWQT PSFPK                                                              15

SEQ ID NO: 69          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 69
PEWQTPSFPK IHKLQE                                                             16

SEQ ID NO: 70          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 70
PSFPKIHKLQ EDIVDR                                                             16

SEQ ID NO: 71          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 71
IHKLQEDIVD RCKQFV                                                             16

SEQ ID NO: 72          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 72
EDIVDRCKQF VGPLTV                                                             16

SEQ ID NO: 73          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 73
RCKQFVGPLT VNEKRR                                                             16

SEQ ID NO: 74          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 74
VGPLTVNEKR RLKLIM                                                             16
```

```
SEQ ID NO: 75          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 75
VNEKRRLKLI MPARFY                                                          16

SEQ ID NO: 76          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 76
RLKLIMPARF YPNVTK                                                          16

SEQ ID NO: 77          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 77
MPARFYPNVT KYLPLD                                                          16

SEQ ID NO: 78          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 78
YPNVTKYLPL DKGIKP                                                          16

SEQ ID NO: 79          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 79
KYLPLDKGIK PYYPEH                                                          16

SEQ ID NO: 80          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 80
DKGIKPYYPE HAVNHY                                                          16

SEQ ID NO: 81          moltype = AA   length = 16
FEATURE                Location/Qualifiers
REGION                 1..16
                       note = source = /note="Description of Artificial Sequence:
                        Synthetic peptide"
source                 1..16
                       mol_type = protein
                       organism = synthetic construct
SEQUENCE: 81
PYYPEHAVNH YFQTRH                                                          16

SEQ ID NO: 82          moltype = AA   length = 16
```

```
FEATURE             Location/Qualifiers
REGION              1..16
                    note = source = /note="Description of Artificial Sequence:
                     Synthetic peptide"
source              1..16
                    mol_type = protein
                    organism = synthetic construct
SEQUENCE: 82
HAVNHYFQTR HYLHTL                                                          16

SEQ ID NO: 83       moltype = AA  length = 16
FEATURE             Location/Qualifiers
REGION              1..16
                    note = source = /note="Description of Artificial Sequence:
                     Synthetic peptide"
source              1..16
                    mol_type = protein
                    organism = synthetic construct
SEQUENCE: 83
YFQTRHYLHT LWKAGI                                                          16

SEQ ID NO: 84       moltype = AA  length = 16
FEATURE             Location/Qualifiers
REGION              1..16
                    note = source = /note="Description of Artificial Sequence:
                     Synthetic peptide"
source              1..16
                    mol_type = protein
                    organism = synthetic construct
SEQUENCE: 84
HYLHTLWKAG ILYKRE                                                          16

SEQ ID NO: 85       moltype = AA  length = 16
FEATURE             Location/Qualifiers
REGION              1..16
                    note = source = /note="Description of Artificial Sequence:
                     Synthetic peptide"
source              1..16
                    mol_type = protein
                    organism = synthetic construct
SEQUENCE: 85
LWKAGILYKR ETTRSA                                                          16

SEQ ID NO: 86       moltype = AA  length = 16
FEATURE             Location/Qualifiers
REGION              1..16
                    note = source = /note="Description of Artificial Sequence:
                     Synthetic peptide"
source              1..16
                    mol_type = protein
                    organism = synthetic construct
SEQUENCE: 86
ILYKRETTRS ASFCGS                                                          16

SEQ ID NO: 87       moltype = AA  length = 16
FEATURE             Location/Qualifiers
REGION              1..16
                    note = source = /note="Description of Artificial Sequence:
                     Synthetic peptide"
source              1..16
                    mol_type = protein
                    organism = synthetic construct
SEQUENCE: 87
ETTRSASFCG SPYSWE                                                          16

SEQ ID NO: 88       moltype = AA  length = 16
FEATURE             Location/Qualifiers
REGION              1..16
                    note = source = /note="Description of Artificial Sequence:
                     Synthetic peptide"
source              1..16
                    mol_type = protein
                    organism = synthetic construct
SEQUENCE: 88
ASFCGSPYSW EQELQH                                                          16

SEQ ID NO: 89       moltype = AA  length = 16
FEATURE             Location/Qualifiers
REGION              1..16
```

```
source                    1..16
                          mol_type = protein
                          organism = synthetic construct
SEQUENCE: 89
SPYSWEQELQ HGSCWW                                                        16

SEQ ID NO: 90             moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 90
EQELQHGSCW WLQFRN                                                        16

SEQ ID NO: 91             moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 91
HGSCWWLQFR NSKPCS                                                        16

SEQ ID NO: 92             moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 92
WLQFRNSKPC SEYCLT                                                        16

SEQ ID NO: 93             moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 93
NSKPCSEYCL THLVNL                                                        16

SEQ ID NO: 94             moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 94
SEYCLTHLVN LLEDWG                                                        16

SEQ ID NO: 95             moltype = AA  length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 95
THLVNLLEDW GPCDEH                                                        16

SEQ ID NO: 96             moltype = AA  length = 16
FEATURE                   Location/Qualifiers
REGION                    1..16
                          note = source = /note="Description of Artificial Sequence:
                          Synthetic peptide"
```

```
source                      1..16
                            mol_type = protein
                            organism = synthetic construct
SEQUENCE: 96
LLEDWGPCDE HGEHHI                                                              16

SEQ ID NO: 97               moltype = AA  length = 16
FEATURE                     Location/Qualifiers
REGION                      1..16
                            note = source = /note="Description of Artificial Sequence:
                            Synthetic peptide"
source                      1..16
                            mol_type = protein
                            organism = synthetic construct
SEQUENCE: 97
GPCDEHGEHH IRIPRT                                                              16

SEQ ID NO: 98               moltype = AA  length = 16
FEATURE                     Location/Qualifiers
REGION                      1..16
                            note = source = /note="Description of Artificial Sequence:
                            Synthetic peptide"
source                      1..16
                            mol_type = protein
                            organism = synthetic construct
SEQUENCE: 98
HGEHHIRIPR TPARVT                                                              16

SEQ ID NO: 99               moltype = AA  length = 16
FEATURE                     Location/Qualifiers
REGION                      1..16
                            note = source = /note="Description of Artificial Sequence:
                            Synthetic peptide"
source                      1..16
                            mol_type = protein
                            organism = synthetic construct
SEQUENCE: 99
IRIPRTPARV TGGVFL                                                              16

SEQ ID NO: 100              moltype = AA  length = 16
FEATURE                     Location/Qualifiers
REGION                      1..16
                            note = source = /note="Description of Artificial Sequence:
                            Synthetic peptide"
source                      1..16
                            mol_type = protein
                            organism = synthetic construct
SEQUENCE: 100
TPARVTGGVF LVDKNP                                                              16

SEQ ID NO: 101              moltype = AA  length = 16
FEATURE                     Location/Qualifiers
REGION                      1..16
                            note = source = /note="Description of Artificial Sequence:
                            Synthetic peptide"
source                      1..16
                            mol_type = protein
                            organism = synthetic construct
SEQUENCE: 101
TGGVFLVDKN PHNTAE                                                              16

SEQ ID NO: 102              moltype = AA  length = 16
FEATURE                     Location/Qualifiers
REGION                      1..16
                            note = source = /note="Description of Artificial Sequence:
                            Synthetic peptide"
source                      1..16
                            mol_type = protein
                            organism = synthetic construct
SEQUENCE: 102
LVDKNPHNTA ESRLVV                                                              16

SEQ ID NO: 103              moltype = AA  length = 16
FEATURE                     Location/Qualifiers
REGION                      1..16
                            note = source = /note="Description of Artificial Sequence:
                            Synthetic peptide"
source                      1..16
                            mol_type = protein
```

```
SEQUENCE: 103
PHNTAESRLV VDFSQF                                                    16

SEQ ID NO: 104          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 104
ESRLVVDFSQ FSRGIT                                                    16

SEQ ID NO: 105          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 105
VDFSQFSRGI TRVSWP                                                    16

SEQ ID NO: 106          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 106
FSRGITRVSW PKFAVP                                                    16

SEQ ID NO: 107          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 107
TRVSWPKFAV PNLQSL                                                    16

SEQ ID NO: 108          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 108
PKFAVPNLQS LTNLLS                                                    16

SEQ ID NO: 109          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 109
PNLQSLTNLL SSNLSW                                                    16

SEQ ID NO: 110          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 110
```

```
LTNLLSSNLS WLSLDV                                                       16

SEQ ID NO: 111          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 111
SSNLSWLSLD VSAAFY                                                       16

SEQ ID NO: 112          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 112
WLSLDVSAAF YHIPLH                                                       16

SEQ ID NO: 113          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 113
VSAAFYHIPL HPAAMP                                                       16

SEQ ID NO: 114          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 114
HLLVGSSGLS RYVAR                                                        15

SEQ ID NO: 115          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 115
SSGLSRYVAR LSSNSR                                                       16

SEQ ID NO: 116          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 116
RYVARLSSNS RIINHQ                                                       16

SEQ ID NO: 117          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 117
LSSNSRIINH QHGTMQ                                                       16
```

-continued

| | | |
|---|---|---|
| SEQ ID NO: 118 | moltype = AA length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |
| SEQUENCE: 118 | | |
| RIINHQHGTM QNLHDS | | 16 |
| | | |
| SEQ ID NO: 119 | moltype = AA length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |
| SEQUENCE: 119 | | |
| QHGTMQNLHD SCSRNL | | 16 |
| | | |
| SEQ ID NO: 120 | moltype = AA length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |
| SEQUENCE: 120 | | |
| QNLHDSCSRN LYVSLL | | 16 |
| | | |
| SEQ ID NO: 121 | moltype = AA length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |
| SEQUENCE: 121 | | |
| SCSRNLYVSL LLLYKT | | 16 |
| | | |
| SEQ ID NO: 122 | moltype = AA length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |
| SEQUENCE: 122 | | |
| LYVSLLLLYK TFGRKL | | 16 |
| | | |
| SEQ ID NO: 123 | moltype = AA length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |
| SEQUENCE: 123 | | |
| LLLYKTFGRK LHLYSH | | 16 |
| | | |
| SEQ ID NO: 124 | moltype = AA length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |
| SEQUENCE: 124 | | |
| TFGRKLHLYS HPIILK | | 16 |
| | | |
| SEQ ID NO: 125 | moltype = AA length = 16 | |
| FEATURE | Location/Qualifiers | |

|   |   |   |
|---|---|---|
| REGION | 1..16<br>note = source = /note="Description of Artificial Sequence:<br>  Synthetic peptide" | |
| source | 1..16<br>mol_type = protein<br>organism = synthetic construct | |
| SEQUENCE: 125<br>LHLYSHPIIL KTKRWG | | 16 |
| SEQ ID NO: 126<br>FEATURE<br>REGION | moltype = AA   length = 16<br>Location/Qualifiers<br>1..16<br>note = source = /note="Description of Artificial Sequence:<br>  Synthetic peptide" | |
| source | 1..16<br>mol_type = protein<br>organism = synthetic construct | |
| SEQUENCE: 126<br>HPIILKTKRW GYSLNF | | 16 |
| SEQ ID NO: 127<br>FEATURE<br>REGION | moltype = AA   length = 16<br>Location/Qualifiers<br>1..16<br>note = source = /note="Description of Artificial Sequence:<br>  Synthetic peptide" | |
| source | 1..16<br>mol_type = protein<br>organism = synthetic construct | |
| SEQUENCE: 127<br>KTKRWGYSLN FMGYVI | | 16 |
| SEQ ID NO: 128<br>FEATURE<br>REGION | moltype = AA   length = 16<br>Location/Qualifiers<br>1..16<br>note = source = /note="Description of Artificial Sequence:<br>  Synthetic peptide" | |
| source | 1..16<br>mol_type = protein<br>organism = synthetic construct | |
| SEQUENCE: 128<br>GYSLNFMGYV IGSWGS | | 16 |
| SEQ ID NO: 129<br>FEATURE<br>REGION | moltype = AA   length = 16<br>Location/Qualifiers<br>1..16<br>note = source = /note="Description of Artificial Sequence:<br>  Synthetic peptide" | |
| source | 1..16<br>mol_type = protein<br>organism = synthetic construct | |
| SEQUENCE: 129<br>FMGYVIGSWG SLPQDH | | 16 |
| SEQ ID NO: 130<br>FEATURE<br>REGION | moltype = AA   length = 16<br>Location/Qualifiers<br>1..16<br>note = source = /note="Description of Artificial Sequence:<br>  Synthetic peptide" | |
| source | 1..16<br>mol_type = protein<br>organism = synthetic construct | |
| SEQUENCE: 130<br>IGSWGSLPQD HIIQKI | | 16 |
| SEQ ID NO: 131<br>FEATURE<br>REGION | moltype = AA   length = 16<br>Location/Qualifiers<br>1..16<br>note = source = /note="Description of Artificial Sequence:<br>  Synthetic peptide" | |
| source | 1..16<br>mol_type = protein<br>organism = synthetic construct | |
| SEQUENCE: 131<br>SLPQDHIIQK IKECFR | | 16 |
| SEQ ID NO: 132<br>FEATURE<br>REGION | moltype = AA   length = 16<br>Location/Qualifiers<br>1..16<br>note = source = /note="Description of Artificial Sequence: | |

```
                          Synthetic peptide"
source                    1..16
                          mol_type = protein
                          organism = synthetic construct
SEQUENCE: 132
HIIQKIKECF RKLPVN                                                           16

SEQ ID NO: 133            moltype = AA   length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 133
IKECFRKLPV NRPIDW                                                           16

SEQ ID NO: 134            moltype = AA   length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 134
RKLPVNRPID WKVCQR                                                           16

SEQ ID NO: 135            moltype = AA   length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 135
NRPIDWKVCQ RIVGLL                                                           16

SEQ ID NO: 136            moltype = AA   length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 136
WKVCQRIVGL LGFAAP                                                           16

SEQ ID NO: 137            moltype = AA   length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 137
RIVGLLGFAA PFTQCG                                                           16

SEQ ID NO: 138            moltype = AA   length = 16
FEATURE                   Location/Qualifiers
REGION                    1..16
                          note = source = /note="Description of Artificial Sequence:
                          Synthetic peptide"
source                    1..16
                          mol_type = protein
                          organism = synthetic construct
SEQUENCE: 138
LGFAAPFTQC GYPALM                                                           16

SEQ ID NO: 139            moltype = AA   length = 16
FEATURE                   Location/Qualifiers
REGION                    1..16
                          note = source = /note="Description of Artificial Sequence:
                          Synthetic peptide"
source                    1..16
```

```
                        mol_type = protein
                        organism = synthetic construct
SEQUENCE: 139
PFTQCGYPAL MPLYAC                                               16

SEQ ID NO: 140          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 140
GYPALMPLYA CIQSKQ                                               16

SEQ ID NO: 141          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 141
MPLYACIQSK QAFTFS                                               16

SEQ ID NO: 142          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 142
CIQSKQAFTF SPTYKA                                               16

SEQ ID NO: 143          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 143
QAFTFSPTYK AFLSKQ                                               16

SEQ ID NO: 144          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 144
SPTYKAFLSK QYLNLY                                               16

SEQ ID NO: 145          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 145
AFLSKQYLNL YPVARQ                                               16

SEQ ID NO: 146          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
```

-continued

| | | |
|---|---|---|
| SEQUENCE: 146<br>QYLNLYPVAR QRPGLC | | 16 |
| SEQ ID NO: 147<br>FEATURE<br>REGION<br><br>source<br><br><br>SEQUENCE: 147<br>YPVARQRPGL CQVFAD | moltype = AA  length = 16<br>Location/Qualifiers<br>1..16<br>note = source = /note="Description of Artificial Sequence:<br>Synthetic peptide"<br>1..16<br>mol_type = protein<br>organism = synthetic construct | 16 |
| SEQ ID NO: 148<br>FEATURE<br>REGION<br><br>source<br><br><br>SEQUENCE: 148<br>QRPGLCQVFA DATPTG | moltype = AA  length = 16<br>Location/Qualifiers<br>1..16<br>note = source = /note="Description of Artificial Sequence:<br>Synthetic peptide"<br>1..16<br>mol_type = protein<br>organism = synthetic construct | 16 |
| SEQ ID NO: 149<br>FEATURE<br>REGION<br><br>source<br><br><br>SEQUENCE: 149<br>CQVFADATPT GWGLAM | moltype = AA  length = 16<br>Location/Qualifiers<br>1..16<br>note = source = /note="Description of Artificial Sequence:<br>Synthetic peptide"<br>1..16<br>mol_type = protein<br>organism = synthetic construct | 16 |
| SEQ ID NO: 150<br>FEATURE<br>REGION<br><br>source<br><br><br>SEQUENCE: 150<br>DATPTGWGLA MGHQRM | moltype = AA  length = 16<br>Location/Qualifiers<br>1..16<br>note = source = /note="Description of Artificial Sequence:<br>Synthetic peptide"<br>1..16<br>mol_type = protein<br>organism = synthetic construct | 16 |
| SEQ ID NO: 151<br>FEATURE<br>REGION<br><br>source<br><br><br>SEQUENCE: 151<br>GWGLAMGHQR MRGTFV | moltype = AA  length = 16<br>Location/Qualifiers<br>1..16<br>note = source = /note="Description of Artificial Sequence:<br>Synthetic peptide"<br>1..16<br>mol_type = protein<br>organism = synthetic construct | 16 |
| SEQ ID NO: 152<br>FEATURE<br>REGION<br><br>source<br><br><br>SEQUENCE: 152<br>MGHQRMRGTF VAPLPI | moltype = AA  length = 16<br>Location/Qualifiers<br>1..16<br>note = source = /note="Description of Artificial Sequence:<br>Synthetic peptide"<br>1..16<br>mol_type = protein<br>organism = synthetic construct | 16 |
| SEQ ID NO: 153<br>FEATURE<br>REGION<br><br>source<br><br><br>SEQUENCE: 153<br>MRGTFVAPLP IHTAEL | moltype = AA  length = 16<br>Location/Qualifiers<br>1..16<br>note = source = /note="Description of Artificial Sequence:<br>Synthetic peptide"<br>1..16<br>mol_type = protein<br>organism = synthetic construct | 16 |

```
SEQ ID NO: 154          moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 154
VAPLPIHTAE LLAACF                                                           16

SEQ ID NO: 155          moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 155
IHTAELLAAC FARSRS                                                           16

SEQ ID NO: 156          moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 156
LLAACFARSR SGAKIL                                                           16

SEQ ID NO: 157          moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 157
FARSRSGAKI LGTDNS                                                           16

SEQ ID NO: 158          moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 158
SGAKILGTDN SVVLSR                                                           16

SEQ ID NO: 159          moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 159
LGTDNSVVLS RKYTSF                                                           16

SEQ ID NO: 160          moltype = AA   length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 160
SVVLSRKYTS FPWLLG                                                           16

SEQ ID NO: 161          moltype = AA   length = 16
```

| | | |
|---|---|---|
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |

SEQUENCE: 161
RKYTSFPWLL GCAANW                                                     16

| | | |
|---|---|---|
| SEQ ID NO: 162 | moltype = AA  length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |

SEQUENCE: 162
FPWLLGCAAN WILRGT                                                     16

| | | |
|---|---|---|
| SEQ ID NO: 163 | moltype = AA  length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |

SEQUENCE: 163
GCAANWILRG TSFVYV                                                     16

| | | |
|---|---|---|
| SEQ ID NO: 164 | moltype = AA  length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |

SEQUENCE: 164
WILRGTSFVY VPSALN                                                     16

| | | |
|---|---|---|
| SEQ ID NO: 165 | moltype = AA  length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |

SEQUENCE: 165
TSFVYVPSAL NPADDP                                                     16

| | | |
|---|---|---|
| SEQ ID NO: 166 | moltype = AA  length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |

SEQUENCE: 166
VPSALNPADD PSRGRL                                                     16

| | | |
|---|---|---|
| SEQ ID NO: 167 | moltype = AA  length = 16 | |
| FEATURE | Location/Qualifiers | |
| REGION | 1..16 | |
| | note = source = /note="Description of Artificial Sequence: Synthetic peptide" | |
| source | 1..16 | |
| | mol_type = protein | |
| | organism = synthetic construct | |

SEQUENCE: 167
NPADDPSRGR LGLSRP                                                     16

| | | |
|---|---|---|
| SEQ ID NO: 168 | moltype = AA  length = 16 | |
| FEATURE | Location/Qualifiers | |
| REGION | 1..16 | |

```
                        note = source = /note="Description of Artificial Sequence:
                         Synthetic peptide"
source                  1..16
                        mol_type = protein
                        organism = synthetic construct
SEQUENCE: 168
PSRGRLGLSR PLLRLP                                                          16

SEQ ID NO: 169          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 169
LGLSRPLLRL PFRPTT                                                          16

SEQ ID NO: 170          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 170
PLLRLPFRPT TGRTSL                                                          16

SEQ ID NO: 171          moltype = AA  length = 16
FEATURE                 Location/Qualifiers
REGION                  1..16
                        note = source = /note="Description of Artificial Sequence:
                         Synthetic peptide"
source                  1..16
                        mol_type = protein
                        organism = synthetic construct
SEQUENCE: 171
PFRPTTGRTS LYAVSP                                                          16

SEQ ID NO: 172          moltype = AA  length = 13
FEATURE                 Location/Qualifiers
REGION                  1..13
                        note = source = /note="Description of Artificial Sequence:
                         Synthetic peptide"
source                  1..13
                        mol_type = protein
                        organism = synthetic construct
SEQUENCE: 172
TGRTSLYAVS PSV                                                             13

SEQ ID NO: 173          moltype = AA  length = 200
FEATURE                 Location/Qualifiers
REGION                  1..200
                        note = source = /note="Description of Artificial Sequence:
                         Synthetic polypeptide"
source                  1..200
                        mol_type = protein
                        organism = synthetic construct
SEQUENCE: 173
HFRKLLLLDE EAGPLEEELP RLADEGLNRR VAEDLNLGNL PEWQTPSFPK IHLQEDIVDR           60
CKQFVGPLTV NEKRRLKLIM PARFYPNVTK YLPLDKGIKP YYPEHAVNHY FQTRHYLHTL          120
WKAGILYKRE TTRSASFCGS PYSWEQELQH GSCWWLQFRN SKPCSEYCLT HLVNLLEDWG          180
PCDEHGEHHI RIPRTPARVT                                                     200

SEQ ID NO: 174          moltype = AA  length = 380
FEATURE                 Location/Qualifiers
REGION                  1..380
                        note = source = /note="Description of Artificial Sequence:
                         Synthetic polypeptide"
source                  1..380
                        mol_type = protein
                        organism = synthetic construct
SEQUENCE: 174
YLPLDKGIKP YYPEHAVNHY FQTRHYLHTL WKAGILYKRE TTRSASFCGS PYSWEQELQH           60
GSCWWLQFRN SKPCSEYCLT HLVNLLEDWG PCDEHGEHHI RIPRTPARVT GGVFLVDKNP          120
HNTAESRLVV DFSQFSRGIT RVSWPKFAVP NLQSLTNLLS SNLSWLSLDV QAFTFSPTYK          180
AFLSKQYLNL YPVARQRPGL CQVFADATPT GWGLAMGHQR MRGTFVAPLP IHTAELLAAC          240
```

```
FARSRSGAKI LGTDNSVVLS RKYTSFPWLL GCAANWILRG TSFVYVPSAL NPADDVGSNL  300
EDPASRELVV SYVNVNMGLK IRQLLWFHIS CLTFGRETVI EYLVSFGVWI RTPPAYRPPN  360
APILSTLPET TVVRRRDRGR                                             380

SEQ ID NO: 175          moltype = AA   length = 410
FEATURE                 Location/Qualifiers
REGION                  1..410
                        note = source = /note="Description of Artificial Sequence:
                         Synthetic polypeptide"
source                  1..410
                        mol_type = protein
                        organism = synthetic construct
SEQUENCE: 175
HFRKLLLLDE EAGPLEEELP RLADEGLNRR VAEDLNLGNL PEWQTPSFPK IHLQEDIVDR  60
CKQFVGPLTV NEKRRLKLIM PARFYPNVTK YLPLDKGIKP YYPEHAVNHY FQTRHYLHTL  120
WKAGILYKRE TTRSASFCGS PYSWEQELQH GSCWWLQFRN SKPCSEYCLT HLVNLLEDWG  180
PCDEHGEHHI RIPRTPARVT QAFTFSPTYK AFLSKQYLNL YPVARQRPGL CQVFADATPT  240
GWGLAMGHQR MRGTFVAPLP IHTAELLAAC FARSRSGAKI LGTDNSVVLS RKYTSFPWLL  300
GCAANWILRG TSFVYVPSAL NPADDVGSNL EDPASRELVV SYVNVNMGLK IRQLLWFHIS  360
CLTFGRETVI EYLVSFGVWI RTPPAYRPPN APILSTLPET TVVRRRDRGR             410

SEQ ID NO: 176          moltype = DNA   length = 1140
FEATURE                 Location/Qualifiers
misc_feature            1..1140
                        note = source = /note="Description of Artificial Sequence:
                         Synthetic polynucleotide"
source                  1..1140
                        mol_type = other DNA
                        organism = synthetic construct
SEQUENCE: 176
tatctgccgc tggataaagg cattaaaccg tattatccgg aacatgcggt gaaccattat  60
tttcagaccc gccattatct gcataccctg tggaaagcgg cattctgta taaacgcgaa   120
accacccgca gcgcgagctt tgcggcagc ccgtatagct gggaacagga actgcagcat   180
ggcagctgct ggtggctgca gtttcgcaac agcaaaccgt gcagcgaata ttgcctgacc   240
catctggtga acctgctgga agattgggga ccgtgcgatg aacatggcga acatcatatt   300
cgcattccgc gcaccccggc gcgcgtgacc ggcggcgtgt ttctggtgga taaaaacccg   360
cataacaccg cggaaagccg cctggtggtg gattttagcc agtttagccg cggcattacc   420
cgcgtgagct ggccgaaatt tgcggtgccg aacctgcaga gcctgaccaa cctgctgagc   480
agcaacctga gctggctgag cctggatgtg caggcgttta cctttagccc gacctataaa   540
gcgtttctga gcaaacagta tctgaacctg tatccggtgg cgcgccagcg cccgggcctg   600
tgccaggtgt ttgcggatgc gaccccgacc ggctggggcc tggcgatggg ccatcagcgc   660
atgcgcggca ccttttgtggc gccgctgccg attcataccg cggaactgct ggcggcgtgc   720
tttgcgcgca gccgcagcgg cgcgaaaatt ctgggcaccg ataacagcgt ggtgctgagc   780
cgcaaatata ccagctttcc gtggctgctg ggctgcgcgg cgaactggat tctgcgcggc   840
accagctttg tgtatgtgcc gagcgcgctg aacccggcgg atgatgtggg cagcaacctg   900
gaaatccgcg cgagccgcga actggtggtg agctatgtga acgtgaacat gggcctgaaa   960
attcgccagc tgctgtggtt tcatattagc tgcctgaccc ttggccgcga aaccgttatt  1020
gaatatctgg tgagctttgg cgtgtggatt cgcaccccgc cggcgtatcg cccgccgaac  1080
gcgccgattc tgagcaccct gccggaaacc accgtggtgc gccgccgcga tcggggccgc  1140

SEQ ID NO: 177          moltype = DNA   length = 1230
FEATURE                 Location/Qualifiers
misc_feature            1..1230
                        note = source = /note="Description of Artificial Sequence:
                         Synthetic polynucleotide"
source                  1..1230
                        mol_type = other DNA
                        organism = synthetic construct
SEQUENCE: 177
cattttcgca aactgctgct gctggatgaa gaagcgggac cgctggaaga agaactgccg   60
cgcctggcgg atgaaggcct gaaccgccgc gtggcggaag atctgaacct gggcaacctg   120
ccggaatggc agaccccgag ctttccgaaa attcatctgc aggaagatat tgtggatcgc   180
tgcaaacagt ttgtgggacc gctgaccgtg aacgaaaaac gccgcctgaa actgattatg   240
ccggcgcgct tttatccgaa cgtgaccaaa tatctgccgc tggataaagg cattaaaccg   300
tattatccgg aacatgcggt gaaccattat tttcagaccc gccattatct gcataccctg   360
tggaaagcgg cattctgta taaacgcgaa accacccgca gcgcgagctt tgcggcagc   420
ccgtatagct gggaacagga actgcagcat ggcagctgct ggtggctgca gtttcgcaac   480
agcaaaccgt gcagcgaata ttgcctgacc catctggtga acctgctgga agattgggga   540
ccgtgcgatg aacatggcga acatcatatt cgcattccgc gcaccccggc gcgcgtgacc   600
ggcggcgttta cctttagccc gacctataaa gcgtttctga gcaaacagta tctgaacctg   660
tatccggtgg cgcgccagcg cccgggcctg tgccaggtgt ttgcggatgc gaccccgacc   720
ggctggggcc tggcgatggg ccatcagcgc atgcgcggca ccttttgtggc gccgctgccg   780
attcataccg cggaactgct ggcggcgtgc tttgcgcgca gccgcagcgg cgcgaaaatt   840
ctgggcaccg ataacagcgt ggtgctgagc cgcaaatata ccagctttcc gtggctgctg   900
ggctgcgcgg cgaactggat tctgcgcggc accagctttg tgtatgtgcc gagcgcgctg   960
aacccggcgg atgatgtggg cagcaacctg gaaatccgcg cgagccgcga actggtggtg  1020
agctatgtga acgtgaacat gggcctgaaa attcgccagc tgctgtggtt tcatattagc  1080
tgcctgaccc ttggccgcga aaccgttatt gaatatctgg tgagctttgg cgtgtggatt  1140
cgcaccccgc cggcgtatcg cccgccgaac gcgccgattc tgagcaccct gccggaaacc  1200
```

```
accgtggtgc gccgccgaga tcgaggccgc                                              1230

SEQ ID NO: 178          moltype = AA  length = 170
FEATURE                 Location/Qualifiers
REGION                  1..170
                        note = source = /note="Description of Artificial Sequence:
                        Synthetic polypeptide"
source                  1..170
                        mol_type = protein
                        organism = synthetic construct
SEQUENCE: 178
YLPLDKGIKP YYPEHAVNHY FQTRHYLHTL WKAGILYKRE TTRSASFCGS PYSWEQELQH   60
GSCWWLQFRN SKPCSEYCLT HLVNLLEDWG PCDEHGEHHI RIPRTPARVT GGVFLVDKNP  120
HNTAESRLVV DFSQFSRGIT RVSWPKFAVP NLQSLTNLLS SNLSWLSLDV            170

SEQ ID NO: 179          moltype = AA  length = 125
FEATURE                 Location/Qualifiers
REGION                  1..125
                        note = source = /note="Description of Artificial Sequence:
                        Synthetic polypeptide"
source                  1..125
                        mol_type = protein
                        organism = synthetic construct
SEQUENCE: 179
QAFTFSPTYK AFLSKQYLNL YPVARQRPGL CQVFADATPT GWGLAMGHQR MRGTFVAPLP   60
IHTAELLAAC FARSRSGAKI LGTDNSVVLS RKYTSFPWLL GCAANWILRG TSFVYVPSAL  120
NPADD                                                              125

SEQ ID NO: 180          moltype = AA  length = 85
FEATURE                 Location/Qualifiers
REGION                  1..85
                        note = source = /note="Description of Artificial Sequence:
                        Synthetic polypeptide"
source                  1..85
                        mol_type = protein
                        organism = synthetic construct
SEQUENCE: 180
VGSNLEDPAS RELVVSYVNV NMGLKIRQLL WFHISCLTFG RETVIEYLVS FGVWIRTPPA   60
YRPPNAPILS TLPETTVVRR RDRGR                                         85

SEQ ID NO: 181          moltype = AA  length = 200
FEATURE                 Location/Qualifiers
REGION                  1..200
                        note = source = /note="Description of Artificial Sequence:
                        Synthetic polypeptide"
source                  1..200
                        mol_type = protein
                        organism = synthetic construct
SEQUENCE: 181
HFRKLLLLDE EAGPLEEELP RLADEGLNRR VAEDLNLGNL PEWQTPSFPK IHLQEDIVDR   60
CKQFVGPLTV NEKRRLKLIM PARFYPNVTK YLPLDKGIKP YYPEHAVNHY FQTRHYLHTL  120
WKAGILYKRE TTRSASFCGS PYSWEQELQH GSCWWLQFRN SKPCSEYCLT HLVNLLEDWG  180
PCDEHGEHHI RIPRTPARVT                                              200

SEQ ID NO: 182          moltype = AA  length = 125
FEATURE                 Location/Qualifiers
REGION                  1..125
                        note = source = /note="Description of Artificial Sequence:
                        Synthetic polypeptide"
source                  1..125
                        mol_type = protein
                        organism = synthetic construct
SEQUENCE: 182
QAFTFSPTYK AFLSKQYLNL YPVARQRPGL CQVFADATPT GWGLAMGHQR MRGTFVAPLP   60
IHTAELLAAC FARSRSGAKI LGTDNSVVLS RKYTSFPWLL GCAANWILRG TSFVYVPSAL  120
NPADD                                                              125

SEQ ID NO: 183          moltype = AA  length = 85
FEATURE                 Location/Qualifiers
REGION                  1..85
                        note = source = /note="Description of Artificial Sequence:
                        Synthetic polypeptide"
source                  1..85
                        mol_type = protein
                        organism = synthetic construct
SEQUENCE: 183
VGSNLEDPAS RELVVSYVNV NMGLKIRQLL WFHISCLTFG RETVIEYLVS FGVWIRTPPA   60
YRPPNAPILS TLPETTVVRR RDRGR                                         85
```

SEQ ID NO: 184          moltype = DNA   length = 2331
FEATURE                 Location/Qualifiers
misc_feature            1..2331
                        note = source = /note="Description of Artificial Sequence:
                        Synthetic polynucleotide"
source                  1..2331
                        mol_type = other DNA
                        organism = synthetic construct
SEQUENCE: 184
atgggggggg ctgccgccag gttgggggcc gtgattttgt tgtcgtcat agtgggcctc    60
catgggtcc gcggcaaata tgccttggcg gatgcctctc tcaagatggc cgaccccaat   120
cgctttcgcg gcaaagacct tccggtcctg gaccagctga ccgaccctcc ggggtccgg   180
cgcgtgtacc acatccaggc gggcctaccg gacccgttcc agcccccag cctcccgatc   240
acggtttact acgccgtgtt ggagcgcgcg tgccgcagcg tgctcctaaa cgcaccgtcg   300
gaggccccc agattgtccg cggggcctcc gaagacgtcc ggaacaacc ctacaacctg    360
accatcgctt ggtttcggat gggaggcaac tgtgctatcc ccatcacggt catggagtac   420
accgaatgct cctacaacaa gtctctgggg gcctgtccca tccgaacgca gccccgctgg   480
aactactatg acagcttcag cgccgtcagc gaggataacc tggggttcct gatgcacgcc   540
cccgcgtttg agaccgccgg cacgtacctg cggctcgtga agataaacga ctggacggag   600
attacacagt ttatcctgga gcaccgagcc aagggctcct gtaagtacgc cctcccgctg   660
cgcatcccc cgtcagcctg cctctcccc caggcctacc agcaggggt gacggtggac   720
agcatcggga tgctgcccg cttcatcccc gagaaccagc gcaccgtcgc cgtatacgcc   780
ttgaagatcg ccgggtggca cgggccctat ctgccgctgg ataaaggcat taaccgtat   840
tatccggaac atgcggtgaa ccattatttt cagaccgcc attatctgca taccctgtgg   900
aaagcgggca ttctgtataa acgcgaaacc accgcagcg cgagctttg cggcagcccg   960
tatagctggg aacaggaact gcagcatggc agctgctggt gctgcagtt tcgcaacagc  1020
aaaccgtgca cgcgaatattg cctgacccat ctggtgaacc tgctggaaga ttggggaccg  1080
tgcgatgaac atggcgaaca tcatattcgc attccgcgca cccggcgcg cgtgaccggc  1140
ggcgtgtttc tggtggataa aaacccgcat aacaccgcgg aaagccgcct ggtggtggat  1200
tttagccagt ttagccgcgg cattacccgc gtgagctggc cgaaatttgc ggtgccgaac  1260
ctgcagagcc tgaccaacct gctgagcagc aacctgagct ggctgagcct ggatgtgcag  1320
gcgtttacct ttagcccgac ctataaagcg tttctgagca aacagtatct gaacctgtat  1380
ccggtggcgc gccagcgccc gggcctgtgc caggtgtttg cggatgcgac cccgaccggc  1440
tggggcctgg cgatgggcca tcagcgcatg cgcggcaccc ttgtggcgcc gctgccgatt  1500
cataccgcga aactgctggc ggcgtgcttt gcgcgcagcc gcagcggcgc gaaaattctg  1560
ggcaccgata cagcgtggt gctgagccgc aaatataccca gctttccgtg gctgctgggc  1620
tgcgcggcga actggattct gcgcggcacc agctttgtgt atgtgccgag cgcgctgaac  1680
ccggcggatg atgtgggcag caacctggaa gatccggcga ccgcgaact ggtggtgagc  1740
tatgtgaacg tgaacatggg cctgaaaatt cgccagctgc tgtggtttca tattagctgc  1800
ctgacctttg gccgcgaaac cgtgattgaa tatctggtga gctttggcgt gtggattcgc  1860
accccgccgg cgtatcgccc gccgaacgcg ccgattctga gcaccctgcc ggaaaccacc  1920
gtggtgcgcc gccgcgatcg gggccgcggg cccaaggccc catacgagc accctgctg   1980
ccccggagc tgtccgagac cccaacgcc acgcagccag aactcgccg ggaagacccc  2040
gaggattcgg ccctcttgga ggaccccgtg gggacggtgg cgccgcaaat cccaccaaac  2100
tggcacatcc cgtcgatcca ggacgccgcg acgccttacc atccccggc caccccgaac  2160
aacatggcc tgatcgccgg cgcggtgggc ggcagtctcc tggcagccct ggtcatttgc  2220
ggaattgtgt actggatgca ccgccgcact cggaaagccc caaagcgcat acgcctcccc  2280
cacatccggg aagacgacca gccgtcctcg caccagccct gttttacta g            2331

SEQ ID NO: 185          moltype = AA    length = 776
FEATURE                 Location/Qualifiers
REGION                  1..776
                        note = source = /note="Description of Artificial Sequence:
                        Synthetic polypeptide"
source                  1..776
                        mol_type = protein
                        organism = synthetic construct
SEQUENCE: 185
MGGAAARLGA VILFVVIVGL HGVRGKYALA DASLKMADPN RFRGKDLPVL DQLTDPPGVR    60
RVYHIQAGLP DPFQPPSLPI TVYYAVLERA CRSVLLNAPS EAPQIVRGAS EDVRKQPYNL   120
TIAWFRMGGN CAIPITVMEY TECSYNKSLG ACPIRTQPRW NYYDSFSAVS EDNLGFLMHA   180
PAFETAGTYL RLVKINDWTE ITQFILEHRA KGSCKYALPL RIPPSACLSP QAYQQGVTVD   240
SIGMLPRFIP ENQRTVAVYS LKIAGWHGPY LPLDKGIKPY YPEHAVNHYF QTRHYLHTLW   300
KAGILYKRET TRSASFCGSP YSWEQELQHG SCWWLQFRNS KPCSEYCLTH LVNLLEDWGP   360
CDEHGEHHIR IPRTPARVTG GVFLVDKNPH NTAESRLVVD FSQFSRGITR VSWPKFAVPN   420
LQSLTNLLSS NLSWLSLDVQ AFTFSPTYKA FLSKQYLNLY PVARQRPGLC QVFADATPTG   480
WGLAMGHQRM RGTFVAPLPI HTAELLAACF ARSRSGAKIL GTDNSVVLSR KYTSFPWLLG   540
CAANWILRGT SFVYVPSALN PADDVGSNLE DPASRELVVS YVNVNMGLKI RQLLWPHISC   600
LTFGRETVIE YLVSFGVWIR TPPAYRPPNA PILSTLPETT VVRRRDRGRG PKAPYTSTLL   660
PPELSETPNA TQPELAPEDP EDSALLEDPV GTVAPQIPPN WHIPSIQDAA TPYHPPATPN   720
NMGLIAGAVG GSLLAALVIC GIVYWMHRRT RKAPKRIRLP HIREDDQPSS HQPLFY       776

SEQ ID NO: 186          moltype = DNA   length = 2421
FEATURE                 Location/Qualifiers
misc_feature            1..2421
                        note = source = /note="Description of Artificial Sequence:
                        Synthetic polynucleotide"
source                  1..2421
                        mol_type = other DNA

```
                        organism = synthetic construct
SEQUENCE: 186
atggggggg    ctgccgccag   gttgggggcc   gtgattttgt   ttgtcgtcat   agtgggcctc    60
catgggtcc    gcggcaaata   tgccttggcg   gatgcctctc   tcaagatggc   cgaccccaat   120
cgctttcgcg   gcaaagacct   tccggtcctg   gaccagctga   ccgaccctcc   ggggtccgg    180
cgcgtgtacc   acatccaggc   gggcctaccg   gacccgttcc   agcccccag    cctcccgatc   240
acggtttact   acgccgtgtt   ggagcgcgcc   tgccgcagcg   tgctcctaaa   cgcaccgtcg   300
gaggccccc    agattgtccg   cggggcctcc   gaagacgtcc   ggaaacaacc   ctacaacctg   360
accatcgctt   ggtttcggat   gggaggcaac   tgtgctatcc   ccatcacggt   catggagtac   420
accgaatgct   cctacaacaa   gtctctgggg   gcctgtccca   tccgaacgca   gcccgctga    480
aactactatg   acagcttcag   cgccgtcagc   gaggataacc   tggggttcct   gatgcacgcc   540
cccgcgtttg   agaccgccgg   cacgtacctg   cggctcgtga   agataaacga   ctggacggag   600
attacacagt   ttatcctgga   gcaccgagcc   aagggctcct   gtaagtacgc   cctcccgctg   660
cgcatccccc   cgtcagcctg   cctctccccc   caggcctacc   agcagggggt   gacggtggac   720
agcatcggga   tgctgccccg   cttcatcccc   gagaaccagc   gcaccgtcgc   cgtatacagc   780
ttgaagatcg   ccgggtggca   cgggccccat   tttcgcaaac   tgctgctgct   ggatgaagaa   840
gcgggaccgc   tggaagaaga   actgccgcgc   ctggcggatg   aaggcctgaa   ccgccgcgtg   900
gcggaagatc   tgaacctggg   caacctgccg   gaatggcaga   ccccgagctt   tccgaaaatt   960
catctgcagg   aagatattgt   ggatcgctgc   aaacagtttg   tgggaccgct   gaccgtgaac  1020
gaaaaacgcc   gcctgaaact   gattatgccg   gcgcgctttt   atccgaacgt   gaccaaatat  1080
ctgccgctga   taaaggcat    taaaccgtat   tatccggaac   atgcggtgaa   ccattatttt  1140
cagacccgcc   attatctgca   tacctgtgg    aaagcgggca   ttctgtataa   acgcgaaacc  1200
acccgcagcg   cgagctttg    cggcagcccc   tatagctggg   aacaggaact   gcagcatggc  1260
agctgctggt   ggctgcagtt   tcgcaacagc   aaaccgtgca   gcgaatattg   cctgacccat  1320
ctggtgaacc   tgctggaaga   ttggggaccg   tgcgatgaac   atggcgaaca   tcatattcgc  1380
attccgcgca   ccccggcgcg   cgtgacccag   gcgtttaccc   ttagcccgac   ctataaagcg  1440
tttctgagca   aacagtatct   gaacctgtat   ccggtggcgc   gccagcgccc   gggcctgtgc  1500
caggtgtttg   cggatgcgac   cccgaccggc   tggggcctgg   cgatgggcca   tcagcgcatg  1560
cgcggcacct   tgtggcgcc    gctgccgatt   cataccgcgg   aactgctggc   ggcgtgcttt  1620
gcgcgcagcc   gcagcggcgc   gaaaattctg   ggcaccgata   acagcgtggt   gctgagccgc  1680
aaatatacca   gctttccgtg   gctgctgggc   tgcgcggcga   actggattct   gcgcggcacc  1740
agctttgtgt   atgtgccgag   cgcgctgaac   ccggcggatg   atgtgggcag   caacctggaa  1800
gatccggcga   gccgcgaact   ggtggtgagc   tatgtgaacg   tgaacatggg   cctgaaaatt  1860
cgccagctgc   tgtggtttca   tattagctgc   ctgacctttg   gccgcgaaac   cgtgattgaa  1920
tatctggtga   gctttggcgt   gtggattcgc   accccgccgg   cgtatcgccc   gccgaacgcg  1980
ccgattctga   gcaccctgcc   ggaaaccacc   gtggtgcgcc   gccagatcg    aggccgcggg  2040
cccaaggccc   catacacgag   caccctgctg   ccccgggagc   tgtccgagac   ccccaacgcc  2100
acgcagccag   aactcgcccc   ggaagacccc   gaggattcgg   ccctcttgga   ggaccccgtg  2160
gggacggtgg   cgccgcaaat   cccaccaaac   tggcacatcc   cgtcgatcca   gacgccgcg   2220
acgccttacc   atccccggc    cacccccgaac   aacatgggcc   tgatcgccgg   cgcggtgggc  2280
ggcagtctcc   tggcagccct   ggtcatttgc   ggaattgtgt   actggatgca   ccgccgcact  2340
cggaaagccc   caaagcgcat   acgcctcccc   cacatccggg   aagacgacca   gccgtcctcg  2400
caccagcct    tgttttacta   g                                                  2421

SEQ ID NO: 187          moltype = AA  length = 806
FEATURE                 Location/Qualifiers
REGION                  1..806
                        note = source = /note="Description of Artificial Sequence:
                        Synthetic polypeptide"
source                  1..806
                        mol_type = protein
                        organism = synthetic construct
SEQUENCE: 187
MGGAAARLGA   VILFVVIVGL   HGVRGKYALA   DASLKMADPN   RFRGKDLPVL   DQLTDPPGVR    60
RVYHIQAGLP   DPFQPPSLPI   TVYYAVLERA   CRSVLLNAPS   EAPQIVRGAS   EDVRKQPYNL   120
TIAWFRMGGN   CAIPITVMEY   TECSYNKSLG   ACPIRTQPRW   NYYDSFSAVS   EDNLGFLMHA   180
PAFETAGTYL   RLVKINDWTE   ITQFILEHRA   KGSCKYALPL   RIPPSACLSP   QAYQQGVTVD   240
SIGMLPRFIP   ENQRTVAVYS   LKIAGWHGPH   FRKLLLLDEE   AGPLEEELPR   LADEGLNRRV   300
AEDLNLGKIL   EWQTPSFPKI   HLQEDIVDRC   KQFVGPLTVN   EKRRLKLIMP   ARFYPNVTKY   360
LPLDKGIKPY   YPEHAVNHYF   QTRHYLHTLW   KAGILYKRET   TRSASFCGSP   YSWEQELQHG   420
SCWWLQFRNS   KPCSEYCLTH   LVNLLEDWGP   CDEHGEHHIR   IPRTPARVTQ   AFTFSPTYKA   480
FLSKQYLNLY   PVARQRPGLC   QVFADATPTG   WGLAMGHQRM   RGTFVAPLPI   HTAELLAACF   540
ARSRSGAKIL   GTDNSVVLSR   KYTSFPWLLG   CAANWILRGT   SFVYVPSALN   PADDVGSNLE   600
DPASRELVVS   YVNVNMGLKI   RQLLWFHISC   LTFGRETVIE   YLVSFGVWIR   TPPAYRPPNA   660
PILSTLPETT   VVRRRDRGRG   PKAPYTSTLL   PPELSETPNA   TQPELAPEDP   EDSALLEDPV   720
GTVAPQIPPN   WHIPSIQDAA   TPYHPPATPN   NMGLIAGAVG   GSLLAALVIC   GIVYWMHRRT   780
RKAPKRIRLP   HIREDDQPSS   HQPLFY                                             806

SEQ ID NO: 188          moltype = AA  length = 9
FEATURE                 Location/Qualifiers
REGION                  1..9
                        note = source = /note="Description of Artificial Sequence:
                        Synthetic peptide"
source                  1..9
                        mol_type = protein
                        organism = synthetic construct
SEQUENCE: 188
FAVPNLQSL                                                                       9
```

```
SEQ ID NO: 189          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 189
PEWQTPSFPK IHLQE                                                          15

SEQ ID NO: 190          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 190
PSFPKIHLQE DIVDR                                                          15

SEQ ID NO: 191          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 191
IHLQEDIVDR CKQFV                                                          15

SEQ ID NO: 192          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 192
DIVDRCKQFV GPLTV                                                          15

SEQ ID NO: 193          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 193
CKQFVGPLTV NEKRR                                                          15

SEQ ID NO: 194          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 194
GPLTVNEKRR LKLIM                                                          15

SEQ ID NO: 195          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 195
NEKRRLKLIM PARFY                                                          15

SEQ ID NO: 196          moltype = AA  length = 15
FEATURE                 Location/Qualifiers
```

```
REGION                    1..15
                          note = source = /note="Description of Artificial Sequence:
                           Synthetic peptide"
source                    1..15
                          mol_type = protein
                          organism = synthetic construct
SEQUENCE: 196
LKLIMPARFY PNVTK                                                              15

SEQ ID NO: 197            moltype = AA   length = 15
FEATURE                   Location/Qualifiers
REGION                    1..15
                          note = source = /note="Description of Artificial Sequence:
                           Synthetic peptide"
source                    1..15
                          mol_type = protein
                          organism = synthetic construct
SEQUENCE: 197
PARFYPNVTK YLPLD                                                              15

SEQ ID NO: 198            moltype = AA   length = 15
FEATURE                   Location/Qualifiers
REGION                    1..15
                          note = source = /note="Description of Artificial Sequence:
                           Synthetic peptide"
source                    1..15
                          mol_type = protein
                          organism = synthetic construct
SEQUENCE: 198
PNVTKYLPLD KGIKP                                                              15

SEQ ID NO: 199            moltype = AA   length = 15
FEATURE                   Location/Qualifiers
REGION                    1..15
                          note = source = /note="Description of Artificial Sequence:
                           Synthetic peptide"
source                    1..15
                          mol_type = protein
                          organism = synthetic construct
SEQUENCE: 199
YLPLDKGIKP YYPEH                                                              15

SEQ ID NO: 200            moltype = AA   length = 15
FEATURE                   Location/Qualifiers
REGION                    1..15
                          note = source = /note="Description of Artificial Sequence:
                           Synthetic peptide"
source                    1..15
                          mol_type = protein
                          organism = synthetic construct
SEQUENCE: 200
KGIKPYYPEH AVNHY                                                              15

SEQ ID NO: 201            moltype = AA   length = 15
FEATURE                   Location/Qualifiers
REGION                    1..15
                          note = source = /note="Description of Artificial Sequence:
                           Synthetic peptide"
source                    1..15
                          mol_type = protein
                          organism = synthetic construct
SEQUENCE: 201
YYPEHAVNHY FQTRH                                                              15

SEQ ID NO: 202            moltype = AA   length = 15
FEATURE                   Location/Qualifiers
REGION                    1..15
                          note = source = /note="Description of Artificial Sequence:
                           Synthetic peptide"
source                    1..15
                          mol_type = protein
                          organism = synthetic construct
SEQUENCE: 202
AVNHYFQTRH YLHTL                                                              15

SEQ ID NO: 203            moltype = AA   length = 15
FEATURE                   Location/Qualifiers
REGION                    1..15
                          note = source = /note="Description of Artificial Sequence:
```

```
                            Synthetic peptide"
source                      1..15
                            mol_type = protein
                            organism = synthetic construct
SEQUENCE: 203
FQTRHYLHTL WKAGI                                                            15

SEQ ID NO: 204              moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 204
YLHTLWKAGI LYKRE                                                            15

SEQ ID NO: 205              moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 205
WKAGILYKRE TTRSA                                                            15

SEQ ID NO: 206              moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 206
LYKRETTRSA SFCGS                                                            15

SEQ ID NO: 207              moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 207
TTRSASFCGS PYSWE                                                            15

SEQ ID NO: 208              moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 208
SFCGSPYSWE QELQH                                                            15

SEQ ID NO: 209              moltype = AA  length = 15
FEATURE                     Location/Qualifiers
REGION                      1..15
                            note = source = /note="Description of Artificial Sequence:
                            Synthetic peptide"
source                      1..15
                            mol_type = protein
                            organism = synthetic construct
SEQUENCE: 209
PYSWEQELQH GSCWW                                                            15

SEQ ID NO: 210              moltype = AA  length = 15
FEATURE                     Location/Qualifiers
REGION                      1..15
                            note = source = /note="Description of Artificial Sequence:
                            Synthetic peptide"
source                      1..15
```

```
                            mol_type = protein
                            organism = synthetic construct
SEQUENCE: 210
QELQHGSCWW LQFRN                                                      15

SEQ ID NO: 211              moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 211
GSCWWLQFRN SKPCS                                                      15

SEQ ID NO: 212              moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 212
LQFRNSKPCS EYCLT                                                      15

SEQ ID NO: 213              moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 213
SKPCSEYCLT HLVNL                                                      15

SEQ ID NO: 214              moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 214
EYCLTHLVNL LEDWG                                                      15

SEQ ID NO: 215              moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 215
HLVNLLEDWG PCDEH                                                      15

SEQ ID NO: 216              moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
SEQUENCE: 216
LEDWGPCDEH GEHHI                                                      15

SEQ ID NO: 217              moltype = AA  length = 15
FEATURE                     Location/Qualifiers
REGION                      1..15
                            note = source = /note="Description of Artificial Sequence:
                             Synthetic peptide"
source                      1..15
                            mol_type = protein
                            organism = synthetic construct
```

```
SEQUENCE: 217
PCDEHGEHHI RIPRT                                                                15

SEQ ID NO: 218          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 218
GEHHIRIPRT PARVT                                                                15

SEQ ID NO: 219          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 219
RIPRTPARVT GGVFL                                                                15

SEQ ID NO: 220          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 220
PARVTGGVFL VDKNP                                                                15

SEQ ID NO: 221          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 221
GGVFLVDKNP HNTAE                                                                15

SEQ ID NO: 222          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 222
VDKNPHNTAE SRLVV                                                                15

SEQ ID NO: 223          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 223
HNTAESRLVV DFSQF                                                                15

SEQ ID NO: 224          moltype = AA  length = 15
FEATURE                 Location/Qualifiers
REGION                  1..15
                        note = source = /note="Description of Artificial Sequence:
                         Synthetic peptide"
source                  1..15
                        mol_type = protein
                        organism = synthetic construct
SEQUENCE: 224
SRLVVDFSQF SRGIT                                                                15
```

```
SEQ ID NO: 225         moltype = AA   length = 15
FEATURE                Location/Qualifiers
REGION                 1..15
                       note = source = /note="Description of Artificial Sequence:
                       Synthetic peptide"
source                 1..15
                       mol_type = protein
                       organism = synthetic construct
SEQUENCE: 225
DFSQFSRGIT RVSWP                                                          15

SEQ ID NO: 226         moltype = AA   length = 15
FEATURE                Location/Qualifiers
REGION                 1..15
                       note = source = /note="Description of Artificial Sequence:
                       Synthetic peptide"
source                 1..15
                       mol_type = protein
                       organism = synthetic construct
SEQUENCE: 226
SRGITRVSWP KFAVP                                                          15

SEQ ID NO: 227         moltype = AA   length = 15
FEATURE                Location/Qualifiers
REGION                 1..15
                       note = source = /note="Description of Artificial Sequence:
                       Synthetic peptide"
source                 1..15
                       mol_type = protein
                       organism = synthetic construct
SEQUENCE: 227
RVSWPKFAVP NLQSL                                                          15

SEQ ID NO: 228         moltype = AA   length = 15
FEATURE                Location/Qualifiers
REGION                 1..15
                       note = source = /note="Description of Artificial Sequence:
                       Synthetic peptide"
source                 1..15
                       mol_type = protein
                       organism = synthetic construct
SEQUENCE: 228
KFAVPNLQSL TNLLS                                                          15

SEQ ID NO: 229         moltype = AA   length = 15
FEATURE                Location/Qualifiers
REGION                 1..15
                       note = source = /note="Description of Artificial Sequence:
                       Synthetic peptide"
source                 1..15
                       mol_type = protein
                       organism = synthetic construct
SEQUENCE: 229
NLQSLTNLLS SNLSW                                                          15

SEQ ID NO: 230         moltype = AA   length = 15
FEATURE                Location/Qualifiers
REGION                 1..15
                       note = source = /note="Description of Artificial Sequence:
                       Synthetic peptide"
source                 1..15
                       mol_type = protein
                       organism = synthetic construct
SEQUENCE: 230
TNLLSSNLSW LSLDV                                                          15

SEQ ID NO: 231         moltype = AA   length = 15
FEATURE                Location/Qualifiers
REGION                 1..15
                       note = source = /note="Description of Artificial Sequence:
                       Synthetic peptide"
source                 1..15
                       mol_type = protein
                       organism = synthetic construct
SEQUENCE: 231
SNLSWLSLDV SAAFY                                                          15

SEQ ID NO: 232         moltype = AA   length = 15
```

```
FEATURE             Location/Qualifiers
REGION              1..15
                    note = source = /note="Description of Artificial Sequence:
                    Synthetic peptide"
source              1..15
                    mol_type = protein
                    organism = synthetic construct
SEQUENCE: 232
LSLDVSAAFY HIPLH                                                            15

SEQ ID NO: 233      moltype = AA  length = 15
FEATURE             Location/Qualifiers
REGION              1..15
                    note = source = /note="Description of Artificial Sequence:
                    Synthetic peptide"
source              1..15
                    mol_type = protein
                    organism = synthetic construct
SEQUENCE: 233
SAAFYHIPLH PAAMP                                                            15
```

ADENOVIRAL VECTORS ENCODING HEPATITIS B VIRAL ANTIGENS FUSED TO HERPES VIRUS GLYCOPROTEIN D AND METHODS OF USING THE SAME

CROSS REFERENCE TO RELATED APPLICATIONS

This application is a continuation of U.S. patent application Ser. No. 17/679,356 filed on Feb. 24, 2022, which is a continuation of U.S. patent application Ser. No. 17/459,313, filed on Aug. 27, 2021 (U.S. Pat. No. 11,291,716), which is a continuation of International Application No. PCT/US2021/012630, filed on Jan. 8, 2021, which claims priority to U.S. Provisional Application No. 62/958,809, filed on Jan. 9, 2020, U.S. Provisional Application No. 62/958,827, filed on Jan. 9, 2020, U.S. Provisional Application No. 62/967,242, filed on Jan. 29, 2020, U.S. Provisional Application No. 62/967,104, filed on Jan. 29, 2020, U.S. Provisional Application No. 63/064,506, filed on Aug. 12, 2020, U.S. Provisional Application No. 63/064,571, filed on Aug. 12, 2020, U.S. Provisional Application No. 63/112,202, filed on Nov. 11, 2020, and U.S. Provisional Application No. 63/112,219, filed on Nov. 11, 2020, the disclosure of each of which is hereby incorporated by reference in their entirety.

SEQUENCE LISTING

The instant application contains a Sequence Listing which has been submitted electronically in XML format and is hereby incorporated by reference in its entirety. The XML copy, created on Nov. 7, 2023, is named 111876_000083_SL_XML.txt and is 326 KB in size.

FIELD OF THE INVENTION

Disclosed herein are non-naturally occurring variants of the hepatitis B virus (HBV) Core protein, the HBV polymerase N-terminal domain, and the HBV polymerase C-terminal domain, as well as immunogenic fragments thereof and fusion proteins comprising the same.

BACKGROUND OF THE INVENTION

The World Health Organization estimates that, in 2015, 257 million people were living with chronic hepatitis B infection (defined as hepatitis B surface antigen positive) and that hepatitis B resulted in an estimated 887,000 deaths, mostly from cirrhosis and hepatocellular carcinoma (i.e., primary liver cancer). Assuming that women of reproductive age constitute 25.3% of the world's population (United Nations data), adults chronically infected may include 65 million women of childbearing age who can potentially transmit HBV to their babies (WHO Global Hepatitis Report 2017. Available at: apps_who_int/iris/bitstream/handle/10665/255016/9789241565455-eng.pdf; jsessionid=D78616700ED7322D4109CA4541FB94EA?sequence=1). The overall incidence rate in 2016 was 1.0 case per 100,000 population (Centers for Disease Control and Prevention. Viral Hepatitis Surveillance—United States, 2017. Atlanta: US Department of Health and Human Services, Centers for Disease Control and Prevention; 2019. Available at: www cdc gov/hepatitis/statistics/2017surveillance/index.htm.). In 2017 alone, a total of 3,407 cases of acute hepatitis B were reported to the Centers for Disease Control and Prevention (CDC).

Despite the availability of a prophylactic HBV vaccine, the burden of chronic HBV infection continues to be a significant unmet worldwide medical problem, due to suboptimal treatment options and sustained rates of new infections in most parts of the developing world.

SUMMARY OF THE INVENTION

Provided herein is a hepatitis B virus (HBV) Core protein comprising the amino acid sequence of SEQ ID NO: 6 or an immunogenic fragment thereof.

Also provided is an HBV polymerase N-terminal domain comprising the amino acid sequence of SEQ ID NO: 8 or an immunogenic fragment thereof.

An HBV polymerase C-terminal domain comprising the amino acid sequence of SEQ ID NO: 10 or an immunogenic fragment thereof is also disclosed.

Fusion proteins comprising: an N-terminal herpes simplex virus (HSV) glycoprotein (gD) sequence or a variant thereof; the disclosed HBV Core protein, HBV polymerase N-terminal domain, HBV polymerase C-terminal domain, or immunogenic fragments thereof; and a C-terminal HSV gD sequence or a variant thereof are also provided.

Also provided herein are fusion proteins comprising: an N-terminal herpes simplex virus (HSV) glycoprotein (gD) sequence or a variant thereof; combinations of the disclosed HBV Core protein, HBV polymerase N-terminal domain, HBV polymerase C-terminal domain, and/or immunogenic fragments thereof; and a C-terminal HSV gD sequence or a variant thereof.

Nucleic acid molecules encoding the disclosed proteins or fusion proteins, vectors comprising the nucleic acid molecules, and vaccines comprising the disclosed vectors are disclosed herein.

Also provided herein are methods of inducing an immune response to HBV in a subject, the method comprising providing to the subject an effective amount of any of the disclosed fusion proteins, nucleic acid molecules, vectors, or vaccines to thereby induce an immune response to HBV.

BRIEF DESCRIPTION OF THE DRAWINGS

The summary, as well as the following detailed description, is further understood when read in conjunction with the appended drawings. For the purpose of illustrating the disclosed proteins, vaccines, and methods, there are shown in the drawings exemplary embodiments of the proteins, vaccines, and methods; however, the proteins, vaccines, and methods are not limited to the specific embodiments disclosed. In the drawings:

FIG. 2A, FIG. 2B, FIG. 2C, FIG. 2D, FIG. 2E, and FIG. 2F illustrate vaccine insert-specific T cell frequencies in C57Bl/6 mice following intramuscular (i.m.) injection with the indicated doses of: replication-defective adenovirus vector of chimpanzee serotype 6 (AdC6) containing the epitope-optimized Core sequence genetically fused into gD (SEQ ID NO: 15) (AdC6-gDCore) (FIG. 2A and FIG. 2D); AdC6 containing the epitope-optimized polymerase C-terminal domain sequence genetically fused into gD (SEQ ID NO: 19) (AdC6-gDPolC) (FIG. 2B and FIG. 2E); and AdC6 containing the epitope-optimized polymerase N-terminal domain sequence genetically fused into gD (SEQ ID NO: 17) (AdC6-gDPolN) (FIG. 2C and FIG. 2F). Mice were bled 14 days after the injection and T cell frequencies to the various HBV inserts were analyzed by intracellular cytokine staining (ICS) for interferon (IFN)-γ upon stimulation of cells with overlapping peptides representing the HBV sequences. Control cells were cultured without peptides. Graphs show results for individual mice with medians indicated by the lines. FIG. 2A-2C show insert-specific CD8+ T cell frequency; FIG. 2D-2F show insert-specific CD4+ T cell frequency.

FIG. 7A, FIG. 7B, FIG. 7C, FIG. 7D, and FIG. 7E illustrate exemplary HBV epitope shifting experiments. FIG. 7A—mice were immunized with the AdC6-gDPolN vaccine. Four weeks later splenocytes were tested by intracellular cytokine staining for IFN-γ responses to peptide pools representing the PolN sequence. T cells after stimulation were stained for T cell markers. FIG. 7B—results obtained with the same assay using splenocytes from mice that were challenged with $1 \times 10^{10}$ vg of AAV8-1.3-HBV. Mice were vaccinated 4 weeks later and T cell responses were tested from spleens 10 weeks later. FIG. 7C—results obtained with the same assay using splenocytes from mice that had been challenged with $1.5 \times 10^{11}$ vg of AAV8-1.3-HBV. Mice were vaccinated 4 weeks later and T cell responses were tested from spleen 10 weeks later. FIGS. 7A, 7B, and 7C show the frequencies of IFN-γ producing CD44+ CD8+ T cells over all CD44+ CD8+ T cells. Background responses obtained by splenocytes incubated without peptide pools were subtracted. FIG. 7D—peptide pools. FIG. 7E—individual peptide sequences. FIG. 7E discloses SEQ ID NOs: 55-68 and 189-233, respectively, in order of appearance.

FIG. 9A, FIG. 9B, and FIG. 9C illustrate the results from exemplary immunogenicity experiments performed on C57Bl/6 mice (n=5 per group) injected with various doses of exemplary AdC6-gDCore, AdC6-gDPolN, or AdC6-gD- PolC vectors and boosted with AdC7 vectors containing the same insert (i.e. AdC7-gDCore, AdC7-gDPolN, or AdC7-gDPolC vectors) two months after the first injection. FIG. 9A illustrates antigen immunogenicity, FIG. 9B illustrates the duration of response, and FIG. 9C illustrates the prime-boost response.

FIG. 12A, FIG. 12B, FIG. 12C, FIG. 12D, FIG. 12E, and FIG. 12F illustrate hematoxylin & eosin staining of liver samples from C57Bl/6 mice injected with the indicated vectors. 20× magnification. Arrows indicate areas of lymphocytic infiltrates.

In FIG. 15B, each slice represents an individual epitope with size showing the proportion of the total; only responses >0.1% were included. Pullouts represent epitopes only recognized in AAV8-1.3HBV infected mice.

FIG. 20A and FIG. 20D show CD8$^+$ T cell responses of mice that received just the AdC6-gDPolN vaccine. FIG. 20B and FIG. 20E show CD8$^+$ T cell responses of mice that were injected with $10^{10}$ vg of AAV8-1.3HBV 4 weeks prior to vaccination with AdC6-gDPolN. FIG. 20C and FIG. 20F show CD8$^+$ T cell responses of mice that were injected with $10^{11}$ vg of AAV8-1.3HBV 4 weeks prior to vaccination with AdC6-gDPolN. FIGS. 20A, 20B and 20C can be used to calculate the breadth of the immune response by individual epitopes using the peptide pools shown in FIG. 7D and the individual peptide sequences recognized using FIG. 7E.

FIG. 21A left panel shows CD8$^+$ T cell responses in spleen of AAV8-1.3HBV injected mice that did or did not receive the AdC6-gDPolN vaccine at 5×10$^{10}$ vp subsequently. FIG. 21A middle panel shows CD8$^+$ T cell frequencies in livers of mice that were treated with different doses of AAV8-1.3HBV and then received vaccines in a prime boost regimen. FIG. 21A right panel shows the levels of Tox-1 expression in PolN-specific CD8$^+$ T cells or naïve CD8$^+$ T cells from the same experiment. FIG. 21B illustrates % IFN-γ$^+$CD8$^+$ T cells.

FIG. 25A illustrates the viral titer for each group at weeks 4 and 8 after AAV challenge; FIG. 25B illustrates the results of the individual mice at weeks 4 and 8 after AAV challenge.

FIG. 30A, FIG. 30B, FIG. 30C, FIG. 30D, FIG. 30E, and FIG. 30F illustrates the phenotypes of the tetramer+CD8+ T cells shown as the mean fluorescent intensity of a dye linked to the indicated antibody: FIG. 30A—anti-PD1 antibody conjugated to BV605; FIG. 30B—anti-LAG3 antibody conjugated to BV650; FIG. 30C—anti-TIM3 antibody conjugated to Pe-Cy7-A; FIG. 30D—anti-CTLA4 antibody conjugated to PE-A; FIG. 30E—anti-EOMES antibody conjugated to AF488; and FIG. 30F—anti-T-bet antibody conjugated to BV786.

DETAILED DESCRIPTION OF ILLUSTRATIVE EMBODIMENTS

Figure 1:
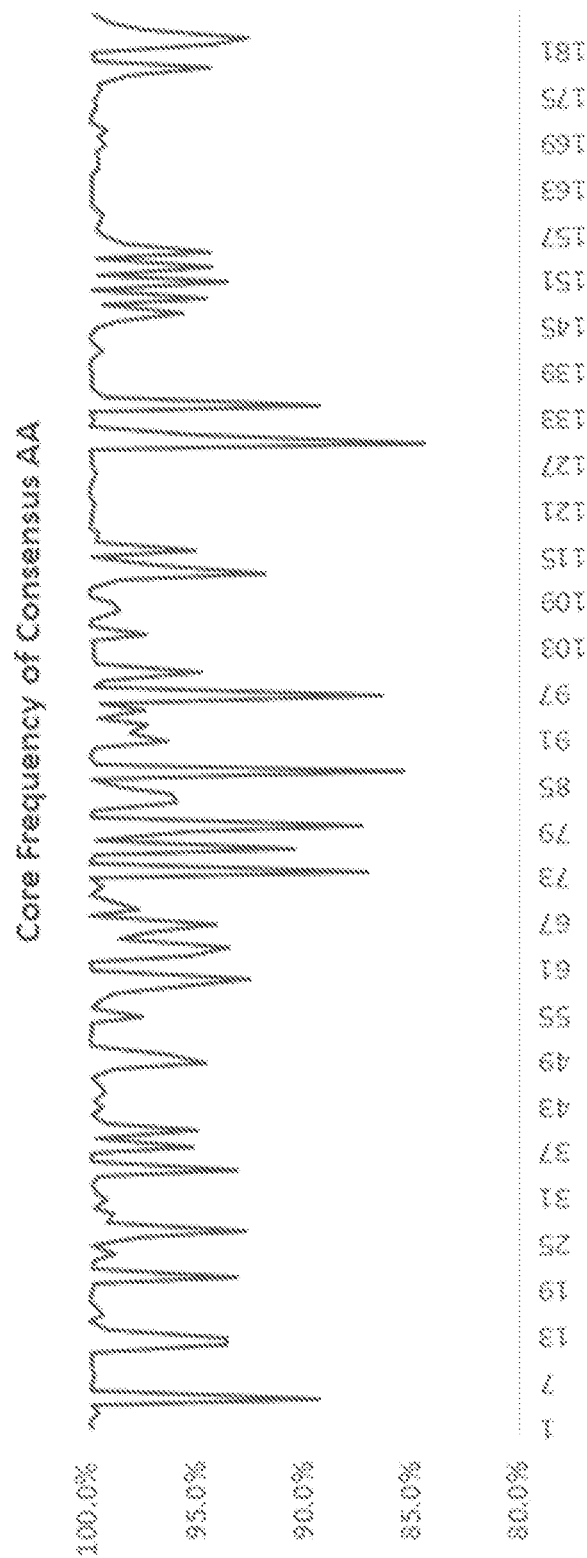
FIG. 1 illustrates the frequency of epitope-optimized Core amino acids. Amino acid residues are indicated on the X-axis; percent sequence similarity across all genomes analyzed is indicated on the Y-axis.
Figure 2D:
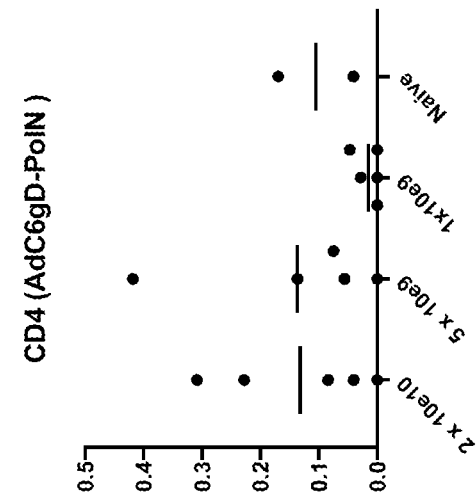
Figure 2E:
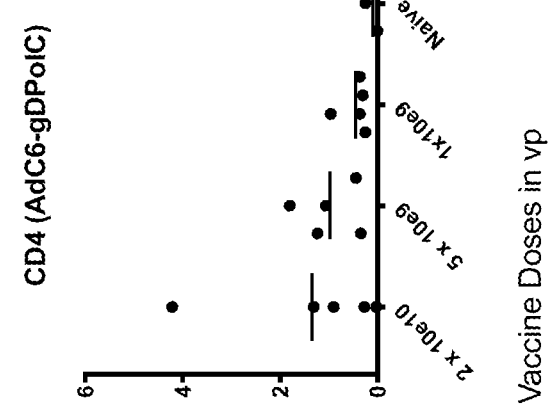
Figure 2F:
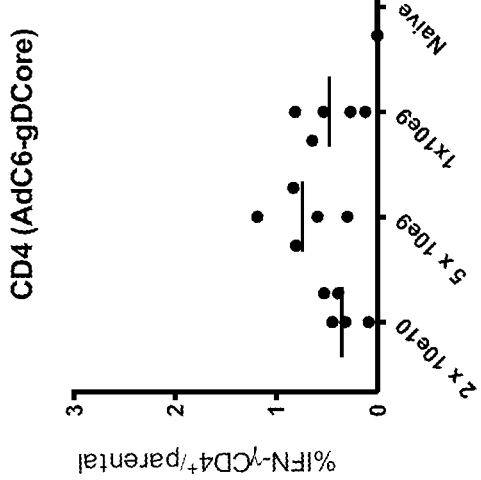

The disclosed proteins, vaccines, and methods may be understood more readily by reference to the following detailed description taken in connection with the accompanying figures, which form a part of this disclosure. It is to be understood that the disclosed proteins, vaccines, and methods are not limited to the specific proteins, vaccines, and methods described and/or shown herein, and that the terminology used herein is for the purpose of describing particular embodiments by way of example only and is not intended to be limiting of the claimed proteins, vaccines, and methods.

Unless specifically stated otherwise, any description as to a possible mechanism or mode of action or reason for improvement is meant to be illustrative only, and the disclosed proteins, vaccines, and methods are not to be constrained by the correctness or incorrectness of any such suggested mechanism or mode of action or reason for improvement.

Throughout this text, the descriptions refer to proteins and methods of using said proteins. Where the disclosure describes or claims a feature or embodiment associated with a proteins, such a feature or embodiment is equally applicable to the methods of using said proteins. Likewise, where the disclosure describes or claims a feature or embodiment associated with a method of using the proteins, such a feature or embodiment is equally applicable to the proteins.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value. It is not intended that the scope of the invention be limited to the specific values recited when defining a range. All ranges are inclusive and combinable.

When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed proteins, vaccines, and methods which are, for clarity, described herein in the context of separate embodiments, may also be provided in combination in a single embodiment. Conversely, various features of the disclosed proteins, vaccines, and methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, "immunogenic fragment thereof" refers to a portion of the disclosed HBV Core (Core), HBV polymerase N-terminal domain (PolN), or HBV polymerase C-terminal domain (PolC) that can produce an immune response in a subject.

As used herein, "providing to the subject" and similar terms indicate a procedure by which the fusion proteins, nucleic acid molecules, vectors, or vaccines are delivered to a subject such that target cells, tissues, or segments of the body of the subject are contacted with the fusion proteins, nucleic acid molecules, vectors, or vaccines. "Providing to the subject" includes parenteral and non-parenteral routes of administration.

The term "biosimilar" (of an approved reference product/biological drug, i.e., reference listed drug) refers to a biological product that is highly similar to the reference product notwithstanding minor differences in clinically inactive components with no clinically meaningful differences between the biosimilar and the reference product in terms of safety, purity and potency, based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biosimilar. The biosimilar may be an interchangeable product that may be substituted for the reference product at the pharmacy without the intervention of the prescribing healthcare professional. To meet the additional standard of "interchangeability," the biosimilar is to be expected to produce the same clinical result as the reference product in any given patient and, if the biosimilar is administered more than once to an individual, the risk in terms of safety or diminished efficacy of alternating or switching between the use of the biosimilar and the reference product is not greater than the risk of using the reference product without such alternation or switch. The biosimilar utilizes the same mechanisms of action for the proposed conditions of use to the extent the mechanisms are known for the reference product. The condition or conditions of use prescribed, recommended, or suggested in the labeling proposed for the biosimilar have been previously approved for the reference product. The route of administration, the dosage form, and/or the strength of the biosimilar are the same as those of the reference product and the biosimilar is manufactured, processed, packed or held in a facility that meets standards designed to assure that the biosimilar continues to be safe, pure and potent. The biosimilar may include minor modifications in the amino acid sequence when compared to the reference product, such as N- or C-terminal truncations that are not expected to change the biosimilar performance. Biosimilars of the disclosed proteins and fusion proteins are included within the scope of this disclosure.

The term "subject" as used herein is intended to mean any animal, in particular, mammals. Although induction of an immune response in mice is exemplified herein, any type of mammal can be treated using the disclosed methods. Thus, the methods are applicable to human and nonhuman animals, although preferably used with mice and humans, and most preferably with humans.

The term "comprising" is intended to include examples encompassed by the terms "consisting essentially of" and "consisting of"; similarly, the term "consisting essentially of" is intended to include examples encompassed by the term "consisting of."

The following abbreviations are used herein: hepatitis B virus (HBV); adenovirus (Ad); herpes simplex virus (HSV); glycoprotein (gD); and virus genomes (vg).

Provided herein is a non-naturally occurring variant of the hepatitis B virus (HBV) Core protein. The disclosed HBV Core protein can comprise the amino acid sequence of SEQ ID NO: 6 or an immunogenic fragment thereof. Exemplary immunogenic fragments of SEQ ID NO: 6 include SEQ ID NOs: 20-54 provided in Table 3, below. In some embodiments, the immunogenic fragment of the HBV Core protein comprises the amino acid sequence of SEQ ID NO: 180. In some embodiments, the immunogenic fragment of the HBV Core protein comprises the amino acid sequence of SEQ ID NO: 183.

Nucleic acid molecules encoding the HBV Core protein or an immunogenic fragment thereof are also provided. The nucleic acid molecule can encode the HBV Core protein comprising the amino acid sequence of SEQ ID NO: 6. In some embodiments, the nucleic acid molecule comprises the nucleotide sequence of SEQ ID NO: 7. The nucleic acid molecules can encode the Core fragments provided in Table 3. In some embodiments, the nucleic acid molecule encodes the amino acid sequence of SEQ ID NO: 180. In some embodiments, the nucleic acid molecule encodes the amino acid sequence of SEQ ID NO: 183.

Vectors comprising the nucleic acid molecules encoding the HBV Core protein or an immunogenic fragment thereof are also provided. Suitable vectors include viral vectors, such as lentiviral vectors, retroviral vectors, adenoviral vectors, adeno-associated viral vectors, alphavirus replicons, herpes virus vectors, pox virus vectors, and rhabdovirus vectors. In some embodiments, the viral vector is an adenoviral vector. The adenoviral vector can be a chimpanzee-derived adenoviral vector. In some aspects, the vector is an AdC68 vector as described in Farina S F, Gao G P, Xiang Z Q, Rux J J, Burnett R M, Alvira M R, Marsh J, Ertl H C, Wilson J M. "Replication-defective vector based on a chimpanzee adenovirus." *J Virol.* 2001 December; 75(23): 11603-13. In some aspects, the vector is an AdC7 vector as described in Reyes-Sandoval A, Fitzgerald J C, Grant R, Roy S, Xiang Z Q, Li Y, Gao G P, Wilson J M, Ertl H C. "Human immunodeficiency virus type 1-specific immune responses in primates upon sequential immunization with adenoviral vaccine carriers of human and simian serotypes"*J Virol.* 2004 July; 78(14): 7392-9. In some aspects, the vector is an AdC6 vector as described in Pinto A R, Fitzgerald J C, Giles-Davis W, Gao G P, Wilson J M, Ertl H C. "Induction of CD8+ T cells to an HIV-1 antigen through a prime boost regimen with heterologous El-deleted adenoviral vaccine carriers" *J Immunol.* 2003 Dec. 15; 171(12): 6774-9.

In some embodiments, the vector comprises the nucleic acid molecule comprising the nucleotide sequence of SEQ ID NO: 7. In some embodiments, the vector is an AdC6 vector comprising the nucleic acid molecule comprising the nucleotide sequence of SEQ ID NO: 7. In some embodiments, the vector is an AdC7 vector comprising the nucleic acid molecule comprising the nucleotide sequence of SEQ ID NO: 7.

In some embodiments, the vector comprises the nucleic acid molecule that encodes the amino acid sequence of SEQ ID NO: 180. In some aspects, the vector is an AdC6 vector. In some aspects, the vector is an AdC7 vector. In some embodiments, the vector comprises the nucleic acid molecule that encodes the amino acid sequence of SEQ ID NO: 183. In some aspects, the vector is an AdC6 vector. In some aspects, the vector is an AdC7 vector.

Vaccines comprising the vectors comprising the nucleic acid molecules encoding the HBV Core protein or an immunogenic fragment thereof are also disclosed. In some embodiments, the vaccine comprises a vector comprising the nucleic acid molecule comprising the nucleotide sequence of SEQ ID NO: 7. In some embodiments, the vaccine comprises an AdC6 vector comprising the nucleic acid molecule comprising the nucleotide sequence of SEQ ID NO: 7. In some embodiments, the vaccine comprises an AdC7 vector comprising the nucleic acid molecule comprising the nucleotide sequence of SEQ ID NO: 7. In some embodiments, the vaccine comprises an AdC6 vector comprising the nucleic acid molecule that encodes the amino acid sequence of SEQ ID NO: 180. In some embodiments, the vaccine comprises an AdC7 vector comprising the nucleic acid molecule that encodes the amino acid sequence of SEQ ID NO: 180. In some embodiments, the vaccine comprises an AdC6 vector that comprises the nucleic acid molecule that encodes the amino acid sequence of SEQ ID NO: 183. In some embodiments, the vaccine comprises an AdC7 vector that comprises the nucleic acid molecule that encodes the amino acid sequence of SEQ ID NO: 183.

The vaccine can further comprise a pharmaceutically acceptable carrier or pharmaceutical acceptable excipient. As used herein, "pharmaceutically acceptable carrier" or "pharmaceutical acceptable excipient" includes any material which, when combined with the disclosed fusion proteins, nucleic acids, or vectors, allows the fusion proteins, nucleic acids, or vectors to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Also disclosed herein are non-naturally occurring variants of the HBV polymerase N-terminal domain (PolN) and the HBV polymerase C-terminal domain (PolC). The disclosed HBV polymerase N-terminal domain can comprise the amino acid sequence of SEQ ID NO: 8 or an immunogenic fragment thereof. Exemplary immunogenic fragments of SEQ ID NO: 8 include SEQ ID NOs: 55-113 provided in Table 4, below. In some embodiments, the immunogenic fragment of the HBV PolN comprises the amino acid sequence of SEQ ID NO: 178. In some embodiments, the immunogenic fragment of the HBV PolN comprises the amino acid sequence of SEQ ID NO: 181. The disclosed HBV polymerase C-terminal domain can comprise the amino acid sequence of SEQ ID NO: 10 or an immunogenic fragment thereof. Exemplary immunogenic fragments of SEQ ID NO: 10 include SEQ ID NOs: 114-172 provided in Table 5, below. In some embodiments, the immunogenic fragment of the HBV PolC comprises the amino acid sequence of SEQ ID NO: 179. In some embodiments, the immunogenic fragment of the HBV PolC comprises the amino acid sequence of SEQ ID NO: 182.

Nucleic acid molecules encoding the HBV polymerase N-terminal domain or an immunogenic fragment thereof, or the HBV polymerase C-terminal domain or an immunogenic fragment thereof, are also provided. The nucleic acid molecule can encode the HBV polymerase N-terminal domain comprising the amino acid sequence of SEQ ID NO: 8. In some embodiments, the nucleic acid molecule encoding the HBV polymerase N-terminal domain comprises the nucleotide sequence of SEQ ID NO: 9. The nucleic acid molecules can encode the HBV polymerase N-terminal domain fragments provided in Table 4. The nucleic acid molecule can encode the HBV polymerase C-terminal domain comprising the amino acid sequence of SEQ ID NO: 10. In some embodiments, the nucleic acid molecule encoding the HBV polymerase C-terminal domain comprises the nucleotide sequence of SEQ ID NO: 11. The nucleic acid molecules can encode the HBV polymerase C-terminal domain fragments provided in Table 5. In some embodiments, the nucleic acid molecule encodes the amino acid sequence of SEQ ID NO: 178. In some embodiments, the nucleic acid molecule encodes the amino acid sequence of SEQ ID NO: 181. In some embodiments, the nucleic acid molecule encodes the amino acid sequence of SEQ ID NO: 179. In some embodiments, the nucleic acid molecule encodes the amino acid sequence of SEQ ID NO: 182.

Vectors comprising the nucleic acid molecules encoding the HBV polymerase N-terminal domain or an immunogenic fragment thereof or C-terminal domain or an immunogenic fragment thereof are also provided. Suitable vectors include those described above. In some embodiments, the vector comprises the nucleic acid molecule comprising the nucleotide sequence of SEQ ID NO: 9. In some embodiments, the vector comprises the nucleic acid molecule comprising the nucleotide sequence of SEQ ID NO: 11. In some aspects, the vector is an adenoviral vector. Suitable adenoviral vectors include, for example, an AdC6 vector or AdC7 vector. In some embodiments, the vector is an AdC6 vector comprising the nucleic acid molecule comprising the nucleotide sequence of SEQ ID NO: 9. In some embodiments, the vector is an AdC7 vector comprising the nucleic acid molecule comprising the nucleotide sequence of SEQ ID NO: 9. In some embodiments, the vector is an AdC6 vector comprising the nucleic acid molecule comprising the nucleotide sequence of SEQ ID NO: 11. In some embodiments, the vector is an AdC7 vector comprising the nucleic acid molecule comprising the nucleotide sequence of SEQ ID NO: 11. In some embodiments, the vector comprises the nucleic acid molecule that encodes the amino acid sequence of SEQ ID NO: 178. In some aspects, the vector is an AdC6 vector. In some aspects, the vector is an AdC7 vector. In some embodiments, the vector comprises the nucleic acid molecule that encodes the amino acid sequence of SEQ ID NO: 181. In some aspects, the vector is an AdC6 vector. In some aspects, the vector is an AdC7 vector. In some embodiments, the vector comprises the nucleic acid molecule that encodes the amino acid sequence of SEQ ID NO: 179. In some aspects, the vector is an AdC6 vector. In some aspects, the vector is an AdC7 vector. In some embodiments, the vector comprises the nucleic acid molecule that encodes the amino acid sequence of SEQ ID NO: 182. In some aspects, the vector is an AdC6 vector. In some aspects, the vector is an AdC7 vector.

Vaccines comprising the vectors comprising the nucleic acid molecules encoding the HBV polymerase N-terminal domain or an immunogenic fragment thereof or HBV polymerase C-terminal domain or an immunogenic fragment thereof are also disclosed. In some embodiments, the vaccine comprises a vector comprising the nucleic acid molecule comprising the nucleotide sequence of SEQ ID NO: 9. The vaccine can comprise an AdC6 vector comprising the nucleic acid molecule comprising the nucleotide sequence of SEQ ID NO: 9. The vaccine can comprise an AdC7 vector comprising the nucleic acid molecule comprising the nucleotide sequence of SEQ ID NO: 9. In some embodiments, the vaccine comprises a vector comprising the nucleic acid molecule comprising the nucleotide sequence of SEQ ID NO: 11. The vaccine can comprise an AdC6 vector comprising the nucleic acid molecule comprising the nucleotide sequence of SEQ ID NO: 11. The vaccine can comprise an AdC7 vector comprising the nucleic acid molecule comprising the nucleotide sequence of SEQ ID NO: 11. The vaccine can further comprise a pharmaceutically acceptable carrier or pharmaceutical acceptable excipient as disclosed above. In some embodiments, the vaccine comprises a vector comprising the nucleic acid molecule that encodes the amino acid sequence of SEQ ID NO: 178. In some aspects, the vector is an AdC6 vector. In some aspects, the vector is an AdC7 vector. In some embodiments, the vaccine comprises a vector comprising the nucleic acid molecule that encodes the amino acid sequence of SEQ ID NO: 181. In some aspects, the vector is an AdC6 vector. In some aspects, the vector is an AdC7 vector. In some embodiments, the vaccine comprises a vector comprising the nucleic acid molecule that encodes the amino acid sequence of SEQ ID NO: 179. In some aspects, the vector is an AdC6 vector. In some aspects, the vector is an AdC7 vector. In some embodiments, the vaccine comprises a vector comprising the nucleic acid molecule that encodes the amino acid sequence of SEQ ID NO: 182. In some aspects, the vector is an AdC6 vector. In some aspects, the vector is an AdC7 vector.

Fusion proteins comprising combinations of the disclosed HBV Core protein or immunogenic fragments thereof, the HBV polymerase N-terminal domain or immunogenic fragments thereof, and/or the HBV polymerase C-terminal domain or immunogenic fragments thereof are also provided herein. For example, the fusion protein can comprise:

(1) an HBV Core protein comprising the amino acid sequence of SEQ ID NO: 6 or an immunogenic fragment thereof and an HBV polymerase N-terminal domain comprising the amino acid sequence of SEQ ID NO: 8 or an immunogenic fragment thereof;

(2) one or more immunogenic fragments of the HBV Core protein comprising the amino acid sequence of SEQ ID NO: 6 and one or more immunogenic fragments of the HBV polymerase N-terminal domain comprising the amino acid sequence of SEQ ID NO: 8. For example, one or more of SEQ ID NOs: 20-54 provided in Table 3 (immunogenic fragments of SEQ ID NO: 6) and one or more of SEQ ID NOs: 55-113 provided in Table 4 (immunogenic fragments of SEQ ID NO: 8);

(3) an HBV Core protein comprising the amino acid sequence of SEQ ID NO: 6 or an immunogenic fragment thereof and an HBV polymerase C-terminal domain comprising the amino acid sequence of SEQ ID NO: 10 or an immunogenic fragment thereof;

(4) one or more immunogenic fragments of the HBV Core protein comprising the amino acid sequence of SEQ ID NO: 6 and one or more immunogenic fragments of the HBV polymerase C-terminal domain comprising the amino acid sequence of SEQ ID NO: 10. For example, one or more of SEQ ID NOs: 20-54 provided in Table 3 (immunogenic fragments of SEQ ID NO: 6) and one or more of SEQ ID NOs: 114-172 provided in Table 5 (immunogenic fragments of SEQ ID NO: 10);

(5) an HBV polymerase N-terminal domain comprising the amino acid sequence of SEQ ID NO: 8 or an immunogenic fragment thereof and an HBV polymerase C-terminal domain comprising the amino acid sequence of SEQ ID NO: 10 or an immunogenic fragment thereof;

(6) one or more immunogenic fragments of the HBV polymerase N-terminal domain comprising the amino acid sequence of SEQ ID NO: 8 and one or more immunogenic fragments of the HBV polymerase C-terminal domain comprising the amino acid sequence of SEQ ID NO: 10. For example, one or more of SEQ ID NOs: 55-113 provided in Table 4 (immunogenic fragments of SEQ ID NO: 8) and one or more of SEQ ID NOs: 114-172 provided in Table 5 (immunogenic fragments of SEQ ID NO: 10);

(7) an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof;

(8) one or more immunogenic fragments of the HBV Core protein comprising the amino acid sequence of SEQ ID NO: 6, one or more immunogenic fragments of the HBV polymerase N-terminal domain comprising the amino acid sequence of SEQ ID NO: 8, and one or more immunogenic fragments of the HBV polymerase C-terminal domain comprising the amino acid sequence of SEQ ID NO: 10. For example, one or more of SEQ ID NOs: 20-54 provided in Table 3 (immunogenic fragments of SEQ ID NO: 6), one or more of SEQ ID NOs: 55-113 provided in Table 4 (immunogenic fragments of SEQ ID NO: 8), and one or more of SEQ ID NOs: 114-172 provided in Table 5 (immunogenic fragments of SEQ ID NO: 10);

(9) An HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof; or

(10) An HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof.

The fusion protein can comprise an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof. In some embodiments, the fusion protein comprises the amino acid sequence of SEQ ID NO: 174.

The fusion protein can comprise an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof. In some embodiments, the fusion protein comprises the amino acid sequence of SEQ ID NO: 175.

Also provided herein are fusion proteins comprising a herpes simplex virus (HSV) glycoprotein (gD) sequence and the disclosed HBV Core protein, the HBV polymerase N-terminal domain, the HBV polymerase C-terminal domain, or various combinations thereof.

The HSV gD is a receptor-binding glycoprotein of HSV. The gD ectodomain is organized in two structurally and functionally differentiated regions: the amino-terminus, which includes the signal sequence and receptor-binding sites; and the carboxy-terminus, which includes the pro-fusion domain and the transmembrane domain. gD interacts with the herpesvirus entry mediator (HVEM) receptor and the nectin receptors. Interaction of gD with the receptors results in the down-regulation of the HVEM receptors binding to BTLA or CD160, which are immunoinhibitory molecules that are expressed on T cells. In some embodiments, the disclosed fusion proteins comprising gD and the disclosed HBV Core protein, the HBV polymerase N-terminal domain, the HBV polymerase C-terminal domain (referred to as "gDCore," "gDPolN" or "gDPolC," respectively), or combinations thereof are expected to enhance a subject's immune response against HBV to a greater extent compared to the HBV Core and/or polymerase antigens alone (i.e. without gD).

Suitable HSV gD proteins for use in the disclosed fusion proteins include wild-type or mutant gD that retains the ability to: 1) augment stimulation of a CD8+ T cell response to an antigen; and/or 2) disrupt an HVEM-BTLA pathway activity.

The fusion proteins can comprise the HBV Core protein or an immunogenic fragment thereof, HBV polymerase N-terminal domain or an immunogenic fragment thereof, HBV polymerase C-terminal domain or an immunogenic fragment thereof disclosed herein, or any combination thereof, an N-terminal HSV gD protein sequence, and a C-terminal HSV gD protein sequence. The HBV Core protein, HBV polymerase N-terminal domain, and HBV polymerase C-terminal domain can be those provided in Table 9 or the immunogenic fragments provided in Tables 3-5. The HBV Core protein, HBV polymerase N-terminal domain, HBV polymerase C-terminal domain, or immunogenic fragments thereof can be inserted between the N-terminal HSV gD protein sequence and the C-terminal HSV gD protein sequence. In some aspects, the N-terminal HSV gD protein sequence comprises the amino acid sequence of SEQ ID NO: 12 and the C-terminal HSV gD protein sequence comprises the amino acid sequence of SEQ ID NO: 13. In some embodiments, the N-terminal HSV gD protein sequence comprises amino acid residues 26-269 of SEQ ID NO: 12.

The fusion protein can comprise:
an N-terminal HSV gD sequence or a variant thereof;
an HBV Core protein comprising the amino acid sequence of SEQ ID NO: 6 or an immunogenic fragment thereof; and
a C-terminal HSV gD sequence or a variant thereof.

The immunogenic fragment of the HBV Core protein can comprise any one of SEQ ID NOs: 20-54, 180, or 183.

The fusion protein can comprise:
an N-terminal HSV gD sequence or a variant thereof;
an HBV Core protein comprising the amino acid sequence of SEQ ID NO: 180 or SEQ ID NO: 183; and
a C-terminal HSV gD sequence or a variant thereof.

The fusion protein can comprise:
an N-terminal HSV gD sequence or a variant thereof;
an HBV polymerase N-terminal domain comprising the amino acid sequence of SEQ ID NO: 8 or an immunogenic fragment thereof; and
a C-terminal HSV gD protein sequence or a variant thereof.

The immunogenic fragment of the HBV polymerase N-terminal domain can comprise any one of SEQ ID NOs: 55-113, 178, or 181.

The fusion protein can comprise:
an N-terminal HSV gD sequence or a variant thereof;
an HBV polymerase N-terminal domain comprising the amino acid sequence of SEQ ID NO: 178 or SEQ ID NO: 181; and
a C-terminal HSV gD protein sequence or a variant thereof.

The fusion protein can comprise:
an N-terminal HSV gD sequence or a variant thereof;
an HBV polymerase C-terminal domain comprising the amino acid sequence of SEQ ID NO: 10 or an immunogenic fragment thereof; and
a C-terminal HSV gD protein sequence or a variant thereof.

The immunogenic fragment of the HBV polymerase C-terminal domain can comprise any one of SEQ ID NOs: 114-172, 179, or 182.

The fusion protein can comprise:
an N-terminal HSV gD sequence or a variant thereof;
an HBV polymerase C-terminal domain comprising the amino acid sequence of SEQ ID NO: 179 or SEQ ID NO: 182; and
a C-terminal HSV gD protein sequence or a variant thereof.

The fusion protein can comprise:
an N-terminal HSV gD sequence or a variant thereof;
an HBV sequence comprising:
  (1) an HBV Core protein comprising the amino acid sequence of SEQ ID NO: 6 or an immunogenic fragment thereof and an HBV polymerase N-terminal domain comprising the amino acid sequence of SEQ ID NO: 8 or an immunogenic fragment thereof;
  (2) one or more immunogenic fragments of the HBV Core protein comprising the amino acid sequence of SEQ ID NO: 6 and one or more immunogenic fragments of the HBV polymerase N-terminal domain comprising the amino acid sequence of SEQ ID NO: 8. For example, one or more of SEQ ID NOs: 20-54 provided in Table 3 (immunogenic fragments of SEQ ID NO: 6) and one or more of SEQ ID NOs: 55-113 provided in Table 4 (immunogenic fragments of SEQ ID NO: 8);
  (3) an HBV Core protein comprising the amino acid sequence of SEQ ID NO: 6 or an immunogenic fragment thereof and an HBV polymerase C-terminal domain comprising the amino acid sequence of SEQ ID NO: 10 or an immunogenic fragment thereof;
  (4) one or more immunogenic fragments of the HBV Core protein comprising the amino acid sequence of SEQ ID NO: 6 and one or more immunogenic fragments of the HBV polymerase C-terminal domain comprising the amino acid sequence of SEQ ID NO: 10. For example, one or more of SEQ ID NOs: 20-54 provided in Table 3 (immunogenic fragments of SEQ ID NO: 6) and one or more of SEQ ID NOs: 114-172 provided in Table 5 (immunogenic fragments of SEQ ID NO: 10);
  (5) an HBV polymerase N-terminal domain comprising the amino acid sequence of SEQ ID NO: 8 or an immunogenic fragment thereof and an HBV polymerase C-terminal domain comprising the amino acid sequence of SEQ ID NO: 10 or an immunogenic fragment thereof;

(6) one or more immunogenic fragments of the HBV polymerase N-terminal domain comprising the amino acid sequence of SEQ ID NO: 8 and one or more immunogenic fragments of the HBV polymerase C-terminal domain comprising the amino acid sequence of SEQ ID NO: 10. For example, one or more of SEQ ID NOs: 55-113 provided in Table 4 (immunogenic fragments of SEQ ID NO: 8) and one or more of SEQ ID NOs: 114-172 provided in Table 5 (immunogenic fragments of SEQ ID NO: 10);

(7) an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof; or (8) one or more immunogenic fragments of the HBV Core protein comprising the amino acid sequence of SEQ ID NO: 6, one or more immunogenic fragments of the HBV polymerase N-terminal domain comprising the amino acid sequence of SEQ ID NO: 8, and one or more immunogenic fragments of the HBV polymerase C-terminal domain comprising the amino acid sequence of SEQ ID NO: 10. For example, one or more of SEQ ID NOs: 20-54 provided in Table 3 (immunogenic fragments of SEQ ID NO: 6), one or more of SEQ ID NOs: 55-113 provided in Table 4 (immunogenic fragments of SEQ ID NO: 8), and one or more of SEQ ID NOs: 114-172 provided in Table 5 (immunogenic fragments of SEQ ID NO: 10);

(9) an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof; or

(10) an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof; and a C-terminal HSV gD protein sequence or a variant thereof.

In some embodiments, the N-terminal HSV gD sequence can comprise at least amino acids 1-269 of HSV gD. The N-terminal HSV gD sequence, for example, can comprise the amino acid sequence of SEQ ID NO: 12. In some embodiments, the N-terminal HSV gD sequence comprises amino acid residues 26-269 of SEQ ID NO: 12.

In some embodiments, the C-terminal HSV gD sequence comprises the transmembrane domain of the HSV gD. The C-terminal HSV gD sequence, for example, can comprise the amino acid sequence of SEQ ID NO: 13.

The fusion protein can comprise the amino acid sequence of SEQ ID NO: 14 (corresponding to gDCore) or an immunogenic fragment thereof. The fusion protein can comprise the amino acid sequence of SEQ ID NO: 16 (corresponding to gDPolN) or an immunogenic fragment thereof. The fusion protein can comprise the amino acid sequence of SEQ ID NO: 18 (corresponding to gDPolC) or an immunogenic fragment thereof. In some embodiments, the amino acid sequence of any one of SEQ ID NOs: 14, 16, or 18, or the immunogenic fragment thereof, does not contain the N-terminal 25 amino acid signal peptide.

The fusion protein can comprise the amino acid sequence of SEQ ID NO: 185 (gDHBV2). The fusion protein can comprise the amino acid sequence of SEQ ID NO: 187 (gDHBV3).

Nucleic acid molecules encoding any of the disclosed fusion proteins are also provided. In some embodiments, the nucleic acid molecule comprises the nucleotide sequence of SEQ ID NO: 15 (corresponding to gDCore). In some embodiments, the nucleic acid molecule comprises the nucleotide sequence of SEQ ID NO: 17 (corresponding to gDPolN). In some embodiments, the nucleic acid molecule comprises the nucleotide sequence of SEQ ID NO: 19 (corresponding to gDPolC).

The nucleic acid molecule can comprise the nucleotide sequence of SEQ ID NO: 184 (gDHBV2). The nucleic acid molecule can comprise the nucleotide sequence of SEQ ID NO: 186 (gDHBV3).

Vectors comprising the nucleic acid molecules encoding the fusion proteins are also disclosed. Suitable vectors include those described above including, for example, an adenoviral vector. In some embodiments, the adenoviral vector is an AdC6 vector. In some embodiments, the adenoviral vector is an AdC7 vector. The vector can comprise the nucleotide sequence of SEQ ID NO: 184 (gDHBV2). In some aspects, the vector is an AdC6 vector that comprises the nucleotide sequence of SEQ ID NO: 184 (gDHBV2). In some aspects, the vector is an AdC7 vector that comprises the nucleotide sequence of SEQ ID NO: 184 (gDHBV2). The vector can comprise the nucleotide sequence of SEQ ID NO: 186 (gDHBV3). In some aspects, the vector is an AdC6 vector that comprises the nucleotide sequence of SEQ ID NO: 186 (gDHBV3). In some aspects, the vector is an AdC7 vector that comprises the nucleotide sequence of SEQ ID NO: 186 (gDHBV3).

Vaccines comprising any of the disclosed vectors are also provided. The vaccine can further comprise a pharmaceutically acceptable carrier or pharmaceutical acceptable excipient as disclosed above. The vaccine can comprise a vector comprising the nucleotide sequence of SEQ ID NO: 184 (gDHBV2). In some aspects, the vaccine comprises an AdC6 vector that comprises the nucleotide sequence of SEQ ID NO: 184 (gDHBV2). In some aspects, the vaccine comprises an AdC7 vector that comprises the nucleotide sequence of SEQ ID NO: 184 (gDHBV2). The vaccine can comprise a vector that comprises the nucleotide sequence of SEQ ID NO: 186 (gDHBV3). In some aspects, the vaccine comprises an AdC6 vector that comprises the nucleotide sequence of SEQ ID NO: 186 (gDHBV3). In some aspects, the vaccine comprises an AdC7 vector that comprises the nucleotide sequence of SEQ ID NO: 186 (gDHBV3).

Provided herein are methods of inducing an immune response to HBV in a subject, the methods comprising providing to the subject an effective amount of any of the disclosed fusion proteins, any of the disclosed nucleic acid molecules, any of the disclosed vectors, or any of the disclosed vaccines to thereby induce an immune response to HBV. In some embodiments, the methods comprise providing to the subject an effective amount of any of the disclosed fusion proteins to thereby induce an immune response to HBV. In some embodiments, the methods comprise providing to the subject an effective amount of any of the disclosed nucleic acid molecules to thereby induce an immune response to HBV. In some embodiments, the methods comprise providing to the subject an effective amount of any of the disclosed vectors to thereby induce an immune response to HBV. In some embodiments, the methods comprise providing to the subject an effective amount of any of the disclosed vaccines to thereby induce an immune response to HBV.

The methods can comprise providing to the subject an effective amount of a vaccine comprising an AdC6 vector, wherein the AdC6 vector comprises a fusion protein comprising the amino acid sequence of any one of SEQ ID NOs: 14, 16, or 18, or an immunogenic fragment thereof. In some embodiments, the methods further comprise providing to the subject, subsequent to providing the vaccine comprising the AdC6 vector, a vaccine comprising an AdC7 vector comprising a fusion protein comprising the amino acid sequence of any one of SEQ ID NOs: 14, 16, or 18, or an immunogenic fragment thereof. Such prime-boost methods can comprise:

Providing to the subject a vaccine comprising an AdC6 vector comprising a fusion protein comprising the amino acid sequence of SEQ ID NO: 14, or an immunogenic fragment thereof, and subsequently providing to the subject a vaccine comprising an AdC7 vector comprising a fusion protein comprising the amino acid sequence of SEQ ID NO: 14, or an immunogenic fragment thereof. In some embodiments, the amino acid sequence of SEQ ID NO: 14, or an immunogenic fragment thereof, does not contain the N-terminal 25 amino acid signal peptide;

Providing to the subject a vaccine comprising an AdC6 vector comprising a fusion protein comprising the amino acid sequence of SEQ ID NO: 16, or an immunogenic fragment thereof, and subsequently providing to the subject a vaccine comprising an AdC7 vector comprising a fusion protein comprising the amino acid sequence of SEQ ID NO: 16, or an immunogenic fragment thereof. In some embodiments, the amino acid sequence of SEQ ID NO: 16, or an immunogenic fragment thereof, does not contain the N-terminal 25 amino acid signal peptide; or Providing to the subject a vaccine comprising an AdC6 vector comprising a fusion protein comprising the amino acid sequence of SEQ ID NO: 18, or an immunogenic fragment thereof, and subsequently providing to the subject a vaccine comprising an AdC7 vector comprising a fusion protein comprising the amino acid sequence of SEQ ID NO: 18, or an immunogenic fragment thereof. In some embodiments, the amino acid sequence of SEQ ID NO: 18, or an immunogenic fragment thereof, does not contain the N-terminal 25 amino acid signal peptide.

The methods can comprise providing to the subject an effective amount of a vaccine comprising an AdC7 vector, wherein the AdC7 vector comprises a fusion protein comprising the amino acid sequence of any one of SEQ ID NOs: 14, 16, or 18, or an immunogenic fragment thereof. In some embodiments, the methods further comprise providing to the subject, subsequent to providing the vaccine comprising the AdC7 vector, a vaccine comprising an AdC6 vector comprising a fusion protein comprising the amino acid sequence of any one of SEQ ID NOs: 14, 16, or 18, or an immunogenic fragment thereof. Such prime-boost methods can comprise:

Providing to the subject a vaccine comprising an AdC7 vector comprising a fusion protein comprising the amino acid sequence of SEQ ID NO: 14, or an immunogenic fragment thereof, and subsequently providing to the subject a vaccine comprising an AdC6 vector comprising a fusion protein comprising the amino acid sequence of SEQ ID NO: 14, or an immunogenic fragment thereof. In some embodiments, the amino acid sequence of SEQ ID NO: 14, or an immunogenic fragment thereof, does not contain the N-terminal 25 amino acid signal peptide;

Providing to the subject a vaccine comprising an AdC7 vector comprising a fusion protein comprising the amino acid sequence of SEQ ID NO: 16, or an immunogenic fragment thereof, and subsequently providing to the subject a vaccine comprising an AdC6 vector comprising a fusion protein comprising the amino acid sequence of SEQ ID NO: 16, or an immunogenic fragment thereof. In some embodiments, the amino acid sequence of SEQ ID NO: 16, or an immunogenic fragment thereof, does not contain the N-terminal 25 amino acid signal peptide; or Providing to the subject a vaccine comprising an AdC7 vector comprising a fusion protein comprising the amino acid sequence of SEQ ID NO: 18, or an immunogenic fragment thereof, and subsequently providing to the subject a vaccine comprising an AdC6 vector comprising a fusion protein comprising the amino acid sequence of SEQ ID NO: 18, or an immunogenic fragment thereof. In some embodiments, the amino acid sequence of SEQ ID NO: 18, or an immunogenic fragment thereof, does not contain the N-terminal 25 amino acid signal peptide.

The methods can comprise providing to the subject an effective amount of a vaccine comprising an AdC6 vector, wherein the AdC6 vector comprises a fusion protein comprising the amino acid sequence of SEQ ID NO: 185 or 187, or an immunogenic fragment thereof. In some embodiments, the methods further comprise providing to the subject, subsequent to providing the vaccine comprising the AdC6 vector, a vaccine comprising an AdC7 vector comprising a fusion protein comprising the amino acid sequence of SEQ ID NO: 185 or 187, or an immunogenic fragment thereof. Such prime-boost methods can comprise:

Providing to the subject a vaccine comprising an AdC6 vector comprising a fusion protein comprising the amino acid sequence of SEQ ID NO: 185, or an immunogenic fragment thereof, and subsequently providing to the subject a vaccine comprising an AdC7 vector comprising a fusion protein comprising the amino acid sequence of SEQ ID NO: 185, or an immunogenic fragment thereof. In some embodiments, the amino acid sequence of SEQ ID NO: 185, or an immunogenic fragment thereof, does not contain the N-terminal 25 amino acid signal peptide; or Providing to the subject a vaccine comprising an AdC6 vector comprising a fusion protein comprising the amino acid sequence of SEQ ID NO: 187, or an immunogenic fragment thereof, and subsequently providing to the subject a vaccine comprising an AdC7 vector comprising a fusion protein comprising the amino acid sequence of SEQ ID NO: 187, or an immunogenic fragment thereof. In some embodiments, the amino acid sequence of SEQ ID NO: 187, or an immunogenic fragment thereof, does not contain the N-terminal 25 amino acid signal peptide.

The methods can comprise providing to the subject an effective amount of a vaccine comprising an AdC7 vector, wherein the AdC7 vector comprises a fusion protein comprising the amino acid sequence of SEQ ID NO: 185 or 187, or an immunogenic fragment thereof. In some embodiments, the methods further comprise providing to the subject, subsequent to providing the vaccine comprising the AdC7 vector, a vaccine comprising an AdC6 vector comprising a fusion protein comprising the amino acid sequence of SEQ ID NO: 185 or 187, or an immunogenic fragment thereof. Such prime-boost methods can comprise:

- Providing to the subject a vaccine comprising an AdC7 vector comprising a fusion protein comprising the amino acid sequence of SEQ ID NO: 185, or an immunogenic fragment thereof, and subsequently providing to the subject a vaccine comprising an AdC6 vector comprising a fusion protein comprising the amino acid sequence of SEQ ID NO: 185, or an immunogenic fragment thereof. In some embodiments, the amino acid sequence of SEQ ID NO: 185, or an immunogenic fragment thereof, does not contain the N-terminal 25 amino acid signal peptide; or
- Providing to the subject a vaccine comprising an AdC7 vector comprising a fusion protein comprising the amino acid sequence of SEQ ID NO: 187, or an immunogenic fragment thereof, and subsequently providing to the subject a vaccine comprising an AdC6 vector comprising a fusion protein comprising the amino acid sequence of SEQ ID NO: 187, or an immunogenic fragment thereof. In some embodiments, the amino acid sequence of SEQ ID NO: 187, or an immunogenic fragment thereof, does not contain the N-terminal 25 amino acid signal peptide.

The immune response induced by the disclosed methods include, but is not limited to, T cell responses, B cell responses, or both (i.e. cellular and/or humoral immune responses). The immune response can be a primary immune response or a secondary immune response. The disclosed methods can induce a subject's immune response against HBV to a greater extent compared to the HBV Core or polymerase antigens alone (i.e. without gD).

The disclosed methods can be used for both therapeutic treatment and prophylactic or preventative measures and can reduce the severity and/or frequency of symptoms, eliminate symptoms and/or the underlying cause of the symptoms, reduce the frequency or likelihood of symptoms and/or their underlying cause, and improve or remediate damage caused, directly or indirectly, by HBV. Treatment also includes prolonging survival as compared to the expected survival of a subject not receiving treatment. Subjects to be treated include those that have HBV as well as those prone to have HBV or those in which HBV is to be prevented.

The amount of the disclosed fusion proteins, nucleic acid molecules, vectors, or vaccines needed to thereby induce an immune response to HBV (e.g. a "effective amount") may vary according to factors such as the disease state, age, sex, and weight of the subject, and the ability of the fusion proteins, nucleic acid molecules, vectors, or vaccines to cause a desired response in the subject. Exemplary indicators of an effective amount include, for example, improved well-being of the subject and reduction, elimination, or prevention of HBV symptoms.

Also provided is the use of any of the disclosed fusion proteins, nucleic acid molecules, vectors, or vaccines in the manufacture of a medicament for inducing an immune response to HBV in a subject.

The disclosed fusion proteins, nucleic acid molecules, vectors, or vaccines for use in inducing an immune response to HBV in a subject is also provided.

EXAMPLES

The following examples are provided to further describe some of the embodiments disclosed herein. The examples are intended to illustrate, not to limit, the disclosed embodiments.

Generation of an Epitope-Optimized Core Sequence

Hepatitis B virus (HBV) can be grouped into several genotypes, based on phylogenic clustering. To assist in the development of an antigen insert for a multi-genotype HBV vaccine for patients with chronic infections, a preliminary bioinformatics evaluation of the genes encoding the HBV Core and HBV polymerase across genotypes A, B, C and D was conducted.

The Core amino acid sequences from the four major HBV clades were downloaded as aligned ClustalW sequences from Hepatitis B Virus database (HBVdb) (release version 45.0; last updated on Aug. 2, 2018). The amino acid sequences represented thousands of HBV genomes inputted from users across Europe, as summarized in the following table.

TABLE 1

Number of unique Core genomes analyzed

| Genotype | HBV Gene | Unique Genomes Analyzed |
| --- | --- | --- |
| HBV genotype A | Core | 1,482 |
| HBV genotype B | | 2,800 |
| HBV genotype C | | 2,768 |
| HBV genotype D | | 1,579 |

"Consensus" Core sequences were first identified for each genotype using the Shannon Entropy tool hosted by the Los Alamos National Laboratory (www.hiv.lanl.gov/content/sequence/ENTROPY/entropy), which calculated the variation and frequency at each amino acid position. These calculations were repeated for each genotype, generating four "consensus" Core sequences, one for each genotype analyzed (SEQ ID NOs: 1-4):

```
Genotype A Consensus
                                          (SEQ ID NO: 1)
MDIDPYKEFGATVELLSFLPSDFFPSVRDLLDTAS

ALYREALESPEHCSPHHTALRQAILCWGELMTLAT

WVGNNLeDPASRDLVVNYVNTNMGLKIRQLLWFHI

SCLTFGRETVLEYLVSFGVWIRTPPAYRPPNAPIL

STLPETTVVRRRDRGRSPRRRTPSPRRRRSQSPRR

RRSQSRESQC-
Genotype B Consensus
                                          (SEQ ID NO: 2)
MDIDpYKEFGASvELLSFLPSDFFPSiRDLLDTAs ALYREALESPEHCSPHHTALRQAIlCWGELMNLAT WVGSNLeDPASRELVVsYVNVNMGLKiRQLLWFHI SCLTFGRETVLEYLVSFGVWIRTPpAYRPpNAPIL

STLPETTVVRRRGRSPRRRIPSPRRRRSQSPRRRR

SQSREsQC-
```

-continued

Genotype C Consensus
(SEQ ID NO: 3)
MDID<u>p</u>YKEFGASVELLSFLPSDFFPSIRDLLDTAS

ALYREALESPEHCSPHHTALRQAILCWGELMNLAT

WVGSNLEDPASRELVV<u>s</u>YVNVNMGLK<u>i</u>RQ1LWFHI

SCLTFGRETVLEYLVSFGVWIRTP<u>p</u>AYRPPNAPIL

STLPETTVVRRRGRSPRRRIPSPRRRRSQSPRRRS

QSRESQC -

Genotype D Consensus
(SEQ ID NO: 4)
MDIDPYKEFGA<u>t</u>VELLSFLP<u>s</u>DFFPSVRDLLDTAS ALYR<u>e</u>ALESPEHCSPHHTALRQAILCWG<u>e</u>LM<u>t</u>LAT WVG<u>g</u>NLEDP<u>a</u>SRDLVVSYVNTN<u>m</u>GLKFRQLLWFHI SCLTFGR<u>e</u>TV<u>i</u>EYLVSFGVWIRTP<u>p</u>AYRPPNAPIL STLPETTV<u>v</u>RRRGRSPRRRIPSPRRRTSQSPRRRR SQSRESQC-
(Bold, underlined residues represent amino
acids having less than 90% frequency).

(Bold, underlined residues represent amino acids having less than 90% frequency).

The above "consensus" Core sequences were combined to generate an epitope-optimized Core sequence. Conserved amino acids were identified at each amino acid residue of the Core protein from each genotype (A, B, C and D) and the frequency and variation within a given sample of genotype genomes was determined. To select amino acids at sites of variation, each variation was tested using epitope prediction algorithms across multiple HLA types and the most immunogenic sequence was selected. Specifically:

(1) Each residue across the four genotypes that was identical were maintained. The genome weighted frequency was also calculated to inform the variability with spacer added, where applicable, to align the sequences for diversity.

(2) Residues that were not identical across the four genotypes were identified and the amino acid diversity was recorded (see Table 2). The initial Core sequence (SEQ ID NO: 5) is provided below, with the residues that were not identical across the four genotypes labeled as $X_1$-$X_{11}$ and the residues having less than 90% frequency in bold, underlined font:

MDID<u>P</u>YKEFGA$X_1$VELLSFLPSDFFPS$X_2$DLLDTASALYREALE

SPEHCSPHHTALRQAILCWGELM$X_3$LATWVG$X_4$NL<u>e</u>DPASR$X_5$L

VV$X_6$YVN$X_7$NMGLK$X_8$RQLLWFHISCLTFGRETV$X_9$EYLVSFGV

WIRTP<u>P</u>AYRP<u>P</u>NAPILSTLPETTVVRRR$X_{10}$$X_{11}$GRSPRRRITS

PRRRRSQSPRRRRSQSRESQC

TABLE 2

| Residues that were not identical across the four genotypes | | | | | | | | | | | |
|---|---|---|---|---|---|---|---|---|---|---|---|
| Residue # | $X_1$ | $X_2$ | $X_3$ | $X_4$ | $X_5$ | $X_6$ | $X_7$ | $X_8$ | $X_9$ | $X_{10}$ | $X_{11}$ |
| Genotype A Consensus | T | V | T | N | D | N | T | I | L | D | R |
| A - Consensus Frequency | 95.4% | 98.2% | 96.0% | 94.0% | 99.5% | 98.9% | 98.3% | 98.8% | 98.2% | 95.8% | 99.5% |
| Genotype B Consensus | S | i | N | S | E | s | V | i | L | — | — |
| B - Consensus Frequency | 97.1% | 89.7% | 93.5% | 90.1% | 91.5% | 75.2% | 93.6% | 80.1% | 99.4% | — | — |
| Genotype C Consensus | S | I | N | S | E | s | V | i | L | — | — |
| C - Consensus Frequency | 99.4% | 90.3% | 97.3% | 96.3% | 97.0% | 83.7% | 97.8% | 78.7% | 98.8% | — | — |
| Genotype D Consensus | t | V | t | g | D | S | T | F | i | — | — |
| D - Consensus Frequency | 75.7% | 97.0% | 87.5% | 58.7% | 98.4% | 93.7% | 96.5% | 99.1% | 77.8% | — | — |

(3) To determine the final amino acid at these positions, epitope prediction algorithms were used to select the appropriate amino acid. For amino acids that showed variability between the genotypes, amino acids that were present in 3 of the genotypes were selected or an MHC class I epitope prediction software was used to select the most immunogenic amino acids. This approach maximized the potential immunogenicity across the greatest number of HLA types. The epitope-optimized Core sequence across all genotypes and within genotypes is shown below (SEQ ID NO: 6):

```
DIDPYKEFGATVELLSFLPSDFFPSIRDLLDTASALYREALESP

EHCSPHHTALRQAILCWGELMTLATWVGSNLEDPASRELVVSYV

NVNMGLKIRQLLWFHISCLTFGRETVIEYLVSFGVWIRTPPAYR

PPNAPILSTLPETTVVRRRDRGRSPRRRTPSPRRRRSQSPRRRR

SQSRESQC
```

The average variation at each site across all genomes, weighted by the number of Glade-specific genomes analyzed, was calculated and showed areas and residues of higher and greater conservation. FIG. 1.

Figure 3A:
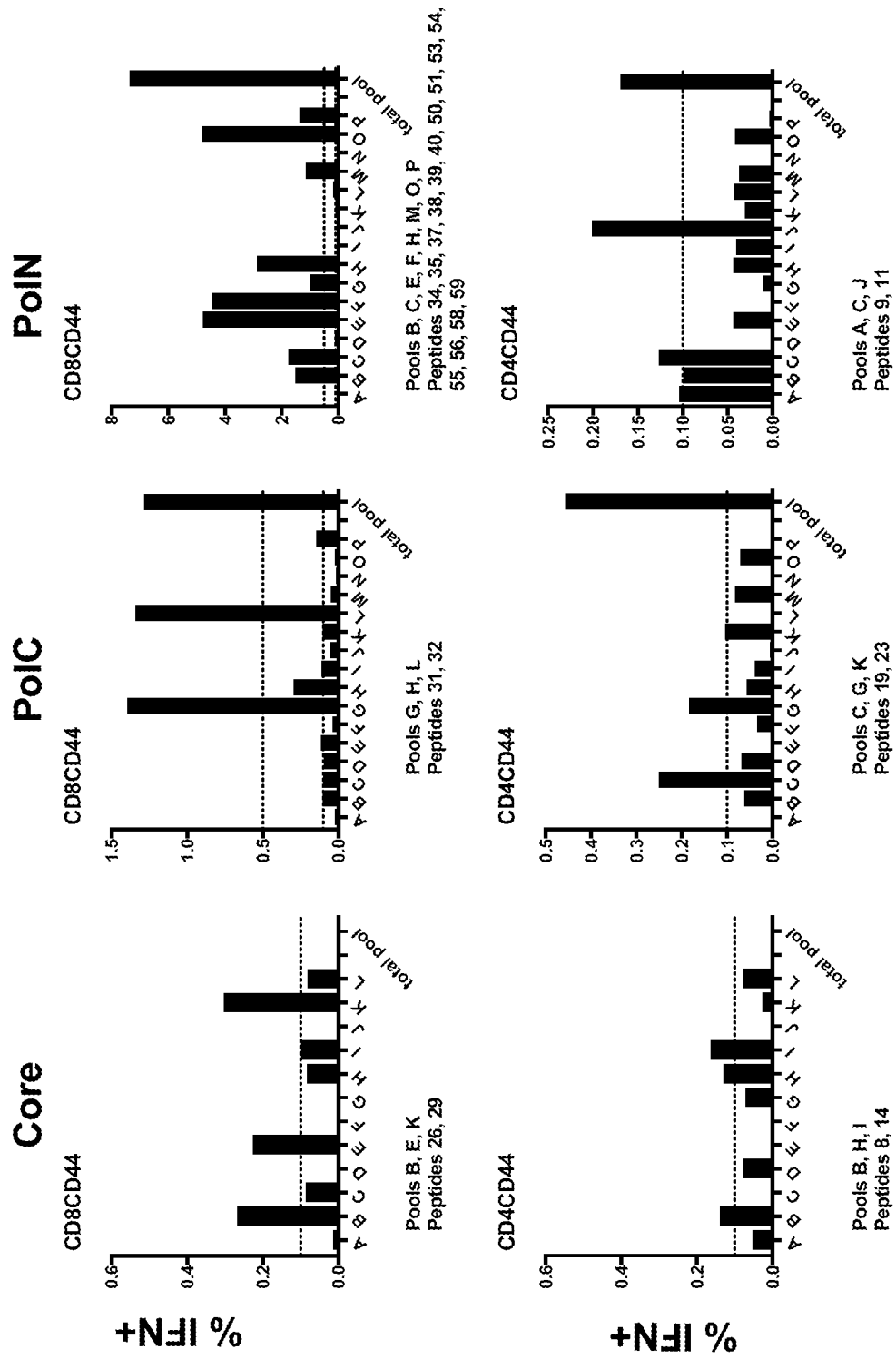
FIG. 3A, FIG. 3B, and FIG. 3C illustrate T cell frequencies in different mouse strains (A: C57Bl/6 mice; B: BALB/c mice; C: HLA-A2 transgenic (tg) mice) to pools of peptides representing the indicated HBV sequence. Results were obtained with splenocytes harvested 4 weeks after immunization and tested by ICS for IFN-γ. Peptides were arranged in matrices so that recognition of 2 pools identified one peptide. The graphs show responses to the different pools; responses to a pool containing all peptides are shown to the right. Background frequencies obtained without the peptides were subtracted. Pools that were deemed to elicit a response and peptides identified in response to different pools are listed at the bottom of each figure. CD8+ T cell and CD4+ T cell responses are shown for BALB/c mice; CD8+ T cell responses are shown for HLA-A2 tg mice, which carry a human MHC class I molecule but mouse MHC class II molecules. T cells were gated on activated CD44+ cells. Each consecutively numbered "peptide" consists of 15 amino acids beginning on the $1^{st}$, $6^{th}$, $11^{th}$, etc. amino acid of the Core, PolN, or PolC sequence. Thus, for example, peptide 1 of Core corresponds to amino acids 1-15 of SEQ ID NO: 6 (i.e. the epitope-optimized Core amino acid sequence), peptide 2 of Core corresponds to amino acids 6-20 of SEQ ID NO: 6, peptide 3 of Core corresponds to amino acids 11-25 of SEQ ID NO: 6, etc. Similarly, peptide 1 of PolN corresponds to amino acids 1-15 of SEQ ID NO: 8 (i.e. the epitope-optimized PolN amino acid sequence), peptide 2 of PolN corresponds to amino acids 6-20 of SEQ ID NO: 8, peptide 3 of PolN corresponds to amino acids 11-25 of SEQ ID NO: 8, etc. Likewise, peptide 1 of PolC corresponds to amino acids 1-15 of SEQ ID NO: 10 (i.e. the epitope-optimized PolC amino acid sequence), peptide 2 of PolC corresponds to amino acids 6-20 of SEQ ID NO: 10, peptide 3 of PolC corresponds to amino acids 11-25 of SEQ ID NO: 10, etc.
Figure 3B:
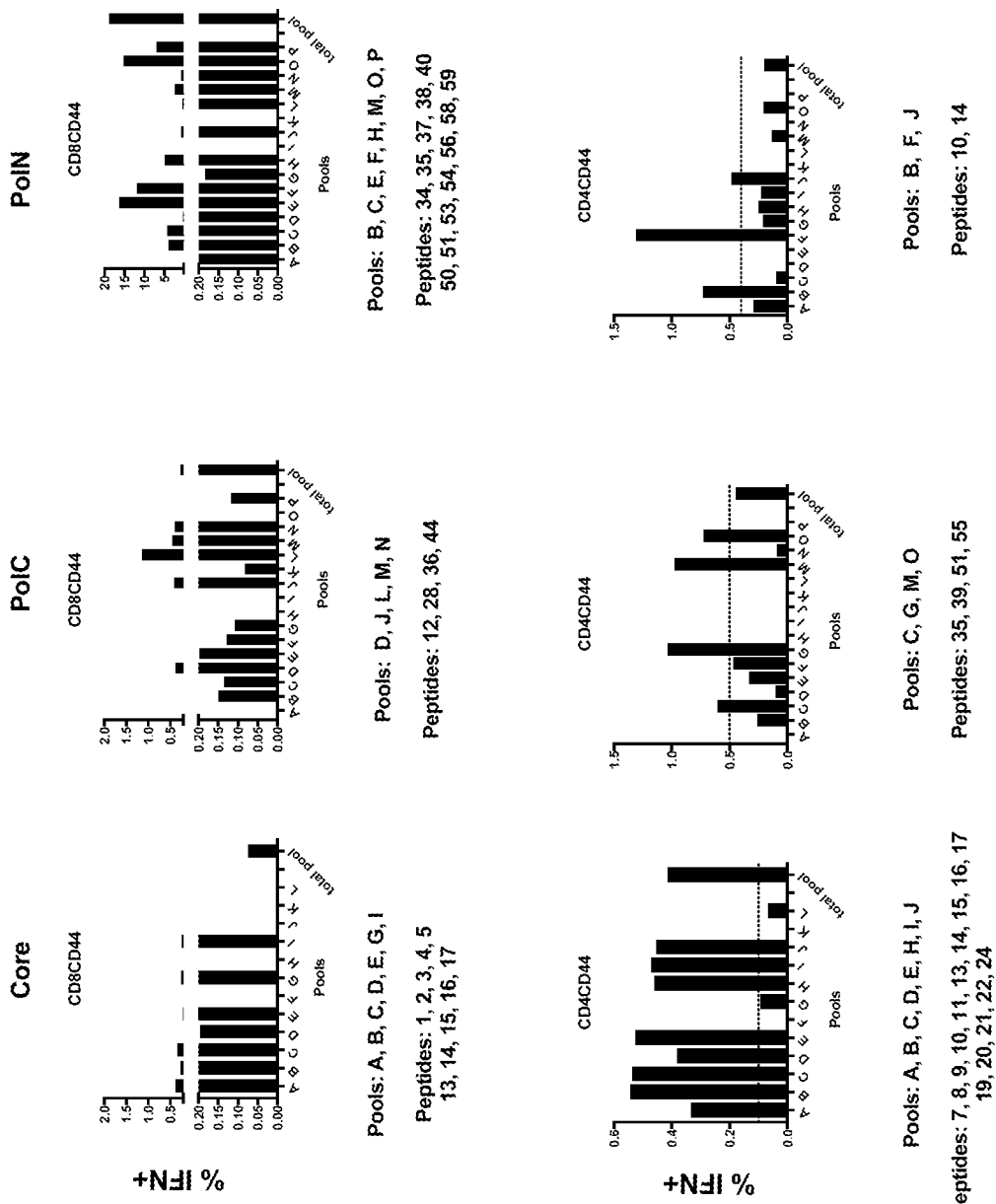
Figure 3C:
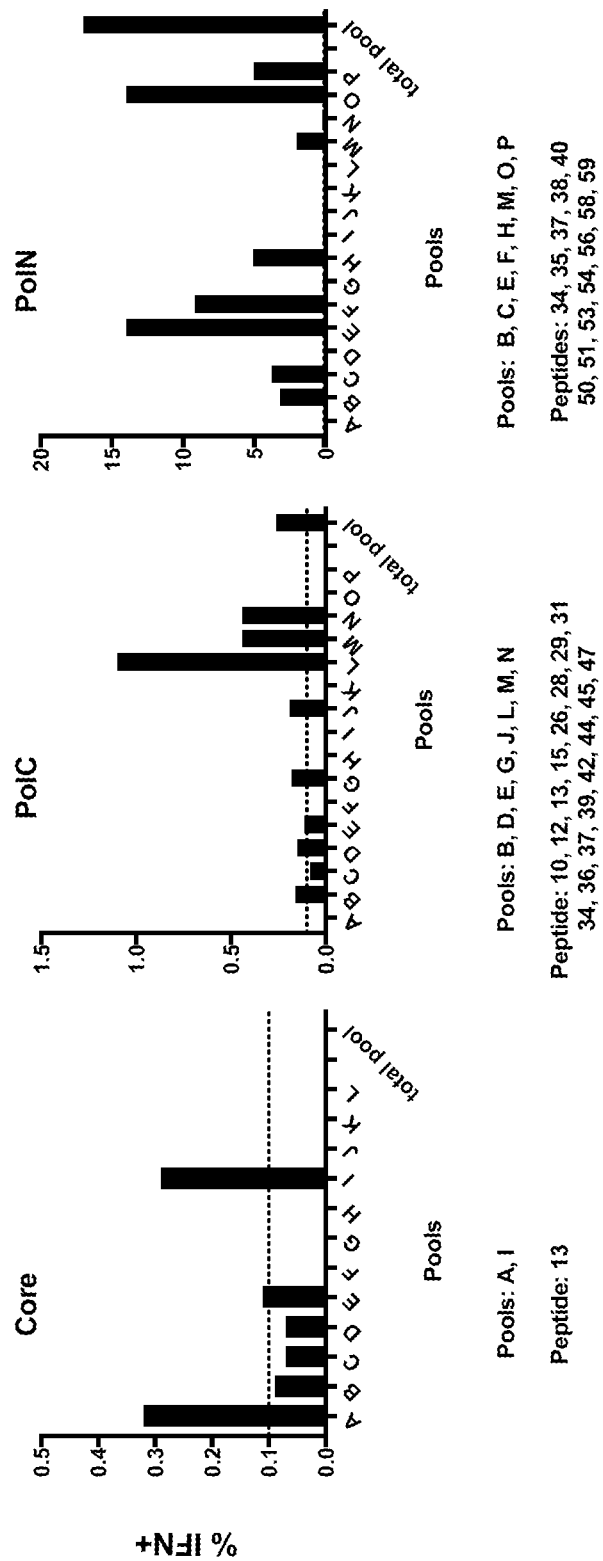

Generation of Epitope-Optimized Polymerase Sequences

An epitope-optimized polymerase sequence was generated from the four major HBV clades as discussed above for the Core sequence. Because the polymerase is long, two fragments—an N-terminal fragment (from which a highly variable segment between the genotypes was removed) and a C-terminal fragment—were generated. Both fragments are approximately 300 amino acids in length. The epitope-optimized polymerase amino acid sequences are shown below and in Table 9:

```
Epitope-optimized HBV polymerase N-terminal
amino acid sequence
(SEQ ID NO: 8):
PLSYQHFRKLLLLDDEEAGPLEEELPRLADEGLNRRVAEDL

NLGNLNVSIPWTHKVGNFTGLYSSTVPVFNPEWQTPSFPK

IHLQEDIVDRCKQFVGPLTVNEKRRLKLIMPARFYPNVTK

YLPLDKGIKPYYPEHAVNHYFQTRHYLHTLWKAGILYKRE

TTRSASFCGSPYSWEQELQHGSCWWLQFRNSKPCSEYCLT

HLVNLLEDWGPCDEHGEHHIRIPRTPARVTGGVFLVDKNP

HNTAESRLVVDFSQFSRGITRVSWPKFAVPNLQSLTNLLS

SNLSWLSLDVSAAFYHIPLHPAAMP
```

```
Epitope-optimized HBV polymerase C-terminal
amino acid sequence
(SEQ ID NO: 10):
HLLVGSSGLSRYVARLSSNSRIINHQHGTMQNLHDSCSRN

LYVSLLLLYKTFGRKLHLYSHPIILKTKRWGYSLNFMGYV

IGSWGSLPQDHIIQKIKECFRKLPVNRPIDWKVCQRIVGL

LGFAAPFTQCGYPALMPLYACIQSKQAFTFSPTYKAFLSK

QYLNLYPVARQRPGLCQVFADATPTGWGLAMGHQRMRGTF
```

-continued

```
VAPLP1HTAELLAACFARSRSGAKILGTDNSVVLSRKYTS

FPWLLGCAANWILRGTSFVYVPSALNPADDPSRGRLGLSR

PLLRLPFRPTTGRTSLYAVSPSV
```

Generation of AdC6 and AdC7 Vectors Expressing the Epitope-Optimized Core and Polymerase Sequences The genes encoding the epitope-optimized Core or polymerase amino acid sequences were cloned into transfer vectors that contained the herpes simplex virus (HSV) glycoprotein D (gD) sequence under the control of the CMV promoter. The genes were then cloned into the El-deleted, E3 ORF 3, 4, 5, 6, and 7-deleted replication deficient adenoviral vector (as described in PCT/US2017/043315) to generate the following vectors:

AdC6 containing the epitope-optimized Core sequence fused to gD (AdC6-gDCore);

AdC6 containing the epitope-optimized polymerase N-terminal sequence fused to gD (AdC6-gDPolN);

AdC6 containing the epitope-optimized polymerase C-terminal sequence fused to gD (AdC6-gDPolC);

AdC7 containing the epitope-optimized Core sequence fused to gD (AdC7-gDCore);

AdC7 containing the epitope-optimized polymerase N-terminal sequence fused to gD (AdC7-gDPolN); and AdC7 containing the epitope-optimized polymerase C-terminal sequence fused to gD (AdC7-gDPolC).

Correct clones were identified by restriction enzyme digest and the cloning sites were sequenced. Vectors were rescued and expanded in HEK 293 cells, purified by cesium chloride (CsC1) gradient centrifugation, and the vector concentration (vp) was determined by spectrophotometry. Vectors were titrated for infectious units upon their expansion in serial dilutions in HEK 293 cells, followed by isolation and reverse transcription of RNA and a nested hexon-specific PCR reaction. Genetic integrity of the vectors was determined by restriction enzyme digest followed by gel electrophoresis of purified viral DNA. Protein expression was determined by Western blotting using gD-specific antibodies. Genetic stability was determined by serial passages (12-15) of the vectors in HEK 293 cells followed by restriction enzyme digest of purified viral DNA and gel electrophoresis.

Testing of Immunogenicity of Vaccines in Mice

C57Bl/6, BALB/c, and HLA-A2 tg mice (n=5 per group) were injected with various concentrations of each of the above vectors. Naïve mice served as controls. Mice were bled at different times after the injection and frequencies of insert-specific CD8+ and CD4+ T cells were determined by intracellular cytokine staining (ICS) for IFN-γ. Two months after the first injection, AdC6-immune mice were boosted with the heterologous vector (AdC7) expressing the same insert. Frequencies of HBV-specific T cells were tested again. Results after priming are shown in FIG. 2A-2F and FIG. 3A (C57Bl/6 mice), FIG. 3B (BALB/c mice) and FIG. 3C (HLA-A2 mice). Results after the boost are shown in FIGS. 4A-4C and 5A-5B.

C57Bl/6 mice showed a very robust CD8+ T cell response to the epitope-optimized polymerase N-terminal sequence and lower responses to the epitope-optimized polymerase C-terminal sequence and the epitope-optimized Core sequence, while CD4+ responses were better against the epitope-optimized Core sequence and the epitope-optimized polymerase C-terminal sequence (FIG. 2A-FIG. 2F). Epitope mapping in C57Bl/6 mice showed higher and broader responses to PolN than PolC (FIG. 3A). Within PolN a total of 14 peptides were recognized by CD8+ T cells while within PolC only two adjacent peptides, which most likely reflect one epitope, were recognized. CD4+ T cells failed to respond to PolN or PolC. This pattern was largely mirrored in BALB/c mice, where CD8+ T cell responses were highest against PolN with recognition of 12 peptides followed by PolC with recognition of 4 peptides (FIG. 3B). Responses to Core were low but surprisingly broad with recognition of 10 peptides (FIG. 3B). BALB/c CD4+ T cells responded best to Core with recognition of 15 peptides with lower recognition of PolC (4 peptides) or PolN (2 peptides). CD8+ T cell responses were also tested in HLA-A2 tg mice where PolN again triggered the highest response involving 12 peptides (FIG. 3C). The response to PolC was lower but broader (16 peptides) while only one peptide of Core was detected (FIG. 3C). The sequences of the peptides tested in the priming experiments are provided in Table 3 (Core peptides), Table 4 (PolN peptides), and Table 5 (PolC peptides). The peptide composition of the peptide pools from the priming experiments are provided in Tables 6-8. Overall these data show that the inserts elicited detectable T cell responses that in most cases were directed against multiple epitopes within each sequence.

TABLE 3

Epitope-Optimized Core Peptides

| Peptide | Amino Acid Sequence | SEQ ID NO: | Prime |
|---|---|---|---|
| 1 | DIDPYKEFGATVELL | 20 | CD8 (B/c) |
| 2 | KEFGATVELLSFLPS | 21 | CD8 (B/c) |
| 3 | TVELLSFLPSDFFPS | 22 | CD8 (B/c) |
| 4 | SFLPSDFFPSIRDLL | 23 | CD8 (B/c) |
| 5 | DFFPSIRDLLDTASA | 24 | CD8 (B/c) |
| 6 | IRDLLDTASALYREA | 25 | |
| 7 | DTASALYREALESPE | 26 | CD4 (B/c) |
| 8 | LYREALESPEHCSPH | 27 | CD4 (B1/6); CD4 (B/c) |
| 9 | LESPEHCSPHHTALR | 28 | CD4 (B/c) |
| 10 | HCSPHHTALRQAILC | 29 | CD4 (B/c) |
| 11 | HTALRQAILCWGELM | 30 | CD4 (B/c) |
| 12 | QAILCWGELMTLATW | 31 | |
| 13 | WGELMTLATWVGSNL | 32 | CD8 (B/c); CD4 (B/c); CD8 (HLA) |
| 14 | TLATWVGSNLEDPAS | 33 | CD8 (B/c); CD4 (B/c) |
| 15 | VGSNLEDPASRELVV | 34 | CD8 (B/c); CD4 (B/c) |
| 16 | EDPASRELVVSYVNV | 35 | CD8 (B/c); CD4 (B/c) |
| 17 | RELVVSYVNVNMGLK | 36 | CD8 (B/c); CD4 (B/c) |
| 18 | SYVNVNMGLKIRQLL | 37 | |

TABLE 3-continued

Epitope-Optimized Core Peptides

| Peptide | Amino Acid Sequence | SEQ ID NO: | Prime |
|---|---|---|---|
| 19 | NMGLKIRQLLWFHIS | 38 | CD4 (B/c) |
| 20 | IRQLLWFHISCLTFG | 39 | CD4 (B/c) |
| 21 | WFHISCLTFGRETVI | 40 | CD4 (B/c) |
| 22 | CLTFGRETVIEYLVS | 41 | CD4 (B/c) |
| 23 | RETVIEYLVSFGVWI | 42 | CD4 (B/c) |
| 24 | EYLVSFGVWIRTPPA | 43 | |
| 25 | FGVWIRTPPAYRPPN | 44 | |
| 26 | RTPPAYRPPNAPILS | 45 | CD8 (B1/6) |
| 27 | YRPPNAPILSTLPET | 46 | |
| 28 | APILSTLPETTVVRR | 47 | CD4 (B1/6) |
| 29 | TLPETTVVRRRDRGR | 48 | CD8 (B1/6) |
| 30 | TVVRRRDRGRSPRRR | 49 | |
| 31 | RDRGRSPRRRTPSPR | 50 | |
| 32 | SPRRRTPSPRRRRSQ | 51 | |
| 33 | TPSPRRRRSQSPRRR | 52 | |
| 34 | RRRSQSPRRRRSQSR | 53 | |
| 35 | SPRRRRSQSRESQC | 54 | |

B/c = BALB/c; B1/6 = C57B1/6; HLA = HLA-A2

TABLE 4

Epitope-Optimized PoIN Peptides

| Peptide | Amino Acid Sequence | SEQ ID NO: | Prime |
|---|---|---|---|
| 1 | PLSYQHFRKLLLLDE | 55 | |
| 2 | HFRKLLLLDEEAGPL | 56 | |
| 3 | LLLDEEAGPLEEELP | 57 | |
| 4 | EAGPLEEELPRLADE | 58 | |
| 5 | EEELPRLADEGLNRR | 59 | |
| 6 | RLADEGLNRRVAEDL | 60 | |
| 7 | GLNRRVAEDLNLGNL | 61 | |
| 8 | VAEDLNLGNLNVSIP | 62 | |
| 9 | NLGNLNVSIPWTHKV | 63 | |
| 10 | NVSIPWTHKVGNFTG | 64 | CD4 (B/c) |
| 11 | WTHKVGNFTGLYSST | 65 | |
| 12 | GNFTGLYSSTVPVFN | 66 | |
| 13 | LYS STVPVFNPEWQT | 67 | |
| 14 | VPVFNPEWQTPSFPK | 68 | CD4 (B/c) |
| 15 | PEWQTPSFPKIHKLQE | 69 | |

TABLE 4-continued

Epitope-Optimized PoIN Peptides

| Peptide | Amino Acid Sequence | SEQ ID NO: | Prime |
|---|---|---|---|
| 16 | PSFPKIHKLQEDIVDR | 70 | |
| 17 | IHKLQEDIVDRCKQFV | 71 | |
| 18 | EDIVDRCKQFVGPLTV | 72 | |
| 19 | RCKQFVGPLTVNEKRR | 73 | |
| 20 | VGPLTVNEKRRLKLIM | 74 | |
| 21 | VNEKRRLKLIMPARFY | 75 | |
| 22 | RLKLIMPARFYPNVTK | 76 | |
| 23 | MPARFYPNVTKYLPLD | 77 | |
| 24 | YPNVTKYLPLDKGIKP | 78 | |
| 25 | KYLPLDKGIKPYYPEH | 79 | |
| 26 | DKGIKPYYPEHAVNHY | 80 | |
| 27 | PYYPEHAVNHYFQTRH | 81 | |
| 28 | HAVNHYFQTRHYLHTL | 82 | |
| 29 | YFQTRHYLHTLWKAGI | 83 | |
| 30 | HYLHTLWKAGILYKRE | 84 | |
| 31 | LWKAGILYKRETTRSA | 85 | |
| 32 | ILYKRETTRSASFCGS | 86 | |
| 33 | ETTRSASFCGSPYSWE | 87 | |
| 34 | ASFCGSPYSWEQELQH | 88 | CD8 (B1/6); CD8 (B/c); CD8 (HLA) |
| 35 | SPYSWEQELQHGSCWW | 89 | CD8 (B1/6); CD8 (B/c); CD8 (HLA) |
| 36 | EQELQHGSCWWLQFRN | 90 | |
| 37 | HGSCWWLQFRNSKPCS | 91 | CD8 (B1/6); CD8 (B/c); CD8 (HLA) |
| 38 | WLQFRNSKPCSEYCLT | 92 | CD8 (B1/6); CD8 (B/c); CD8 (HLA) |
| 39 | NSKPCSEYCLTHLVNL | 93 | CD8 (B1/6) |
| 40 | SEYCLTHLVNLLEDWG | 94 | CD8 (B1/6); CD8 (B/c); CD8 (HLA) |
| 41 | THLVNLLEDWGPCDEH | 95 | |
| 42 | LLEDWGPCDEHGEHHI | 96 | |
| 43 | GPCDEHGEHHIRIPRT | 97 | |
| 44 | HGEHHIRIPRTPARVT | 98 | |
| 45 | IRIPRTPARVTGGVFL | 99 | |
| 46 | TPARVTGGVFLVDKNP | 100 | |
| 47 | TGGVFLVDKNPHNTAE | 101 | |
| 48 | LVDKNPHNTAESRLVV | 102 | |
| 49 | PHNTAESRLVVDFSQF | 103 | |
| 50 | ESRLVVDFSQFSRGIT | 104 | CD8 (B1/6); CD8 (B/c); CD8 (HLA) |
| 51 | VDFSQFSRGITRVSWP | 105 | CD8 (B1/6); CD8 (B/c); CD8 (HLA) |
| 52 | FSRGITRVSWPKFAVP | 106 | |
| 53 | TRVSWPKFAVPNLQSL | 107 | CD8 (B1/6); CD8 (B/c); CD8 HLA) |
| 54 | PKFAVPNLQSLTNLLS | 108 | CD8 (B1/6); CD8 (B/c); CD8 (HLA) |
| 55 | PNLQSLTNLLSSNLSW | 109 | CD8 (B1/6) |
| 56 | LTNLLSSNLSWLSLDV | 110 | CD8 (B1/6); CD8 (B/c); CD8 (HLA) |
| 57 | SSNLSWLSLDVSAAFY | 111 | |
| 58 | WLSLDVSAAFYHIPLH | 112 | CD8 (B1/6); CD8 (B/c); CD8 (HLA) |
| 59 | VSAAFYHIPLHPAAMP | 113 | CD8 (B1/6); CD8 (B/c); CD8 (HLA) |

B/c = BALB/c; B1/6 = C57B1/6; HLA = HLA-A2

TABLE 5

Epitope-Optimized PoIC Peptides

| Peptide | Amino Acid Sequence | SEQ ID NO: | Prime |
|---|---|---|---|
| 1 | HLLVGSSGLSRYVAR | 114 | |
| 2 | SSGLSRYVARLSSNSR | 115 | |
| 3 | RYVARLSSNSRIINHQ | 116 | |
| 4 | LSSNSRIINHQHGTMQ | 117 | |
| 5 | RIINHQHGTMQNLHDS | 118 | |
| 6 | QHGTMQNLHDSCSRNL | 119 | |
| 7 | QNLHDSCSRNLYVSLL | 120 | |
| 8 | SCSRNLYVSLLLLYKT | 121 | |
| 9 | LYVSLLLLYKTFGRKL | 122 | |
| 10 | LLLYKTFGRKLHLYSH | 123 | CD8 (HLA) |
| 11 | TFGRKLHLYSHPIILK | 124 | |
| 12 | LHLYSHPIILKTKRWG | 125 | CD8 (B/c); CD8 (HLA) |
| 13 | HPIILKTKRWGYSLNF | 126 | CD8 (HLA) |

TABLE 5-continued

Epitope-Optimized PolC Peptides

| Peptide | Amino Acid Sequence | SEQ ID NO: | Prime |
|---|---|---|---|
| 14 | KTKRWGYSLNFMGYVI | 127 | |
| 15 | GYSLNFMGYVIGSWGS | 128 | CD8 (HLA) |
| 16 | FMGYVIGSWGSLPQDH | 129 | |
| 17 | IGSWGSLPQDHIIQKI | 130 | |
| 18 | SLPQDHIIQKIKECFR | 131 | |
| 19 | HIIQKIKECFRKLPVN | 132 | |
| 20 | IKECFRKLPVNRPIDW | 133 | |
| 21 | RKLPVNRPIDWKVCQR | 134 | |
| 22 | NRPIDWKVCQRIVGLL | 135 | |
| 23 | WKVCQRIVGLLGFAAP | 136 | |
| 24 | RIVGLLGFAAPFTQCG | 137 | |
| 25 | LGFAAPFTQCGYPALM | 138 | |
| 26 | PFTQCGYPALMPLYAC | 139 | CD8 (HLA) |
| 27 | GYPALMPLYACIQSKQ | 140 | |
| 28 | MPLYACIQSKQAFTFS | 141 | CD8 (B/c); CD8 (HLA) |
| 29 | CIQSKQAFTFSPTYKA | 142 | CD8 (HLA) |
| 30 | QAFTFSPTYKAFLSKQ | 143 | |
| 31 | SPTYKAFLSKQYLNLY | 144 | CD8 (Bl/6); CD8 (HLA) |
| 32 | AFLSKQYLNLYPVARQ | 145 | CD8 (Bl/6) |
| 33 | QYLNLYPVARQRPGLC | 146 | |
| 34 | YPVARQRPGLCQVFAD | 147 | CD8 (HLA) |
| 35 | QRPGLCQVFADATPTG | 148 | CD4 (B/c) |
| 36 | CQVFADATPTGWGLAM | 149 | CD8 (B/c); CD8 (HLA) |
| 37 | DATPTGWGLAMGHQRM | 150 | CD8 (HLA) |
| 38 | GWGLAMGHQRMRGTFV | 151 | |
| 39 | MGHQRMRGTFVAPLPI | 152 | CD4 (B/c); CD8 (HLA) |
| 40 | MRGTFVAPLPIHTAEL | 153 | |
| 41 | VAPLPIHTAELLAACF | 154 | |
| 42 | IHTAELLAACFARSRS | 155 | CD8 (HLA) |
| 43 | LLAACFARSRSGAKIL | 156 | |
| 44 | FARSRSGAKILGTDNS | 157 | CD8 (B/c); CD8 (HLA) |
| 45 | SGAKILGTDNSVVLSR | 158 | CD8 (HLA) |
| 46 | LGTDNSVVLSRKYTSF | 159 | |
| 47 | SVVLSRKYTSFPWLLG | 160 | |
| 48 | RKYTSFPWLLGCAANW | 161 | |
| 49 | FPWLLGCAANWILRGT | 162 | |
| 50 | GCAANWILRGTSFVYV | 163 | |
| 51 | WILRGTSFVYVPSALN | 164 | CD4 (B/c) |
| 52 | TSFVYVPSALNPADDP | 165 | |
| 53 | VPSALNPADDPSRGRL | 166 | |
| 54 | NPADDPSRGRLGLSRP | 167 | |
| 55 | PSRGRLGLSRPLLRLP | 168 | CD4 (B/c) |
| 56 | LGLSRPLLRLPFRPTT | 169 | |
| 57 | PLLRLPFRPTTGRTSL | 170 | |
| 58 | PFRPTTGRTSLYAVSP | 171 | |
| 59 | TGRTSLYAVSPSV | 172 | |

B/c = BALB/c; Bl/6 = C57Bl/6; HLA = HLA-A2

TABLE 6

Epitope-Optimized Core Pool

| Core Matrix | A | B | C | D | E | F |
|---|---|---|---|---|---|---|
| G | 1 | 2 | 3 | 4 | 5 | 6 |
| H | 7 | 8 | 9 | 10 | 11 | 12 |
| I | 13 | 14 | 15 | 16 | 17 | 18 |
| J | 19 | 20 | 21 | 22 | 23 | 24 |
| K | 25 | 26 | 27 | 28 | 29 | 30 |
| L | 31 | 32 | 33 | 34 | 35 | |

TABLE 7

Epitope-Optimized PolN Pool

| Pol N Matrix | A | B | C | D | E | F | G | H |
|---|---|---|---|---|---|---|---|---|
| I | 1 | 2 | 3 | 4 | 5 | 6 | 7 | 8 |
| J | 9 | 10 | 11 | 12 | 13 | 14 | 15 | 16 |
| K | 17 | 18 | 19 | 20 | 21 | 22 | 23 | 24 |
| L | 25 | 26 | 27 | 28 | 29 | 30 | 31 | 32 |
| M | 33 | 34 | 35 | 36 | 37 | 38 | 39 | 40 |
| N | 41 | 42 | 43 | 44 | 45 | 46 | 47 | 48 |
| O | 49 | 50 | 51 | 52 | 53 | 54 | 55 | 56 |
| P | 57 | 58 | 59 | | | | | |

TABLE 8

Epitope-Optimized PolC Pool

| Pol C Matrix | A | B | C | D | E | F | G | H |
|---|---|---|---|---|---|---|---|---|
| I | 1 | 2 | 3 | 4 | 5 | 6 | 7 | 8 |
| J | 9 | 10 | 11 | 12 | 13 | 14 | 15 | 16 |
| K | 17 | 18 | 19 | 20 | 21 | 22 | 23 | 24 |
| L | 25 | 26 | 27 | 28 | 29 | 30 | 31 | 32 |
| M | 33 | 34 | 35 | 36 | 37 | 38 | 39 | 40 |
| N | 41 | 42 | 43 | 44 | 45 | 46 | 47 | 48 |
| O | 49 | 50 | 51 | 52 | 53 | 54 | 55 | 56 |
| P | 57 | 58 | | | | | | |

Figure 4A:
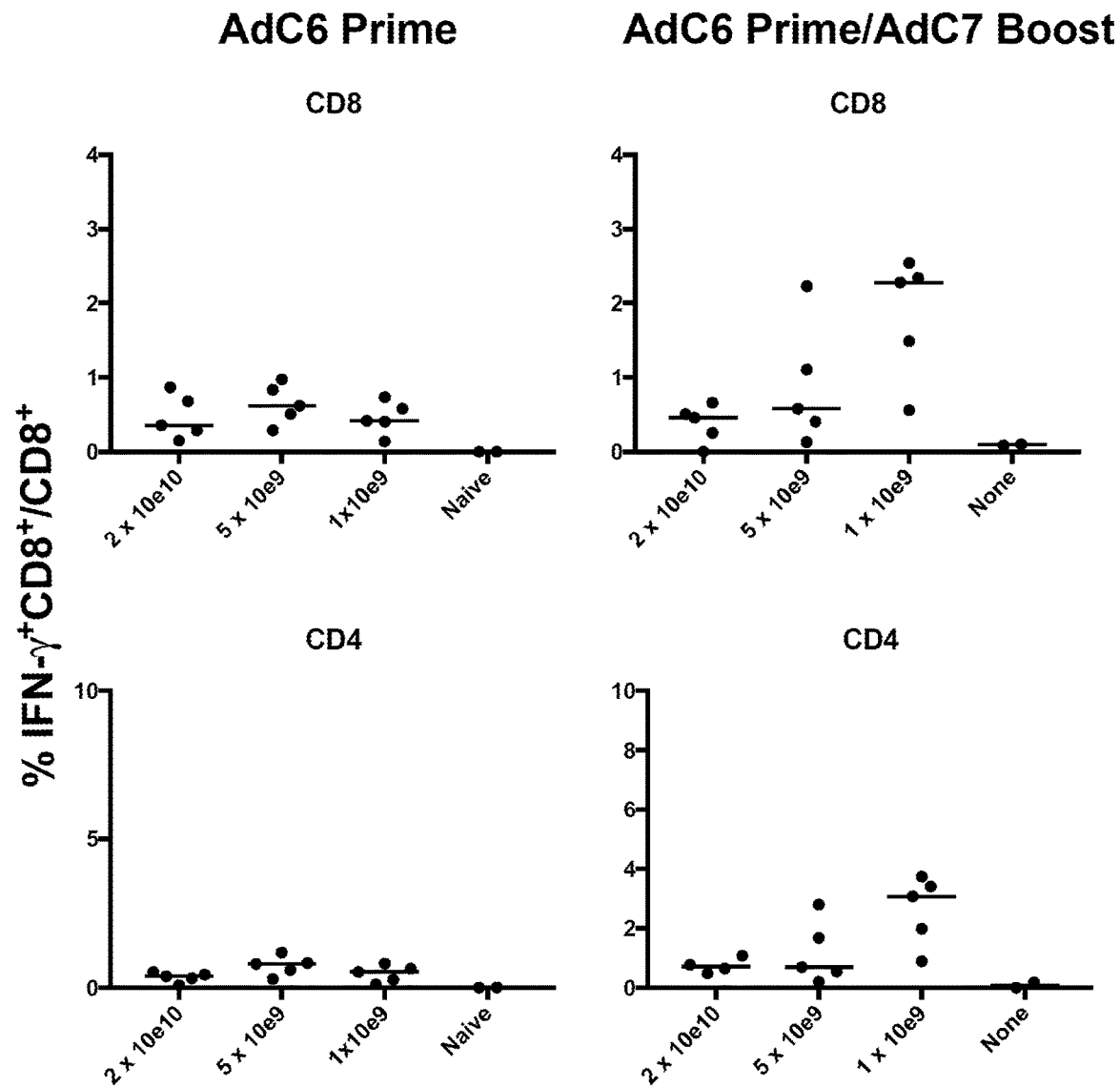
FIG. 4A, FIG. 4B and FIG. 4C show the IFN-γ response upon boosting with AdC6-gDCore (A), AdC6-gDPolC (B), and AdC6-gDPolN (C) in C57Bl/6 mice immunized with various doses of the indicated vectors. The left graphs show responses tested from blood 2 weeks after priming with AdC6 vector. Mice were boosted 8 weeks later with the same doses of AdC7 vectors expressing the same inserts. The right graphs show responses at 2 weeks after the boost in blood.
Figure 4B:
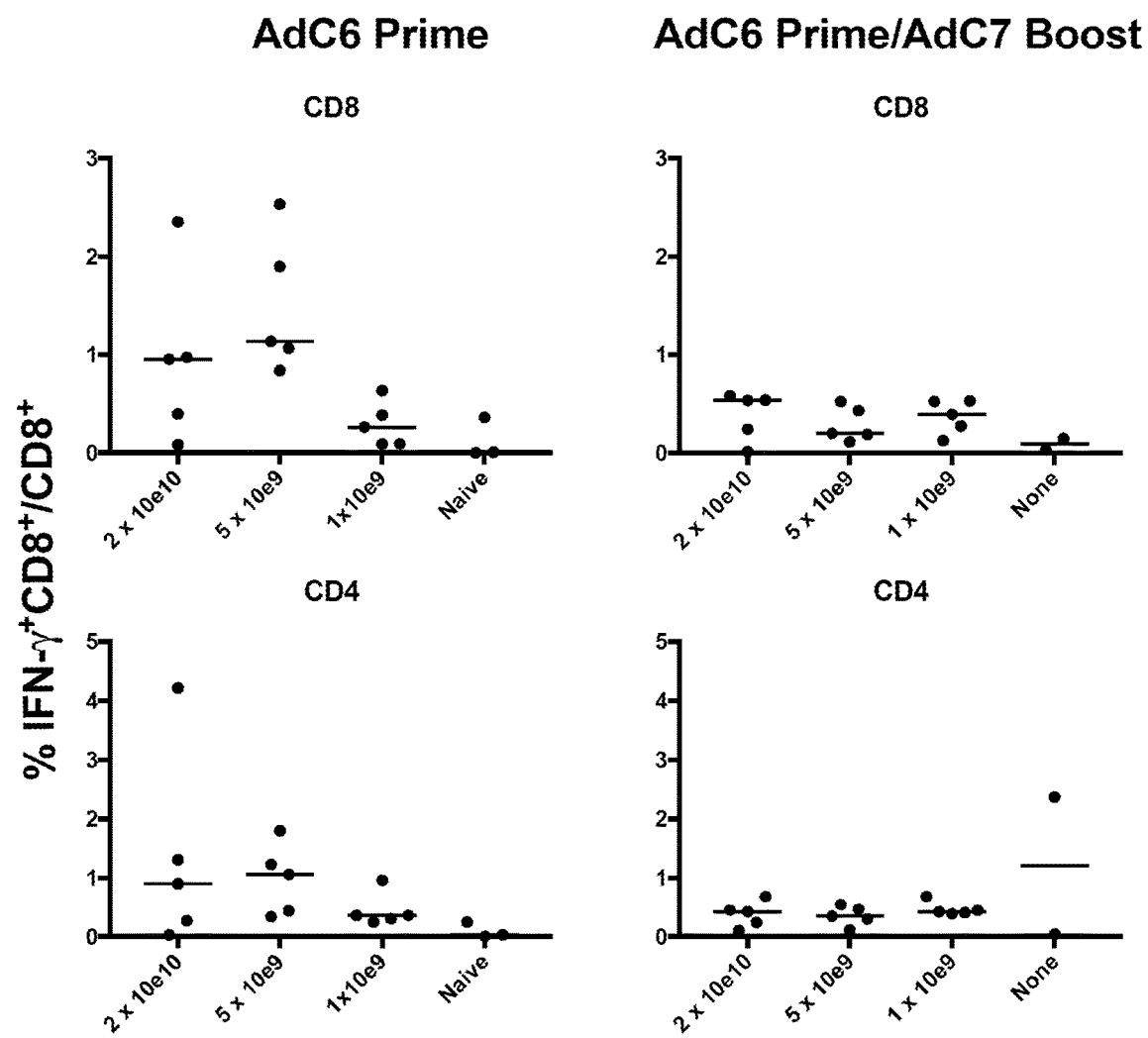
Figure 4C:
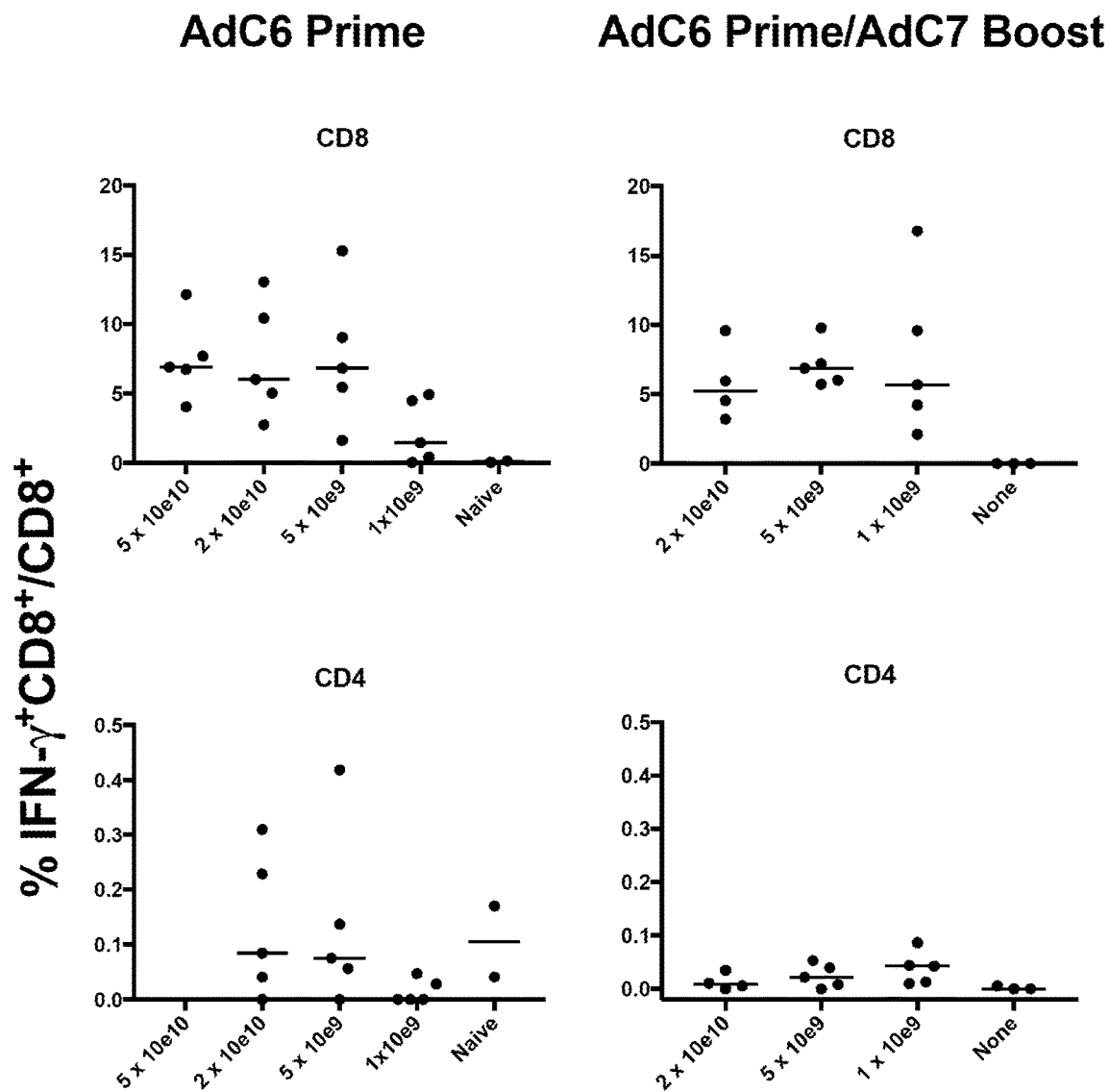
Figure 5A:
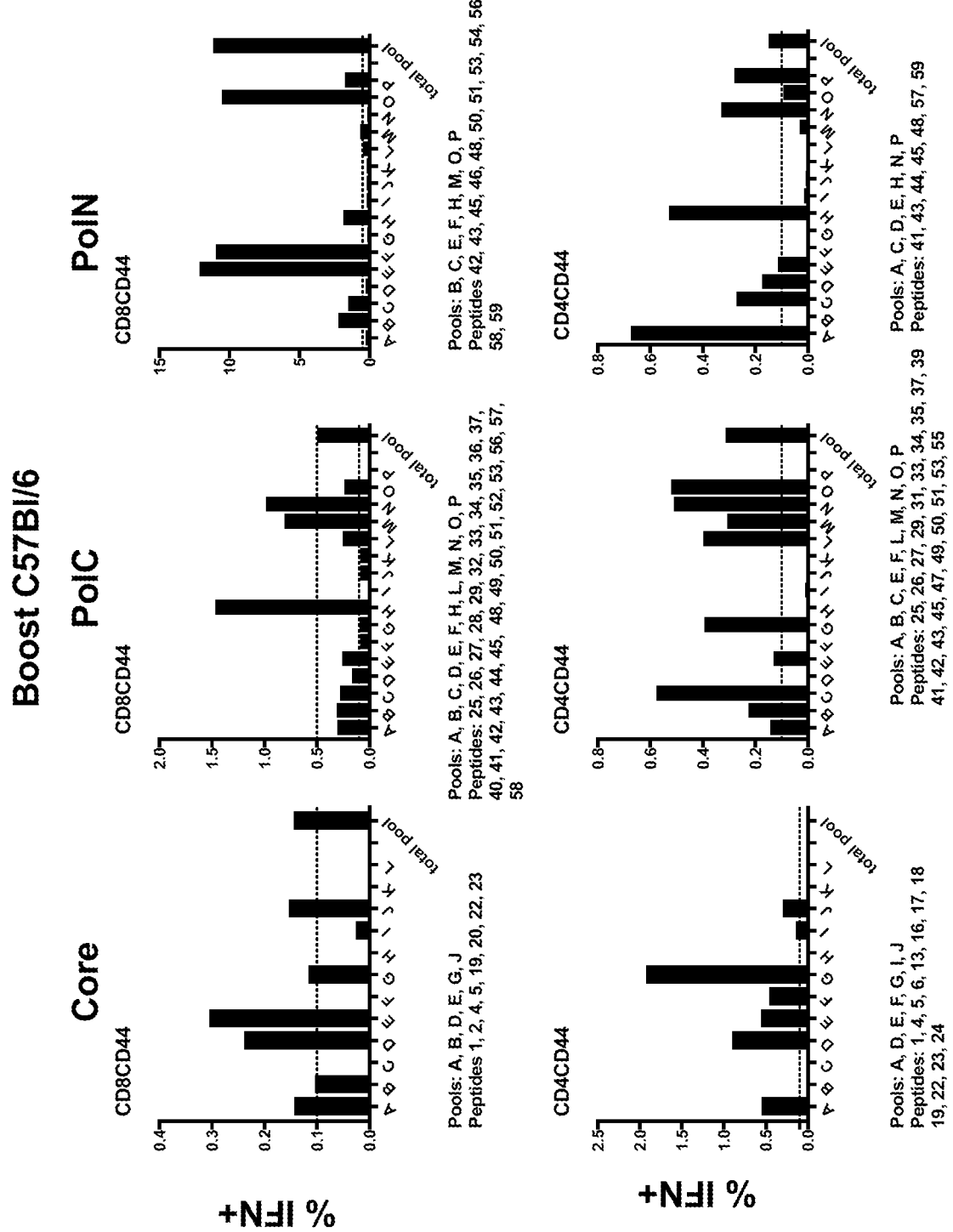
FIG. 5A, FIG. 5B, and FIG. 5C illustrate T cell frequencies in different mouse strains (A: C57Bl/6 mice; B: BALB/c mice; C: HLA-A2 tg mice) to pools of peptides representing the indicated HBV sequence. Mice were primed with AdC6 vectors expressing either of the 3 inserts (i.e., Core, PolC, or PolN) and were boosted 8 weeks later with AdC7 vectors expressing the same inserts. Results were obtained with splenocytes harvested 4 weeks after the immunization and tested by ICS for IFN-γ. Peptides were arranged in matrices so that recognition of 2 pools identified one peptide. The graphs show responses to the different pools; responses to a pool containing all peptides are shown to the right. Background frequencies obtained without the peptides were subtracted. Pools that were deemed to elicit a response and peptides identified in response to different pools are listed at the bottom of each figure. CD8+ T cell and CD4+ T cell responses are shown for BALB/c mice; CD8+ T cell responses are shown for HLA-A2 tg mice which carry a human MHC class I molecule but mouse MHC class II molecules. T cells were gated on activated CD44+ cells. Each consecutively numbered "peptide" consists of 15 amino acids beginning on the $1^{st}$, $6^{th}$, $11^{th}$, etc. amino acid of the Core, PolN, or PolC sequence. Thus, for example, peptide 1 of Core corresponds to amino acids 1-15 of SEQ ID NO: 6 (i.e. the epitope-optimized Core amino acid sequence), peptide 2 of Core corresponds to amino acids 6-20 of SEQ ID NO: 6, peptide 3 of Core corresponds to amino acids 11-25 of SEQ ID NO: 6, etc. Similarly, peptide 1 of PolN corresponds to amino acids 1-15 of SEQ ID NO: 8 (i.e. the epitope-optimized PolN amino acid sequence), peptide 2 of PolN corresponds to amino acids 6-20 of SEQ ID NO: 8, peptide 3 of PolN corresponds to amino acids 11-25 of SEQ ID NO: 8, etc. Likewise, peptide 1 of PolC corresponds to amino acids 1-15 of SEQ ID NO: 10 (i.e. the epitope-optimized PolC amino acid sequence), peptide 2 of PolC corresponds to amino acids 6-20 of SEQ ID NO: 10, peptide 3 of PolC corresponds to amino acids 11-25 of SEQ ID NO: 10, etc.
Figure 5B:
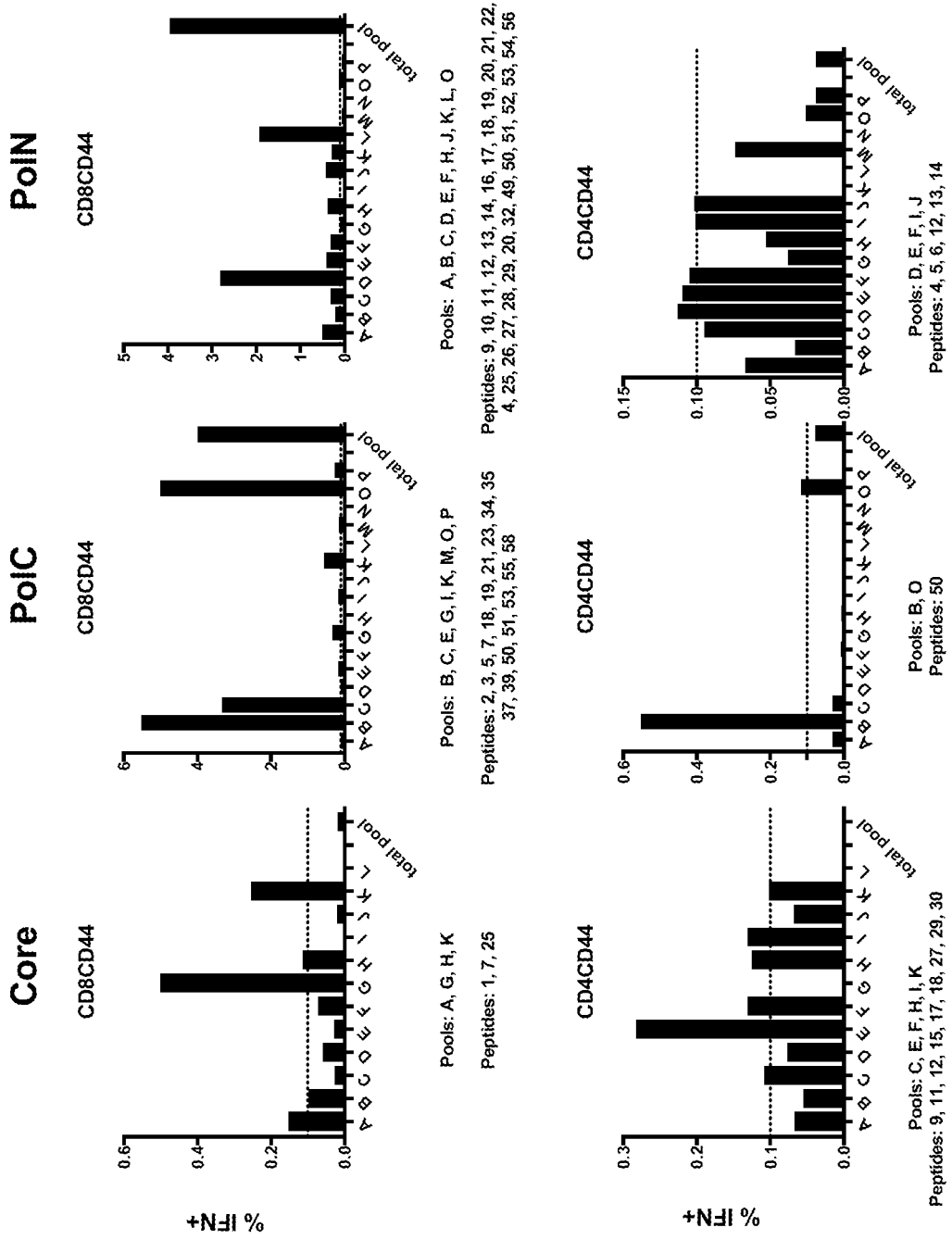
Figure 5C:
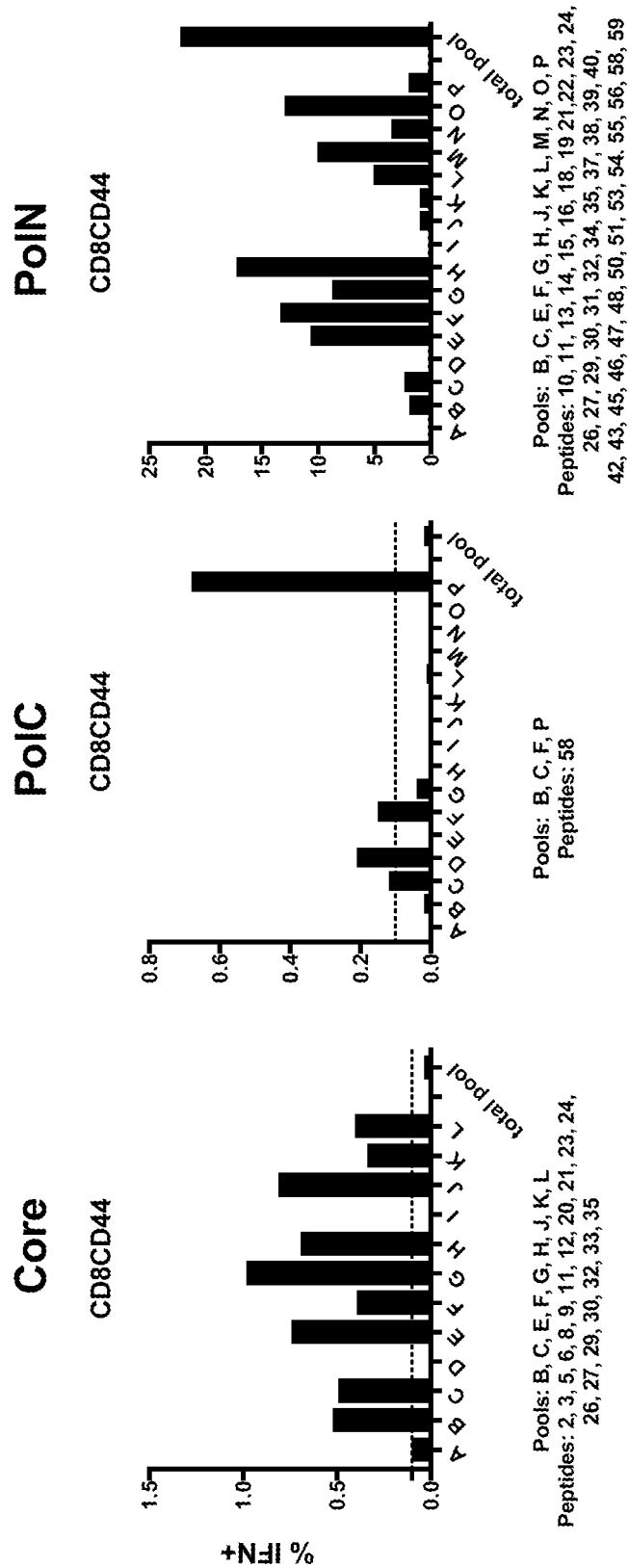

After the boost, which was tested in C57Bl/6, BALB/c and HLA-A2 tg mice, increases in responses were mainly seen for inserts and at vector doses that upon priming induced suboptimal responses, i.e., for Core tested at the $1\times10^9$ vp vector dose (FIG. 4A-4C). Although booster immunization failed to increase the response to PolN or PolC when vectors were injected at high doses, the boost nevertheless broadened the T cell responses (FIG. 5A-5C)

Immunogenicity Summary

The above results illustrate that:
  The vaccines are immunogenic: PolN>PolC>Core for CD8+ T cells; Core>PolC>PolN for CD4+ T cell responses;
  Immune responses can be boosted by a heterologous vaccine carrier;
  Immune responses are broad; and
  The breadth of the T cell responses increases after the boost.

Effect of Vaccination on HBV Titers Low Dose AAV-1.3HBV Challenge

Figure 6:
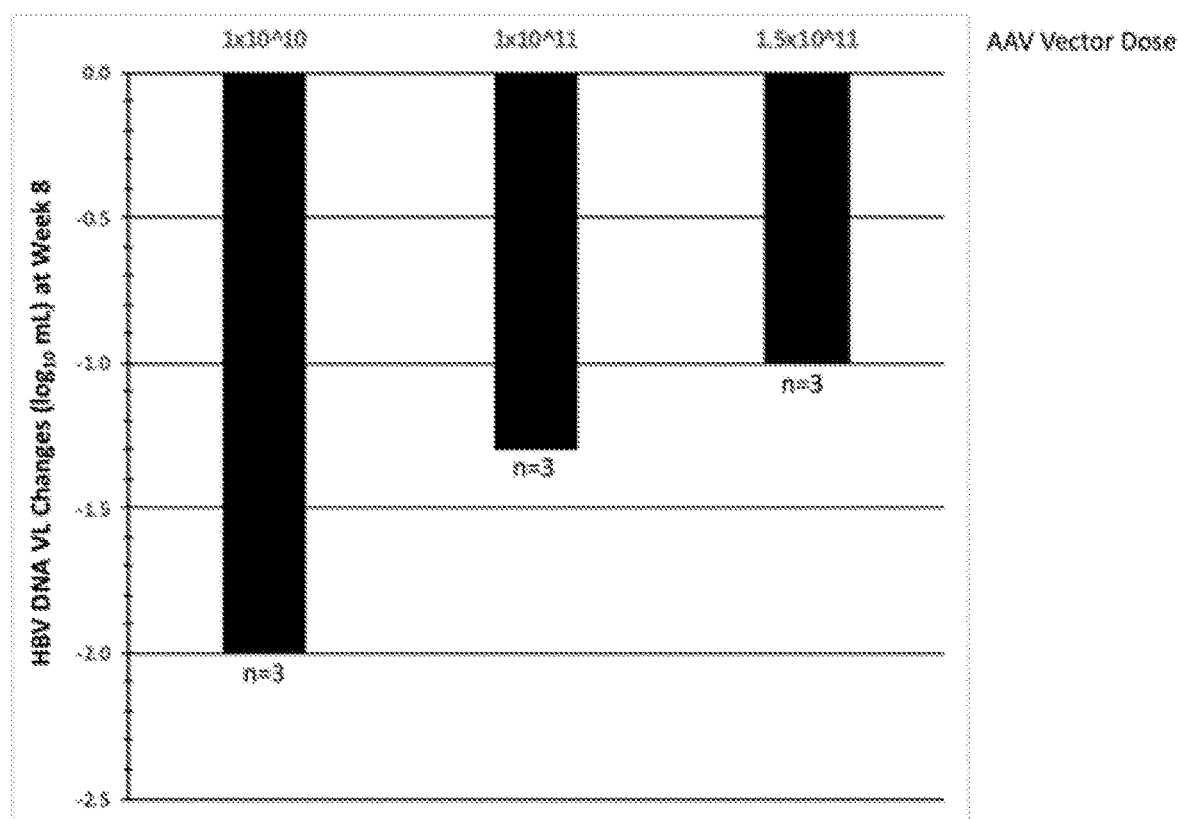
FIG. 6 illustrates the effect of vaccination on HBV genome copy numbers in serum upon AAV-1.3HBV challenge. A group of 3 mice were challenged with $1 \times 10^{10}$, $1 \times 10^{11}$ or $1.5 \times 10^{11}$ virus genomes (vg) of an adeno-associated virus 8 (AAV8)-1.3HBV vector and 8 weeks later were vaccinated with AdC6-gDPolN. Viral titers were tested 8 weeks after vaccination and compared to pre-vaccination titers. Viral changes from baseline for each treatment group are shown.

A group of 3 mice were challenged with $1\times10^{10}$, $1\times10^{11}$ or $1.5\times10^{11}$ vg of AAV-1.3HBV and were vaccinated with AdC6-gDPolN 8 weeks later. Viral titers were tested 8 weeks after vaccination and compared to pre-vaccination titers. FIG. 6 shows viral changes from baseline for each treatment group.

Epitope Shifting

CD8+ T cells to HBV antigens become exhausted during chronic HBV infections. Progression towards exhaustion is more rapid and pronounced for CD8+ T cells to dominant, as compared to subdominant, epitopes. The underlying reason is that exhaustion is driven by overwhelming antigen-driven stimulation through the T cell receptor; dominant epitopes are presented at higher levels on MHC class I antigens expressed by antigen presenting cells than subdominant epitopes with lower avidity to their restricting elements. Typical vaccine approaches primarily induce immune responses to dominant epitopes. Therapeutic vaccines should take into account loss of T cells to dominant epitopes during chronic virus infections and should be designed to favor expansion of CD8+ T cells to subdominant epitopes, which have a higher likelihood of resisting disease-driven exhaustion, translating to superior disease control.

The epitope profile in naïve mice immunized with an adenovirus vector comprising a nucleic acid sequence encoding the HBV polymerase N-terminal domain (PolN) fused to the herpes simplex virus glycoprotein D ("AdC6-gDPolN", wherein the amino acid sequence of gDPolN is SEQ ID NO: 16) was determined. Responses in mice that had not been pre-treated with the AAV8-1.3HBV vector were compared to those obtained in mice infected with an AAV8 vector expressing the 1.3HBV genome prior to vaccination with the AdC6-gDPolN. The AAV8-1.3HBV vector induced high titers of HBV in serum, which could drive CD8+ T cell exhaustion.

Figure 8A:
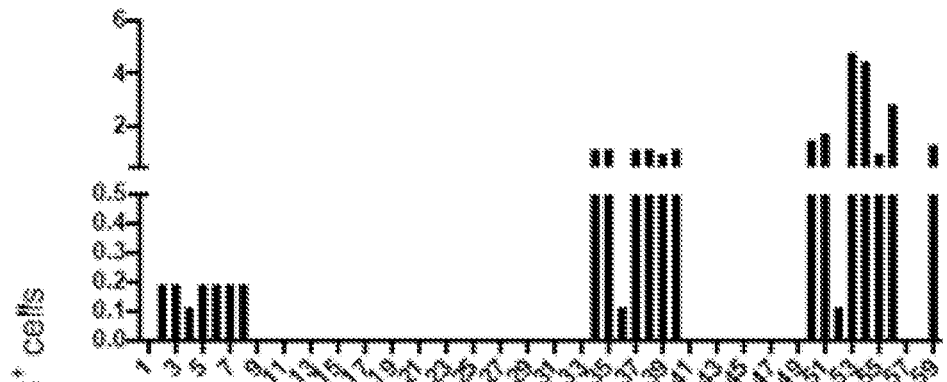
FIG. 8A, FIG. 8B, and FIG. 8C show data from the same experiment described above in FIG. 7. Based on the responses to the peptide pools, it was determined which individual peptides (both pools and peptides shown in FIG. 7) were positive. The graphs show responses to all of the peptides. Each peptide was present in two pools and therefore two values for frequencies were obtained for each peptide; only the lower data points are shown in this figure.
Figure 8B:
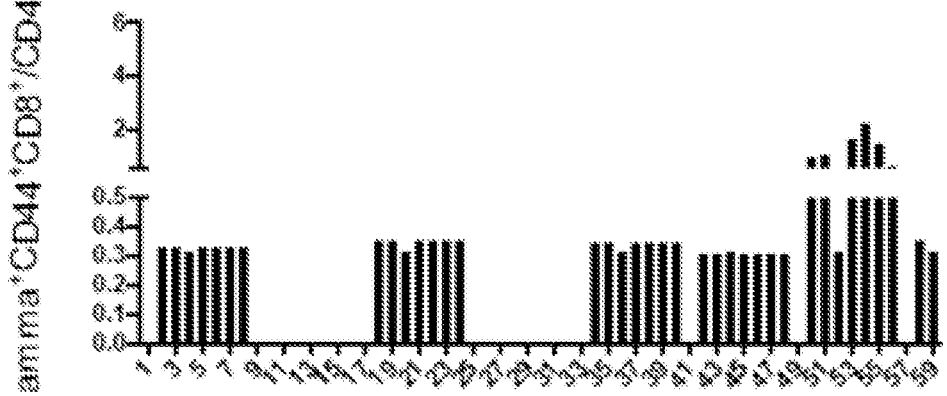
Figure 8C:
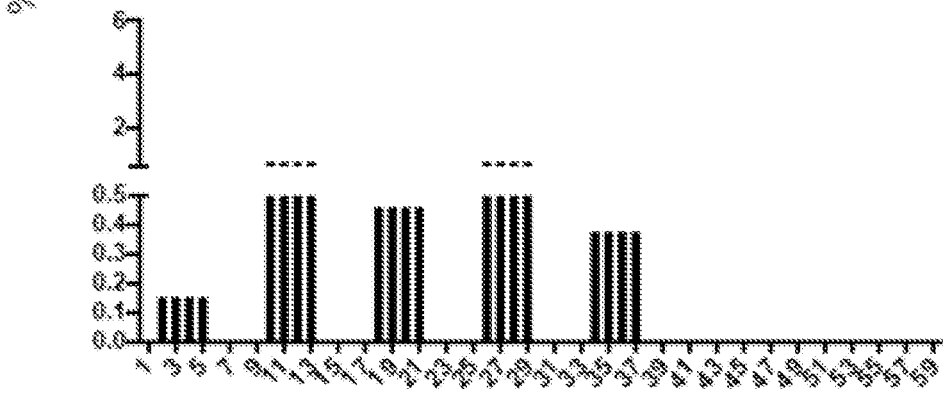

In the first series of experiments a peptide pool matrix was used to identify epitopes in mice vaccinated with the AdC6-gDPolN vector, but not challenged with an AAV-1.3HBV vector. A number of regions in these naïve mice were identified that elicited potent responses (e.g. greater than 1% IFN-γ production CD8+CD44+ T cells. FIG. 7A and FIG. 8A. In the second experiment, mice were challenged with $1\times10^{10}$ virus genomes (vg) of the AAV-1.3HBV vector, were vaccinated 4 weeks later with an AdC6 vector expressing the same HBV polymerase sequence (gDPolN) as in the initial experiment in non-challenged mice, and ten weeks thereafter the HBV PolN-specific CD8+ T cell epitope profile was determined using peptide pool matrices on splenocytes from the mice that had been challenged prior to vaccination. FIG. 7B and FIG. 8B. The experiment was repeated using more stringent conditions by challenging mice with a $1.5\times10^{11}$ vg dose of the AAV8-1.3HBV vector. Mice were again vaccinated 4 weeks later and were tested approximately 10 weeks after vaccination for CD8+ T cell responses to the peptide pool matrices. FIG. 7C and FIG. 8C. In both experiments, compared to the results obtained from unvaccinated mice, a shift was observed in the epitope profile in AAV8-1.3HBV infected mice, which at the time of vaccination had high viral loads between $10^7$-$10^9$ vg per ml of serum. The effect was more pronounced in mice that had been challenged with a high dose of the AAV8-1.3HBV vector. In both experiments a reduction in responses were observed. Furthermore, especially in mice challenged with the high dose of AAV8-1.3HBV, the results showed a loss of CD8+ T cells to many of the epitopes that showed immunodominance in uninfected vaccinated mice (e.g. within region represented by peptides 50 to 59, FIG. 8), a better preservation of epitopes that were subdominant (such as those within the region represented by peptides 2 to 8) as well as new epitopes, such as in the region presented by peptides 10 to 29. These data confirm a shift from recognition of dominant to recognition of subdominant epitopes.

```
Based on these data a new HBV polymerase N-
terminal domain insert (HBV PolN v2) was generated
(SEQ ID NO: 173):
HFRKLLLLDEEAGPLEEELPRLADEGLNRRVAEDLNLGNLPEWQTPSFPK

IHLQEDIVDRCKQFVGPLIVNEKRRLKLIMPARFYPNVIKYLPLDKGIKP

YYPEHAVNHYFQTRHYLHTLWKAGILYKRETTRSASFCGSPYSWEQELQH

GSCWWLQFRNSKPCSEYCLTHLVNLLEDWGPCDEHGEHHIRIPRTPARVT
```

This insert induced CD8+ T cell responses mainly to subdominant epitopes to which responses remain intact in mice with high HBV viral loads.

Immunogenicity and Efficacy of gDCore, gDPo1N, and gDPo1C Vaccines

The immunogenicity and efficacy the AdC6-gDCore, AdC6-gDPolN, AdC6-gDPolC, AdC7-gDCore, AdC7-gDPolN, and AdC7-gDPolC vaccines in an AAV8-HBV mouse model were analyzed.

Methods—Immunogenicity

C57Bl/6 mice (n=5 per group) were injected with various doses of: AdC6-gDCore (gDCore nucleic acid sequence corresponding to SEQ ID NO: 15); AdC6-gDPolN (gDPolN nucleic acid sequence corresponding to SEQ ID NO: 17); or AdC6-gDPolC (gDPolC nucleic acid sequence corresponding to SEQ ID NO: 19). Two months after the first injection, AdC6 vector-immunized mice were boosted with AdC7 vectors containing the same insert (e.g. AdC7-gDCore, AdC7-gDPolN, or AdC7-gDPolC). Mice were bled at 14 days and 56 days after the injection and T cell frequencies to the various HBV inserts were analyzed by intracellular cytokine staining (ICS) for interferon (IFN)-γ upon stimulation of cells with overlapping peptides representing the HBV sequences. Control cells were cultured without peptides. Frequencies and phenotype of CD8+ T cells to one immunodominant epitope within PolN were tested for by staining with an MHC I tetramer. The breadth and specificity of CD8+ T cell responses to individual peptides within a target sequence was performed via epitope mapping of splenocytes (CD8+ T cells tested by ICS for IFN-γ).

To assess CD8+ T cells in the liver, C57Bl/6 mice (n=8 per group) received intravenous administration of $1\times10^{10}$ viral genomes (vg) of AAV8-1.3HBV, $1\times10^{11}$ vg of AAV8-1.3HBV, or nothing via their tail vein, and 4 weeks later received a single IM injection of $5\times10^9$ viral particles (vp) of AdC6-gDPolN. Eight weeks after the IM injection, mice were sacrificed, livers were removed, and lymphocytes were isolated and stained with T cell markers and a tetramer recognizing the T cell receptor to an immunodominant epitope present in the PolN sequence.

In a separate experiment, three groups of C57Bl/6 mice (n=4 per group) received a single IM injection of $5\times10^9$ vp of AdC6-gDPolN at four weeks (-) or received either intravenous administration of $1\times10^{11}$ viral genomes (vg) of AAV8-1.3HBV via their tail vein with or without a single IM injection of $5\times10^9$ vp of AdC6-gDPolN four weeks later. Approximately 2 months after administration of AAV8-1.3HBV, mice were sacrificed, livers were removed and liver slices were prepared from each of the three groups, stained with hematoxylin and eosin and evaluated for lymphocytic infiltrates. From the same experiment, cells were stained with a specific tetramer and fluorochrome labeled antibodies to T-bet (clone 4B10, BV785 stain) or antibodies to PD-1 (clone 29F.1Al2, BF605 stain), TIM-3 (clone RMT3-23, Pe/Cy7 stain), CTLA-4 (clone UC10-4B9, PE stain), or LAG-3 (clone C9B7W, BV650 stain). Cells were analyzed by flow cytometry and gated on CD44+CD8 tetramer positive cells, which were then gated on the markers. Percent marker positive cells were identified from histograms in comparison to naïve T cells.

Methods—Efficacy

AAV8-1.3HBV Vector Studies—To assess the impact of AdC6-gDPolN on chronic HBV virus exposure, C57Bl/6 mice (n=8 per group) were challenged intravenously via their tail vein with $1\times10^{10}$ vg of AAV8-1.3HBV and four weeks later immunized with a single IM injection of $5\times10^9$ vp of AdC6-gDPolN. HBV DNA viral titers were evaluated by qPCR; pre- and post-vaccination changes from baseline ($\log_{10}$ copies/mL) were reported. Viral genome copy numbers were assessed at four, six, eight, ten, and twelve weeks after AAV8 challenge. Viral dynamics were assessed by PCR over time and the change in log 10 in HBV copies per mL were assessed. The number of mice showing a one, two or three log reductions at different points after treatment was assessed.

Impact of chronic HBV virus exposure on CD8+ T cell antigen recognition over time—The effect of AAV8-1.3HBV on vaccine-induced hepatic CD8+ T cells was assessed. The epitope profile in splenocytes of naïve mice immunized with a single IM injection of $5\times10^9$ vp of AdC6-gDPolN was determined 4 weeks after vaccination. Mice challenged with $1\times10^{10}$ and $1.5\times10^{11}$ vg of AAV8-1.3HBV and subsequently vaccinated with $5\times10^9$ vp of AdC6-gDPolN 4 weeks later had CD8+ T cell epitope profiles in splenocytes performed 10 weeks after vaccination (14 weeks after AAV injection). Epitope profiles between AAV-naïve and AAV-treated vaccinated animals were compared. PolN-specific CD8+ T cells from liver were analyzed for differentiation markers.

Results

Figure 10:
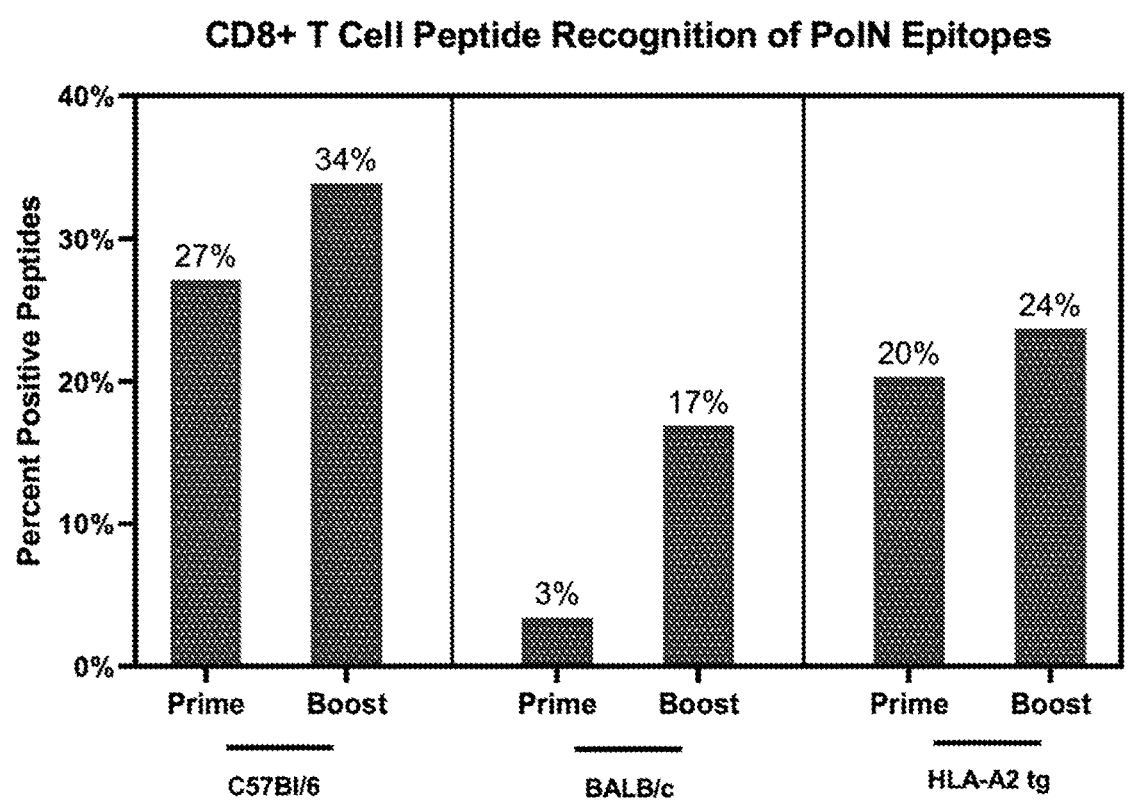
FIG. 10 illustrates the CD8+ T cell peptide recognition of PolN epitopes in BALB/c, C57Bl/6, and HLA-A2 transgenic mice after vaccination with a prime of AdC6-gDPolN and a boost of AdC7-gDPolN. CD8+ T cell peptide recognition was calculated as the fraction of positive peptides recognized two weeks after either the prime or the boost by the total number of overlapping 8 peptides from PolN (59 peptides total).

Immunogenicity—Vaccination induced robust and sustained CD8+ T cell responses to PolN (median frequencies over all circulating CD8+ T cells: 6.0%) and lower responses to PolC and core (median frequencies: 1.0% & 0.4%, respectively; FIG. 9A and FIG. 9B). Boosting at 8 weeks increased responses to all regions with significant changes being observed for core (p=0.007) (FIG. 9C). FIGS. 9A-9C show % CD8+ T cells over all CD8+ T cells for individual mice with medians indicated by the lines. Vaccination induced broad epitope recognition by CD8+ T cells that was further enhanced after boosting (27% to 34%; FIG. 10).

Figure 11B:
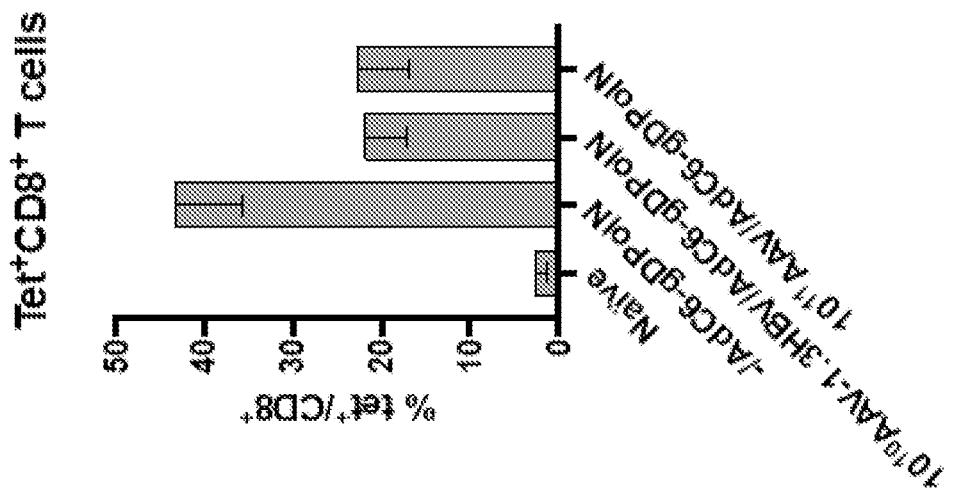
FIG. 11A and FIG. 11B illustrate vaccine-induced HBV-specific CD8+ T cell response in the liver of C57Bl/6 mice injected with the indicated vectors. * p-value between 0.01-0.05; *** p-value between 0.0001-0.001; via 1-way ANOVA.
Figure 11A:
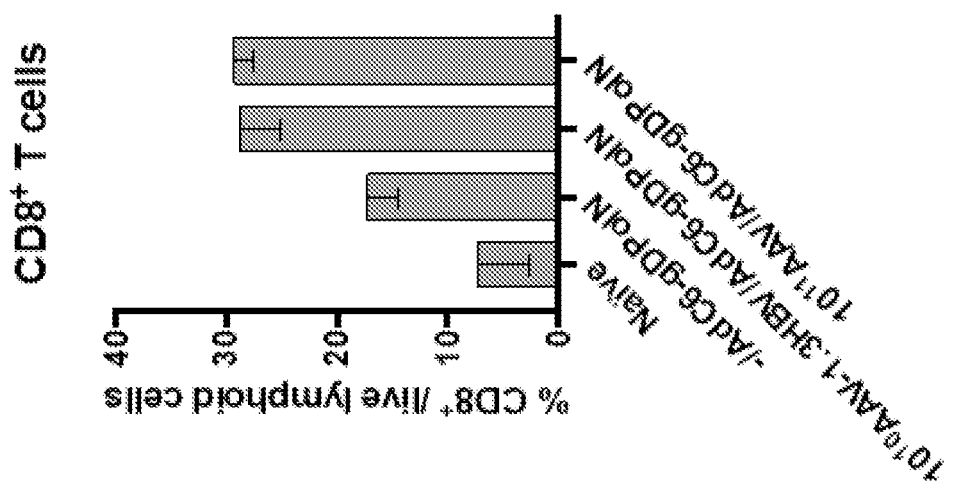
Figure 13A:
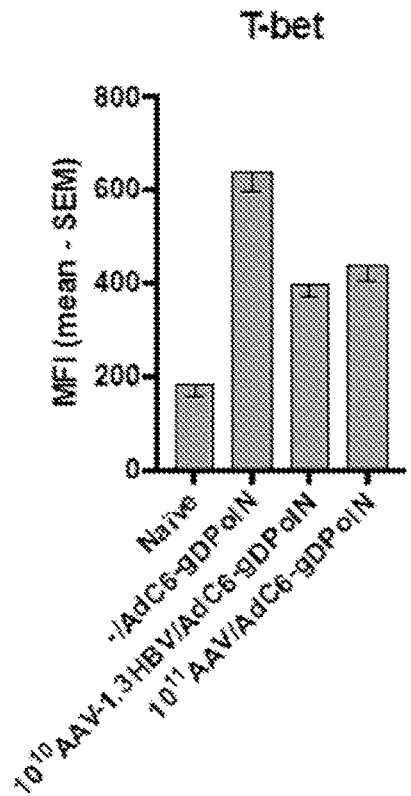
FIG. 13A and FIG. 13B illustrate vaccine-induced markers of CD8+ T cell activation/exhaustion in the liver of C57Bl/6 mice injected with the indicated vectors.  p-value between 0.001-0.01; * p-value between 0.0001-0.001; via 1-way ANOVA.
Figure 13B:
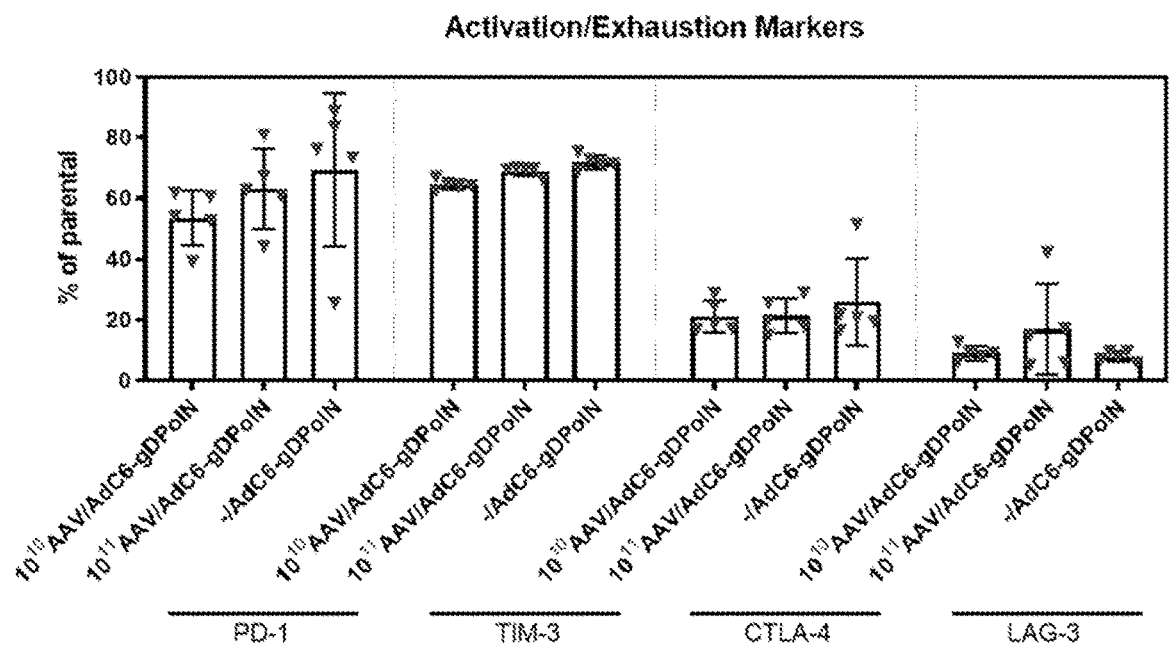

At week 12 following AdC6-gDPolN vaccination, AAV8-1.3HBV-infected vaccinated mice showed a preferential increase in hepatic CD8+ infiltrates (FIGS. 11A-11B and FIGS. 12A-12F), a decreased presence of vaccine-induced HBV-specific CD8+ T cells (FIGS. 11A and FIG. 11B) and slightly reduced levels of T-bet (suggestive of loss of effector functions) (FIGS. 13A-13B). FIG. 11A shows the % CD8+ T cells over all recovered lymphocytes from individual livers. FIG. 11B shows percent tetramer positive CD8+ cells, which were identified from histograms in comparison to naïve T cells. No clear pattern of cellular markers suggestive of T cell differentiation to an exhaustion phenotype was observed, however, between vaccinated AAV1.3HBV-infected and -uninfected mice (FIGS. 13A-13B).

Figure 14A:
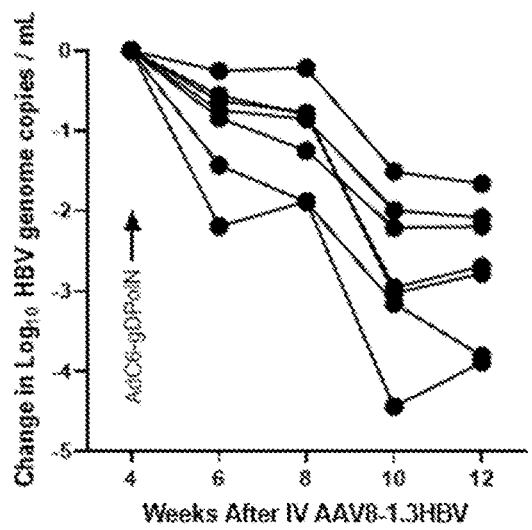
FIG. 14A and FIG. 14B illustrate HBV viral dynamics in C57Bl/6 mice injected with an exemplary AdC6-gDPolN vector. The median HBV DNA VL/ml at week 4-7.3 $\log_{10}$ cps/mL are provided. n=7; one mouse excluded for missing data.
Figure 14B:
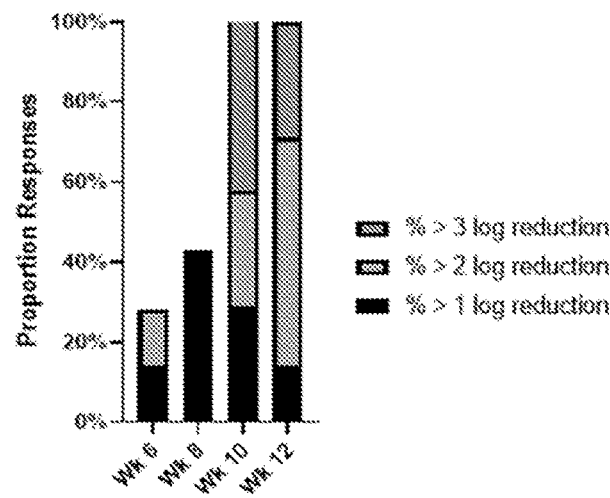

Efficacy—Following a single IM injection of the AdC6-gDPolN vector, AAV8-1.3HBV-infected mice had multi-log HBV DNA declines in serum that persisted throughout the 8-week post vaccination period (FIG. 14). Post vaccination, median declines in serum HBV DNA viral load levels at four and eight weeks were 0.86 and 2.69 $\log_{10}$ cps/mL, respectively (FIG. 14A). At week 8, all animals had a >1 $\log_{10}$ cps/mL, 6/7 (86%) had >2 $\log_{10}$ cps/mL, and 2/7 (29%) had >3 $\log_{10}$ cps/mL declines from baseline (FIG. 14B).

Figure 15A:
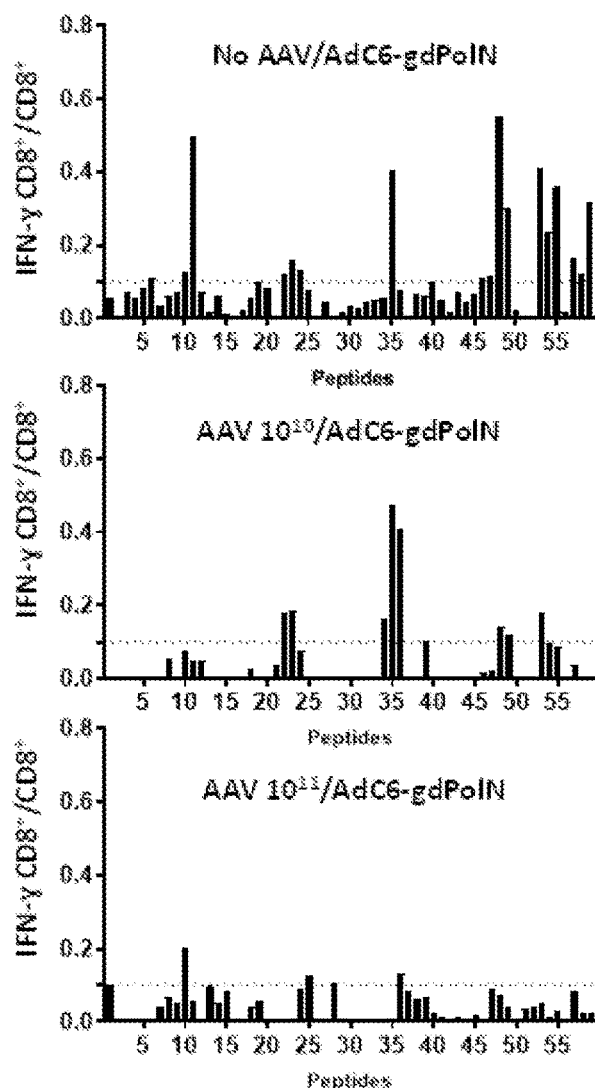
FIG. 15A and FIG. 15B illustrate the impact of AAV-induced HBV on CD8+ T cell responses in C57Bl/6 mice first injected with $10^{10}$ or $10^{11}$ vg of AAV-1.3HBV and then four weeks later boosted with $10^{10}$ vp of an exemplary AdC6-gDPolN vector.
Figure 15B:
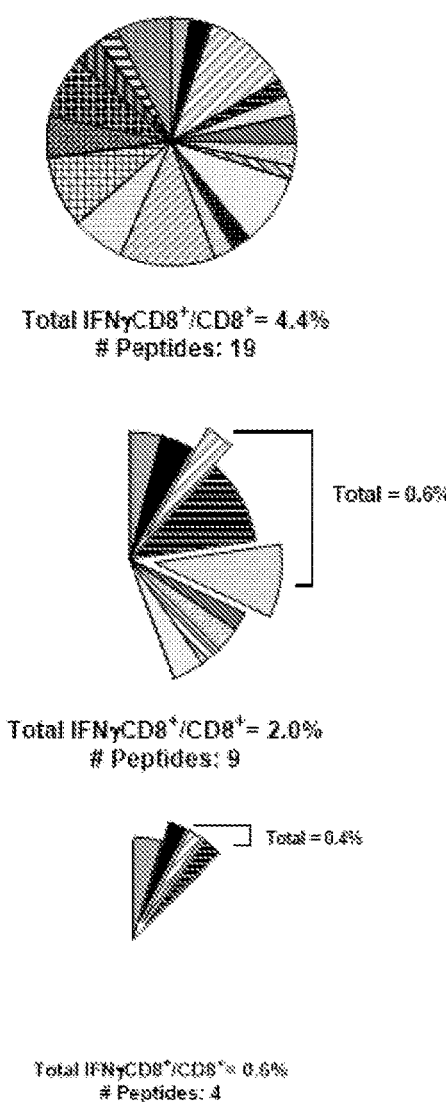

Following a single AdC6-gDPolN vector injection, distinct CD8+ T cell recognition patterns to PolN peptides in splenocytes were observed when AAV-HBV-infected and naïve mice were compared. FIG. 15A and FIG. 15B illustrate the results from experiments in which mice were first injected with AAV-1.3HBV and then four weeks later boosted with $10^{10}$ vp of the AdC6-gDPolN vector, splenocytes were harvested 8 weeks after the immunization and tested by ICS for IFN-γ upon a short in vitro stimulation with individual peptides spanning the sequence of PolN. Background frequencies obtained without peptide were subtracted. FIG. 15A shows the peptide recognition profile of mice that received the AdC6-gDPolN vaccine only followed by those that were first injected with the indicated doses of the AAV8-1.3HBV vector. The pie graphs in FIG. 15B show the corresponding responses to peptides that reached the threshold of 0.1% of all CD44+ CD8+ cells (data correspond to those in FIG. 15A). Each slice/color represents the frequency of the response to an individual peptide with size showing the proportion of the total; only responses greater than 0.1% were included. Pullouts indicate epitopes only recognized in AAV8-1.3HBV infected mice. It was found that pre-treatment with AAV reduced both the number of epitopes recognized after a single IM prime and the magnitude of the immune response as the sum total of IFN-γ producing CD8+ T cells over the pool of CD8+ T cells. AAV pre-treatment shifted the T cell recognition to new epitopes, which represent roughly a third of the detectable CD8+ T cell response. The percentage of functional HBV-specific CD8+ T cell responses were highest in naïve mice (4.4%, FIG. 15B) but decreased in the presence of low and high dose AAV8-1.3HBV (2.0% & 0.6%; respectively, FIG. 15B). AAV8-1.3HBV-uninfected animals showed strong CD8+ T cell responses to a number of epitopes, which were decreased and shifted in AAV-HBV-infected animals to include T cell recognition of new epitopes.

Discussion

An HBV therapeutic vaccine that targets early CD8+ T cell activation using gD as a genetically encoded checkpoint inhibitor was generated and was shown to:

Induce potent and durable CD8+ T cell responses to key HBV antigens (FIG. 9);

Stimulate very broad CD8+ T cell responses (FIG. 10) that included sub-dominant epitope recognition (FIG. 15); and Achieve sustained multi-log HBV DNA viral load reductions in an AAV mouse model (FIG. 14) with preferential trafficking of functional CD8+ T cells to the liver (FIGS. 11 and 12).

In the disclosed AAV studies, AAV-induced HBV infection caused loss of CD8+ T cell recognition to dominant epitopes of PolN following vaccination with AdC6-gDPolN (FIG. 15). Without intending to be bound by theory, it is believed that it is the breadth of the CD8+ T cells induced by gD and their ability to recognize subdominant epitopes that led to a sustained immune response and multi-log suppression of HBV.

Immunogenicity of AdC6/7-gDPoIN in Blood and Liver Following Vaccination in AAV-Induced HBV-Infected Animals The following studies were performed to evaluate $CD8^+$ T cell responses to the AdC6-gDPolN vaccine in blood, spleens, and livers of animals in the presence of pre-existing AAV-induced HBV infection.

Experiment #1—$CD8^+$ T cell responses in AAV8-1.3HBV Infected Mice: Response Kinetics in Blood Purpose—To assess the effect of sustained titers of HBV antigen on $CD8^+$ T cell responses to the gDPolN antigen as expressed within the AdC6 vector.

Methods—C57Bl/6 mice were injected i.v. with the $10^{10}$ of the AAV8-1.3HBV vector. Four weeks later they were vaccinated with $5 \times 10^9$ vp of the AdC6-gDPolN vector. Control mice received only the AdC6-gDPolN vector. Naïve mice served as additional controls. Mice were boosted 2 months later with the same dose of the AdC7-gDPolN vaccine. Blood was collected at various times after the prime and the boost and PBMCs were tested for IFN-γ-producing $CD8^+$ T cells.

Figure 16:
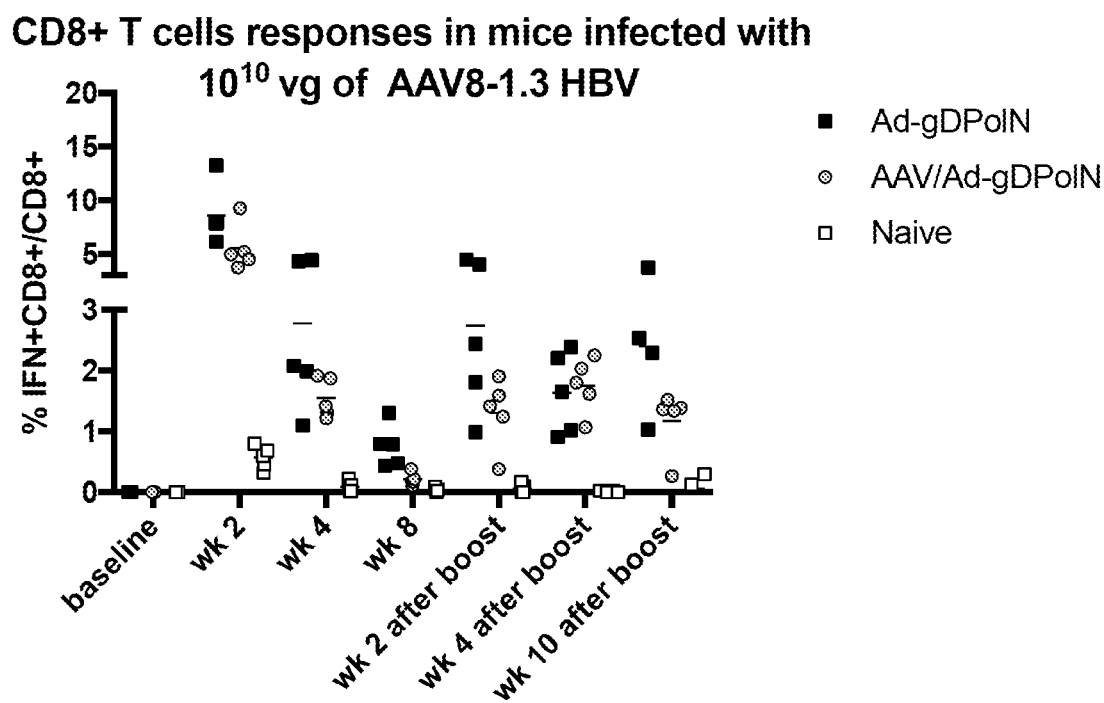
FIG. 16 illustrates the frequencies of IFN-γ-producing CD8+ T cells for individual C57Bl/6 mice that were injected i.v. with the $10^{10}$ vg of the AAV8-1.3HBV vectors, vaccinated 4 weeks later with 5×10 9 vp of the AdC6-gDPolN vector, and boosted 2 months later with the same dose of the AdC7-gDPolN vaccine. Control mice only received the vaccine. Naïve mice served as additional controls.

Results—As shown in FIG. 16, mice mounted a vigorous PolN-specific $CD8^+$ T cell response 2 weeks after vaccination, which gradually declined by week 8 and then increased again after the boost. The $CD8^+$ T cell response was more stable after the boost than after the prime. At most time points tested responses were lower in mice that had been injected with the AAV8-1.3HBV vector than in the controls that had not been injected with an AAV vector.

Experiment #2—$CD8^+$ T Cell Responses in AAV8-1.3HBV Infected Mice: Responses in Liver Purpose—To assess $CD8^+$ T cell responses including markers indicative of T cell exhaustion in livers of AAV8-1.3HBV-infected, vaccinated mice.

Methods—C57Bl/6 mice were injected i.v. with the $10^{10}$ or $10^{11}$ vg of the AAV8-1.3HBV vectors. Four weeks later they were vaccinated with $5 \times 10^9$ vp of the AdC6-gDPolN vector. Control mice received only the AdC6-gDPolN vector. Naïve mice served as additional controls. Mice were boosted 2 months later with the same dose of the AdC7-gDPolN vaccine.

To obtain hepatic lymphocytes, livers were cut into small fragments and treated with 2 mg/ml Collagenase P, 1 mg/ml DNase I (all from Roche, Basel Switzerland) and 2% FBS (Tissue Culture Biologicals, Tulare, CA) in L15 under agitation for 1 hour. Liver fragments were homogenized, filtrated through 70 µm strainers and lymphocytes were purified by Percoll-gradient centrifugation and washed with DMEM supplemented with 10% FBS. Lymphocytes were stained with a violet live/dead dye (Thermo Fisher Scientific), anti-CD8-APC (clone 53-6.7, BioLegend), anti-CD44-Alexa Flour 700 (clone IM7, BioLegend), anti-EOMES-Alexa Fluor 488 (clone Danl lmag, eBioscience), anti-PD1-BV605 (clone 29F.1Al2, BioLegend), anti-LAG3-BV650 (clone C9B7W, BioLegend), anti-T-bet-BV786 (clone 4B10, BioLegend), anti-CTLA-4-PE-A (clone UC10-4B9, BioLegend), anti-TIM-3-Pe-Cy7-A (clone RMT3-23, BioLegend), and an APC-labeled MHC class I tetramer (NIH tetramer Facility, Emory University, Atlanta GA) corresponding to amino acids 396-404 FAVPNLQSL (SEQ ID NO: 188) (peptide 55) of the HBV polymerase at +4° C. for 30 min in the dark. Cells were washed and were analyzed by a BD FACS Celesta (BD Biosciences, San Jose, CA) and DiVa software. Post-acquisition analyses were performed with FlowJo (TreeStar, Ashland, OR).

Figure 17A:
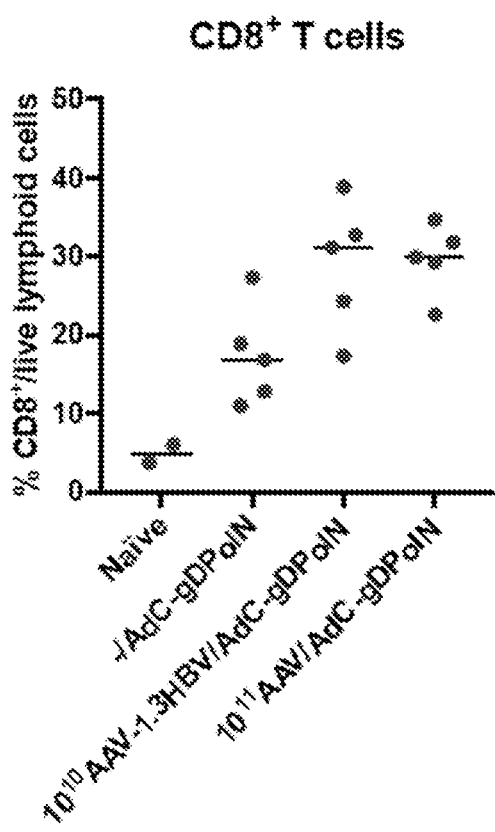
FIG. 17A and FIG. 17B illustrate: A) % of CD8$^+$ T cells within the lymphatic infiltrates of livers of individual mice; and B) the frequencies of PolN-tetramer$^+$CD8$^+$ T cells within the same infiltrates. C57Bl/6 mice were injected i.v. with the $10^{10}$ or $10^{11}$ vg of the AAV8-1.3HBV vector, were vaccinated 4 weeks later with 5×10 9 vp of the AdC6-gDPolN vector, and were boosted 2 months later with the same dose of the AdC7-gDPolN vaccine. Control mice only received the vaccine. Naïve mice served as additional controls.
Figure 17B:
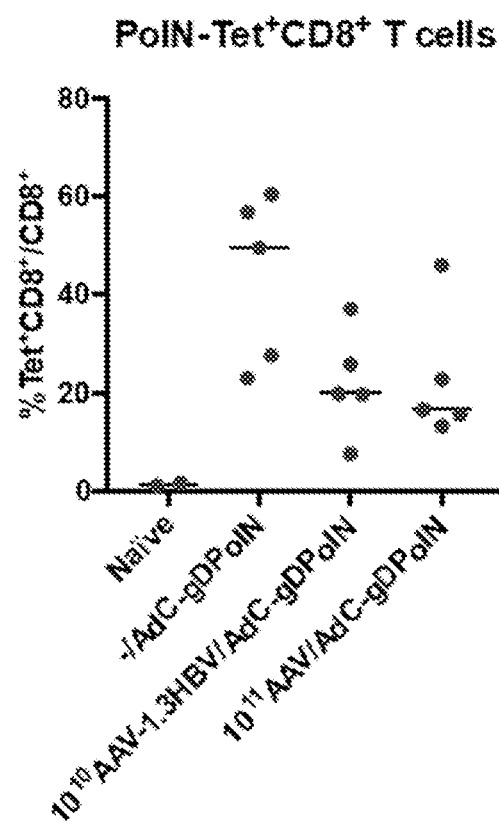
Figure 18A:
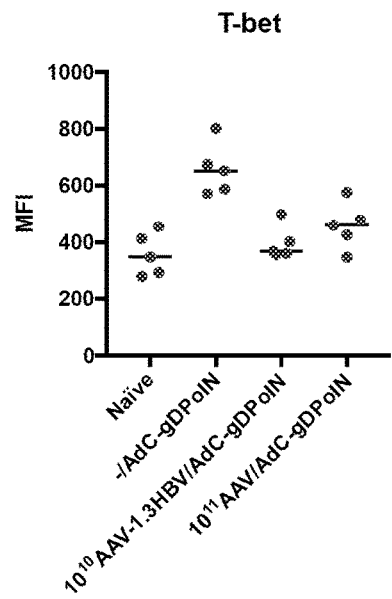
FIG. 18A, FIG. 18B, FIG. 18C, FIG. 18D, FIG. 18E, and FIG. 18F illustrate the phenotypes of the infiltrating tetramer+CD8$^+$ T cells in comparison to naïve (i.e., tetramer CD44$^-$CD8$^+$) T cells analyzed with the mean fluorescent intensity (MFI) of the indicated markers. Lines with stars above indicate significant differences by multiple t-test. (*) p≤0.05-0.01, () p≤0.01-0.001, (*) p≤0.001-0.0001, (****) p≤0.0001.
Figure 18B:
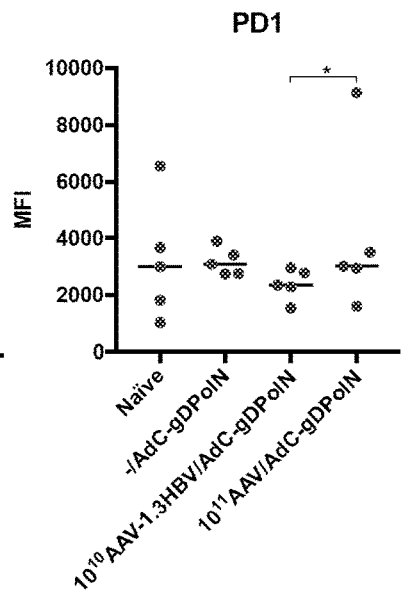
Figure 18C:
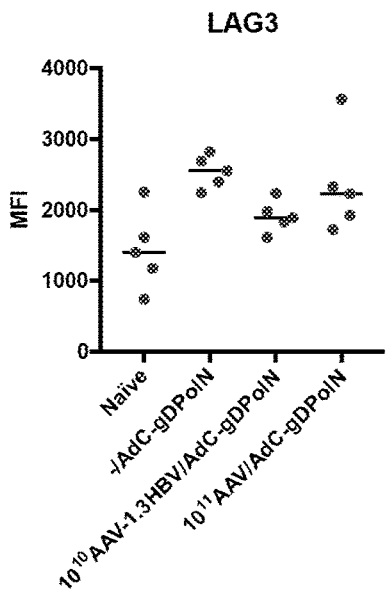
Figure 18D:
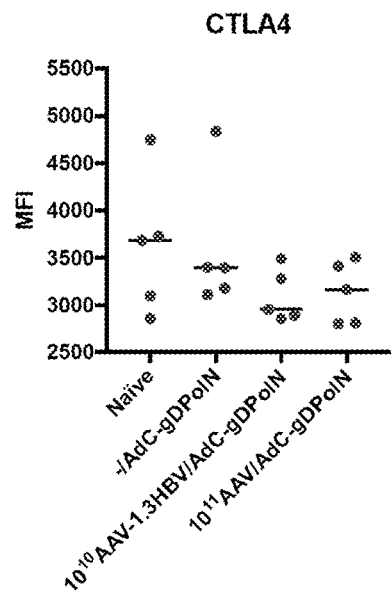
Figure 18E:
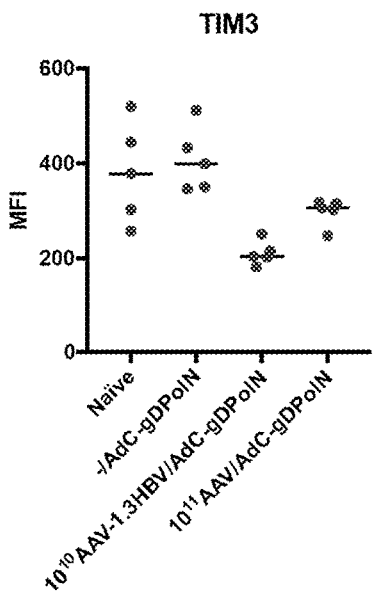
Figure 18F:
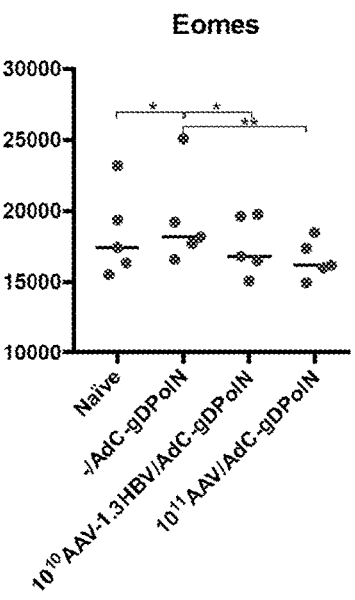
Figure 19A:
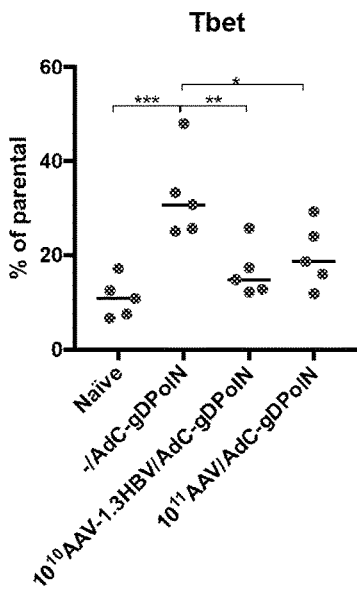
FIG. 19A, FIG. 19B, FIG. 19C, FIG. 19D, FIG. 19E, and FIG. 19F illustrate the percentage of Tet$^+$ or naïve CD8$^+$ T cells positive for the indicated markers. Lines with stars above indicate significant differences by multiple t-test. (*) p≤0.05-0.01, () p≤0.01-0.001, (*) p≤0.001-0.0001, (****) p≤0.0001.
Figure 19B:
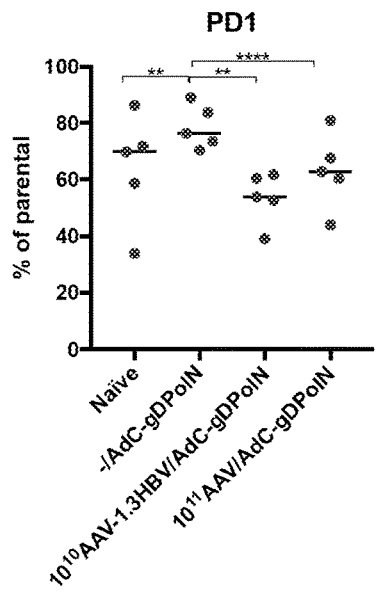
Figure 19C:
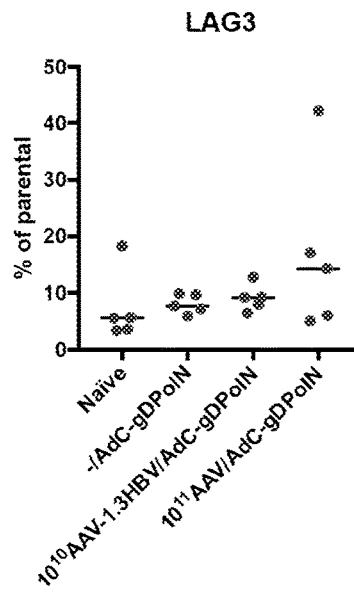
Figure 19D:
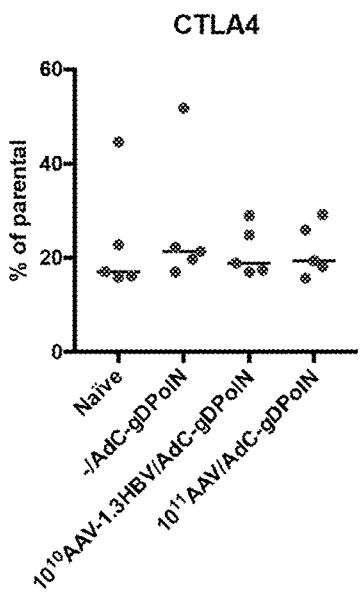
Figure 19E:
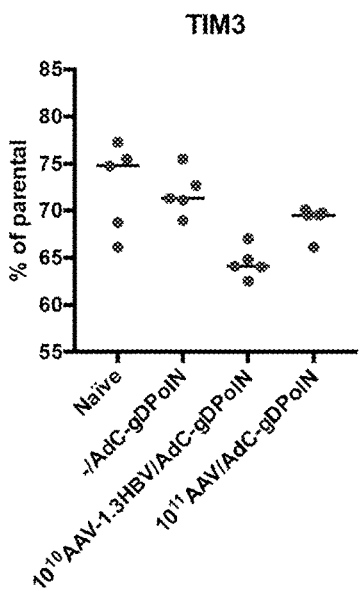
Figure 19F:
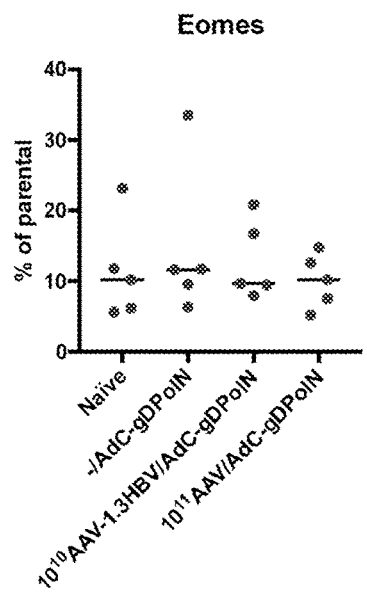

Results—The frequencies of $CD8^+$ T cells within the lymphocytic liver infiltrates were analyzed. Frequencies of $CD8^+$ T cells within the lymphocytic liver infiltrates were increased in vaccinated mice as compared to naïve mice, and further increases were seen in mice that prior to vaccination had been injected with the AAV8-1.3HBV vector (FIG. 17A). Frequencies of PolN-specific $CD8^+$ T cells identified by staining with a tetramer specific for an epitope present in the PolN insert were reduced in AAV-1.3HBV-injected mice (FIG. 17B).

The phenotypes of the infiltrating tetramer$^+$CD8+ T cells in comparison to naïve (i.e., tetramer$^-$CD44$^-$CD8$^+$ T cells) were assessed by determining the mean fluorescent intensity of a dye linked to a given antibody (FIG. 18A-FIG. 18F) and by assessing the percentages (FIG. 19A-FIG. 19F) of $CD8^+$ T cells that were positive for the indicated markers.

T-bet which controls a number of $CD8^+$ T cell functions, was reduced on hepatic $CD8^+$ T cells from mice that had been injected with AAV8-1.3HBV prior to vaccination in comparison the vaccine only group. Exhaustion markers were not increased in AAV8-1.3HBV-pre-treated groups suggesting that the observed loss of PolN-specific $CD8^+$ T cells in presence of HBV was unlikely to be caused by classical $CD8^+$ T cell exhaustion (FIG. 18A-FIG. 18F and FIG. 19A-FIG. 19F).

Experiment #3—Breadth of the PolN-Specific CD8+ T Cell Response in AAV8-1.3HBV Infected Mice Purpose—To assess if the presence of HBV affects the breadth of the $CD8^+$ T cell response to PolN expressed within gD by the AdC vaccines.

Figure 20A:
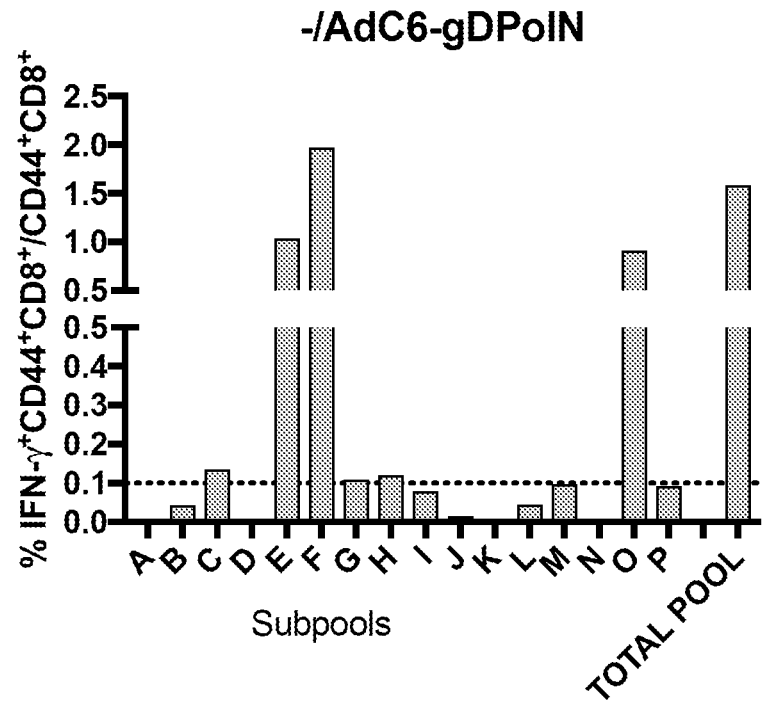
FIG. 20A, FIG. 20B, FIG. 20C, FIG. 20D, FIG. 20E, and FIG. 20F illustrate the CD8$^+$ T cell response to individual peptides spanning the PolN sequence. Total pool—response to mixtures of all PolN peptides; Naïve—response of naïve mice to mixtures of all PolN peptides.
Figure 20B:
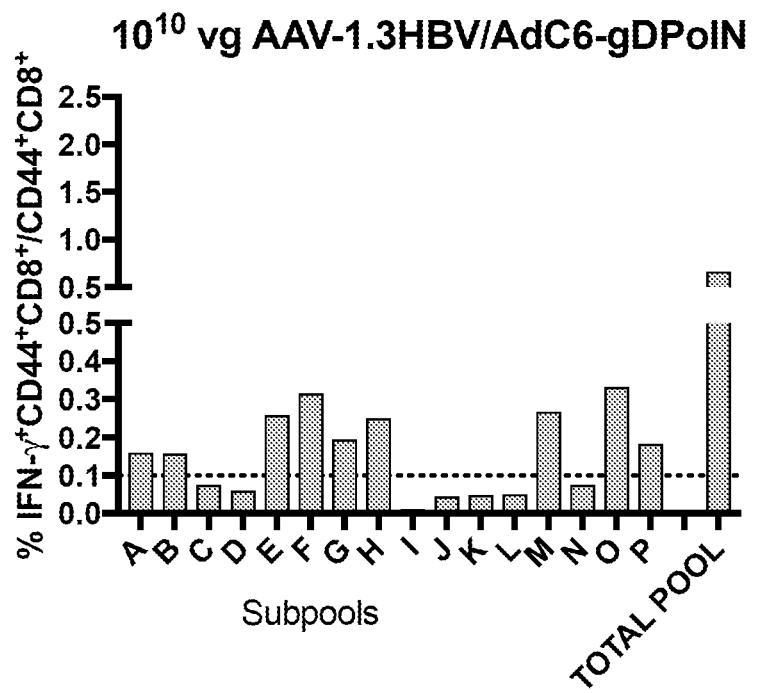
Figure 20C:
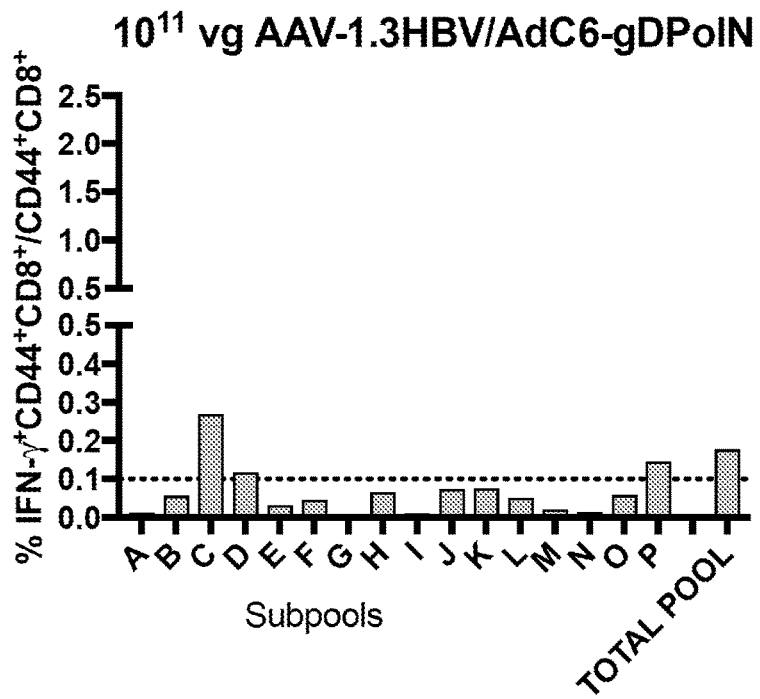

Methods—Mice were injected i.v. with the $10^{10}$ or $10^{11}$ vg of the AAV8-1.3HBV vectors and were boosted 2 months later with the corresponding AdC7 vectors. Control mice received only the AdC6-gDPolN vector. Mice were euthanized 10 weeks later and the pooled splenocytes were tested against pools of peptides in the non-AAV infected animal study. Results are provided in FIG. 20A-FIG. 20C.

Figure 20D:
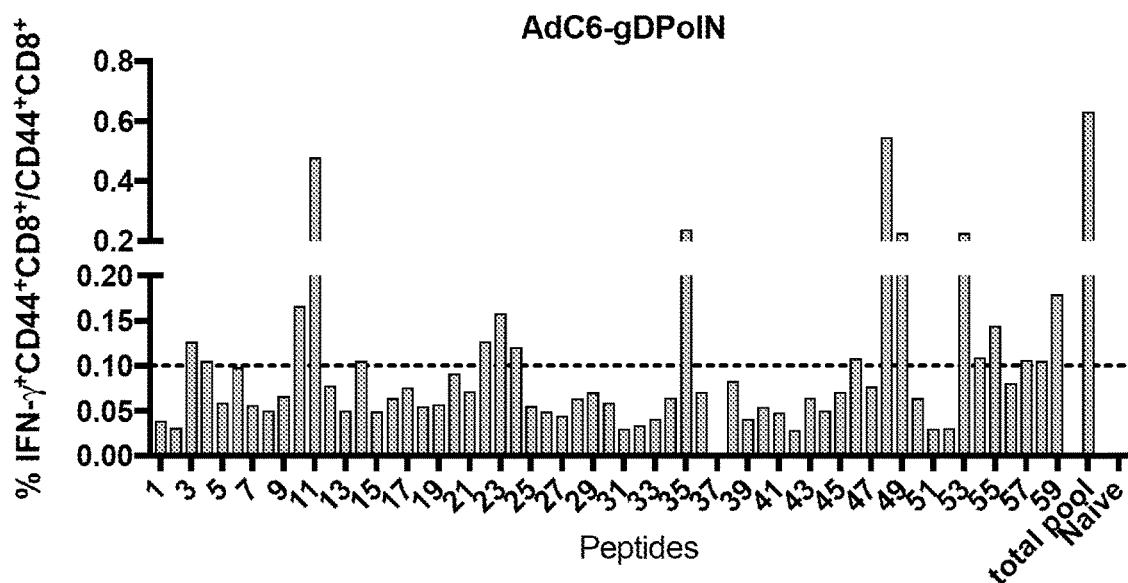
Figure 20E:
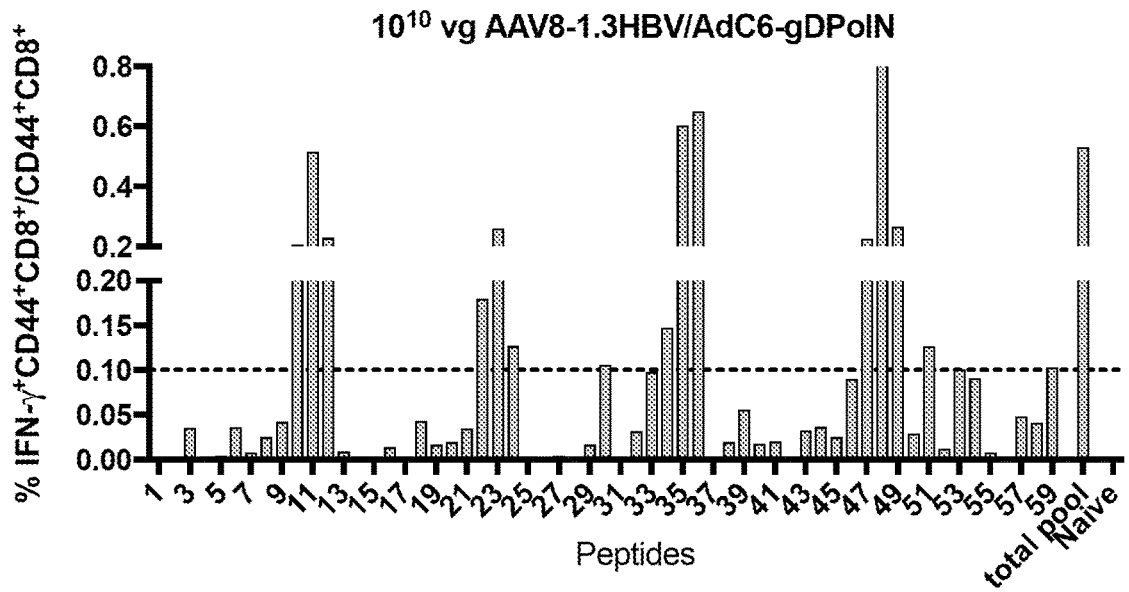
Figure 20F:
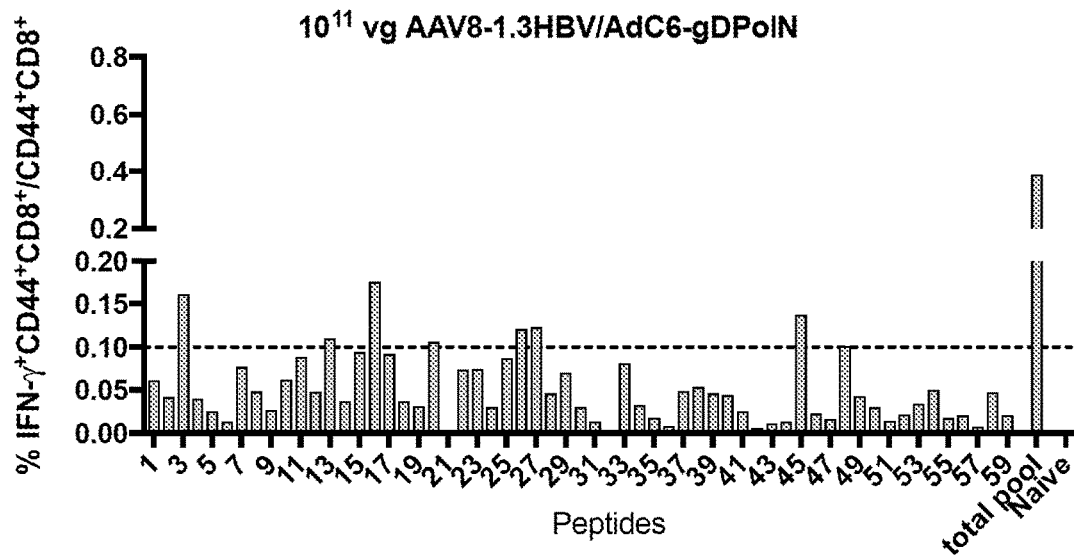

In a second experiment, mice were injected i.v. with the $10^{10}$ or $10^{11}$ vg of the AAV8-1.3HBV vectors. Four weeks later they were vaccinated with $5 \times 10^{10}$ vp of the AdC6-gDPolN vector. Control mice received only the AdC6-gDPolN vector. Naïve mice served as additional controls. Splenocytes were analyzed 6 weeks later for IFN-γ-producing CD8+ T cells in response to individual peptides spanning the PolN sequence. Results are provided in FIG. 20D-FIG. 20F.

Results—The presence of HBV, especially high titers of HBV such as after injection with the $10^{11}$ vg dose of AAV8-HBV1.3, not only reduced overall $CD8^+$ T cell responses to the PolN sequence as presented by the AdC6-gDPolN vaccine but also caused a shift in the epitope recognition profile.

Experiment #4—Functions of Hepatic PolN-Specific CD8+ T Cells in AAV8-1.3HBV Infected Mice Purpose—To evaluate if liver-infiltrating PolN-specific CD8⁺ T cells remain functional in AAV8-1.3HBV infected mice.

Methods—In the first experiment, C57BL/6 mice were injected i.v. with 3×10¹¹ vg of AAV8-1.3HBV. One group was vaccinated 8 weeks later with 5×10¹⁰ vp of AdC6-gDPolN vector. The other group was left unvaccinated. Mice were euthanized 4.5 months later and splenocytes were tested for frequencies of CD8⁺ T cells producing IFN-γ in response to the PolN peptide pool.

In the second experiment, mice were injected with graded concentrations of AAV8-1.3HBV (1×10¹⁰, 4×10¹⁰, or 1×10¹¹). All mice were vaccinated 4 weeks later with 5×10¹⁰ vp of the AdC6-gDPolN vector. The mice were boosted 2 months later with the same dose of the AdC7-gDPolN vector. Mice were euthanized 2 months later and lymphocytes were isolated from livers and tested for CD8⁺ T cells producing IFN-γ in response to the PolN peptide pool. Cells were also stained with an antibody to Tox, a transcription factor that increases in exhausted T cells.

Figure 21A:
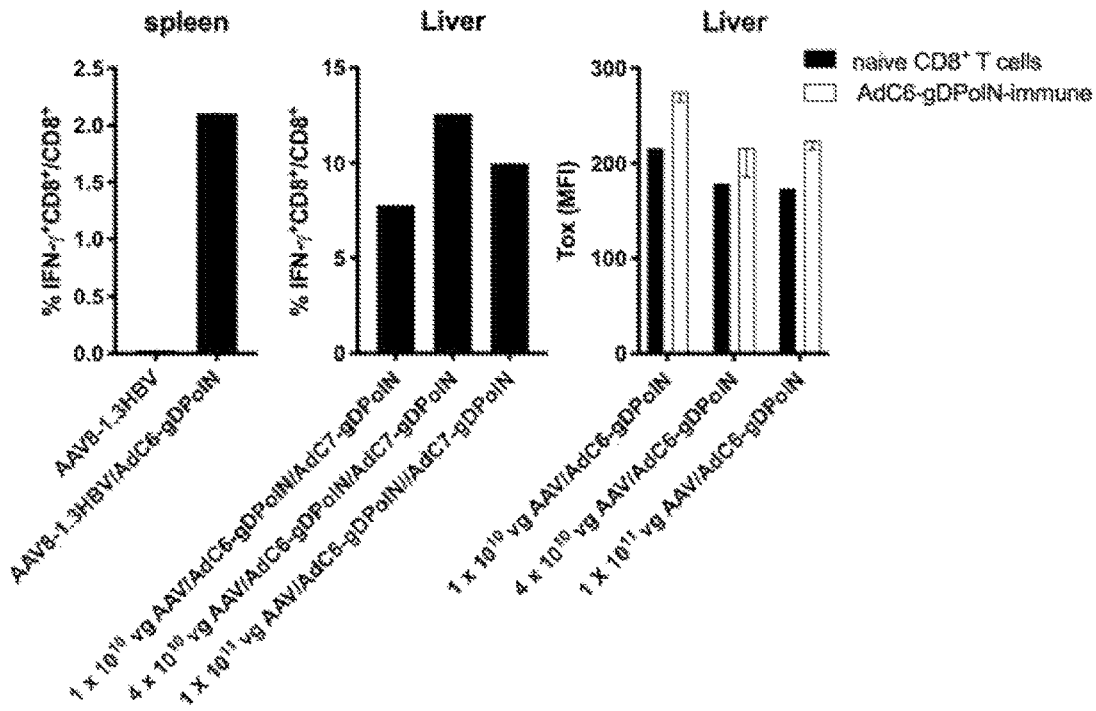
FIG. 21A and FIG. 21B illustrate the PolN-specific CD8+ T cells in the spleen or liver of mice.

Results—As shown in FIG. 21, vaccine-induced CD8⁺ T cells remained functional in mice that had been injected with the AAV8-1.3HBV vector.

Experiment #5—Effect of Vaccination of AAV8-1.3HBV Infected Mice on Liver Histology Purpose—To assess if AdC6/7-gDPolN vaccination of AAV.8-1.3HBV-vaccinated mice causes sustained liver damage.

Methods—Mice were injected with 10¹⁰ vg of the AAV8-1.3HPV given i.v. One month later they were vaccinated with 5×10⁹ vp of the AdC6-gDPolN vector. The mice were boosted 2 months later with the same dose of the AdC7-gDPolN vector given at the same dose. The mice were euthanized ~2 months later. Liver sections were collected and fixed in 10% formaldehyde. Sections (~3 µm in thickness) were prepared and stained with Hematoxylin Eosin (H&E). They were reviewed under a light microscope at 20× magnification.

Results—One out of 33 sections from mice that had received both the AAV vector and the vaccine showed a small lymphocytic infiltrate that was at the margin of the liver section.

Figure 21B:
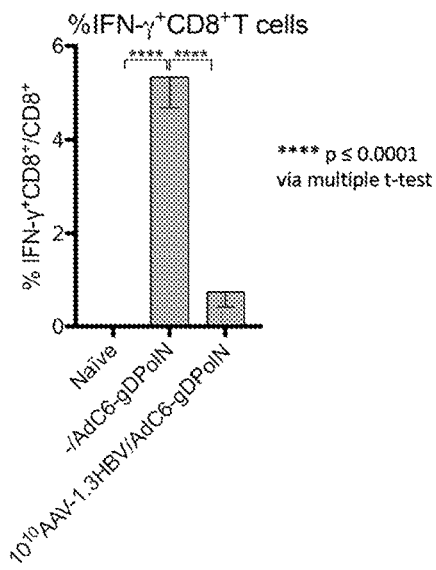

As shown in FIG. 21B, following a single gDPolN vaccination in HLA-A2-tg mice, frequencies of IFN-γ producing hepatic CD8⁺ T cells were reduced in mice receiving AAV as compared to those that had only been vaccinated.

Conclusions
- CD8⁺ T cell responses to PolN were reduced in AAV8-1.3HBV infected mice. Nevertheless, they remained detectable.
- Exhaustion markers were not increased in AAV8-1.3HBV pre-treated animals suggesting that the observed loss of PolN-specific CD8⁺ T cells in the presence of HBV was unlikely to be caused by classical CD8⁺ T cell exhaustion.
- AAV-induced HBV-infection caused a shift in the epitope recognition profile of CD8⁺ T cell responses to PolN.
- Vaccine-induced CD8⁺ T cells remained functional in mice that had been previously infected with the AAV8-1.3HBV vector.
- The vaccine used in a prime boost regimen did not cause overt liver damage in HBV positive mice.

Generation of HBV PolN-PolC-Core Constructs

Two multi-antigen inserts (second generation PolN-PolC-Core and third generation PolN-PolC-Core) were generated. The sequences of these inserts are shown below:

```
2nd generation HBV vaccine insert ("HBV2")
(Pol N (italics)-Pol C (underlined)-Core)
                               (SEQ ID NO: 174)
YIPLDKGIKPYYPEHAVNHYFQTRHYLHTLWK

AGILYKRETTRSASFCGSPYSWEQELQHGSCW

WLQFRNSKPCSEYCITHLVNILEDWGPCDEHG

EHHIRIPRTPARVTGGVFLVDKNPHNTAESRL

VVDFSQFSRGITRVSWPKFAVPNIQSLTNLLS

SNLSWESLDVQAFTFSPTYKAFLSKQYLNLYP

VARQRPGLCQVFADATPTGWGLAMGHQRMRGT

FVAPLPIHTAELLAACFARSRSGAKILGTDNS

VVLSRKYTSFPWLLGCAANWILRGTSFVYVPS

ALNPADDVGSNLEDPASRELVVSYVNVNMGLK

IRQLLWFHISCLTFGRETVIEYLVSFGVWIRT

PPAYRPPNAPILSTLPETTVVRRRDRGR

3rd generation HBV vaccine insert ("HBV3")
(Pol N (italics)-Pol C (underlined)-Core)
                               (SEQ ID NO: 175)
HFRKLLLLDEEAGPLEEELPRLADEGLNRRVA

EDLNIGNLPEWQTPSFPKIHLQEDIVDRCKQF

VGPLTVNEKRRLKLIMPARFYPNVTKYLPLDK

GIKPYYPEHAVNHYFQTRHYLHTLWKAGILYK

RETTRSASFCGSPYSWEQELQHGSCWWLQFRN

SKPCSEYCLTHLVNLLEDWGPCDEHGEHHIRI

PRTPARVTQAFTFSPTYKAFLSKQYLNLYPVA

RQRPGLCQVFADATPTGWGLAMGHQRMRGTFV

APLPIHTAELLAACFARSRSGAKILGTDNSVV

LSRKYTSFPWLLGCAANWILRGTSFVYVPSAL

NPADDVGSNLEDPASRELVVSYVNVNMGLKIR

QLLWFHISCLTFGRETVIEYLVSFGVWIRTPP

AYRPPNAPILSTLPETTVVRRRDRGR
```

The second generation HBV ("HBV2") insert includes immuno-dominant PolN epitopes identified from mice that had not been infected with the AAV8-1.3HBV vector prior to vaccination. Many of these epitopes were found to be lost in a mouse model of chronic HBV infection brought about by pre-administering an AAV8-1.3HBV vector (as defined in "Epitope Shifting" above). The third generation HBV ("HBV3") insert selects for contiguous regions of PolN that were preferentially recognized by mice with high loads of HBV (see above). Regions of Core and PolC were selected for both constructs using the following general formula: regions with the highest immune responses on either prime (FIG. 3) or boost (FIG. 5) regions in C57Bl/6, BALBc and HLA-A2 tg mice, and with the aim of selecting a large contiguous region instead of selecting unique epitopes and inserting spacer sequences between them.

Genetic Integrity and Stability of the 2$^{nd}$ and 3$^{rd}$ Generation HBV Inserts (HBV2 and HBV3)

Western Blot—Purified recombinant viral vector preparations (AdC6-gDHBV2, AdC6-gDHBV3, AdC7-gDHBV2, and AdC7-gDHBV3) were evaluated for their ability to elicit transgene-product expression in vitro. To that end, Western Blot assays were performed to assess the expression of gD protein in cell lysates following cell culture infection with the vector of interest. Adherent HEK293 cell monolayers were infected with known quantities of the purified vector and harvested at 48 hours post-infection, resuspended in lysis and extraction buffer containing protease inhibitors, and lysed by sonication. The total protein extracts were denatured by the use of dithiothreitol as a redox agent and submitted to electrophoresis in a 12% Bis-Tris polyacrylamide gel (PAGE). Subsequent to protein separation by SDS-PAGE, the samples were transferred onto an activated polyvinylidene difluoride membrane by wet electrophoretic transfer. The membrane was immunostained for the detection of gD protein using the primary antibody to gD diluted to 1:1000 in saline (clone PA1-30233, Invitrogen, Carlsbad, CA) for 1 h at room temperature. Membranes were washed with 1× TBS-T prior to incubating with HRP-conjugated goat anti-rabbit secondary IgG (ab6721, Abcam, Cambridge UK) for 1 h at room temperature. This was followed by the addition of a luminol-based chemiluminescent substrate. The stained membrane was exposed to an autoradiography film and signal emission was evaluated after processing by an automated film developer. Following documentation of the gD protein expression in infected HEK293 cell lysates, the membrane was stripped and re-probed for the presence of β-actin in the total protein extract samples. This staining step was employed to evaluate the consistency of the PAGE sample loading step and thus better support the semi-quantitative analysis of the in vitro stimulation of gD protein expression by the recombinant viral vector.

Stability—To ensure the genetic integrity of the viral construct, the genetic stability of each recombinant viral vector lot was assessed through sequential viral passages in adherent HEK293 cell cultures. The recombinant virus pool resulting from each transfection was cultured under standard growing conditions for a total of 12 passages. In the last passage, the virus pool was expanded and the crude harvest purified by cesium chloride gradient. Following vector purification, viral DNA was isolated using the QIAGEN DNeasy Blood & Tissue Kit and evaluated by restriction enzyme digest with Ase I and Bgl II, two restriction enzymes that cleave the DNA template in distinct construct-specific pre-defined banding patterns. After digestion, samples were submitted to electrophoresis in 1% agarose gel containing ethidium bromide to allow for the visualization of the digested bands, followed by documentation of results using a digital gel imaging system. Viral preparations that exhibited banding patterns identical to those of an early passage virus were considered to have maintained the original molecular clone structure and thus deemed stable at the end of 12 viral passages.

Results—The banding patterns of viral vector DNAs remained stable after 12 passages compared to that after 5 passages indicating the vector genomes were stable (data not shown).

Immunogenicity of the 2$^{nd}$ and 3$^{rd}$ Generation HBV Inserts (HBV2 and HBV3) as Expressed by AdC6 or AdC7 Vectors Purpose—To assess CD8$^+$ T cell responses to the HBV2 and HBV3 inserts expressed by AdC6 vectors or AdC7 vectors.

Methods—Groups of C57Bl/6 mice were injected with 5×10$^9$ or 5×10$^{10}$ vp of AdC6-gDHBV2 or AdC6-gDHBV3 vector. Mice injected with the same doses of the AdC6-gDPolN vector served as positive controls; naïve mice served as negative controls. Mice were bled 14 days later and PBMCs were tested for frequencies of CD8$^+$ T cells producing IFN-γ in response to peptide pools corresponding to the HBV inserts. Four weeks later (6 weeks after vaccination) mice were bled again and tested with the PolN-specific tetramer. AdC6-gDHBV3 immunized mice were excluded as this insert lacks the epitope that corresponds to the tetramer.

Groups of C57Bl/6 mice were injected with 5×10$^9$ or 5×10$^{10}$ vp of AdC7-gDHBV2 or 5×10$^{10}$ vp of AdC7-gDHBV3 vector. Naïve mice served as negative controls. Mice were bled 14 days later and PBMCs were tested for frequencies of CD8$^+$ T cells producing IFN-γ in response to peptide pools corresponding to the HBV inserts.

Immunogenicity of AdC7 Prime/AdC6 Boost

Mice were bled ~4 weeks later and PBMCs were retested by ICS for CD8$^+$ T cells producing IFN-γ and/or TNF-α in response to the peptides for the inserts. Mice were boosted two months after the prime with the same dose of the heterologous vector expressing the same insert. PBMCs were tested by ICS 2 weeks later and pre- and post-boost CD8$^+$ and CD4$^+$ T cell responses were compared. The AdC7-gDHBV2 vector induced robust frequencies of CD8$^+$ T cells producing IFN-γ and/or TNF-α after the prime. Frequencies increased after the AdC6-gDHBV2 boost and this was especially pronounced after the low vector doses and for CD8$^+$ T cells producing IFN-γ. The AdC7-gDHBV3 vector was poorly immunogenic but CD8+ T cell responses became positive after the AdC6-gDHBV3 boost. In the same token CD4+ T cell responses were marginal after the prime but increased after the boost. There was no marked difference in CD4 responses to the HBV2 or HBV3 insert.

Figure 22A:
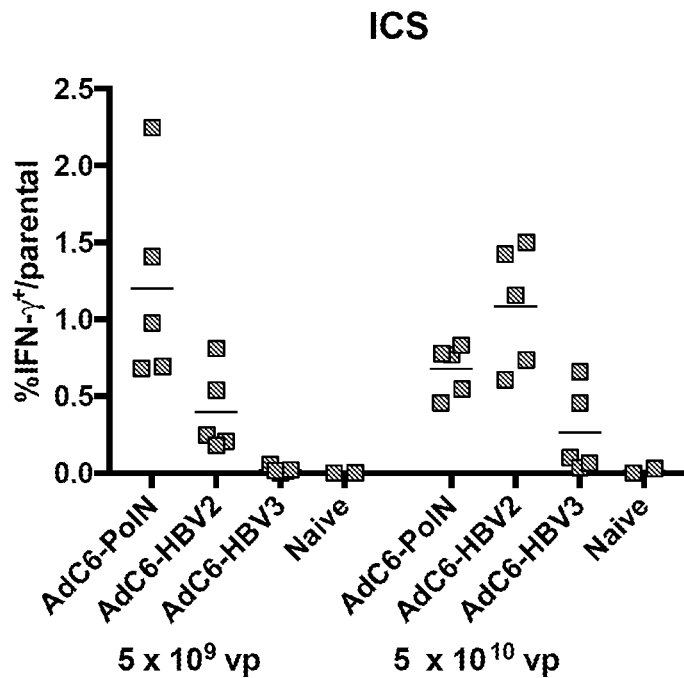
FIG. 22A and FIG. 22B illustrate A) CD8+ T cell frequencies in the blood of mice injected with the indicated AdC6 vectors; and B) frequencies of tetramer+CD8+ T cells.
Figure 22B:
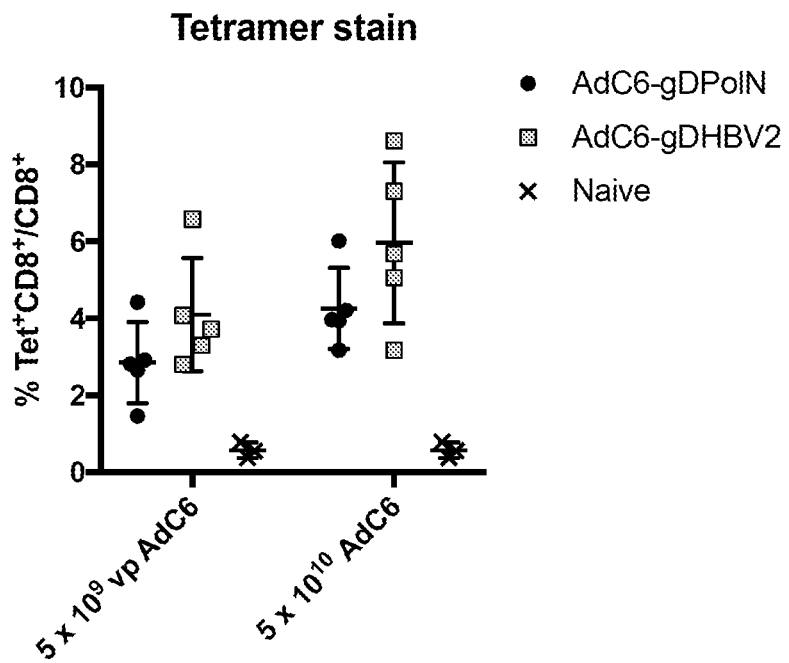
Figure 23:
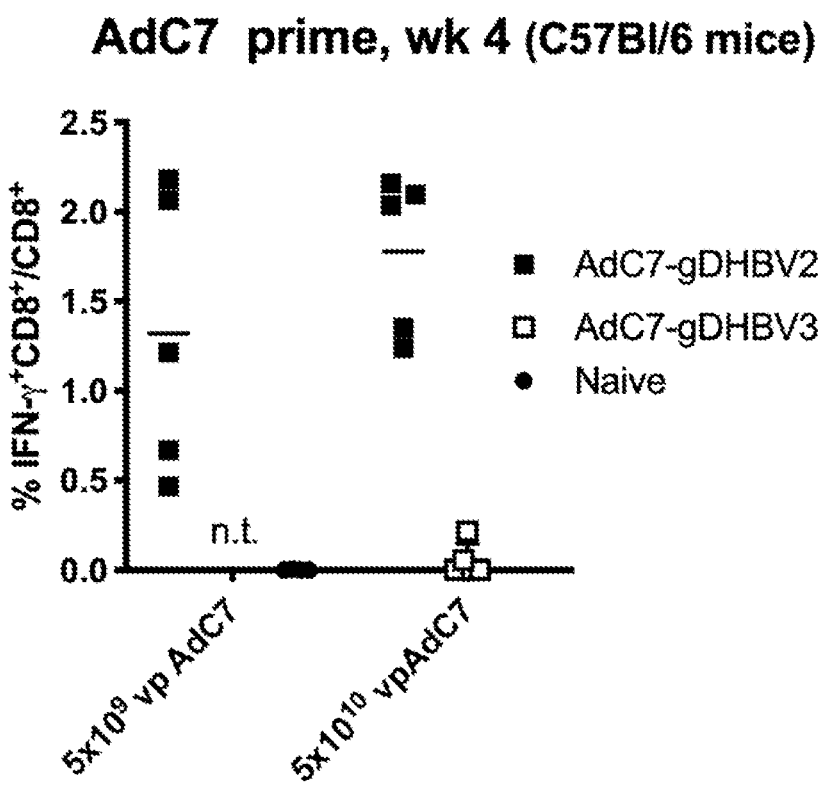
FIG. 23 illustrates CD8+ T cell frequencies in the blood of mice injected with the indicated AdC7 vectors.
Figure 24A:
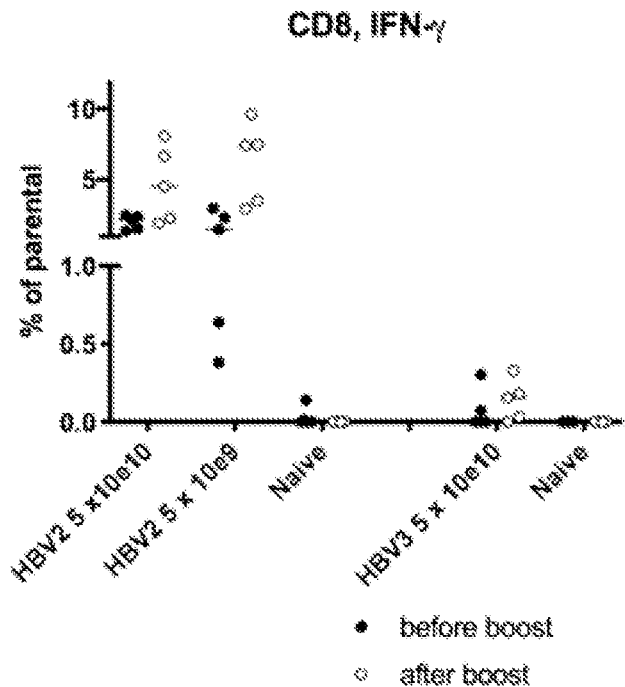
FIG. 24A, FIG. 24B, FIG. 24C, FIG. 24D, FIG. 24E, and FIG. 24F illustrate CD8$^+$ (FIG. 24A-FIG. 24C) and CD4+ (FIG. 24D-FIG. 24F) T cell frequencies to the gDHBV2 and gDHBV3 inserts in blood of mice injected with the indicated AdC7 vectors ("after prime") and then boosted with the corresponding AdC6 vectors ("after boost"). Graphs show frequencies of T cells producing IFN-γ, frequencies of T cells producing TNF-α, and the sum of frequencies of T cells producing either cytokine.
Figure 24B:
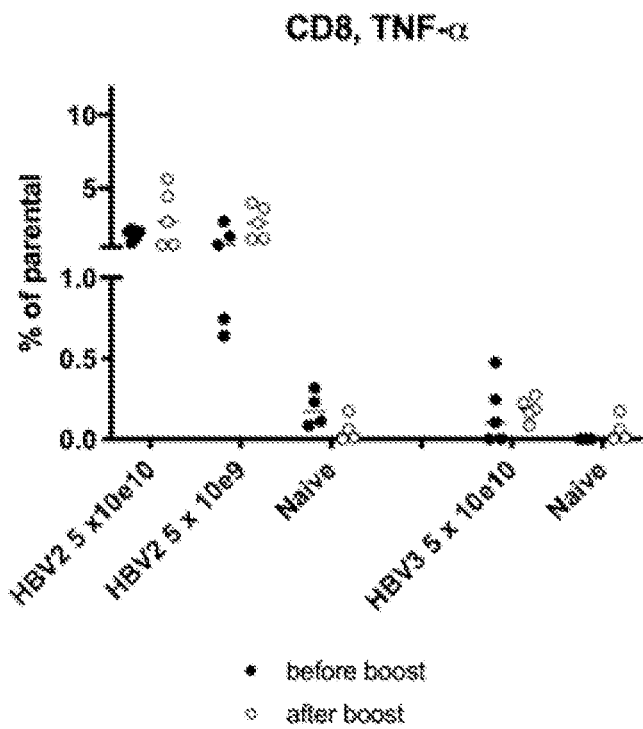
Figure 24C:
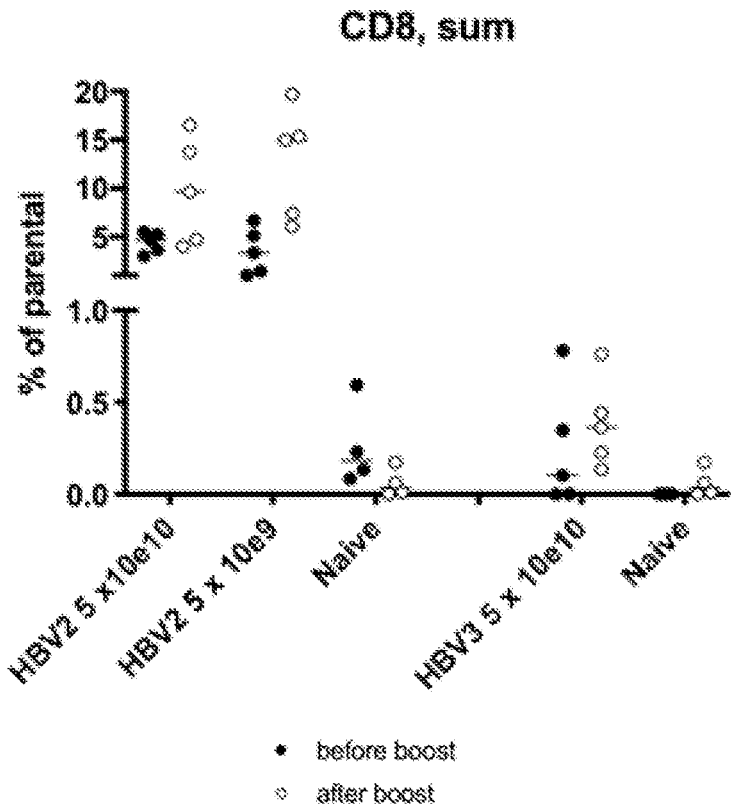
Figure 24D:
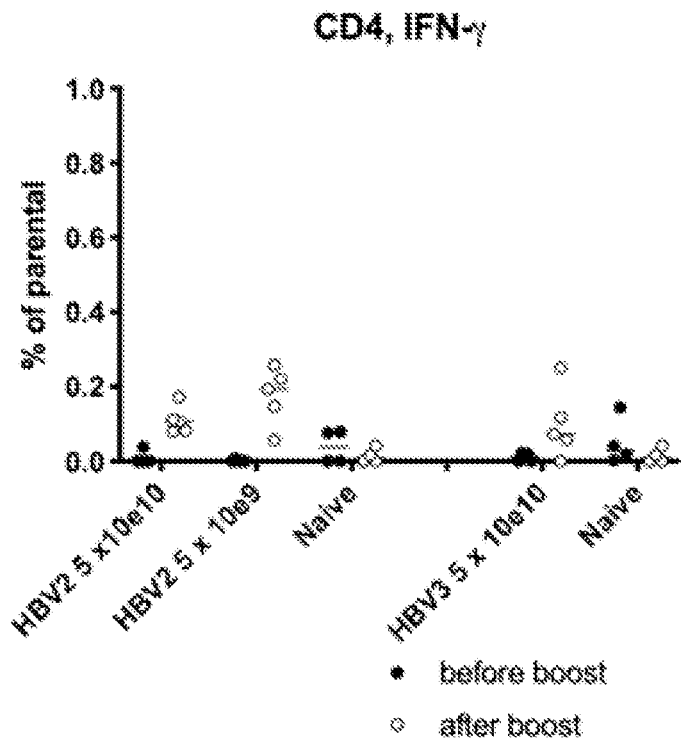
Figure 24E:
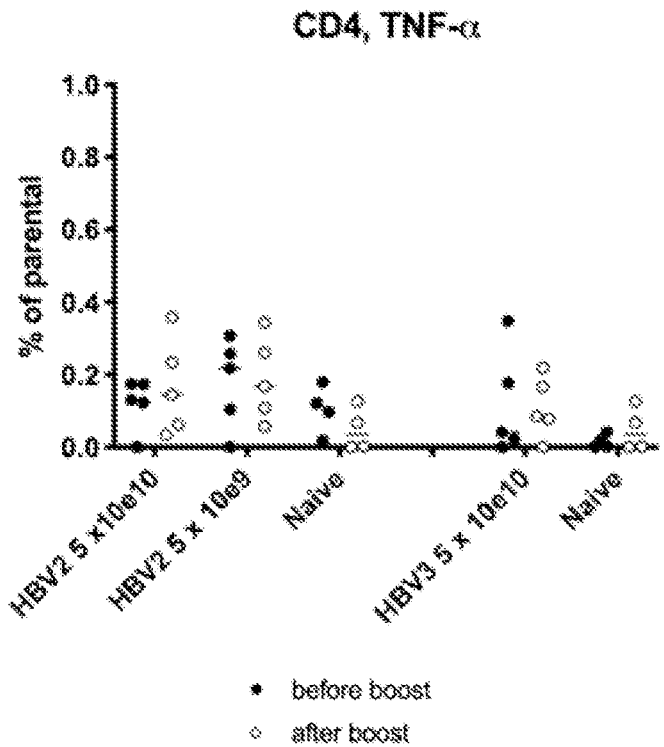
Figure 24F:
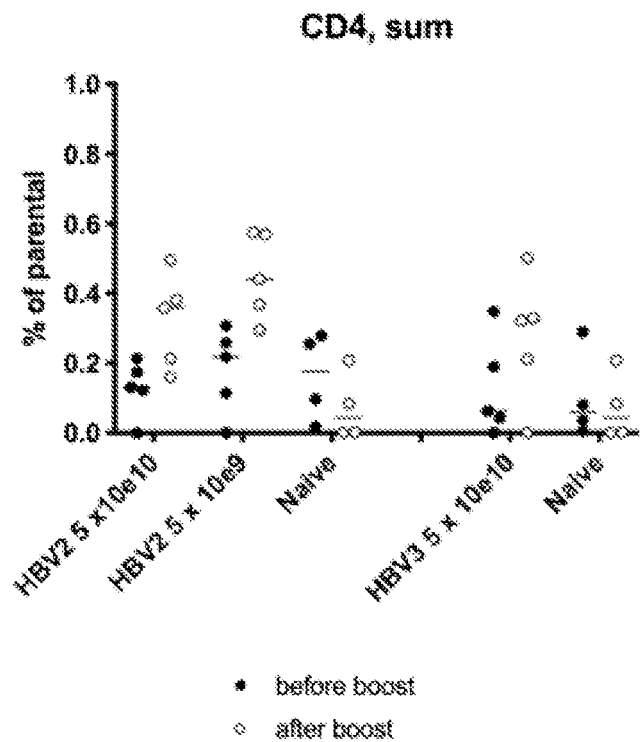

Conclusions
  Both the AdC6-gDHBV2 and AdC7-gDHBV2 vectors were highly immunogenic (FIG. 22A, FIG. 22B, and FIG. 23) and responses increased after a boost with a heterologous AdC vector expressing the same insert (FIG. 24).
  The AdC7-gDHBV2 and AdC7-gDHBV3 vectors displayed borderline immunogenicity consistent with their design as they lack the epitope that corresponds to the tetramer being used (FIG. 22A and FIG. 23).
  Boosting AdC7-gDHBV2 with AdC6-gDHBV2 enhances CD8$^+$ T cell responses.

Comparison of HBV DNA Viral Titers in AdC6-gDPolN, AdC6-gDHBV2, AdC6-gDHBV3, or AdC6-HBV2 AAV-Infected Mice Methods Five groups of C57Bl/6 mice were challenged with 1×10$^9$ vg of AAV8-1.3HBV and were vaccinated 4 weeks later with 1×10$^{10}$ vp of either AdC6-gDPolN (n=10), AdC6-gDHBV2 (n=10), AdC6-gDHBV3 (n=10), or AdC6-HBV2 without gD (n=10); AAV-infected, non-vaccinated animals ("naive") (n=10) and non-AAV-infected, non-vaccinated animals (n=2-5) served as controls. Viral titers were tested 4 weeks after AAV injection (before vaccination) and compared to levels 4 weeks after vaccination (week 8 after AAV injection).

Results

Figure 25A:
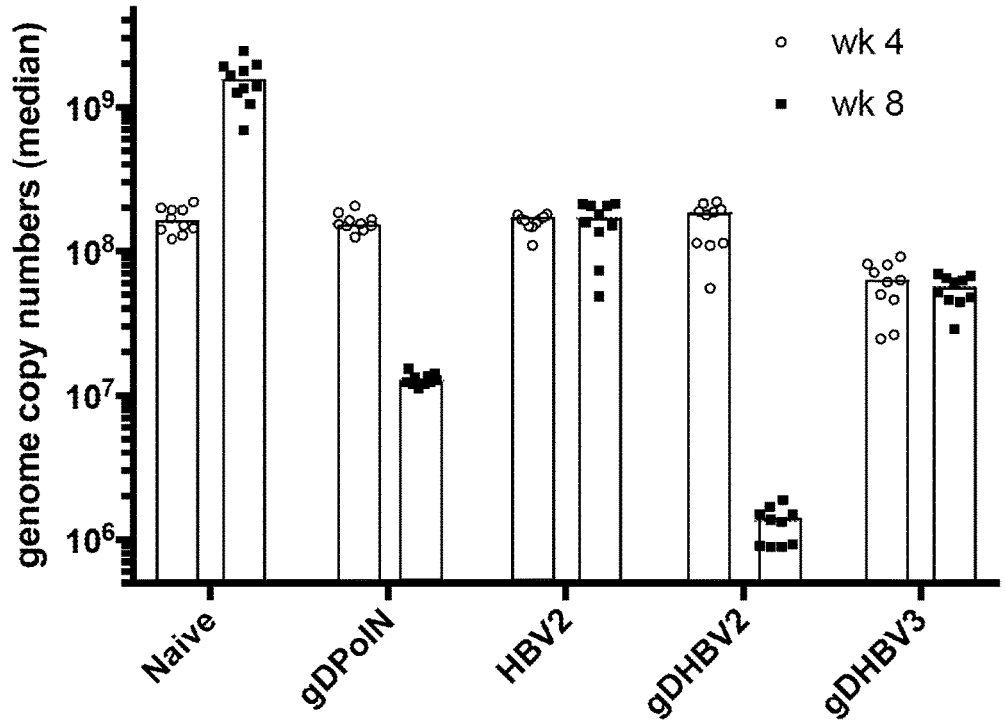
FIG. 25A and FIG. 25B illustrate the HBV DNA viral titer in C57Bl/6 mice that were challenged with 1×10 9 vg of AAV8-1.3HBV and were vaccinated 4 weeks later with 1×10$^{10}$ vp of AdC6-gDPolN ("gDPolN"), AdC6-gDHBV2 ("gDHBV2"), AdC6-gDHBV3 ("gDHBV3"), or AdC6-HBV2 without gD ("HBV2"); AAV-infected, non-vaccinated animals ("naïve"), and non-AAV-infected, non-vaccinated animals (data not shown) served as controls.
Figure 25B:
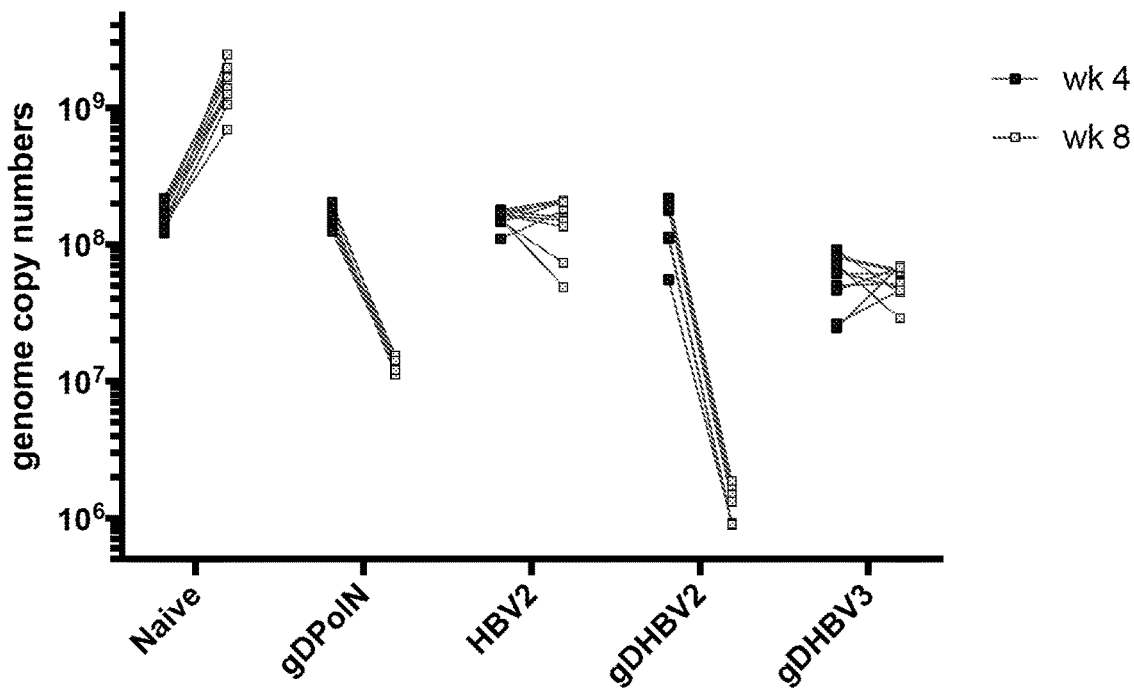

At week 8, the median HBV viral titers increased by 0.98 log$_{10}$ cps/mL in naïve mice, remained unchanged in AdC6-HBV2 vaccinated mice, and declined by −0.04, −1.09 and −2.13 log$_{10}$ cps/mL in AdC6-gDHBV3, AdC6-gDPolN and AdC6-gDHBV2 vaccinated animals, respectively (FIG. 25A). The results for individual mice are shown in FIG. 25B—all AdC6-gDPolN and AdC6-gDHBV2 vaccinated animals had greater than 1 and 2 $\log_{10}$ copies/mL declines, respectively; in contrast, none of the naïve, AdC6-HBV2, or AdC6-gDHBV3 vaccinated animals had a 1 $\log_{10}$ copies/mL or greater decline at Week 8.

Immunogenicity Studies for gDHBV2 and gDHBV3

The induction of CD8+ T cell responses and their breadth to segments of HBV core and polymerase contained in either gDHBV2 or gDHBV3 following a single prime injection or prime followed by a boost vaccination with a heterologous vector containing the same insert were evaluated.

Experiment 1

Purpose: Assess IFN-γ+ CD8+ T cell responses following prime and boost vaccinations with gD-HBV2 and gD-HBV3 expressed by heterologous chimpanzee adenoviral vectors (AdC6 and AdC7) in C57Bl/6 mice.

Methods: Four groups of five C57Bl/6 mice were immunized via intramuscular injection as follows: (a) $5 \times 10^{10}$ vp AdC7-gDHBV2 followed two months later by $5 \times 10^{10}$ vp AdC6-gDHBV2; (b) $5 \times 10^{9}$ vp AdC7-gDHBV2 followed two months later by $5 \times 10^{9}$ vp AdC6-gDHBV2; (c) $5 \times 10^{10}$ vp AdC7-gDHBV3 followed two months later by $5 \times 10^{10}$ vp AdC6-gDHBV3; or (d) no vaccine. Blood was assessed by ICS for IFN-γ+ CD8+ T cell responses 2 and 6 weeks after the prime, prior to the boost, and then 2 and 4 weeks after the boost.

Figure 26B:
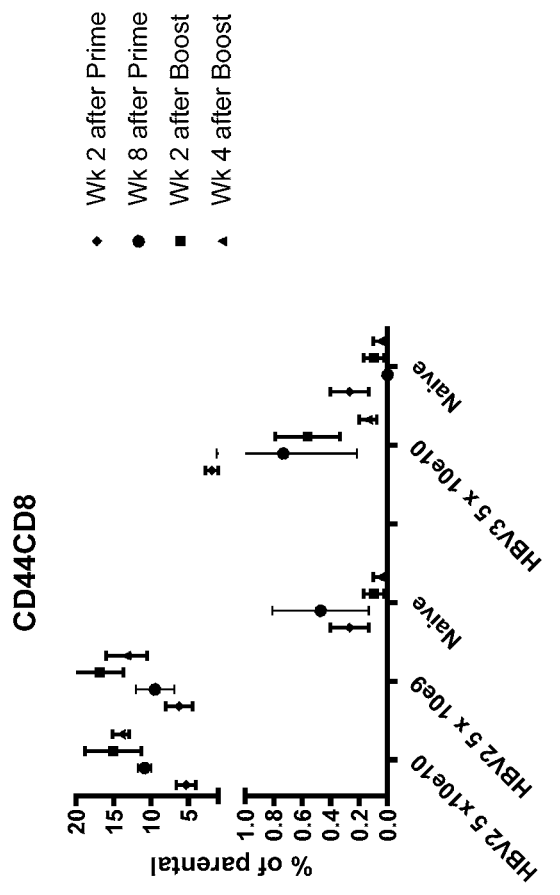
FIG. 26A, FIG. 26B, FIG. 26C, and FIG. 26D illustrate the percent of parental IFN-γ and/or TNF-α producing CD8$^+$ T cells (FIG. 26A), CD44+ CD8+ T cells (FIG. 26B), CD4+ T cells (FIG. 26C) or CD44+CD4+ T cells (FIG. 26D) two and eight weeks after prime and two and four weeks after the boost (as the mean) using the indicated construct.
Figure 26A:
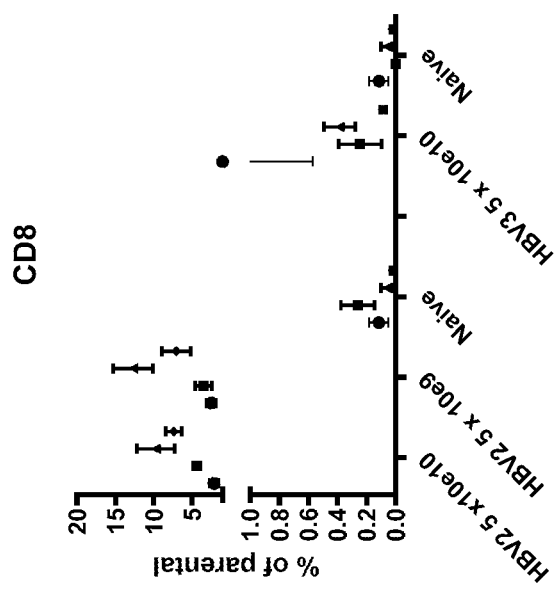
Figure 26D:
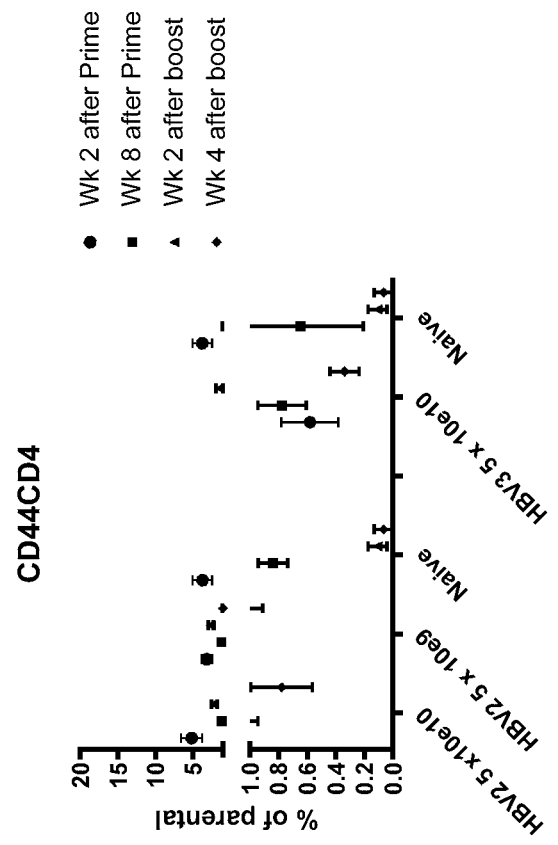
Figure 26C:
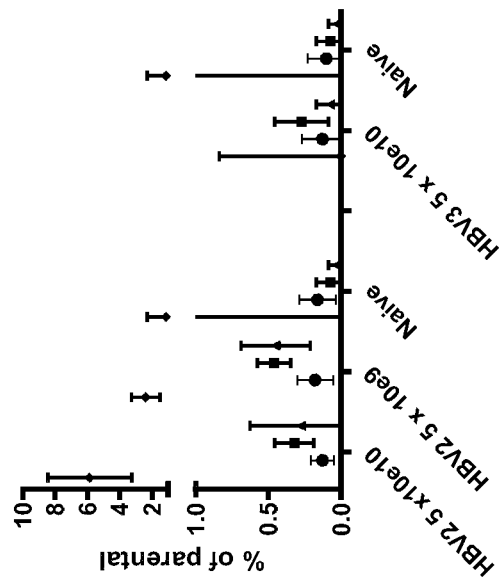

Results: At all time points tested each vaccine construct was found to induce IFN-γ+ CD8+ T cells. FIG. 26 shows the percent of parental IFN-γ and/or TNF-α producing CD8+ T cells (FIG. 26A), CD44+CD8+ T cells (FIG. 26B), CD4+ T cells (FIG. 26C) or CD44+CD4+ T cells (FIG. 26D). Immune responses as assessed by ICS from PBMCs of individual mice are shown two and eight weeks after the prime, as well as two and four weeks after the boost as the mean.

Experiment 2

Purpose: Compare IFN-γ+ CD8+ T cell responses following different doses of prime and boost vaccinations with gD-HBV2 and gD-HBV3 to that with gD-PolN using heterologous chimpanzee adenoviral vectors (AdC6 and AdC7) in C57Bl/6 mice.

Methods: Groups of C57Bl/6 mice (n=5 mice/group) were immunized as follows:

gDPolN Groups
(a) $5 \times 10^{9}$ vp AdC6-gDPolN followed three months later by $5 \times 10^{9}$ vp AdC7-gDPolN; and
(b) $5 \times 10^{10}$ vp AdC6-gDPolN followed three months later by $5 \times 10^{10}$ vp AdC7-gDPolN gDHBV2 Groups
(c) $5 \times 10^{9}$ vp AdC6-gDHBV2 followed three months later by $5 \times 10^{9}$ vp AdC7-gDHBV2 and;
(d) $5 \times 10^{10}$ vp AdC6-gDHBV2 followed three months later by $5 \times 10^{10}$ vp AdC7-gDHBV2 gDHBV3 Groups
(e) $5 \times 10^{9}$ vp AdC6-gDHBV3 followed three months later by $5 \times 10^{9}$ vp AdC7-gDHBV3 and;
(f) $5 \times 10^{10}$ vp AdC6-gDHBV3 followed three months later by $5 \times 10^{10}$ vp AdC7-gDHBV3

No Treatment Served as Controls

For all treatment groups, immunogenicity CD8+ T cell responses was from blood assessed by ICS for IFN-γ+ at two and six weeks after the prime, prior to the boost, and then two and six weeks after the boost. Immunogenicity was also assessed by tetramer staining using an APC-labeled MHC class I tetramer (NIH tetramer Facility, Emory University, Atlanta GA) corresponding to amino acids 396-404 FAVPNLQSL (peptide 55) of the HBV polymerase at week four after the prime. HBV3 does not contain the FAVPNLQSL peptide.

Figures 27A, 27B, 27C:
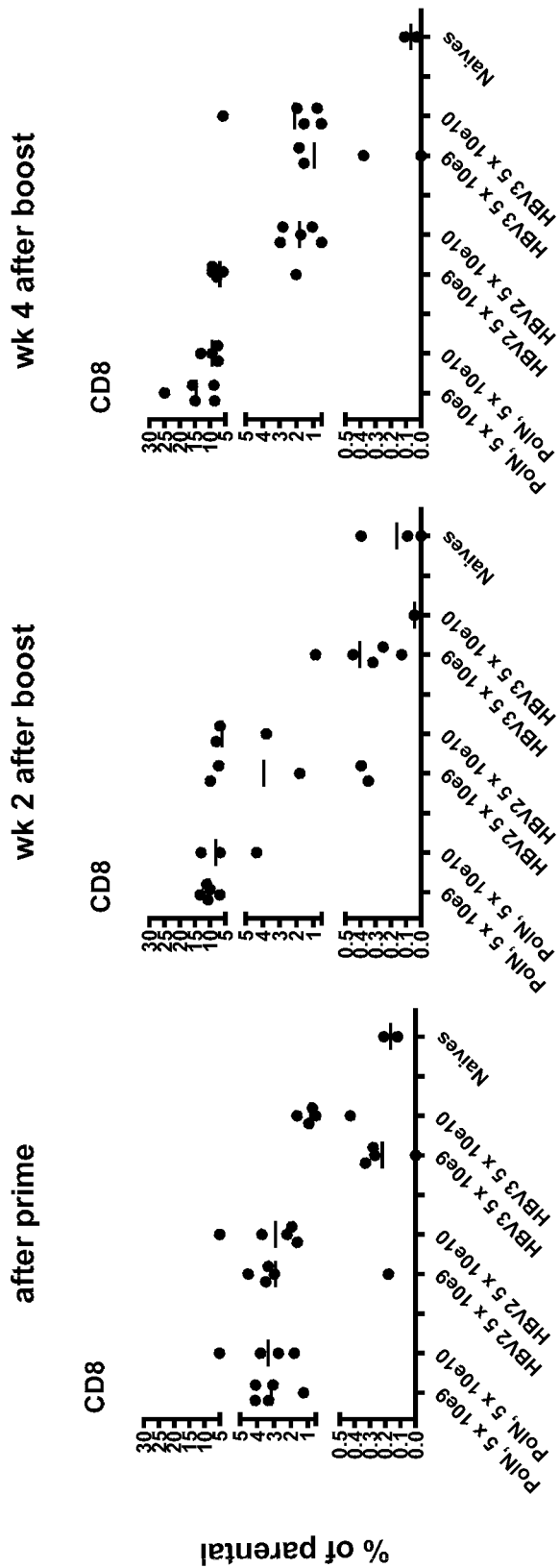
FIG. 27A, FIG. 27B, and FIG. 27C illustrate CD8+ T cells at multiple time points: four weeks after prime (FIG. 27A); two weeks after the boost (FIG. 27B); and four weeks after the boost (FIG. 27C) with the indicated constructs (PolN=gDPolN; HBV2=gDHBV2; HBV3=gDHBV3). The graph shows the overall frequencies of CD8+ T cells producing IFN-γ+ as assessed by ICS.

Results: At all time points, each vaccine tested was found to induce IFN-γ+ CD8+ T cells. Results obtained with the gDHBV2 vaccine were similar to those obtained with the gDPolN vaccine; the gDHBV3 vaccine was less immunogenic. Upon tetramer staining, frequencies of the specific CD8+ T cells were comparable between the two vaccines; a number of activation markers tended to be more highly expressed on tetramer+CD8+ T cells from the gDHBV2-immunized groups. FIG. 27 shows CD8+ T cells at multiple time points: four weeks after prime (FIG. 27A); two weeks after the boost (FIG. 27B); and four weeks after the boost (FIG. 27C). The graph shows the overall frequencies of CD8+ T cells producing IFN-γ+ as assessed by ICS.

Figures 28A, 28B, 28C:
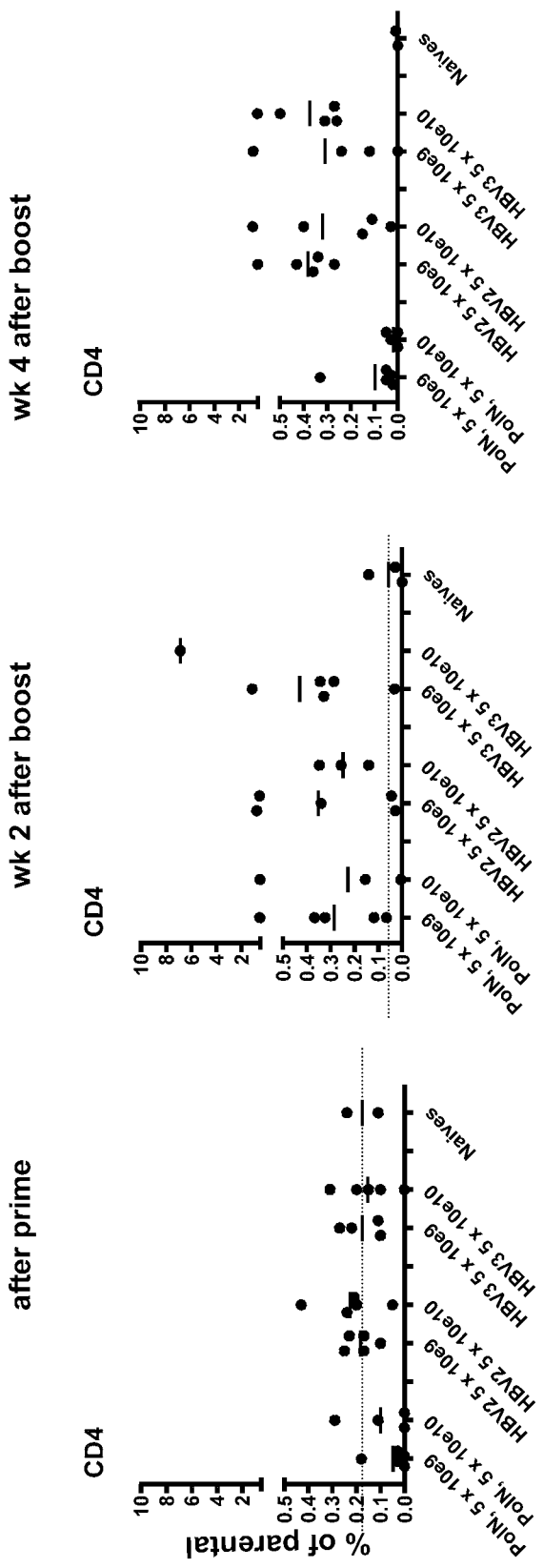
FIG. 28A, FIG. 28B, and FIG. 28C illustrate cytokine-producing CD4+ T cells at multiple time points: four weeks after prime (FIG. 28A); two weeks after the boost (FIG. 28B); and four weeks after the boost (FIG. 28C) with the indicated constructs (PolN=gDPolN; HBV2=gDHBV2; HBV3=gDHBV3) as assessed by ICS. The dashed line indicates the cut-off for positive responses, based on the results from the naïve mice.

FIG. 28 shows cytokine-producing CD4+ T cells at multiple time points: four weeks after prime (FIG. 28A); two weeks after the boost (FIG. 28B); and four weeks after the boost (FIG. 28C) as assessed by ICS. The dashed line indicates the cut-off for positive responses, based on the results from the naïve mice.

Figure 29A:
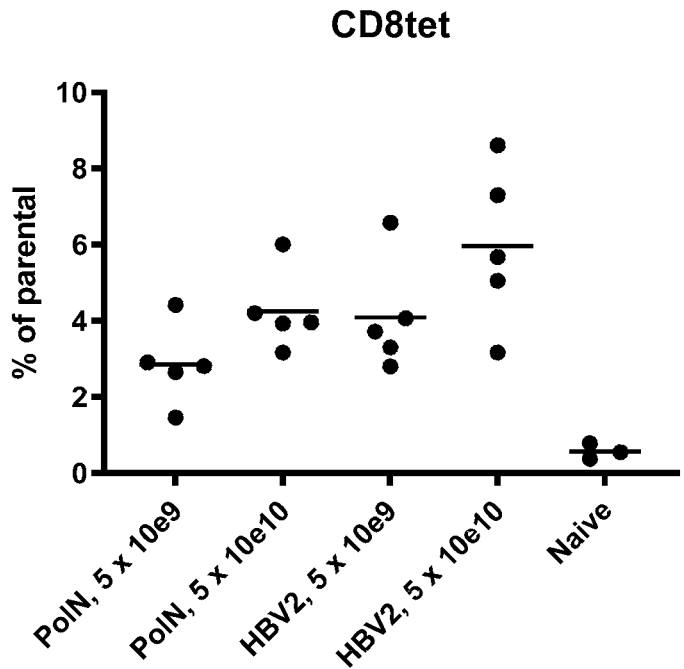
FIG. 29A and FIG. 29B illustrate the results of tetramer staining gated on either CD8+ T cells (FIG. 29A) or CD44+ CD8+ T cells (FIG. 29B) at four weeks after the prime with the indicated construct (PolN=gDPolN; HBV2=gDHBV2).
Figure 29B:
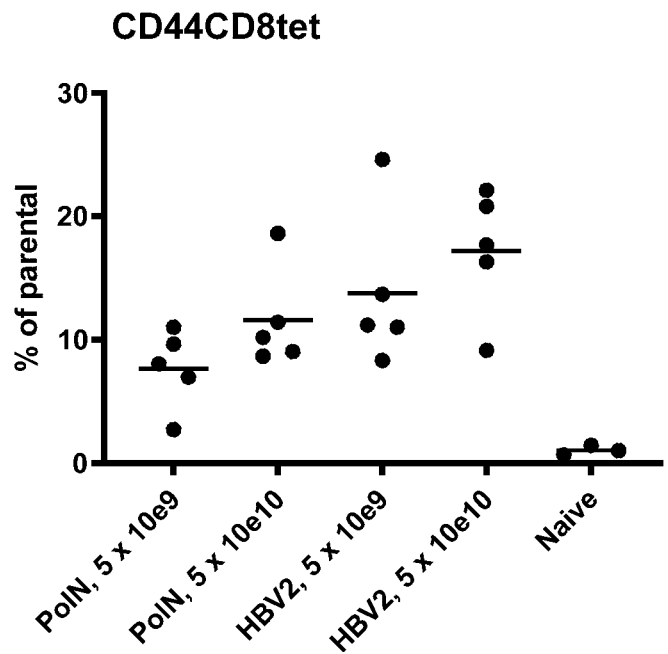

FIG. 29 shows the results of tetramer staining gated on either CD8+ T cells (FIG. 29A) or CD44+CD8+ T cells (FIG. 29B) at four weeks after the prime.

Figures 30A, 30B, 30C:
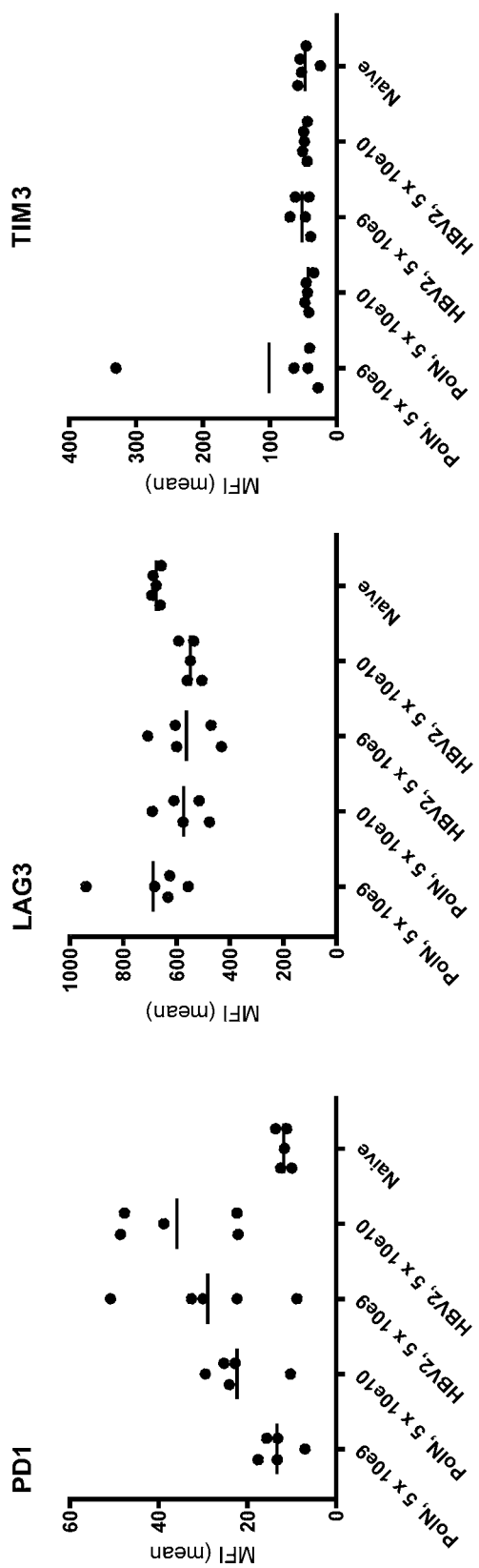

FIG. 30 shows the phenotypes of the tetramer+CD8+ T cells shown as the mean fluorescent intensity of a dye linked to the indicated antibody: FIG. 30A anti-PD1 antibody conjugated to BV605; FIG. 30B anti-LAG3 antibody conjugated to BV650; FIG. 30C anti-TIM3 antibody conjugated to Pe-Cy7-A; FIG. 30D anti-CTLA4 antibody conjugated to PE-A; FIG. 30E anti-EOMES antibody conjugated to AF488; and FIG. 30F anti-T-bet antibody conjugated to BV786.

Experiment 3

The breadth of responses were assessed from pooled splenocytes of vaccinated C57BL/6 mice which were tested by ICS against the individual peptides present in the HBV vaccine inserts.

Methods: Four groups of five C57Bl/6 mice were immunized via intramuscular injection as follows: (a) $5 \times 10^{10}$ vp AdC7-gDHBV2 followed two months later by $5 \times 10^{10}$ vp AdC6-gDHBV2; (b) $5 \times 10^{9}$ vp AdC7-gDHBV2 followed two months later by $5 \times 10^{9}$ vp AdC6-gDHBV2; (c) $5 \times 10^{10}$ vp AdC7-gDHBV3 followed two months later by $5 \times 10^{10}$ vp AdC6-gDHBV3; or (3) no vaccine. Animals were sacrificed eight weeks after the boost and pooled splenocytes were assessed by ICS for IFN-γ+ CD8+ T cell responses to individual HBV2 or HBV3 peptides (cut-off for positive responses set at 0.1%).

Figure 31:
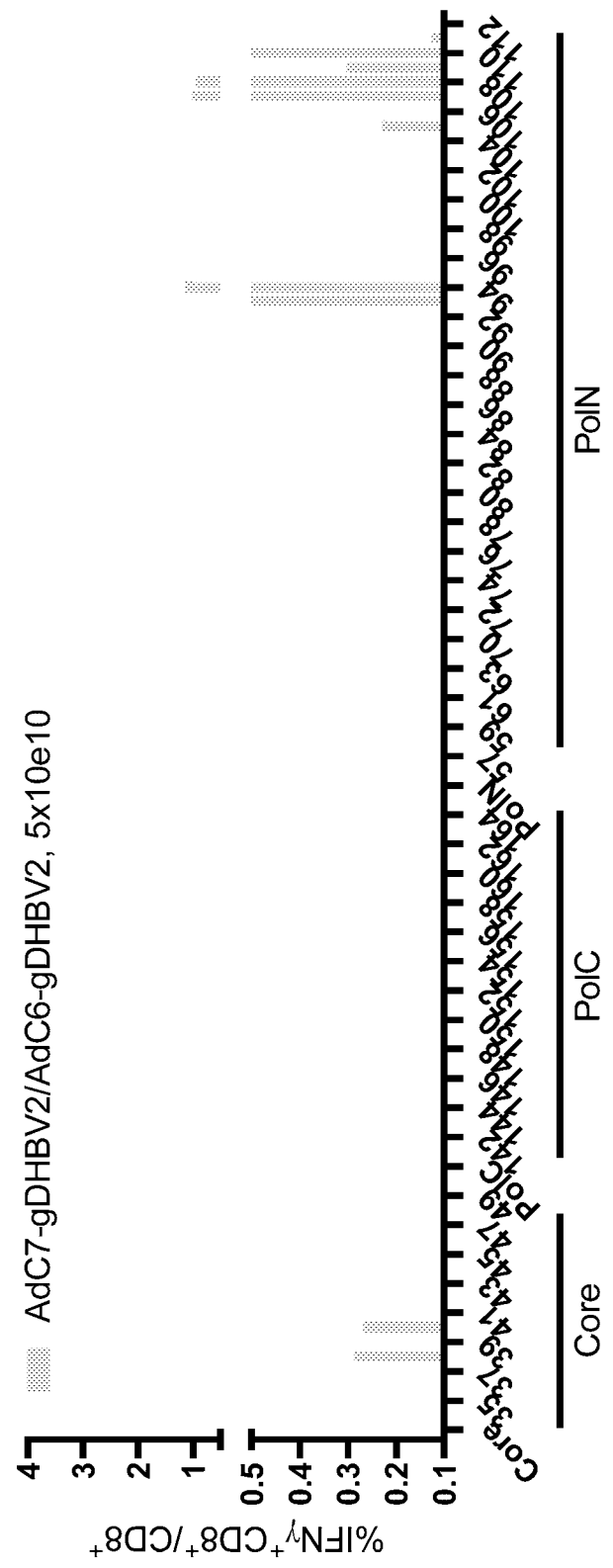
FIG. 31 illustrates the CD8+ T cell responses after a prime vaccination of $5\times10^{10}$ vp AdC7-gDHBV2 followed two months later by vaccination with $5\times10^{10}$ vp AdC6-gDHBV2. Numbers on the X axis correspond to the SEQ ID NO as provided herein.
Figure 32:
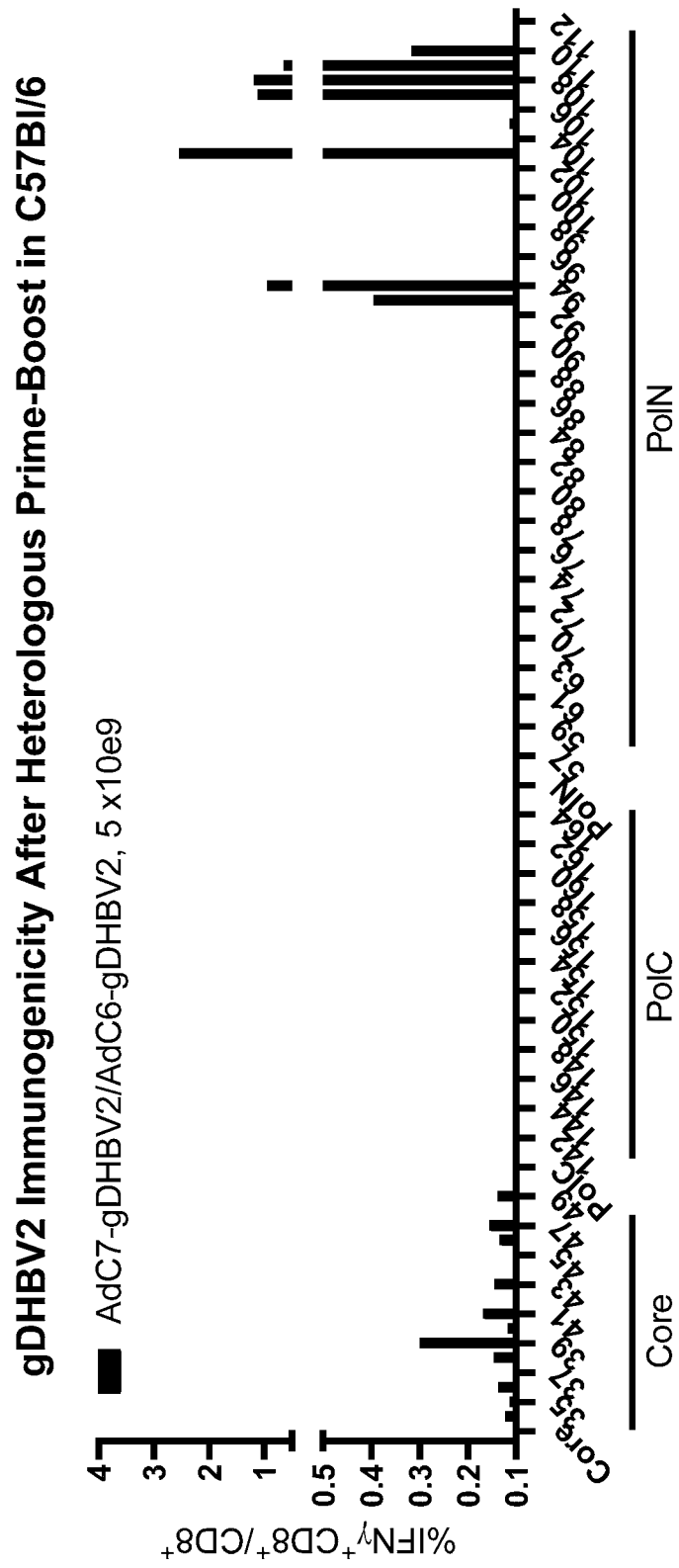
FIG. 32 illustrates the CD8+ T cell responses after a prime vaccination with $5\times10^9$ vp AdC7-gDHBV2 followed two months later by vaccination with $5\times10^9$ vp AdC6-gDHBV2. Numbers on the X axis correspond to the SEQ ID NO as provided herein.
Figure 33:
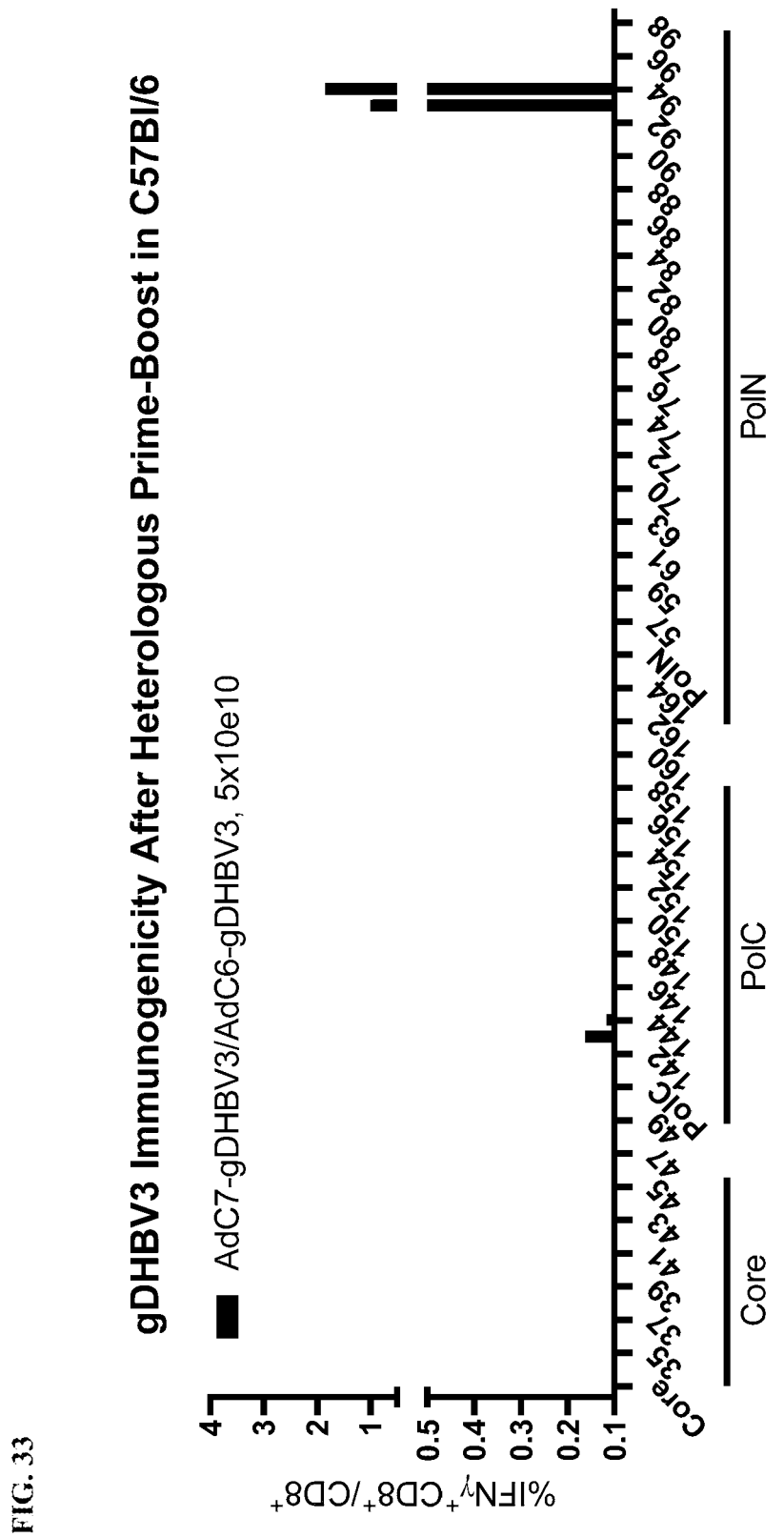
FIG. 33 shows the immunogenicity after a prime vaccination with $5\times10^{10}$ vp AdC7-gDHBV3 followed two months later by vaccination with $5\times10^{10}$ vp AdC6-gDHBV3. Numbers on the X axis correspond to the SEQ ID NO as provided herein.

Results: Independent of the dose, the prime boost regimen with the gDHBV2 vaccines induced responses to several epitopes within core and polymerase. FIG. 31 shows the CD8+ T cell responses after a prime vaccination of $5 \times 10^{10}$ vp AdC7-gDHBV2 followed two months later by vaccination with $5 \times 10^{10}$ vp AdC6-gDHBV2. Numbers on the X axis correspond to the SEQ ID NO as provided herein. FIG. 32 shows the CD8+ T cell responses after a prime vaccination with $5 \times 10^{9}$ vp AdC7-gDHBV2 followed two months later by vaccination with $5 \times 10^{9}$ vp AdC6-gDHBV2. Numbers on the X axis correspond to the SEQ ID NO as provided herein. FIG. 33 shows the immunogenicity after a prime vaccination with $5 \times 10^{10}$ vp AdC7-gDHBV3 followed two months later by vaccination with $5 \times 10^{10}$ vp AdC6-gDHBV3. Numbers on the X axis correspond to the SEQ ID NO as provided herein.

Experiment 4

The breadth of responses were assessed from pooled splenocytes of vaccinated BALB/c mice which were tested by ICS against the individual peptides present in the HBV vaccine inserts.

Methods: Five groups of five BALB/c mice were immunized via intramuscular injection as follows: (a) $5\times10^{10}$ vp AdC6-gDHBV2; (b) $5\times10^{10}$ vp AdC6-gDHBV3; (c) $5\times10^{10}$ vp AdC7-gDHBV2; (d) $5\times10^{10}$ vp AdC7-gDHBV3; or (e) no vaccine. 12 weeks post vaccination animals were sacrificed, spleens were collected and pooled splenocytes were assessed by ICS for IFN-$\gamma^+$ CD8+ T cell responses to individual HBV2 or HBV3 peptides (cut-off for positive responses set at 0.1%).

Figure 34:
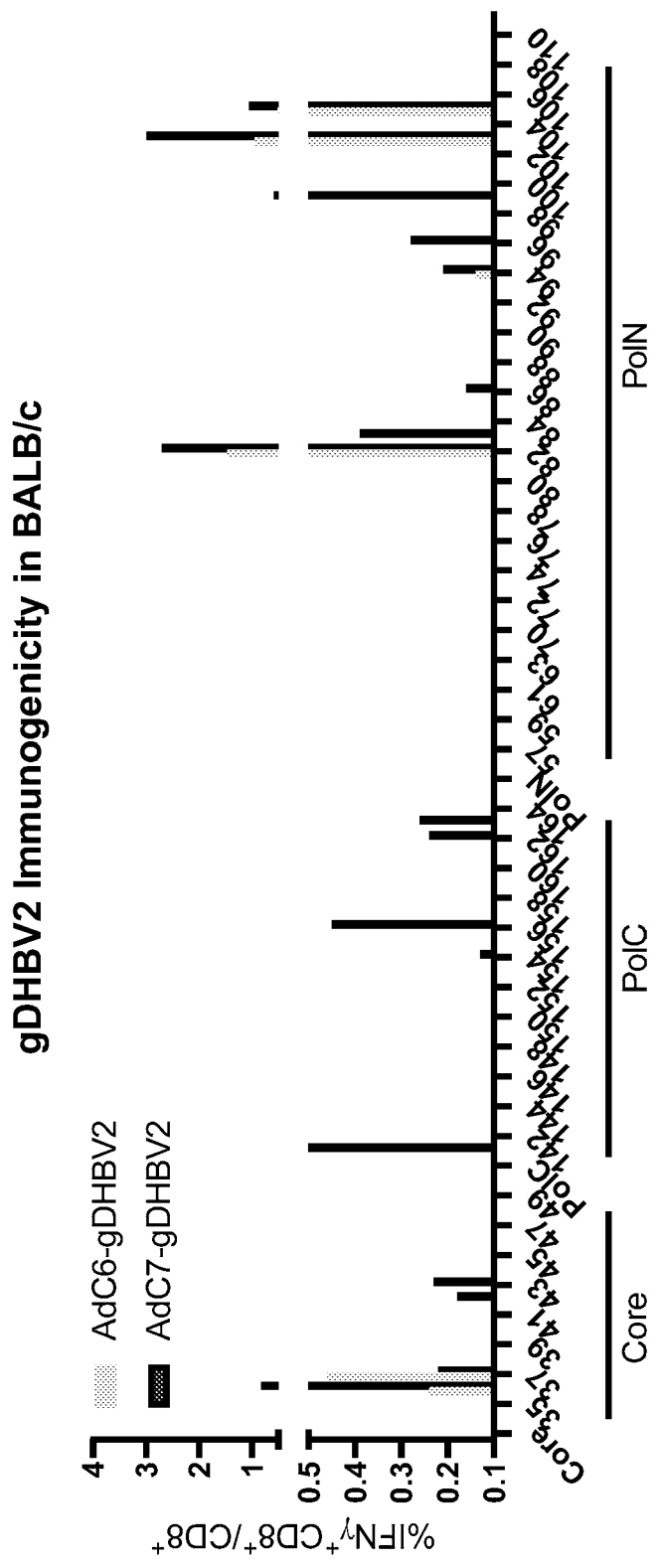
FIG. 34 illustrates the immunogenicity of the AdC6-gDHBV2 and AdC7-gDHBV2 vaccines corresponding to the SEQ ID NO (X axis) as provided herein. Core, PolC, and PolN regions in both HBV2 constructs were immunogenic.
Figure 35:
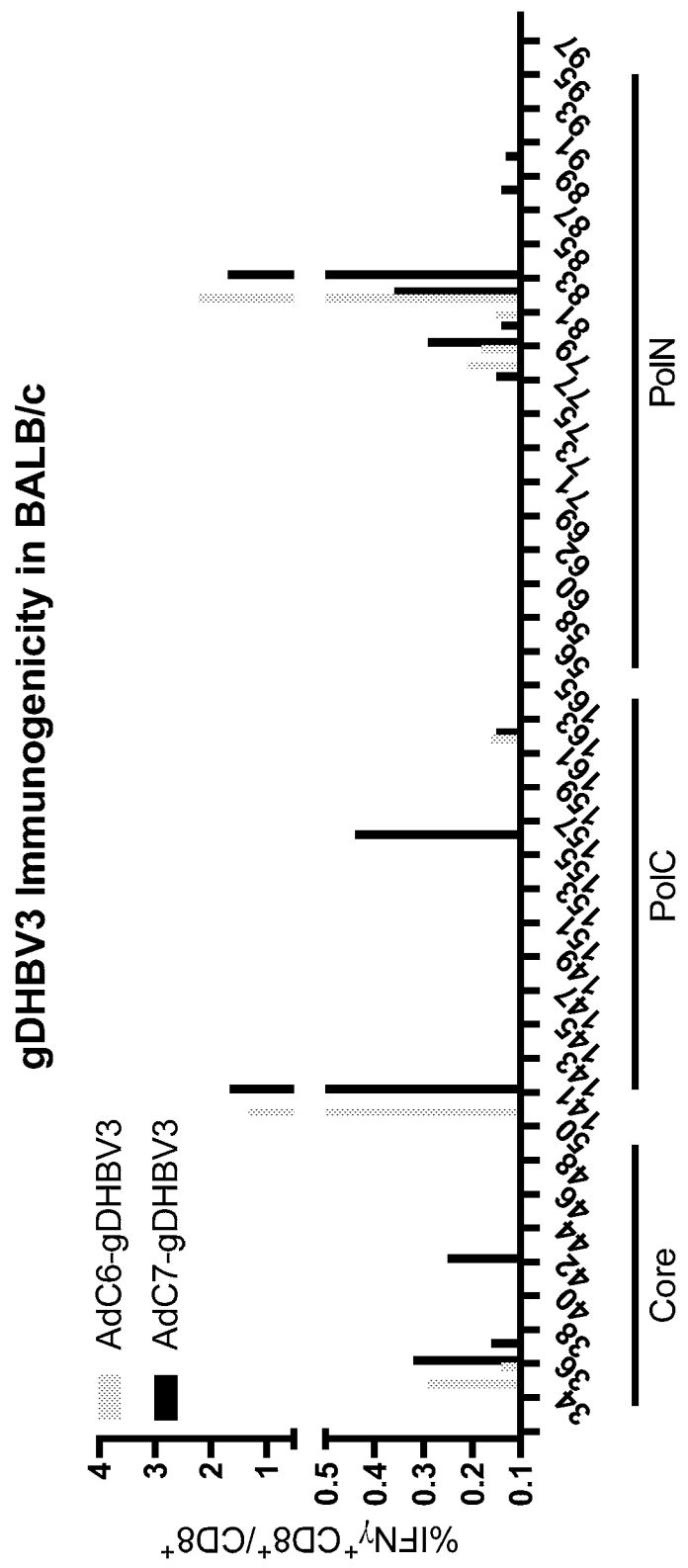
FIG. 35 illustrates the immunogenicity of the AdC6-gDHBV3 and AdC7-gDHBV3 vaccines corresponding to the SEQ ID NO (X axis) as provided herein. Core, PolC, and PolN regions in both HBV3 constructs were immunogenic.

Results: At week 12, each vaccine construct was found to be immunogenic across multiple regions of the Core and Polymerase genes delivered by the vaccine. FIG. 34 shows the immunogenicity of the AdC6-gDHBV2 and AdC7-gDHBV2 vaccines corresponding to the SEQ ID NO (X axis) as provided herein. Core, PolC, and PolN regions in both HBV2 constructs were immunogenic. FIG. 35 shows the immunogenicity of the AdC6-gDHBV3 and AdC7-gDHBV3 vaccines corresponding to the SEQ ID NO (X axis) as provided herein. Core, PolC, and PolN regions in both HBV3 constructs were immunogenic.

Experiment 5

Methods: Five groups of C57Bl/6 mice were challenged with $1\times10^9$ vg of AAV8-1.3HBV and were vaccinated 4 weeks later ("prime vaccination") with $1\times10^{10}$ vp of either AdC6-gDPolN (n=10), AdC6-gDHBV2 (n=10), AdC6-gDHBV3 (n=10), or AdC6-HBV2 without gD (n=10); AAV-infected, non-vaccinated animals (n=10) and non-AAV-infected, non-vaccinated animals (n=2-5) serve as controls. Mice will be bled at various times after the injection and frequencies of insert-specific CD8+ and CD4+ T cells will be determined by intracellular cytokine staining (ICS) for IFN-$\gamma$. PCR will be performed at 2 weeks, 6 weeks, and 8 weeks after the prime vaccination, and a T cell assay will be performed at 4 weeks after the prime vaccination.

At 8 weeks following the prime vaccination, mice will be boosted with AdC7 vectors containing the same antigenic insert used in the prime vaccination ("boost vaccination") and blood and serum will be tested for CD8+/CD4+ T cell as previously described at different time points after vaccination. PCR will be performed at 2 weeks, 6 weeks, and 10 weeks after the boost vaccination, and a T cell assay will be performed at 4 weeks and 12 weeks after the boost vaccination.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in their entirety.

TABLE 9

Sequences

| | Sequence |
|---|---|
| Genotype A Consensus (SEQ ID NO: 1) | MDIDPYKEFGATVELLSFLPSDFFPSVRDLLDTASAL YREALESPEHCSPHHTALRQAILCWGELMTLATWVGN NLeDPASRDLVVNYVNTNMGLKIRQLLWFHISCLTFG RETVLEYLVSFGVWIRTPPAYRPPNAPILSTLPETTV VRRRDRGRSPRRRTPSPRRRRSQSPRRRRSQSRESQC |
| Genotype B Consensus (SEQ ID NO: 2) | MDIDpYKEFGASvELLSFLPSDFFPSiRDLLDTAsAL YREALESPEHCSPHHTALRQAIlCWGELMNLATWVGS NLeDPASRELVVsYVNVNMGLKiRQLLWFHISCLTFG RETVLEYLVSFGVWIRTPpAYRPpNAPILSTLPETTV VRRRGRSPRRRTPSPRRRRSQSPRRRRSQSREsQC |
| Genotype C Consensus (SEQ ID NO: 3) | MDIDpYKEFGASVELLSFLPSDFFPSIRDLLDTASAL YREALESPEHCSPHHTALRQAILCWGELMNLATWVGS NLEDPASRELVVsYVNVNMGLKiRQlLWFHISCLTFG RETVLEYLVSFGVWIRTPpAYRPPNAPILSTLPETTV VRRRGRSPRRRTPSPRRRRSQSPRRRRSQSRESQC |
| Genotype D Consensus (SEQ ID NO: 4) | MDIDPYKEFGAtVELLSFLPsDFFPSVRDLLDTASALYReAL ESPEHCSPHHTALRQAILCWGeLMtLATWVGgNLEDPaSRDL VVSYVNTNmGLKFRQLLWFHISCLTFGReTViEYLVSFGVWI RTPpAYRPPNAPILSTLPETTVvRRRGRSPRRRTPSPRRRRS QSPRRRRSQSRESQC |
| Initial Core sequence (SEQ ID NO: 5) | MDID<u>P</u>YKEFGAX$_1$VELLSFLPSDFFPSX$_2$DLLDTASALYREA LES<u>P</u>EHCSPHHTALRQAILCWGELMX$_3$LATWVGX$_4$NLeDPAS RX$_5$LVVX$_6$YVNX$_7$NMGLKX$_8$RQLLWFHISCLTFGRETVX$_9$EY LVSFGVWIRT<u>P</u>PAYRP<u>P</u>NAPILSTLPETTVVRRRX$_{10}$X$_{11}$GR SPRRRTPSPRR<u>R</u>RSQS<u>P</u>RRRRSQSRESQC |
| Epitope-optimized Core amino acid sequence (SEQ ID NO: 6) | DIDPYKEFGATVELLSFLPSDFFPSIRDLLDTASALYREALE SPEHCSPHHTALRQAILCWGELMTLATWVGSNLEDPASRELV VSYVNVNMGLKIRQLLWFHISCLTFGRETVIEYLVSFGVWIR TPPAYRPPNAPILSTLPETTVVRRRDRGRSPRRRTPSPRRRR SQSPRRRRSQSRESQC |
| Epitope-optimized Core nucleotide | GACATCGACCCCTACAAGGAGTTCGGCGCCACCGTGGAGCTG CTGAGCTTCCTGCCCAGCGACTTCTTCCCCAGCATCAGGGAC CTGCTGGACACCGCCAGCGCCCTGTACAGGGAGGCCCTGGAG |

TABLE 9-continued

Sequences

| | Sequence |
|---|---|
| sequence (SEQ ID NO: 7) | AGCCCCGAGCACTGCAGCCCCCACCACACCGCCCTGAGGCAG GCCATCCTGTGCTGGGGCGAGCTGATGACCCTGGCCACCTGG GTGGGCAGCAACCTGGAGGACCCCGCCAGCAGGGAGCTGGTG GTGAGCTACGTGAACGTGAACATGGGCCTGAAGATCAGGCA CTGCTGTGGTTCCACATCAGCTGCCTGACCTTCGGCAGGGAG ACCGTGATCGAGTACCTGGTGAGCTTCGGCGTGTGGATCAGG ACCCCCCCCGCCTACAGGCCCCCCAACGCCCCCATCCTGAGC ACCCTGCCCGAGACCACCGTGGTGAGGAGGAGGGACAGGGGC AGGAGCCCCAGGAGGAGGACCCCCAGCCCCAGGAGGAGGAGG AGCCAGAGCCCCAGGAGGAGGAGGAGCCAGAGCAGGGAGAGC CAGTGC |
| Epitope-optimized polymerase N-terminal amino acid sequence (SEQ ID NO: 8) | PLSYQHFRKLLLLDEEAGPL TABLE 9-continued Sequences

| | Sequence |
|---|---|
| N-terminal HSV gD sequence (SEQ ID NO: 12) Signal peptide in italics | *MGGAAARLGAVILFVVIVGLHGVRG*KYALADASLKMADPNRF RGKDLPVLDQLTDPPGVRRVYHIQAGLPDPFQPPSLPITVYY AVLERACRSVLLNAPSEAPQIVRGASEDVRKQPYNLTIAWFR MGGNCAIPITVMEYTECSYNKSLGACPIRTQPRWNYYDSFSA VSEDNLGFLMHAPAFETAGTYLRLVKINDWTEITQFILEHRA KGSCKYALPLRIPPSACLSPQAYQQGVTVDSIGMLPRFIPEN QRTVAVYSLKIAGWHGP |
| C-terminal HSV gD sequence (SEQ ID NO: 13) | GPKAPYTSTLLPPELSETPNATQPELAPEDPEDSALLEDPVG TVAPQIPPNWHIPSIQDAATPYHPPATPNNMGLIAGAVGGSL LAALVICGIVYWMHRRTRKAPKRIRLPHIREDDQPSSHQPLF Y |
| gDCore amino acid sequence Core underlined (SEQ ID NO: 14) Signal peptide in italics | *MGGAAARLGAVILFVVIVGLHGVRG*KYALADASLKMADPNRF RGKDLPVLDQLTDPPGVRRVYHIQAGLPDPFQPPSLPITVYY AVLERACRSVLLNAPSEAPQIVRGASEDVRKQPYNLTIAWFR MGGNCAIPITVMEYTECSYNKSLGACPIRTQPRWNYYDSFSA VSEDNLGFLMHAPAFETAGTYLRLVKINDWTEITQFILEHRA KGSCKYALPLRIPPSACLSPQAYQQGVTVDSIGMLPRFIPEN QRTVAVYSLKIAGWHGP<u>DIDPYKEFGATVELLSFLPSDFFPS IRDLLDTASALYREALESPEHCSPHHTALRQAILCWGELMTL ATWVGSNLEDPASRELVVSYVNVNMGLKIRQLLWFHISCLTF GRETVIEYLVSFGVWIRTPPAYRPPNAPILSTLPETTVVRRR DRGRSPRRRTPSPRRRRSQSPRRRRSQSRESQCGPKAPYTST LLPPELSETPNATQPELAPEDPEDSALLEDPVGTVAPQIPPN WHIPSIQDAATPYHPPATPNNMGLIAGAVGGSLLAALVICGI VYWMHRRTRKAPKRIRLPHIREDDQPSSHQPLFY</u> |
| gDCore nucleic acid sequence Core underlined (SEQ ID NO: 15) | atggggggggctgccgccaggttgggggccgtgattttgttt gtcgtcatagtgggcctccatggggtccgcggcaaatatgcc ttggcggatgcctctctcaagatggccgaccccaatcgcttt cgcggcaaagaccttccggtcctggaccagctgaccgaccct ccggggcgtccggcgcgtgtaccacatccaggcgggcctaccg gacccgttccagccccccagcctcccgatcacggtttactac gccgtgttggagcgcgcctgccgcagcgtgctcctaaacgca ccgtcggaggccccccagattgtccgcggggcctccgaagac gtccggaaacaaccctacaacctgaccatcgcttggtttcgg atgggaggcaactgtgctatcccatcacggtcatggagtac accgaatgctcctacaacaagtctctggggcctgtcccatc cgaacgcagccccgctggaactactatgacagcttcagcgcc gtcagcgaggataacctgggttcctgatgcacgcccccgcg tttgagaccgccggcacgtacctgcgggctcgtgaagataaac gactgacggagattacacagtttatcctggagcaccgagcc aagggctcctgtaagtacgccctcccgctgcgcatccccccg tcagcctgcctctcccccaggcctaccagcaggggtgacg gtggacagcatcgggatgctgccccgcttcatccccgagaac cagcgcaccgtcgccgtatacagcttgaagatcgccgggtgg cacgggccc<u>gacatcgacccctacaaggagttcggcgccacc gtggagctgctgagcttcctgcccagcgacttcttcccagc atcagggacctgctggacaccgccagcgccctgtacagggag gccctggagagccccgagcactgcagcccccaccacaccgcc ctgaggcaggccatcctgtgctggggcgagctgatgaccctg gccacctgggtgggcagcaacctggaggaccccgccagcagg gagctggtggtgagctacgtgaacgtgaacatgggcctgaag atcaggcagctgctgtggttccacatcagctgcctgaccttc ggcaggagaccgtgatcgagtacctggtgagcttcggcgtg tggatcaggaccccccccgcctacaggccccccaacgccccc atcctgagcaccctgcccgagaccaccgtggtgaggaggagg gacaggggcaggagccccaggaggaggaccccagccccagg aggaggaggagccagagccccaggaggaggaggagccagagc agggagagccagtgcgggcccaaggccccatacacgagcacc ctgctgccccggagctgtccgagaccccaacgccacgcag ccagaactcgccccggaagaccccgaggattcggccctcttg gaggacccgtggggacggtggcgccgcaaatcccaccaaac tggcacatcccgtcgatccaggacgccgcgacgccttaccat cccccggccacccgaacaacatgggcctgatcgccggcgcg gtgggcggcagtctcctggcagcctggtcatttgcggaatt gtgtactggatgcaccgccgcactcggaaagcccccaaagcgc atacgcctcccccacatccgggaagacgaccagccgtcctcg caccagcccttgttttactag</u> |
| gDPolN amino acid sequence PolN underlined (SEQ ID NO: 16) Signal peptide | *MGGAAARLGAVILFVVIVGLHGVRG*KYALADASLKMADPNRF RGKDLPVLDQLTDPPGVRRVYHIQAGLPDPFQPPSLPITVYY AVLERACRSVLLNAPSEAPQIVRGASEDVRKQPYNLTIAWFR MGGNCAIPITVMEYTECSYNKSLGACPIRTQPRWNYYDSFSA VSEDNLGFLMHAPAFETAGTYLRLVKINDWTEITQFILEHRA |

TABLE 9-continued

| | Sequences |
|---|---|
| | Sequence |
| in italics | KGSCKYALPLRIPPSACLSPQAYQQGVTVDSIGMLPRFIPEN<br>QRTVAVYSLKIAGWHGPPLSYQHFRKLLLLDEEAGPLEEELP<br>RLADEGLNRRVAEDLNLGNLNVSIPWTHKVGNFTGLYSSTVP<br>VFNPEWQTPSFPKIHLQEDIVDRCKQFVGPLTVNEKRRLKLI<br>MPARFYPNVTKYLPLDKGIKPYYPEHAVNHYFQTRHYLHTLW<br>KAGILYKRETTRSASFCGSPYSWEQELQHGSCWWLQFRNSKP<br>CSEYCLTHLVNLLEDWGPCDEHGEHHIRIPRTPARVTGGVFL<br>VDKNPHNTAESRLVVDFSQFSRGITRVSWPKFAVPNLQSLTN<br>LLSSNLSWLSLDVSAAFYHIPLHPAAMPGPKAPYTSTLLPPE<br>LSETPNATQPELAPEDPEDSALLEDPVGTVAPQIPPNWHIPS<br>IQDAATPYHPPATPNNMGLIAGAVGGSLLAALVICGIVYWMH<br>RRTRKAPKRIRLPHIREDDQPSSHQPLFY* |
| gDPolN nucleic<br>acid sequence<br>PolN underlined<br>(SEQ ID NO: 17) | atggggggggctgccgccaggttgggggccgtgattttgttt<br>gtcgtcatagtgggcctccatggggtccgcggcaaatatgcc<br>ttggcggatgcctctctcaagatggccgaccccaatcgcttt<br>cgcggcaaagaccttccggtcctggaccagctgaccgaccct<br>ccggggggtccggcgcgtgtaccacatccaggcgggcctaccg<br>gacccgttccagccccccagcctcccgatcacggtttactac<br>gccgtgttggagcgcgcctgccgcagcgtgctcctaaacgca<br>ccgtcggaggcccccagattgtccgcggggcctccgaagac<br>gtccggaaacaaccctacaacctgaccatcgcttggtttcgg<br>atgggaggcaactgtgctatccccatcacggtcatggagtac<br>accgaatgctcctacaacaagtctctgggggcctgtcccatc<br>cgaacgcagccccgctggaactactatgacagcttcagcgcc<br>gtcagcgaggataacctggggttcctgatgcacgcccccgcg<br>tttgagaccgccggcacgtacctgcggctcgtgaagataaac<br>gactggacggagattacacagtttatcctggagcaccgagcc<br>aagggctcctgtaagtacgccctcccgctgcgcatcccccg<br>tcagcctgcctctcccccaggcctaccagcaggggtgacg<br>gtggacagcatcgggatgctgcccgcttcatccccgagaac<br>cagcgcaccgtcgccgtatacagcttgaagatcgccgggtgg<br>cacgggccccccctgagctaccagcacttcaggaagctgctg<br>ctgctggacgaggaggccggccccctggaggagagctgccc<br>aggctggccgacgagggcctgaacaggagggtggccgaggac<br>ctgaacctgggcaacctgaacgtgagcatcccctggacccac<br>aaggtgggcaacttcaccggcctgtacagcagcaccgtgccc<br>gtgttcaaccccgagtggcagaccccagcttccccaagatc<br>cacctgcaggaggacatcgtggacaggtgcaagcagttcgtg<br>ggtcccctgaccgtgaacgagaagaggaggctgaagctgatc<br>atgcccgccaggttctaccccaacgtgaccaagtacctgccc<br>ctggacaagggcatcaagccctactaccccgagcacgccgtg<br>aaccactacttccagaccaggcactacctgcacaccctgtgg<br>aaggccggcatcctgtacaagagggagaccaccaggagcgcc<br>agcttctgcggcagccctacagctgggagcaggagctgcag<br>cacggcagctgctggtggctgcagttcaggaacagcaagccc<br>tgcagcgagtactgcctgacccacctggtgaacctgctggag<br>gactggggtccctgccgacgagcacggcgagcaccacatcagg<br>atccccaggaccccgccagggtgaccggcggcgtgttcctg<br>gtggacaagaaccccacaacaccgccgagagcaggctggtg<br>gtggacttcagccagttcagcaggggcatcaccagggtgagc<br>tggcccaagttcgccgtgcccaacctgcagagcctgaccaac<br>ctgctgagcagcaacctgagctggctgagcctggacgtgagc<br>gccgccttctaccacatcccctgcacccgccgccatgccc<br>gggcccaaggccccatacacgagcaccctgctgcccccggag<br>ctgtccgagacccccaacgccacgcagccagaactcgccccg<br>gaagaccccgaggattcggccctcttggaggaccccgtgggg<br>acggtggccgccaaatcccaccaaactggcacatcccgtcg<br>atccaggacgccgcgacgccttaccatccccggccacccg<br>aacaacatgggcctgatcgccggcgcggtgggcggcagtctc<br>ctggcagccctggtcatttgcggaattgtgtactggatgcac<br>cgccgcactcggaaagccccaaagcgcatacgcctcccccac<br>atccgggaagacgaccagccgtcctcgcaccagcccttgttt<br>tactag |
| gDPolC amino<br>acid sequence<br>PolC underlined<br>(SEQ ID NO: 18)<br>Signal peptide<br>in italics | *MGGAAARLGAVILFVVIVGLHGVRG*KYALADASLKMADPNRF<br>RGKDLPVLDQLTDPPGVRRVYHIQAGLPDPFQPPSLPITVYY<br>AVLERACRSVLLNAPSEAPQIVRGASEDVRKQPYNLTIAWFR<br>MGGNCAIPITVMEYTECSYNKSLGACPIRTQPRWNYYDSFSA<br>VSEDNLGFLMHAPAFETAGTYLRLVKINDWTEITQFILEHRA<br>KGSCKYALPLRIPPSACLSPQAYQQGVTVDSIGMLPRFIPEN<br>QRTVAVYSLKIAGWHGPPHLLVGSSGLSRYVARLSSNSRIINH<br>QHGTMQNLHDSCSRNLYVSLLLLYKTFGRKLHLYSHPIILKT<br>KRWGYSLNFMGYVIGSWGSLPQDHIIQKIKECFRKLPVNRPI<br>DWKVCQRIVGLLGFAAPFTQCGYPALMPLYACIQSKQAFTFS<br>PTYKAFLSKQYLNLYPVARQRPGLCQVFADATPTGWGLAMGH |

TABLE 9-continued

| | Sequences |
|---|---|
| | Sequence |
| | QRMRGTFVAPLPIHTAELLAACFARSRSGAKILGTDNSVVLS<br>RKYTSFPWLLGCAANWILRGTSFVYVPSALNPADDPSRGRLG<br>LSRPLLRLPFRPTTGRTSLYAVSPSVGPKAPYTSTLLPPELS<br>ETPNATQPELAPEDPEDSALLEDPVGTVAPQIPPNWHIPSIQ<br>DAATPYHPPATPNNMGLIAGAVGGSLLAALVICGIVYWMHRR<br>TRKAPKRIRLPHIREDDQPSSHQPLFY |
| gDPolC nucleic acid sequence PolC underlined (SEQ ID NO: 19) | atggggggggctgccgccaggttgggggccgtgattttgttt<br>gtcgtcatagtgggcctccatggggtccgcggcaaatatgcc<br>ttggcggatgcctctctcaagatggccgaccccaatcgcttt<br>cgcggcaaagaccttccggtcctggaccagctgaccgaccct<br>ccggggggtccggcgcgtgtaccacatccaggcgggcctaccg<br>gacccgttccagccccccagcctcccgatcacggtttactac<br>gccgtgttggagcgcgcctgccgcagcgtgctcctaaacgca<br>ccgtcggaggcccccagattgtccgcggggcctccgaagac<br>gtccggaaacaaccctacaacctgaccatcgcttggtttcgg<br>atgggaggcaactgtgctatcccatcacggtcatggagtac<br>accgaatgctcctacaacaagtctctggggcctgtcccatc<br>cgaacgcagccccgctggaactactatgacagcttcagcgcc<br>gtcagcgaggataacctggggttcctgatgcacgcccccgcg<br>tttgagaccgccggcacgtacctgcggctcgtgaagataaac<br>gactggacggagattacacagtttatcctggagcaccgagcc<br>aagggctcctgtaagtacgccctcccgctgcgcatccccccg<br>tcagcctgcctctcccccaggcctaccagcaggggtgacg<br>gtggacagcatcgggatgctgccccgcttcatccccgagaac<br>cagcgcaccgtcgccgtatacagcttgaagatcgccgggtgg<br>cacgggcccaccctgctggtgggcagcagcggcctgagcagg<br>tacgtggccaggctgagcagcaacagcaggatcatcaaccac<br>cagcacggcaccatgcagaacctgcacgacagctgcagcagg<br>aacctgtacgtgagcctgctgctgctgtacaagaccttcggc<br>aggaagctgcacctgtacagccaccccatcatcctgaagacc<br>aagaggtgggctacagcctgaacttcatgggctacgtgatc<br>ggcagctggggcagcctgcccaggaccacatcatccagaag<br>atcaaggagtgcttcaggaagctgcccgtgaacaggcccatc<br>gactggaaggtgtgccagaggatcgtgggcctgctgggcttc<br>gccgccccttcacccagtgcggctaccccgccctgatgccc<br>ctgtacgcctgcatccagagcaagcaggccttcaccttcagc<br>cccacctacaaggccttcctgagcaagcagtacctgaacctg<br>taccccgtggccaggcagaggccggcctgtgccaggtgttc<br>gccgacgccaccccaccggctggggcctggccatgggccac<br>cagaggatgaggggcaccttcgtggccccctgcccatccac<br>accgccgagctgctggccgcctgcttcgccaggagcaggagc<br>ggcgccaagatcctgggcaccgacaacagcgtggtgetgage<br>aggaagtacaccagcttcccctggctgctgggctgcgccgcc<br>aactggatcctgaggggcaccagcttcgtgtacgtgcccagc<br>gccctgaacccgccgacgaccccagcaggggcaggctgggc<br>ctgagcaggcccctgctgaggctgcccttcaggcccaccacc<br>ggcaggaccagcctgtacgccgtgagccccagcgtgggcc<br>aaggccccatacacgagcaccctgctgccccggagctgtcc<br>gagacccccaacgccacgcagccagaactcgccccggaagac<br>cccgaggattcggccctcttggaggacccgtggggacggtg<br>gcgccgcaaatcccaccaaactggcacatcccgtcgatccag<br>gacgccgcgacgccttaccatcccccggccaccccgaacaac<br>atgggcctgatcgccggcgcggtgggcggcagtctcctggca<br>gccctggtcatttgcggaattgtgtactggatgcaccgccgc<br>actcggaaagcccaaagcgcatacgcctccccacatccgg<br>gaagacgaccagccgtcctcgcaccagcccttgttttactag |
| HBV PolN v2 amino acid sequence (SEQ ID NO: 173) | HFRKLLLLDEEAGPLEEELPRLADEGLNRRVAEDLNLGNLPE<br>WQTPSFPKIHLQEDIVDRCKQFVGPLTVNEKRRLKLIMPARF<br>YPNVTKYLPLDKGIKPYYPEHAVNHYFQTRHYLHTLWKAGIL<br>YKRETTRSASFCGSPYSWEQELQHGSCWWLQFRNSKPCSEYC<br>LTHLVNLLEDWGPCDEHGEHHIRIPRTPARVT |
| HBV2 amino acid sequence (SEQ ID NO: 174) (Pol N (italics)-Pol C (underlined)-Core) | *YLPLDKGIKPYYPEHAVNHYFQTRHYLHTLWKAGILYKRETT*<br>*RSASFCGSPYSNEQELQHGSCWNLQFRNSKPCSEYCLTHLVN*<br>*LLEDWGPCDEHGEHHIRIPRTPARVTGGVFLVDKNPHNTAES*<br>*RLWDFSQFSRGITRVSWPKFAVPNLQSLTNLLSSNLSVVLSL*<br>*DVQAFTFSPTYKAFLSKQYLNLYPVARQRPGLCQVFADATPT*<br>GWGLAMGHQRMRGTFVAPLPIHTAELLAACFARSRSGAKILG<br>TDNSVVLSRKYTSFPWLLGCAANWILRGTSFVYVPSALNPAD<br>DVGSNLEDPASRELVVSYVNVNMGLKIRQLLWFHISCLTFGR<br>ETVIEYLVSFGVWIRTPPAYRPPNAPILSTLPETTVWRRRDR<br>GR |

TABLE 9-continued

Sequences

| | Sequence |
|---|---|
| HBV3 amino acid sequence (SEQ ID NO: 175) (Pol N (italics)-Pol C (underlined)-Core) | *HFRKLLLLDEEAGPLEEELPRLADEGLNRRVAEDLNLGNLPE WQTPSFPKIHLQEDIVDRCKQFVGPLTVNEKRRLKLIMPARF YPNVTKYLPLDKGIKPYYPEHAVNHYFQTRHYHLTLWKAGIL YKRETTRSASFCGSPYSWEQELQHGSCWWLQFRNSKPCSEYC LTHLVNLLEDWGPCDEHGEHHIRIPRTPARVT*<u>QAFTFSPTYK AFLSKQYLNLYPVARQRPGLCQVFADATPTGWGLAMGHQRMR GTFVAPLPIHTAELLAACFARSRSGAKILGTDNSVVLSRKYT SFPWLLGCAANWILRGTSFVYVPSALNPADDVGSNLEDPASR</u>ELWSYVNVNMGLKIRQLLWFHISCLTFGRETVIEYLVSFGV WIRTPPAYRPPNAPILSTLPETTWRRRDRGR |
| HBV2 nucleic acid sequence (SEQ ID NO: 176) | tatctgccgctggataaaggcattaaaccgtattatccggaa catgcggtgaaccattattttcagacccgccattatctgcat accctgtggaaagcgggcattctgtataaacgcgaaaccacc cgcagcgcgagcttttgcggcagcccgtatagctgggaacag gaactgcagcatggcagctgctggtggctgcagtttcgcaac agcaaaccgtgcagcgaatattgcctgacccatctggtgaac ctgctggaagattggggaccgtgcgatgaacatggcgaacat catattcgcattccgcgcacccggcgcgcgtgaccggcggc gtgtttctggtggataaaaacccgcataacaccgcggaaagc cgcctggtggtggattttagccagtttagccgcggcattacc cgcgtgagctggccgaaatttgcggtgccgaacctgcagagc ctgaccaacctgctgagcagcaacctgagctggctgagcctg gatgtgcaggcgtttacctUagcccgacctataaagcgtttc tgagcaaacagtatctgaacctgtatccggtggcgcgccagc gcccgggcctgtgccaggtgtttgcggatgcgaccccgaccg gctgggcctggcgatgggccatcagcgcatgcgcggcacct ttgtggcgccgctgccgattcataccgcggaactgctggcgg cgtgctttgcgcgcagccgcagcggcgcgaaaattctgggca ccgataacagcgtggtgctgagccgcaaatataccagctttc cgtggctgctgggctgcgcggcgaactggattctgcgcggca ccagctttgtgtatgtgccgagcgcgctgaaccggcggatg atgtgggcagcaacctggaagatccggcgagccgcgaactgg tggtgagctatgtgaacgtgaacatgggcctgaaaattcgcc agctgctgtggtttcatattagctgcctgacctttggccgcg aaaccgtgattgaatatctggtgagctttggcgtgtggattc gcaccccgccggcgtatcgcccgccgaacgcgccgattctga gcaccctgccggaaaccaccgtggtgcgccgccgcgatcggg gccgc |
| HBV3 nucleic acid sequence (SEQ ID NO: 177) | cattttcgcaaactgctgctgctggatgaagaagcgggaccg ctggaagaagaactgccgcgcctggcggatgaaggcctgaac cgccgcgtggcggaagatctgaacctgggcaacctgccggaa tggcagacccccgagctttccgaaaattcatctgcaggaagat attgtggatcgctgcaaacagtttgtgggaccgctgaccgtg aacgaaaaacgccgcctgaaactgattatgccggcgcgcttt tatccgaacgtgaccaaatatctgccgctggataaaggcatt aaaccgtattatccggaacatgcggtgaaccattattttcag acccgccattatctgcataccctgtggaaagcgggcattctg tataaacgcgaaaccacccgcagcgcgagcttttgcggcagc ccgtatagctgggaacaggaactgcagcatggcagctgctgg tggctgcagtttcgcaacagcaaaccgtgcagcgaatattgc ctgacccatctggtgaacctgctggaagattggggaccgtg gatgaacatggcgaacatcatattcgcattccgcgcacccg gcgcgcgtgacccaggcgtttaccttttagcccgacctataaa gcgtttctgagcaaacagtatctgaacctgtatccggtggcg cgccagcgcccgggcctgtgccaggtgtttgcggatgcgacc ccgaccggctgggcctggcgatgggccatcagcgcatgcgc ggcacctttgtggcgccgctgccgattcataccgcggaactg ctggcggcgtgctttgcgcgcagccgcagcggcgcgaaaatt ctgggcaccgataacagcgtggtgctgagccgcaaatatacc agctttccgtggctgctgggctgcgcggcgaactggattctg cgcggcaccagctttgtgtatgtgccgagcgcgctgaacccg gcggatgatgtgggcagcaacctggaagatccggcgagccgc gaactggtggtgagctatgtgaacgtgaacatgggcctgaaa attcgccagctgctgtggtttcatattagctgcctgaccttt ggccgcgaaaccgtgattgaatatctggtgagctttggcgtg tggattcgcaccccgccggcgtatcgcccgccgaacgcgccg attctgagcaccctgccggaaaccaccgtggtgcgccgcgca gatcgaggccgc |

TABLE 9-continued

Sequences

| | Sequence |
|---|---|
| HBV2 PolN amino acid sequence (SEQ ID NO: 178) | YLPLDKGIKPYYPEHAVNHYFQTRHYLHTLWKAGILYKRETT RSASFCGSPYSWEQELQHGSCWWLQFRNSKPCSEYCLTHLVN LLEDWGPCDEHGEHHIRIPRTPARVTGGVFLVDKNPHNTAES RLVVDFSQFSRGITRVSWPKFAVPNLQSLTNLLSSNLSWLSL DV |
| HBV2 PolC amino acid sequence (SEQ ID NO: 179) | QAFTFSPTYKAFLSKQYLNLYPVARQRPGLCQVFADATPTGW GLAMGHQRMRGTFVAPLPIHTAELLAACFARSRSGAKILGTD NSVVLSRKYTSFPWLLGCAANWILRGTSFVYVPSALNPADD |
| HBV2 Core amino acid sequence (SEQ ID NO: 180) | VGSNLEDPASRELVVSYVNVNMGLKIRQLLWFHISCLTFGRE TVIEYLVSFGVWIRTPPAYRPPNAPILSTLPETTVVRRRDRG R |
| HBV3 PolN amino acid sequence (SEQ ID NO: 181) | HFRKLLLLDEEAGPLEEELPRLADEGLNRRVAEDLNLGNLPE WQTPSFPKIHLQEDIVDRCKQFVGPLTVNEKRRLKLIMPARF YPNVTKYLPLDKGIKPYYPEHAVNHYFQTRHYLHTLWKAGIL YKRETTRSASFCGSPYSWEQELQHGSCWWLQFRNSKPCSEYC LTHLVNLLEDWGPCDEHGEHHIRIPRTPARVT |
| HBV3 PolC amino acid sequence (SEQ ID NO: 182) | QAFTFSPTYKAFLSKQYLNLYPVARQRPGLCQVFADATPTGW GLAMGHQRMRGTFVAPLPIHTAELLAACFARSRSGAKILGTD NSWLSRKYTSFPWLLGCAANWILRGTSFVYVPSALNPADD |
| HBV3 Core amino acid sequence (SEQ ID NO: 183) | VGSNLEDPASRELWSYVNVNMGLKIRQLLWFHISCLTFGRE TVIEYLVSFGVWIRTPPAYRPPNAPILSTLPETTWRRRDRG R |
| gD-HBV2 nucleic acid sequence (SEQ ID NO: 184) | atggggggggctgccgccaggttgggggccgtgattttgttt gtcgtcatagtgggcctccatggggtccgcggcaaatatgcc ttggcggatgcctctctcaagatggccgaccccaatcgcttt cgcggcaaagaccttccggtcctggaccagctgaccgaccct ccggggggtccggcgcgtgtaccacatccaggcgggcctaccg gacccgttccagccccccagcctcccgatcacggtttactac gccgtgttggagcgcgcctgccgcagcgtgctcctaaacgca ccgtcggaggccccccagattgtccgcggggcctccgaagac gtccggaaacaaccctacaacctgaccatcgcttggtttcgg atgggaggcaactgtgctatccccatcacggtcatggagtac accgaatgctcctacaacaagtctctgggggcctgtcccatc cgaacgcagccccgctggaactactatgacagcttcagcgcc gtcagcgaggataacctggggttcctgatgcacgccccccgcg tttgagaccgccggcacgtacctgcggctcgtgaagataaac gactggacggagattacacagtttatcctggagcaccgagcc aagggctcctgtaagtacgccctcccgctgcgcatccccccg tcagcctgcctctcccccaggcctaccagcaggggtgacg gtggacagcatcgggatgctgccccgcttcatccccgagaac cagcgcaccgtcgcgtatacagcttgaagatcgccgggtgg cacgggccctatctgccgctggataaaggcattaaaccgtat tatccggaacatgcggtgaaccattattttcagacccgccat tatctgcataccctgtggaaagcgggcattctgtataaacgc gaaaccacccgcagcgcgagcttttgcggcagcccgtatagc tgggaacaggaactgcagcatggcagctgctggtggctgcag tttcgcaacagcaaaccgtgcagcgaatattgcctgacccat ctggtgaacctgctggaagattggggaccgtgcgatgaacat ggcgaacatcatattcgcattccgcgcacccccggccgcgtg accggcggcgtgtttctggtggataaaaacccgcataacacc gcggaaagccgcctggtggtggattttagccagtttagccgc ggcattacccgcgtgagctggccgaaatttgcggtgccgaac ctgcagagcctgaccaacctgctgagcagcaacctgagctgg ctgagcctggatgtgcaggcgtttacctttagcccgacctat aaagcgtttctgagcaaacagtatctgaacctgtatccggtg gcgcgccagcgcccgggcctgtgccaggtgtttgcggatgcg accccgaccggctggggcctggcgatgggccatcagcgcatg cgcggcacctttgtggcgccgctgccgattcataccgcggaa ctgctggcggcgtgctttgcgcgcagccgcagcggcgcgaaa attctgggcaccgataacagcgtggtgctgagccgcaaatat accagctttccgtggctgctgggctgcgcggcaaactggatt ctgcgcggcaccagctttgtgtatgtgccgagcgcgctgaac ccggcggatgatgtgggcagcaacctggaagatccggcgagc cgcgaactggtggtgagctatgtgaacgtgaacatgggcctg aaaattcgccagctgctgtggtttcatattagctgcctgacc tttggccgcgaaaccgtgattgaaatatctggtgagctttggc |

TABLE 9-continued

Sequences

| | Sequence |
|---|---|
| | gtgtggattcgcaccccgccggcgtatcgcccgccgaacgcg<br>ccgattctgagcaccctgccggaaaccaccgtggtgcgccgc<br>cgcgatcggggccgcgggcccaaggccccatacacgagcacc<br>ctgctgccccggagctgtccgagaccccaacgccacgcag<br>ccagaactcgccccggaagaccccgaggattcggccctcttg<br>gaggacccccgtggggacggtggcgccgcaaatcccaccaaac<br>tggcacatcccgtcgatccaggacgccgcgacgccttaccat<br>cccccggccaccccgaacaacatgggcctgatcgccggcgcg<br>gtgggcggcagtctcctggcagccctggtcatttgcggaatt<br>gtgtactggatgcaccgccgcactcggaaagccccaaagcgc<br>atacgcctccccacatccgggaagacgaccagccgtcctcg<br>caccagcccttgttttactag |
| gD-HBV2 amino<br>acid sequence<br>(SEQ ID NO:<br>185) | *MGGAAARLGAVILFVVIVGLHGVRG*KYALADASLKMADPNRF<br>RGKDLPVLDQLTDPPGVRRVYHIQAGLPDPFQPPSLPITVYY<br>AVLERACRSVLLNAPSEAPQIVRGASEDVRKQPYNLTIAWFR<br>MGGNCAIPITVMEYTECSYNKSLGACPIRTQPRWNYYDSFSA<br>VSEDNLGFLMHAPAFETAGTYLRLVKINDWTEITQFILEHRA<br>KGSCKYALPLRIPPSACLSPQAYQQGVTVDSIGMLPRFIPEN<br>QRTVAVYSLKIAGWHGPYLPLDKGIKPYYPEHAVNHYFQTRH<br>YLHTLWKAGILYKRETTRSASFCGSPYSWEQELQHGSCWWLQ<br>FRNSKPCSEYCLTHLVNLLEDWGPCDEHGEHHIRIPRTPARV<br>TGGVFLVDKNPHNTAESRLVVDFSQFSRGITRVSWPKFAVPN<br>LQSLTNLLSSNLSWLSLDVQAFTFSPTYKAFLSKQYLNLYPV<br>ARQRPGLCQVFADATPTGWGLAMGHQRMRGTFVAPLPIHTAE<br>LLAACFARSRSGAKILGTDNSVVLSRKYTSFPWLLGCAANWI<br>LRGTSFVYVPSALNPADDVGSNLEDPASRELVVSYVNVNMGL<br>KIRQLLWFHISCLTFGRETVIEYLVSFGVWIRTPPAYRPPNA<br>PILSTLPETTVVRRRDRGRGPKAPYTSTLLPPELSETPNATQ<br>PELAPEDPEDSALLEDPVGTVAPQIPPNWHIPSIQDAATPYH<br>PPATPNNMGLIAGAVGGSLLAALVICGIVYWMHRRTRKAPKR<br>IRLPHIREDDQPSSHQPLFY* |
| gD-HBV3 nucleic<br>acid sequence<br>(SEQ ID NO:<br>186) | atggggggggctgccgccaggttgggggccgtgattttgttt<br>gtcgtcatagtgggcctccatggggtccgcggcaaatatgcc<br>ttggcggatgcctctctcaagatggccgaccccaatcgcttt<br>cgcggcaaagaccttccggtcctggaccagctgaccgaccct<br>ccggggtccggcgcgtgtaccacatccaggcgggcctaccg<br>gacccgttccagccccccagcctcccgatcacggtttactac<br>gccgtgttggagcgcgcctgccgcagcgtgctcctaaacgca<br>ccgtcggaggcccccagattgtccgcggggcctccgaagac<br>gtccggaaacaaccctacaacctgaccatcgcttggtttcgg<br>atgggaggcaactgtgctatcccatcacggtcatggagtac<br>accgaatgctcctacaacaagtctctgggggcctgtcccatc<br>cgaacgcagccccgctggaactactatgacagcttcagcgcc<br>gtcagcgaggataacctggggttcctgatgcacgccccgcg<br>tttgagaccgccggcacgtacctgcggctcgtgaagataaac<br>gactggacggagattacacagtttatcctggagcaccgagcc<br>aagggctcctgtaagtacgccctcccgctgcgcatcccccg<br>tcagcctgcctctccccccaggcctaccagcaggggtgacg<br>gtggacagcatcgggatgctgccccgcttcatccccgagaac<br>cagcgcaccgtcgccgtatacagcttgaagatcgccgggtgg<br>cacgggccccattttcgcaaactgctgctgctggatgaagaa<br>gcgggaccgctggaagaagaactgccgcgcctggcggatgaa<br>ggcctgaaccgccgcgtggcggaagatctgaacctgggcaac<br>ctgccggaatggcagaccccgagctttccgaaaattcatctg<br>caggaagatattgtggatcgctgcaaacagtttgtgggaccg<br>ctgaccgtgaacgaaaaacgccgcctgaaactgattatgccg<br>gcgcgcttttatccgaacgtgaccaaatatctgccgctggat<br>aaaggcattaaaccgtattatccggaacatgcggtgaaccat<br>tattttcagacccgccattatctgcatacccctgtggaaagcg<br>ggcattctgtataaacgcgaaaccacccgcagcgcgagcttt<br>tgcggcagcccgtatagctgggaacaggaactgcagcatggc<br>agctgctggtggctgcagtttcgcaacagcaaaccgtgcagc<br>gaatattgcctgacccatctggtgaacctgctggaagattgg<br>ggaccgtgcgatgaacatggcgaacatcatattcgcattccg<br>cgcacccccggcgcgtgacccaggcgtttacctttagcccg<br>acctataaagcgtttctgagcaaacagtatctgaacctgtat<br>ccggtggcgcgccagcgcccgggcctgtgccaggtgtttgcg<br>gatgcgaccccgaccggctggggcctggcgatgggccatcag<br>cgcatgcgcggcaccttttgtggcgccgctgccgattcatacc<br>gcggaactgctggcggcgtgctttgcgcgcagccgcagcggc<br>gcgaaaattctgggcaccgataacagcgtggtgctgagccgc<br>aaatataccagcttccgtggctgctgggctgcgcggcgaac<br>tggattctgcgcggcaccagctttgtgtatgtgccgagcgcg<br>ctgaacccggcggatgatgtgggcagcaacctggaagatccg |

TABLE 9-continued

Sequences

| | Sequence |
|---|---|
| | gcgagccgcgaactggtggtgagctatgtgaacgtgaacatg<br>ggcctgaaaattcgccagctgctgtggtttcatattagctgc<br>ctgacctttggccgcgaaaccgtgattgaatatctggtgagc<br>tttggcgtgtggattcgcaccccgccggcgtatcgcccgccg<br>aacgcgccgattctgagcaccctgccggaaaccaccgtggtg<br>cgccgccgagatcgaggccgcgggcccaaggccccatacacg<br>agcaccctgctgccccggagctgtccgagacccccaacgcc<br>acgcagccagaactcgcccggaagaccccgaggattcggcc<br>ctcttggaggacccgtggggacggtggcgccgcaaatccca<br>ccaaactggcacatcccgtcgatccaggacgccgcgacgcct<br>taccatccccggccaccccgaacaacatgggcctgatcgcc<br>ggcgcggtgggcggcagtctcctggcagccctggtcatttgc<br>ggaattgtgtactggatgcaccgccgcactcggaaagcccca<br>aagcgcatacgcctccccacatccgggaagacgaccagccg<br>tcctcgcaccagcccttgttttactag |
| gD-HBV3 amino acid sequence (SEQ ID NO: 187) | MGGAAARLGAVILFVVIVGLHGVRGKYALADASLKMADPNRF<br>RGKDLPVLDQLTDPPGVRRVYHIQAGLPDPFQPPSLPITVYY<br>AVLERACRSVLLNAPSEAPQIVRGASEDVRKQPYNLTIAWFR<br>MGGNCAIPITVMEYTECSYNKSLGACPIRTQPRWNYYDSFSA<br>VSEDNLGFLMHAPAFETAGTYLRLVKINDWTEITQFILEHRA<br>KGSCKYALPLRIPPSACLSPQAYQQGVTVDSIGMLPRFIPEN<br>QRTVAVYSLKIAGWHGPHFRKLLLLDEEAGPLEEELPRLADE<br>GLNRRVAEDLNLGNLPEWQTPSFPKIHLQEDIVDRCKQFVGP<br>LTVNEKRRLKLIMPARFYPNVTKYLPLDKGIKPYYPEHAVNH<br>YFQTRHYLHTLWKAGILYKRETTRSASFCGSPYSWEQELQHG<br>SCWWLQFRNSKPCSEYCLTHLVNLLEDWGPCDEHGEHHIRIP<br>RTPARVTQAFTFSPTYKAFLSKQYLNLYPVARQRPGLCQVFA<br>DATPTGWGLAMGHQRMRGTFVAPLPIHTAELLAACFARSRSG<br>AKILGTDNSVVLSRKYTSFPWLLGCAANWILRGTSFVYVPSA<br>LNPADDVGSNLEDPASRELVVSYVNVNMGLKIRQLLWFHISC<br>LTFGRETVIEYLVSFGVWIRTPPAYRPPNAPILSTLPETTVV<br>RRRDRGRGPKAPYTSTLLPPELSETPNATQPELAPEDPEDSA<br>LLEDPVGTVAPQIPPNWHIPSIQDAATPYHPPATPNNMGLIA<br>GAVGGSLLAALVICGIVYWMHRRTRKAPKRIRLPHIREDDQP<br>SSHQPLFY* |

Embodiments

The following list of embodiments is intended to complement, rather than displace or supersede, the previous descriptions.

Embodiment 1. A hepatitis B virus (HBV) Core protein comprising the amino acid sequence of SEQ ID NO: 6 or an immunogenic fragment thereof.

Embodiment 2. The HBV Core protein of embodiment 1, wherein the immunogenic fragment comprises any one of SEQ ID NOs: 20-54.

Embodiment 3. A hepatitis B virus (HBV) Core protein comprising the amino acid sequence of SEQ ID NO: 180 or an immunogenic fragment thereof, or the amino acid sequence of SEQ ID NO: 183 or an immunogenic fragment thereof.

Embodiment 4. A nucleic acid molecule encoding the HBV Core protein of any one of embodiments 1-3.

Embodiment 5. The nucleic acid molecule of embodiment 4, wherein the nucleic acid molecule comprises the nucleotide sequence of SEQ ID NO: 7.

Embodiment 6. A vector comprising the nucleic acid molecule of embodiment 4 or 5.

Embodiment 7. The vector of embodiment 6, wherein the vector is an adenoviral vector.

Embodiment 8. The vector of embodiment 7, wherein the adenoviral vector is an AdC6 vector or AdC7 vector.

Embodiment 9. A vaccine comprising the vector of any one of embodiments 6-8.

Embodiment 10. A HBV polymerase N-terminal domain comprising the amino acid sequence of SEQ ID NO: 8 or an immunogenic fragment thereof.

Embodiment 11. The HBV polymerase N-terminal domain of embodiment 10, wherein the immunogenic fragment comprises any one of SEQ ID NOs: 55-113.

Embodiment 12. A HBV polymerase N-terminal domain comprising the amino acid sequence of SEQ ID NO: 178 or an immunogenic fragment thereof, or the amino acid sequence of SEQ ID NO: 181 or an immunogenic fragment thereof.

Embodiment 13. A HBV polymerase C-terminal domain comprising the amino acid sequence of SEQ ID NO: 10 or an immunogenic fragment thereof.

Embodiment 14. The HBV polymerase C-terminal domain of embodiment 13, wherein the immunogenic fragment comprises any one of SEQ ID NOs: 114-172.

Embodiment 15. A HBV polymerase C-terminal domain comprising the amino acid sequence of SEQ ID NO: 179 or an immunogenic fragment thereof, or the amino acid sequence of SEQ ID NO: 182 or an immunogenic fragment thereof.

Embodiment 16. A nucleic acid molecule encoding the HBV polymerase of any one of embodiments 10-15.

Embodiment 17. The nucleic acid molecule of embodiment 16, wherein the nucleic acid molecule comprises the nucleotide sequence of SEQ ID NO: 9.

Embodiment 18. The nucleic acid molecule of embodiment 16, wherein the nucleic acid molecule comprises the nucleotide sequence of SEQ ID NO: 11.

Embodiment 19. A vector comprising the nucleic acid molecule of any one of embodiments 16-18.

Embodiment 20. The vector of embodiment 19, wherein the vector is an adenoviral vector.

Embodiment 21. The vector of embodiment 20, wherein the adenoviral vector is an AdC6 vector or AdC7 vector.

Embodiment 22. A vaccine comprising the vector of any one of embodiments 19-21.

Embodiment 23. A fusion protein comprising:
one or more of an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof.

Embodiment 24. The fusion protein of embodiment 23, comprising:
(1) an HBV Core protein comprising the amino acid sequence of SEQ ID NO: 6 or an immunogenic fragment thereof and an HBV polymerase N-terminal domain comprising the amino acid sequence of SEQ ID NO: 8 or an immunogenic fragment thereof;
(2) one or more of SEQ ID NOs: 20-54 (immunogenic fragments of SEQ ID NO: 6) and one or more of SEQ ID NOs: 55-113 (immunogenic fragments of SEQ ID NO: 8);
(3) an HBV Core protein comprising the amino acid sequence of SEQ ID NO: 6 or an immunogenic fragment thereof and an HBV polymerase C-terminal domain comprising the amino acid sequence of SEQ ID NO: 10 or an immunogenic fragment thereof;
(4) one or more of SEQ ID NOs: 20-54 (immunogenic fragments of SEQ ID NO: 6) and one or more of SEQ ID NOs: 114-172 (immunogenic fragments of SEQ ID NO: 10);
(5) an HBV polymerase N-terminal domain comprising the amino acid sequence of SEQ ID NO: 8 or an immunogenic fragment thereof and an HBV polymerase C-terminal domain comprising the amino acid sequence of SEQ ID NO: 10 or an immunogenic fragment thereof;
(6) one or more of SEQ ID NOs: 55-113 (immunogenic fragments of SEQ ID NO: 8) and one or more of SEQ ID NOs: 114-172 (immunogenic fragments of SEQ ID NO: 10);
(7) an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof; or
(8) one or more of SEQ ID NOs: 20-54 (immunogenic fragments of SEQ ID NO: 6), one or more of SEQ ID NOs: 55-113 (immunogenic fragments of SEQ ID NO: 8), and one or more of SEQ ID NOs: 114-172 (immunogenic fragments of SEQ ID NO: 10).

Embodiment 25. A fusion protein comprising:
an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof.

Embodiment 26. The fusion protein of embodiment 25, comprising the amino acid sequence of SEQ ID NO: 174.

Embodiment 27. A fusion protein comprising:
an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof.

Embodiment 28. The fusion protein of embodiment 27, comprising the amino acid sequence of SEQ ID NO: 175.

Embodiment 29. A fusion protein comprising:
an N-terminal herpes simplex virus (HSV) glycoprotein (gD) sequence or a variant thereof;
an HBV Core protein comprising the amino acid sequence of SEQ ID NO: 6 or an immunogenic fragment thereof; and
a C-terminal HSV gD sequence or a variant thereof.

Embodiment 30. The fusion protein of embodiment 29, wherein the immunogenic fragment comprises any one of SEQ ID NOs: 20-54.

Embodiment 31. A fusion protein comprising:
an N-terminal HSV gD sequence or a variant thereof;
an HBV polymerase N-terminal domain comprising the amino acid sequence of SEQ ID NO: 8 or an immunogenic fragment thereof; and
a C-terminal HSV gD protein sequence or a variant thereof.

Embodiment 32. The fusion protein of embodiment 31, wherein the immunogenic fragment comprises any one of SEQ ID NOs: 55-113.

Embodiment 33. A fusion protein comprising:
an N-terminal HSV gD sequence or a variant thereof;
an HBV polymerase C-terminal domain comprising the amino acid sequence of SEQ ID NO: 10 or an immunogenic fragment thereof; and
a C-terminal HSV gD protein sequence or a variant thereof.

Embodiment 34. The fusion protein of embodiment 33, wherein the immunogenic fragment comprises any one of SEQ ID NOs: 114-172.

Embodiment 35. A fusion protein comprising:
an N-terminal HSV gD sequence or a variant thereof;
an HBV sequence comprising:
(1) an HBV Core protein comprising the amino acid sequence of SEQ ID NO: 6 or an immunogenic fragment thereof and an HBV polymerase N-terminal domain comprising the amino acid sequence of SEQ ID NO: 8 or an immunogenic fragment thereof;
(2) one or more of SEQ ID NOs: 20-54 (immunogenic fragments of SEQ ID NO: 6) and one or more of SEQ ID NOs: 55-113 (immunogenic fragments of SEQ ID NO: 8);
(3) an HBV Core protein comprising the amino acid sequence of SEQ ID NO: 6 or an immunogenic fragment thereof and an HBV polymerase C-terminal domain comprising the amino acid sequence of SEQ ID NO: 10 or an immunogenic fragment thereof;

(4) one or more of SEQ ID NOs: 20-54 (immunogenic fragments of SEQ ID NO: 6) and one or more of SEQ ID NOs: 114-172 (immunogenic fragments of SEQ ID NO: 10);

(5) an HBV polymerase N-terminal domain comprising the amino acid sequence of SEQ ID NO: 8 or an immunogenic fragment thereof and an HBV polymerase C-terminal domain comprising the amino acid sequence of SEQ ID NO: 10 or an immunogenic fragment thereof;

(6) one or more of SEQ ID NOs: 55-113 (immunogenic fragments of SEQ ID NO: 8) and one or more of SEQ ID NOs: 114-172 (immunogenic fragments of SEQ ID NO: 10);

(7) an HBV Core protein comprising the amino acid sequence of SEQ ID NO: 6 or an immunogenic fragment thereof, an HBV polymerase N-terminal domain comprising the amino acid sequence of SEQ ID NO: 8 or an immunogenic fragment thereof, and an HBV polymerase C-terminal domain comprising the amino acid sequence of SEQ ID NO: 10 or an immunogenic fragment thereof; or (8) one or more of SEQ ID NOs: 20-54 (immunogenic fragments of SEQ ID NO: 6), one or more of SEQ ID NOs: 55-113 (immunogenic fragments of SEQ ID NO: 8), and one or more of SEQ ID NOs: 114-172 (immunogenic fragments of SEQ ID NO: 10) and a C-terminal HSV gD protein sequence or a variant thereof.

Embodiment 36. A fusion protein comprising:
an N-terminal HSV gD sequence or a variant thereof;
an HBV Core protein comprising the amino acid sequence of SEQ ID NO: 180 or an immunogenic fragment thereof, or the amino acid sequence of SEQ ID NO: 183 or an immunogenic fragment thereof; and
a C-terminal HSV gD sequence or a variant thereof.

Embodiment 37. A fusion protein comprising:
an N-terminal HSV gD sequence or a variant thereof;
an HBV polymerase N-terminal domain comprising the amino acid sequence of SEQ ID NO: 178 or an immunogenic fragment thereof, or the amino acid sequence of SEQ ID NO: 181 or an immunogenic fragment thereof; and
a C-terminal HSV gD protein sequence or a variant thereof.

Embodiment 38. A fusion protein comprising:
an N-terminal HSV gD sequence or a variant thereof;
an HBV polymerase C-terminal domain comprising the amino acid sequence of SEQ ID NO: 179 or an immunogenic fragment thereof, or the amino acid sequence of SEQ ID NO: 182 or an immunogenic fragment thereof; and
a C-terminal HSV gD protein sequence or a variant thereof.

Embodiment 39. A fusion protein comprising:
an N-terminal HSV gD sequence or a variant thereof;
an HBV sequence comprising:
(1) an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof; or (2) an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof; and a C-terminal HSV gD protein sequence or a variant thereof.

Embodiment 40. The fusion protein of embodiment 39, wherein the HBV sequence comprises an HBV polymerase N-terminal domain comprising the amino acid sequence of SEQ ID NO: 178 or an immunogenic fragment thereof, an HBV polymerase C-terminal domain comprising the amino acid sequence of SEQ ID NO: 179 or an immunogenic fragment thereof, and an HBV Core protein comprising the amino acid sequence of SEQ ID NO: 180 or an immunogenic fragment thereof.

Embodiment 41. The fusion protein of embodiment 40, wherein the HBV sequence comprises the amino acid sequence of SEQ ID NO: 174.

Embodiment 42. The fusion protein of embodiment 39, wherein the HBV sequence comprises an HBV polymerase N-terminal domain comprising the amino acid sequence of SEQ ID NO: 181 or an immunogenic fragment thereof, an HBV polymerase C-terminal domain comprising the amino acid sequence of SEQ ID NO: 182 or an immunogenic fragment thereof, and an HBV Core protein comprising the amino acid sequence of SEQ ID NO: 183 or an immunogenic fragment thereof Embodiment 43. The fusion protein of embodiment 42, wherein the HBV sequence comprises the amino acid sequence of SEQ ID NO: 175.

Embodiment 44. The fusion protein of any one of embodiments 29-43, wherein the N-terminal HSV gD sequence comprises the amino acid sequence of SEQ ID NO: 12.

Embodiment 45. The fusion protein of any one of embodiments 29-43, wherein the N-terminal HSV gD sequence comprises amino acid residues 26-269 of SEQ ID NO: 12.

Embodiment 46. The fusion protein of any one of embodiments 29-45, wherein the C-terminal HSV gD sequence comprises the transmembrane domain of the HSV gD.

Embodiment 47. The fusion protein of any one of embodiments 29-46, wherein the C-terminal HSV gD sequence comprises the amino acid sequence of SEQ ID NO: 13.

Embodiment 48. The fusion protein of any one of embodiments 29-47, wherein the fusion protein comprises the amino acid sequence of any one of SEQ ID NO: 14 or an immunogenic fragment thereof, SEQ ID NO: 16 or an immunogenic fragment thereof, or SEQ ID NO: 18 or an immunogenic fragment thereof.

Embodiment 49. The fusion protein of any one of embodiments 39-47, wherein the fusion protein comprises the amino acid sequence of SEQ ID NO: 185.

Embodiment 50. The fusion protein of any one of embodiments 39-47, wherein the fusion protein comprises the amino acid sequence of SEQ ID NO: 187.

Embodiment 51. A nucleic acid molecule encoding the fusion protein of any one of embodiments 23-50.

Embodiment 52. The nucleic acid molecule of embodiment 51, wherein the nucleic acid molecule comprises the nucleotide sequence of any one of SEQ ID NOs: 15, 17, or 19.

Embodiment 53. The nucleic acid molecule of embodiment 51, wherein the nucleic acid molecule comprises the nucleotide sequence of SEQ ID NO: 176.

Embodiment 54. The nucleic acid molecule of embodiment 51, wherein the nucleic acid molecule comprises the nucleotide sequence of SEQ ID NO: 177.

Embodiment 55. The nucleic acid molecule of embodiment 51, wherein the nucleic acid molecule comprises the nucleotide sequence of SEQ ID NO: 184.

Embodiment 56. The nucleic acid molecule of embodiment 51, wherein the nucleic acid molecule comprises the nucleotide sequence of SEQ ID NO: 186.

Embodiment 57. A vector comprising the nucleic acid molecule of any one of embodiments 51-56.

Embodiment 58. The vector of embodiment 57, wherein the vector is an adenoviral vector.

Embodiment 59. The vector of embodiment 58, wherein the adenoviral vector is an AdC6 vector or AdC7 vector.

Embodiment 60. A vaccine comprising the vector of any one of embodiments 57-59.

Embodiment 61. A method of inducing an immune response to HBV in a subject, the method comprising providing to the subject an effective amount of the fusion protein of any one of embodiments 23-50, the nucleic acid molecule of any one of embodiments 51-56, the vector of any one of embodiments 57-59, or the vaccine of embodiment 60 to thereby induce an immune response to HBV.

Embodiment 62. The method of embodiment 61, wherein the vaccine comprises an AdC6 vector comprising a fusion protein comprising the amino acid sequence of any one of SEQ ID NOs: 14, 16, or 18, or an immunogenic fragment thereof.

Embodiment 63. The method of embodiment 62, further comprising providing to the subject, subsequent to providing the vaccine comprising the AdC6 vector, a vaccine comprising an AdC7 vector comprising a fusion protein comprising the amino acid sequence of any one of SEQ ID NOs: 14, 16, or 18, or an immunogenic fragment thereof.

Embodiment 64. The method of embodiment 61, wherein the vaccine comprises an AdC7 vector comprising a fusion protein comprising the amino acid sequence of any one of SEQ ID NOs: 14, 16, or 18, or an immunogenic fragment thereof.

Embodiment 65. The method of embodiment 64, further comprising providing to the subject, subsequent to providing the vaccine comprising the AdC7 vector, a vaccine comprising an AdC6 vector comprising a fusion protein comprising the amino acid sequence of any one of SEQ ID NOs: 14, 16, or 18, or an immunogenic fragment thereof.

Embodiment 66. The method of embodiment 61, wherein the vaccine comprises an AdC6 vector comprising a fusion protein comprising the amino acid sequence of SEQ ID NO: 185.

Embodiment 67. The method of embodiment 66, further comprising providing to the subject, subsequent to providing the vaccine comprising the AdC6 vector, a vaccine comprising an AdC7 vector comprising a fusion protein comprising the amino acid sequence of SEQ ID NO: 185.

Embodiment 68. The method of embodiment 61, wherein the vaccine comprises an AdC7 vector comprising a fusion protein comprising the amino acid sequence of SEQ ID NO: 185.

Embodiment 69. The method of embodiment 68, further comprising providing to the subject, subsequent to providing the vaccine comprising the AdC7 vector, a vaccine comprising an AdC6 vector comprising a fusion protein comprising the amino acid sequence of SEQ ID NO: 185.

Embodiment 70. The method of embodiment 61, wherein the vaccine comprises an AdC6 vector comprising a fusion protein comprising the amino acid sequence of SEQ ID NO: 187.

Embodiment 71. The method of embodiment 70, further comprising providing to the subject, subsequent to providing the vaccine comprising the AdC6 vector, a vaccine comprising an AdC7 vector comprising a fusion protein comprising the amino acid sequence of SEQ ID NO: 187.

Embodiment 72. The method of embodiment 61, wherein the vaccine comprises an AdC7 vector comprising a fusion protein comprising the amino acid sequence of SEQ ID NO: 187.

Embodiment 73. The method of embodiment 72, further comprising providing to the subject, subsequent to providing the vaccine comprising the AdC7 vector, a vaccine comprising an AdC6 vector comprising a fusion protein comprising the amino acid sequence of SEQ ID NO: 187.

Embodiment 74. The method of any one of embodiments 61-73, wherein the amino acid sequence of any one of SEQ ID NOs: 14, 16, 18, 185, or 187, or an immunogenic fragment thereof, does not contain the N-terminal 25 amino acid signal peptide.

What is claimed:

1. A method of inducing an immune response to HBV in a subject, the method comprising:
providing to the subject an effective amount of a first vaccine comprising a nucleic acid molecule that comprises a nucleotide sequence encoding an HBV polymerase N-terminal domain comprising the amino acid sequence of SEQ ID NO: 178 or an immunogenic fragment thereof, a nucleotide sequence encoding an HBV polymerase C-terminal domain comprising the amino acid sequence of SEQ ID NO: 179 or an immunogenic fragment thereof, and a nucleotide sequence encoding an HBV Core protein comprising the amino acid sequence of SEQ ID NO: 180 or an immunogenic fragment thereof, and
providing to the subject an effective amount of a second vaccine comprising a nucleic acid molecule that comprises a nucleotide sequence encoding an HBV polymerase N-terminal domain comprising the amino acid sequence of SEQ ID NO: 178 or an immunogenic fragment thereof, a nucleotide sequence encoding an HBV polymerase C-terminal domain comprising the amino acid sequence of SEQ ID NO: 179 or an immunogenic fragment thereof, and a nucleotide sequence encoding an HBV Core protein comprising the amino acid sequence of SEQ ID NO: 180 or an immunogenic fragment thereof,
to thereby induce an immune response to HBV.

2. The method of claim 1, wherein the nucleic acid molecule of the first vaccine encodes a fusion protein comprising the amino acid sequence of SEQ ID NO: 174, the nucleic acid molecule of the second vaccine encodes a fusion protein comprising the amino acid sequence of SEQ ID NO: 174, or the nucleic acid molecule of the first vaccine and the nucleic acid molecule of the second vaccine encode a fusion protein comprising the amino acid sequence of SEQ ID NO: 174.

3. The method of claim 1, wherein the nucleic acid molecule of the first vaccine, the nucleic acid molecule of the second vaccine, or the nucleic acid molecule of the first vaccine and the nucleic acid molecule of the second vaccine further comprise a nucleotide sequence encoding:
an N-terminal HSV gD sequence or a variant thereof,
a C-terminal HSV gD sequence or a variant thereof, or both.

4. The method of claim 3, comprising:
providing to the subject an effective amount of a first vaccine comprising a nucleic acid molecule that comprises a nucleotide sequence encoding an N-terminal HSV gD sequence or a variant thereof, a nucleotide sequence encoding an HBV polymerase N-terminal domain comprising the amino acid sequence of SEQ ID NO: 178 or an immunogenic fragment thereof, a nucleotide sequence encoding an HBV polymerase C-terminal domain comprising the amino acid sequence of SEQ ID NO: 179 or an immunogenic fragment thereof, a nucleotide sequence encoding an HBV Core protein comprising the amino acid sequence of SEQ ID NO: 180 or an immunogenic fragment thereof, and a nucleotide sequence encoding a C-terminal HSV gD sequence or a variant thereof, and
providing to the subject an effective amount of a second vaccine comprising a nucleic acid molecule that comprises a nucleotide sequence encoding an N-terminal HSV gD sequence or a variant thereof, a nucleotide sequence encoding an HBV polymerase N-terminal domain comprising the amino acid sequence of SEQ ID NO: 178 or an immunogenic fragment thereof, a nucleotide sequence encoding an HBV polymerase C-terminal domain comprising the amino acid sequence of SEQ ID NO: 179 or an immunogenic fragment thereof, a nucleotide sequence encoding an HBV Core protein comprising the amino acid sequence of SEQ ID NO: 180 or an immunogenic fragment thereof, and a nucleotide sequence encoding a C-terminal HSV gD sequence or a variant thereof,
to thereby induce an immune response to HBV.

5. The method of claim 4, wherein the nucleic acid molecule of the first vaccine, the nucleic acid molecule of the second vaccine, or the nucleic acid molecule of the first vaccine and the nucleic acid molecule of the second vaccine encode an HBV fusion protein comprising the amino acid sequence of SEQ ID NO: 174.

6. The method of claim 5, wherein the N-terminal HSV gD sequence of the first vaccine, the N-terminal HSV gD sequence of the second vaccine, or the N-terminal HSV gD sequence of the first vaccine and the N-terminal HSV gD sequence of the second vaccine comprise the amino acid sequence of SEQ ID NO: 12.

7. The method of claim 5, wherein the N-terminal HSV gD sequence of the first vaccine, the N-terminal HSV gD sequence of the second vaccine, or the N-terminal HSV gD sequence of the first vaccine and the N-terminal HSV gD sequence of the second vaccine comprise amino acid residues 26-269 of SEQ ID NO: 12.

8. The method of claim 5, wherein the C-terminal HSV gD sequence of the first vaccine, the C-terminal HSV gD sequence of the second vaccine, or the C-terminal HSV gD sequence of the first vaccine and the C-terminal HSV gD sequence of the second vaccine comprise the transmembrane domain of the HSV gD.

9. The method of claim 8, wherein the C-terminal HSV gD sequence of the first vaccine, the C-terminal HSV gD sequence of the second vaccine, or the C-terminal HSV gD sequence of the first vaccine and the C-terminal HSV gD sequence of the second vaccine comprise the amino acid sequence of SEQ ID NO: 13.

10. The method of claim 4, comprising:
providing to the subject an effective amount of a first vaccine comprising a nucleic acid molecule that comprises a nucleotide sequence encoding an N-terminal HSV gD sequence comprising amino acid residues 26-269 of SEQ ID NO: 12, a nucleotide sequence encoding an HBV polymerase N-terminal domain comprising the amino acid sequence of SEQ ID NO: 178 or an immunogenic fragment thereof, a nucleotide sequence encoding an HBV polymerase C-terminal domain comprising the amino acid sequence of SEQ ID NO: 179 or an immunogenic fragment thereof, a nucleotide sequence encoding an HBV Core protein comprising the amino acid sequence of SEQ ID NO: 180 or an immunogenic fragment thereof, and a nucleotide sequence encoding a C-terminal HSV gD sequence comprising the amino acid sequence of SEQ ID NO: 13, and
providing to the subject an effective amount of a second vaccine comprising a nucleic acid molecule that comprises a nucleotide sequence encoding an N-terminal HSV gD sequence comprising amino acid residues 26-269 of SEQ ID NO: 12, a nucleotide sequence encoding an HBV polymerase N-terminal domain comprising the amino acid sequence of SEQ ID NO: 178 or an immunogenic fragment thereof, a nucleotide sequence encoding an HBV polymerase C-terminal domain comprising the amino acid sequence of SEQ ID NO: 179 or an immunogenic fragment thereof, a nucleotide sequence encoding an HBV Core protein comprising the amino acid sequence of SEQ ID NO: 180 or an immunogenic fragment thereof, and a nucleotide sequence encoding a C-terminal HSV gD sequence comprising the amino acid sequence of SEQ ID NO: 13,
to thereby induce an immune response to HBV.

11. The method of claim 10, wherein the N-terminal HSV gD sequence of the first vaccine, the N-terminal HSV gD sequence of the second vaccine, or the N-terminal HSV gD sequence of the first vaccine and the N-terminal HSV gD sequence of the second vaccine comprise the amino acid sequence of SEQ ID NO: 12.

12. The method of claim 10, wherein the nucleic acid molecule of the first vaccine, the nucleic acid molecule of the second vaccine, or the nucleic acid molecule of the first vaccine and the nucleic acid molecule of the second vaccine encode an HBV fusion protein comprising the amino acid sequence of SEQ ID NO: 174.

13. The method of claim 12, wherein the nucleic acid molecule of the first vaccine, the nucleic acid molecule of the second vaccine, or the nucleic acid molecule of the first vaccine and the nucleic acid molecule of the second vaccine comprise the nucleotide sequence of SEQ ID NO: 176.

14. The method of claim 10, wherein the nucleic acid molecule of the first vaccine, the nucleic acid molecule of the second vaccine, or the nucleic acid molecule of the first vaccine and the nucleic acid molecule of the second vaccine encode a fusion protein comprising the amino acid sequence of SEQ ID NO: 185.

15. The method of claim 14, wherein the nucleic acid molecule of the first vaccine, the nucleic acid molecule of the second vaccine, or the nucleic acid molecule of the first vaccine and the nucleic acid molecule of the second vaccine comprise the nucleotide sequence of SEQ ID NO: 184.

16. The method of claim 14, wherein the first vaccine comprises an AdC6 vector comprising a nucleic acid molecule encoding a fusion protein comprising the amino acid sequence of SEQ ID NO: 185.

17. The method of claim 16, comprising
providing to the subject an effective amount of a first vaccine comprising an AdC6 vector comprising a nucleic acid molecule encoding a fusion protein comprising the amino acid sequence of SEQ ID NO: 185, and
subsequent to providing the first vaccine, providing to the subject an effective amount of a second vaccine comprising an AdC7 vector comprising a nucleic acid molecule encoding a fusion protein comprising the amino acid sequence of SEQ ID NO: 185,
to thereby induce an immune response to HBV.

18. The method of claim 14, wherein the first vaccine comprises an AdC7 vector comprising a nucleic acid molecule encoding a fusion protein comprising the amino acid sequence of SEQ ID NO: 185.

19. The method of claim 18, comprising
providing to the subject an effective amount of a first vaccine comprising an AdC7 vector comprising a nucleic acid molecule encoding a fusion protein comprising the amino acid sequence of SEQ ID NO: 185, and
subsequent to providing the first vaccine, providing to the subject an effective amount of a second vaccine comprising an AdC6 vector comprising a nucleic acid molecule encoding a fusion protein comprising the amino acid sequence of SEQ ID NO: 185,
to thereby induce an immune response to HBV.

20. The method of claim 14, wherein the nucleic acid molecule of the first vaccine, the nucleic acid molecule of the second vaccine, or the nucleic acid molecule of the first vaccine and the nucleic acid molecule of the second vaccine encode a fusion protein comprising the amino acid sequence of SEQ ID NO: 185, or an immunogenic fragment thereof, without the N-terminal 25 amino acid signal peptide.

* * * * *